(12) United States Patent
Roizman et al.

(10) Patent No.: US 10,905,770 B2
(45) Date of Patent: Feb. 2, 2021

(54) TOPICAL DELIVERY OF THERAPEUTIC AGENTS USING CELL-PENETRATING PEPTIDES FOR THE TREATMENT OF AGE-RELATED MACULAR DEGENERATION AND OTHER EYE DISEASES

(71) Applicant: MacRegen, Inc., Birmingham, AL (US)

(72) Inventors: Keith Roizman, San Jose, CA (US); John Jacob Requard, III, Apex, NC (US); Felicity Jane De Cogan, Ely (GB)

(73) Assignee: MacRegen, Inc., Birmingham, AL (US)

( * ) Notice: Subject to any disclaimer, the term of this patent is extended or adjusted under 35 U.S.C. 154(b) by 43 days.

(21) Appl. No.: 16/037,432

(22) Filed: Jul. 17, 2018

(65) Prior Publication Data

US 2019/0015521 A1 Jan. 17, 2019

Related U.S. Application Data

(60) Provisional application No. 62/533,231, filed on Jul. 17, 2017.

(51) Int. Cl.

| | |
|---|---|
| *A61K 47/64* | (2017.01) |
| *A61K 9/00* | (2006.01) |
| *A61K 45/06* | (2006.01) |
| *A61P 29/00* | (2006.01) |
| *A61P 3/06* | (2006.01) |
| *A61P 39/06* | (2006.01) |
| *A61K 31/047* | (2006.01) |
| *A61K 31/065* | (2006.01) |
| *A61K 47/42* | (2017.01) |
| *A61K 31/573* | (2006.01) |
| *A61K 39/395* | (2006.01) |
| *A61K 31/7004* | (2006.01) |
| *A61K 31/436* | (2006.01) |
| *A61K 31/366* | (2006.01) |
| *A61K 31/40* | (2006.01) |
| *A61K 38/17* | (2006.01) |
| *C07K 16/22* | (2006.01) |
| *C07K 16/24* | (2006.01) |
| *A61K 39/00* | (2006.01) |

(52) U.S. Cl.
CPC ......... *A61K 47/645* (2017.08); *A61K 9/0048* (2013.01); *A61K 9/0051* (2013.01); *A61K 31/047* (2013.01); *A61K 31/065* (2013.01); *A61K 31/366* (2013.01); *A61K 31/40* (2013.01); *A61K 31/436* (2013.01); *A61K 31/573* (2013.01); *A61K 31/7004* (2013.01); *A61K 38/1709* (2013.01); *A61K 39/3955* (2013.01); *A61K 45/06* (2013.01); *A61K 47/42* (2013.01); *A61P 3/06* (2018.01); *A61P 29/00* (2018.01); *A61P 39/06* (2018.01); *C07K 16/22* (2013.01); *C07K 16/241* (2013.01); *A61K 2039/505* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 2003/0022831 A1 | 1/2003 | Rothbard et al. | |
| 2004/0266663 A1* | 12/2004 | Schwartz | A61K 31/66 514/7.4 |
| 2008/0234183 A1 | 9/2008 | Hallbrink et al. | |

(Continued)

FOREIGN PATENT DOCUMENTS

| | | |
|---|---|---|
| CN | 106668860 A | 5/2017 |
| WO | WO 97/23240 A2 | 7/1997 |

(Continued)

OTHER PUBLICATIONS

Kent "Treating Wet AMD with Anti-VEGF Drugs," Review of Ophthalmology, Aug. 5, 2016 (Year: 2016).*
Akahoshi et al., "Enhanced cellular uptake of lactosomes using cell-penetrating peptides", Science and Technology of Advanced Materials, vol. 17 (1), 2016, pp. 245-252.
Bhattacharya et al., "Differentially cleaving peptides as a strategy for controlled drug release in human retinal pigment epithelial cells", Journal of Controlled Release, vol. 251 (2017), pp. 37-48.
Chen et al., "Anti-angiogenesis through noninvasive to minimally invasive intraocular delivery of the peptide CC12 identified by in vivo-directed evolution", Biomaterials, vol. 112 (2017), pp. 218-233.

(Continued)

*Primary Examiner* — Christina Bradley
(74) *Attorney, Agent, or Firm* — The Marbury Law Group, PLLC

(57) ABSTRACT

The present disclosure provides therapeutic agents for the treatment of age-related macular degeneration (AMD) and other eye disorders. One or more therapeutic agents can be used to treat any stages (including the early, intermediate and advance stages) of AMD, and any phenotypes of AMD, including geographic atrophy (including non-central GA and central GA) and neovascularization (including types 1, 2 and 3 NV). In some embodiments, the one or more therapeutic agents are or include an anti-dyslipidemic agent, an antioxidant, an anti-inflammatory agent, a complement inhibitor, a neuroprotector or an anti-angiogenic agent, or any combination thereof. In certain embodiments, the one or more therapeutic agents are or include an anti-dyslipidemic agent (e.g., an apolipoprotein mimetic or/and a statin). In some embodiments, the one or more therapeutic agents are mixed with, non-covalently associated with or covalently bonded to a cell-penetrating peptide (CPP), encapsulated in CPP-conjugated nanoparticles, micelles or liposomes, or modified (e.g., stapled, prenylated, lipidated or coupled to a small-molecule α-helix mimic) to acquire membrane-translocating ability. In certain embodiments, the one or more therapeutic agents are administered by eye drop.

19 Claims, 18 Drawing Sheets

Specification includes a Sequence Listing.

(56) References Cited

U.S. PATENT DOCUMENTS

| | | |
|---|---|---|
| 2013/0041133 A1 | 2/2013 | Aaronson et al. |
| 2014/0357563 A1 | 12/2014 | Poncz et al. |
| 2016/0339079 A1 | 11/2016 | Stamboulis et al. |
| 2017/0000730 A1 | 1/2017 | Peyman |
| 2017/0157038 A1 | 1/2017 | Peyman |
| 2017/0057998 A1 | 3/2017 | Stamboulis et al. |
| 2018/0296525 A1* | 10/2018 | Roizman ............ A61K 38/1866 |

FOREIGN PATENT DOCUMENTS

| | | |
|---|---|---|
| WO | WO 98/52614 A2 | 11/1998 |
| WO | WO 2015/114324 A1 | 8/2015 |

OTHER PUBLICATIONS

Chu et al., "Topical ocular delivery to laser-induced choroidal neovascularization by dual internalizing RG D and TAT peptide-modified nanoparticles", International Journal of Nanomedicine, vol. 12, 2017, pp. 1353-1368.

Chugh et al., "Critical Review: Cell-Penetrating Peptides: Nanocarrier for Macromolecule Delivery in Living Cells", Life, vol. 62(3), Mar. 2010, pp. 183-193.

Crombez et al., "A New Potent Secondary Amphipathic Cell-penetrating Peptide for siRNA Delivery Into Mammalian Cells", Molecular Therapy, vol. 17 (1), Jan. 2009, pp. 95-103.

Davis et al., "Topical Delivery of Avastin to the Posterior Segment of the Eye In Vivo Using Annexin A5-associated Liposomes", Small (2014), vol. 10, No. 8, pp. 1575-1584.

deCogan et al., "Topical Treatment for AMD: Non-Invasive Delivery and Efficacy of Ranibuzumab and Bevacizumab in Rabbit and Porcine Eyes", University of Birmingham; presented at the ARVO Conference in Honolulu, Hawaii on Apr. 30, 2018.

De Cogan et al.," Topical Delivery of Anti-VEGF Drugs to the Ocular Posterior Segment Using Cell-Penetrating Peptides", Nanotechnology and Regenerative Medicine, Investigative Ophthalmology and Visual Science, vol. 58 (5), 2017, pp. 2578-2590.

De Coupade et al. "Novel human-derived cell-penetrating peptides for specific subcellular delivery of therapeutic biomolecules", Biochem. J. (2005) 390, pp. 407-418.

Desai et al., "Interaction of nanoparticles and cell-penetrating peptides with skin for transdermal drug delivery", Mol Membr Biol., 27(7), Oct. 2010, pp. 247-259.

Deshayes et al., "Cell-penetrating peptides: tools for intracellular delivery of therapeutics", CMLS, Cell Mol. Life Sci., 62 (2005), pp. 1839-1849.

Deshayes et al., "Structural polymorphism of non-covalent peptide-based delivery systems: Highway to cellular uptake", Biochimica et Biophysica Acta 1798, (2010), pp. 2304-2314.

Dom et al., "Cellular uptake of Antennapedia Penetratin peptides is a two-step process in which phase transfer precedes a tryptophan-dependent translocation", Nucleic Acids Research, vol. 31, No. 2, 2003, pp. 556-561.

Duchardt et al., "A Cell-penetrating Peptide Derived from Human Lactoferrin with Conformation-dependent Uptake Efficiency", J. of Biological Chemistry, vol. 284 (52), 2009, pp. 36099-36108.

El-Andaloussi et al., "A Novel Cell-penetrating Peptide, M918, for Efficient Delivery of Proteins and Peptide Nucleic Acids", Molecular Therapy, vol. 15(10) (2007) pp. 1820-1826.

Elliott et al., "Intercellular Trafficking and Protein Delivery by a Herpesvirus Structural Protein", Cell, vol. 88, (1997) pp. 223-233.

Ezzat et al., "PepFect 14, a novel cell-penetrating peptide for oligonucleotide delivery in solution and as solid formulation", Nucleic Acids Research, vol. 39, No. 12, (2011) pp. 5284-5298.

Fischer et al., "A quantitative validation of fluorophore-labelled cell-permeable peptide conjugates: fluorophore and cargo dependence of import", Biochimica et Biophysica Acta 1564 (2002) pp. 365-374.

Futaki et al., "Arginine-rich Peptides: An Abundant Source of Membrane-Permeable Peptides Having Potential As Carriers for Intracellular Protein Delivery", J. of Biological Chemistry, vol. 276, No. 8 (2001), pp. 5836-5840.

Futaki et al., "Structural Variety of Membrane Permeable Peptides", Current Protein and Peptide Science, vol. 4, (2003), pp. 87-96.

Futaki, "Membrane-permeable arginine-rich peptides and the translocation mechanisms", Advanced Drug Delivery Reviews, 57, (2005) pp. 547-558.

Gautam et al., "Topical Delivery of Protein and Peptide Using Novel Cell Penetrating Peptide IMT-P8", Nature, Scientific Reports , 6: 26278 (pp. 1-13), 2016.

George et al., "Corneal Penetrating Elastin-Like Polypeptide Carriers", Journal of Ocular Pharmacology and Therapeutics, vol. 32, No. 3, 2016, pp. 163-171.

Godet et al., "PP2A$_1$ Binding, Cell Transducing and Apoptotic Properties of Vpr$_{77-92}$: A New Functional Domain of HIV-1 Vpr Proteins" PLOS One, vol. 5, Issue 11, (2010), e13760 (1-10).

Gottschalk et al., "A Novel DNA-peptide complex for efficient gene transfer and expression in mammalian cells", Gene Therapy, (1996), vol. 3, pp. 448-457.

Gros et al., "A non-covalent peptide-based strategy for protein and peptide nucleic acid transduction", Biochimica et Biophysica Acta 1758 (2006) pp. 384-393.

Heitz et al., Themed Section: Vector Design and Drug Delivery-Review: Twenty years of cell-penetrating peptides: from molecular mechanisms to therapeutics, British Journal of Pharmacology (2009), 157, pp. 195-206.

Herbig et al., "Membrane Surface-Associated Helices Promote Lipid Interactions and Cellular Uptake of Human Calcitonin-Derived Cell Penetrating Peptides", Biophysical Journal, vol. 89, Dec. 2005, pp. 4056-4066.

Hou et al., "Transdermal delivery of proteins mediated by non-covalently associated arginine-rich intracellular delivery peptide", Experimental Dermatology, 2007; 16: 999-1006.

Hou et al., "Mechanisms of Nanoparticle Mediated siRNA Transfection by Melittin-Derived Peptides", Final Edited Form—ACS Nano. vol. 7(10) 2013, pp. 8605-8615 [NIH Public Access, pp. 1-21].

Hou et al., "Melittin Derived Peptides for Nanoparticle Based siRNA Transfection", Final Edited Form—Biomaterials, vol. 34(12) 2013, pp. 3110-3119 [NIH Public Access, pp. 1-20].

Hu et al., "Reprogramming Human Retinal Pigmented Epithelial Cells to Neurons Using Recombinant Proteins", Stem Cells Translationalmedicine, 2014;3: pp. 1526-1534.

Jain et al., "Cell Penetrating Peptides as Efficient Nanocarriers for Delivery of Antifungal Compound, Natamycin for the Treatment of Fungal Keratitis", Pharm Res (2015) vol. 32:pp. 1920-1930.

Johnson et al., "Cell-penetrating Peptide for Enhanced Delivery of Nucleic Acids and Drugs to Ocular Tissues Including Retina and Cornea", Molecular Therapy vol. 16 No. 1, (2008), pp. 107-114.

Johnson et al., "Cell Penetrating Peptide POD Mediates Delivery of Recombinant Proteins to Retina, Cornea and Skin", Final Edited Form: Vision Res. Mar. 31, 2010; 50(7): pp. 686-697 [NIH Public Access, pp. 1-20].

Jones et al., "Characterisation of cell-penetrating peptide-mediated peptide delivery", British Journal of Pharmacology (2005) 145, 1093-1102.

Kamada et al., "Creation of Novel Cell-Penetrating Peptides for Intracellular Drug Delivery Using Systematic Phage Display Technology Originated from Tat Transduction Domain", Biol. Pharm. Bull. 30(2) 218-223 (2007).

Kamei et al., "Permeation characteristics of oligoarginine through intestinal epithelium and its usefulness for intestinal peptide drug delivery", Journal of Controlled Release, 131, (2008), pp. 94-99.

Kamei et al., "Usefulness of cell-penetrating peptides to improve intestinal insulin absorption", Journal of Controlled Release, 132, (2008), pp. 21-25.

Kamei et al., "Importance of intermolecular interaction on the improvement of intestinal therapeutic peptide/protein absorption using cell-penetrating peptides", Journal of Controlled Release, 136, (2009), pp. 179-186.

Kerkis et al., "Review Article: State of the Art in the Studies on Crotamine, a Cell Penetrating Peptide from South American Rattle-

(56) References Cited

OTHER PUBLICATIONS snake", Hindawi Publishing Corporation, BioMed Research International, vol. 2014, Article ID 675985, 9 pages, http://dx.doi.org/10.1155/2014/675985.

Khafagy et al., "Efficiency of cell-penetrating peptides on the nasal and intestinal absorption of therapeutic peptides and proteins", International Journal of Pharmaceutics, 381, (2009), pp. 49-55.

Kim et al., Cholesteryl Oligoarginine Delivering Vascular Endothelial Growth Factor siRNA Effectively Inhibits Tumor Growth in Colon Adenocarcinoma°, Molecular Therapy vol. 14, No. 3, Sep. 2006, pp. 343-350.

Kim et al., "Discovery of a non-cationic cell penetrating peptide derived from membrane-interacting human proteins and its potential as a protein delivery carrier" Nature, Scientific Reports, 5:11719 (pp. 1-15) (2015).

Kramer et al., "Reinventing Cell Penetrating Peptides Using Glycosylated Methionine Sulfonium Ion Sequences", ACS Publications, ACS Cent. Sci., 2015, 1, pp. 83-88.

Langedijk et al., "Translocation Activity of C-terminal Domain of Pestivirus $E^{rns}$ and Ribotoxin L3 Loop", J. of Biological Chemistry, vol. 277, No. 7, (2002), pp. 5308-5314.

Lin et al., "Communication: Inhibition of Nuclear Translocation of Transcription Factor NF-kB by a Synthetic Peptide Containing a Cell Membrane-permeable Motif and Nuclear Localization Sequence", J. of Biological Chemistry, vol. 270, No. 24, (1995), pp. 14255-14258.

Lindberg et al., "PepFect15, a novel endosomolytic cell-penetrating peptide for oligonucleotide delivery via scavenger receptors", International Journal of Pharmaceutics, vol. 441 (2013), pp. 242-247.

Liu et al., "Penetratin, a Potentially Powerful Absorption Enhancer for Noninvasive Intraocular Drug Delivery", ACS Publications, Mol. Pharmaceutics, 2014, 11, 1218-1227.

Lopes et al., "Enhanced skin penetration of P20 phosphopeptide using protein transduction domains", Final Edited Form: Eur J Pharm Biopharm., Feb. 2008; 68(2): 441 [NIH Public Access, pp. 1-8].

Lundberg et al., "Delivery of short interfering RNA using endosomolytic cell-penetrating peptides", FASEB Journal, vol. 21, pp. 2664-2671 (2007).

Mae et al., "A stearylated CPP for delivery of splice correcting oligonucleotides using a non-covalent co-incubation strategy", Journal of Controlled Release, 134, (2009), pp. 221-227.

Magzoub et al., "Membrane perturbation effects of peptides derived from the N-termini of unprocessed prion proteins", Biochimica et Biophysica Acta, 1716 (2005) pp. 126-136.

Maiolo et al., "Effects of cargo molecules on the cellular uptake of arginine-rich cell-penetrating peptides", Biochimica et Biophysica Acta, 1712 (2005), pp. 161-172.

Mano et al., "Cellular uptake of $S4_{13}$-PV peptide occurs upon conformational changes induced by peptide-membrane interactions", Biochimica et Biophysica Acta 1758 (2006) pp. 336-346.

Marks et al., "Spontaneous Membrane-Translocating Peptides by Orthogonal High-throughput Screening", Final Edited Form: J Am Chem Soc., Jun. 15, 2011; 133(23): 8995-9004 [NIH Public Access, pp. 1-21].

McGeady et al., "The Farnesyl Group of H-Ras Facilitates the Activation of a Soluble Upstream Activator of Mitogen-activated Protein Kinase", J. of Biological Chemistry, vol. 270, No. 44, (1995) pp. 26347-26351.

Mehta et al., "A cell penetrating peptide derived from azurin inhibits angiogenesis and tumor growth by inhibiting phosphorylation of VEGFR-2, FAK and Akt", Angiogenesis (2011) vol. 14:355-369.

Mickan et al., "Rational Design of CPP-based Drug Delivery Systems: Considerations from Pharmacokinetics", Current Pharmaceutical Biotechnology, 2014, vol. 15(3), pp. 1-10.

Milletti, "Cell-penetrating peptides: classes, origin, and current landscape", Drug Discovery Today, vol. 17, Nos. 15/16, Aug. 2012, pp. 850-860.

Mitchell et al., "Polyarginine enters cells more efficiently than other polycationic homopolymers", J. Peptide Res., 2000, 56, pp. 318-325.

Morris et al., "A new peptide vector for efficient delivery of oligonucleotides into mammalian cells", Nucleic Acids Research, 1997, vol. 25, No. 14, pp. 2730-2736.

Morris et al. "A non-covalent peptide-based carrier for in vivo delivery of DNA mimics", Nucleic Acids Research, 2007, vol. 35, No. 7, e49 (pp. 1-10).

Mueller et al., "Cell Penetration Peptides for Enhanced Entry of αB-Crystallin into Lens Cells", Investigative Ophthalmology & Visual Science, Jan. 2013, vol. 54, No. 1, pp. 2-8.

Munyendo et al., "Cell Penetrating Peptides in the Delivery of Biopharmaceuticals", Biomolecules 2012, 2, 187-202; doi:10.3390/biom2020187.

Myrberg et al., "Protein Delivery by the Cell-Penetrating Peptide YTA2", Bioconjugate Chem. (2007), vol. 18, pp. 170-174.

Nascimento et al., "Crotamine Mediates Gene Delivery into Cells through the Binding to Heparan Sulfate Proteoglycans", J. of Biological Chemistry, vol. 282, No. 29, (2007) pp. 21349-21360.

Nasrollahi et al., "Cell-penetrating Peptides as a Novel Transdermal Drug Delivery System", Chem Biol Drug Des 2012; 80: pp. 639-646.

Ochocki et al., "Evaluation of a Cell Penetrating Prenylated Peptide Lacking an Intrinsic Fluorophore via in situ Click Reaction", Final Edited Form: Bioorg Med Chem Lett., Sep. 1, 2011; 21(17): pp. 4998-5001 [NIH Public Access, pp. 1-9].

Oehlke et al., "Extensive cellular uptake into endothelial cells of an amphipathic β-sheet forming peptide", FEBS Letters 415 (1997) 196-199.

Oess et al., "Novel cell permeable motif derived from the PreS2-domain of hepatitis-B virus surface antigens", Gene Therapy (2000) 7, 750-758.

Okuyama et al, "Small-molecule mimics of an α-helix for efficient transport of proteins into cells", Nature Methods, vol. 4, No. 2, (2007), 153-159.

Park et al., "Structure-activity analysis of buforin II, a histone H2A-derived antimicrobial peptide: The proline hinge is responsible for the cell-penetrating ability of buforin II", PNAS, vol. 97, No. 15 (Jul. 18, 2000), pp. 8245-8250.

Pescina et al., "Design and Synthesis of New Cell Penetrating Peptides: Diffusion and Distribution Inside the Cornea", ACS Publications, Mol. Pharmaceutics, 2016, 13, pp. 3876-3883.

Rittner et al., "New Basic Membrane-Destabilizing Peptides for Plasmid-Based Gene Delivery in Vitro and in Vivo", Molecular Therapy vol. 5, No. 2, Feb. 2002, pp. 104-114.

Rousselle et al., "New Advances in the Transport of Doxorubicin through the Blood-Brain Barrier by a Peptide Vector-Mediated Strategy", Molecular Pharmacology, 57:679-686 (2000).

Rousselle et al., "Enhanced Delivery of Doxorubicin into the Brain via a Peptide-Vector-Mediated Strategy: Saturation Kinetics and Specificity", The Journal of Pharmacology and Experimental Therapeutics, vol. 296, No. 1, (2001), pp. 124-131.

Rousselle et al., "Improved Brain Uptake and Pharmacological Activity of Dalargin Using a Peptide-Vector-Mediated Strategy", The Journal of Pharmacology and Experimental Therapeutics, vol. 306, No. 1 (2003), pp. 371-376.

Ruan et al., "Recent advances in peptides for enhancing transdermal macromolecular drug delivery", Ther. Deliv. (2016), vol. 7(2), pp. 89-100.

Rudolph et al., "Oligomers of the Arginine-rich Motif of the HIV-1 TAT Protein Are Capable of Transferring Plasmid DNA into Cells", J. of Biological Chemistry, vol. 278, No. 13, 2003, pp. 11411-11418.

Rydstrom et al., "Direct Translocation as Major Cellular Uptake for CADY Self-Assembling Peptide-Based Nanoparticles", PLoS ONE, vol. 6(10): e25924. (2011) doi:10.1371/journal.pone.0025924.

Sanders et al., "Prediction of Cell Penetrating Peptides by Support Vector Machines", PLoS Comput Biol 7(7): e1002101. (2011) doi:10.1371/journal.pcbi.1002101.

Schmidt et al., "Arginine-rich cell-penetrating peptides", FEBS Letters 584 (2010), pp. 1806-1813.

(56) References Cited

OTHER PUBLICATIONS

Schmidt et al., "Identification of Short Hydrophobic Cell-Penetrating Peptides for Cytosolic Peptide Delivery by Rational Design", ACS Publications, Bioconjugate Chem., 2017, 28, pp. 382-389.
Shah et al., "Enhanced skin permeation using polyarginine modified nanostructured lipid carriers", Final Edited Form: J Control Release. Aug. 10, 2012; 161(3): pp. 735-745 [NIH Public Access, pp. 1-28].
Sheldon et al., "Loligomers: Design of de novo peptide-based intracellular vehicles", Proc. Natl. Acad. Sci. USA, vol. 92, pp. 2056-2060, Mar. 1995.
Shen et al., "Conjugation of poly-L-lysine to albumin and horseradish peroxidase: A novel method of enhancing the cellular uptake of proteins", Proc. Nati. Acad. Sci. USA, vol. 75, No. 4, pp. 1872-1876, Apr. 1978.
Simeoni et al., "Insight into the mechanism of the peptide-based gene delivery system MPG: implications for delivery of siRNA into mammalian cells", Nucleic Acids Research, 2003, vol. 31, No. 11, pp. 2717-2724.
Soler et al., "Identification of BP16 as a non-toxic cell-penetrating peptide with highly efficient drug delivery properties", Org. Biomol. Chem., 2014, vol. 12, pp. 1652-1663.
Soomets et al., "Deletion analogues of transportan", Biochimica et Biophysica Acta 1467 (2000) 165-176.
Stalmans et al., "Chemical-Functional Diversity in Cell-Penetrating Peptides", PLoS ONE 8(8): e71752. (2013) doi:10.1371/journal.pone.0071752.
Stalmans et al., "Cell-Penetrating Peptides Selectively Cross the Blood-Brain Barrier In Vivo", PLoS ONE 10(10): e0139652. (2015) doi:10.1371/journal.pone.0139652.
Sun et al., "A Promising Future for Peptides in Ophthalmology: Work Effectively and Smartly" Current Medicinal Chemistry, 2015, 22, 1030-1040.
Suzuki et al., "Possible Existence of Common Internalization Mechanisms among Arginine-rich Peptides", J. of Biological Chemistry, vol. 277, No. 4, (2002) pp. 2437-2443.
Takayama et al., "Enhanced intracellular delivery using arginine-rich peptides by the addition of penetration accelerating sequences (PAS)", Journal of Controlled Release, 138, (2009), pp. 128-133.
Takayama et al., "Effect of the Attachment of a Penetration Accelerating Sequence and the Influence of Hydrophobicity on Octaarginine-Mediated Intracellular Delivery", ACS Publications, Mol. Pharmaceutics, (2012), vol. 9, pp. 1222-1230.
Takayama, "Development of an Oligoarginine Peptide Displaying Rapid Cell Penetration for Improved Intestinal Absorption", Yakugaku Zasshi, 134(1), (2014), pp. 55-61—English Abstract.
Takeda et al., "Protein transduction therapy into cochleae via the round window niche in guinea pigs", Molecular Therapy—Methods & Clinical Development (2016) 3, 16055; doi:10.1038/mtm.2016.55.
Takeshima et al., "Translocation of Analogues of the Antimicrobial Peptides Magainin and Buforin across Human Cell Membranes", J. of Biological Chemistry, vol. 278, No. 2, (2003), pp. 1310-1315.
Tan et al., "Cell-Penetrating Peptide-Mediated Topical Delivery of Biomacromolecular Drugs", Current Pharmaceutical Biotechnology, 2014, 15, pp. 231-239.
Tang et al., "Helical Poly(arginine) Mimics with Superior Cell-Penetrating and Molecular Transporting Properties", Final Edited Form: Chem Sci. Oct. 2013; 4(10): pp. 3839-3844 [NIH Public Access, pp. 1-16].
Temsamani et al., "Improved Brain Uptake and Pharmacological Activity Profile of Morphine-6-Glucuronide Using a Peptide Vector-Mediated Strategy", The Journal of Pharmacology and Experimental Therapeutics, vol. 313, No. 2 (2005), pp. 712-719.
Uchida et al., "Development of an Efficient Transdermal Delivery System of Small Interfering RNA Using Functional Peptides, Tat and AT-1002", Chem. Pharm. Bull. 59(2) 196-201 (2011).
Uemura et al., "Short polymers of Arginine Rapidly Translocate Into Vascular Cells-Effects on Nitric Oxide Synthesis" Circulation Journal., (2002), vol. 66, pp. 1155-1160.

Vasconcelos et al., "Conjugation of cell-penetrating peptides with poly(lactic-co-glycolic acid)-polyethylene glycol nanoparticles improves ocular drug delivery", International Journal of Nanomedicine (2015): vol. 10, pp. 609-631.
Wadhwani et al., "Antimicrobial and cell-penetrating peptides induce lipid vesicle fusion by folding and aggregation", Eur Biophys J (2012), vol. 41:pp. 177-187.
Wagstaff et al., "Protein Transduction: Cell Penetrating Peptides and Their Therapeutic Applications", Current Medicinal Chemistry, (2006), 13, pp. 1371-1387.
Walensky et al., "Activation of Apoptosis in Vivo by a Hydrocarbon-Stapled BH3 Helix", Final Edited Form: Science. Sep. 3, 2004; 305(5689): pp. 1466-1470 [NIH Public Access, pp. 1-10].
Wang et al., "Cell-penetrating peptide TAT-mediated delivery of acidic FGF to retina and protection against ischemia-reperfusion injury in rats", J. Cell. Mol. Med., vol. 14, No. 7, (2010) pp. 1998-2005.
Wender et al., "The design, synthesis, and evaluation of molecules that enable or enhance cellular uptake: Peptoid molecular transporters", PNAS, Nov. 21, 2000, vol. 97, No. 24, pp. 13003-13008.
Wollack et al., "Investigation of the Sequence and Length Dependence for Cell-Penetrating Prenylated Peptides", Final Edited Form: Bioorg Med Chem Lett., Jan. 1, 2010; 20(1): pp. 161-163 [NIH Public Access, pp. 1-9].
Wyman et al., "Design, Synthesis, and Characterization of a Cationic Peptide That Binds to Nucleic Acids and Permeabilizes Bilayers", Biochemistry, 1997, 36, pp. 3008-3017.
Yao et al., "Design of new acid-activated cell-penetrating peptides for tumor drug delivery", (2017), PeerJ 5:e3429; DOI 10.7717/peerj.3429.
Zhang et al., "Dual functions of the human antimicrobial peptide LL-37—Target membrane perturbation and host cell cargo delivery", Biochimica et Biophysica Acta 1798 (2010) pp. 2201-2208.
Zhang et al., "Design of Acid-Activated Cell Penetrating Peptide for Delivery of Active Molecules into Cancer Cells", ACS Publications, Bioconjugate Chem., (2011), vol. 22, pp. 1410-1415.
International Search Report issued in connection with international application No. PCT/DE96/02487 (publication No. WO 97/23240); dated Aug. 27, 1997.
International Search Report issued in connection with international application No. PCT/US98/10571 (publication No. WO 98/52614); dated Sep. 12, 1998.
International Search Report and Written Opinion for International Application No. PCT/US2018/042410, dated Nov. 15, 2018.
Anantharamaiah, G. M., et al. "Novel Method for Reducing Plasma Cholesterol: A Ligand Replacement Therapy." Clin. Lipidol vol. 10 No. 1 pp. 83-90, Jan. 1, 2015.
Ananyeva, Natalya, et al. "Low Density Lipoproteins Interact With Acidic Fibroblast Growth Factor and Modify Its Function." Arterioscler. Thromb. Vasc. Biol., 2003; 21:601-607 (Apr. 2003). DOI: 0.1161/01.ATV.0000065193.27491.5B.
AnaSpec catalog pp. For Atrial Natriuretic Peptides (ANP). https://www.anaspec.com/products/promotions.asp?id=98&col=2&row=2, downloaded Jul. 7, 2017.
GenBank entry CAA47464 (entered 2005), "Histone [Homo sapiens]."
Haugland, Richard P. Handbook of Fluorescent Probes and Research Products (2002). ISBN 0-97 10636-0-5, pp. 11-18.
Hsieh, Joseph C., et al. "Infusion Therapy for Movement Disorders." Chapter 44 in Neuromodulation, vol. 2; Krames, Elliott S. et al., eds., pp. 561-570 (2009).
Kieselbach, G., et al. "Inhibitory effect of certain neuropeptides on the proliferation of human retinal pigment epithelial cells ." ARVO annual meeting abstract (2003), published in Invest. Opthalmal. Vis. Sci. (2003) 44 p. 1637.
Mishra, Gyan P., et al. "Recent applications of liposomes in opthalmic drug delivery." J. Drug Deliv. (2011) article ID 863734.
Mybiospace catalog page for VIP. https://www.mybiospace.com/vip-recombinant-protein/vasoactive-intestinal-peptide-vip/2018754, downloaded Aug. 29, 2019.
Pinto, Ricardo, et al. "Quantification of the CBD-FITC conjugates surface coating on cellulose fibres." BMC Biotechnology (2008) 8:1, Jan. 9, 2008, http://www.biomedcentral.com/1_472-6750/8/1.

(56) References Cited

OTHER PUBLICATIONS

Sasi, Manju, et al. "Neurobiology of local and intercellular BDNF signaling." Pflugers Arch—Eur J Physiol (2017) 469:593-610 (Mar. 9, 2017). Published with open access at Springerlink.com. DOI 10.1007/s00424-017-1964-4.

Takashima, Yusuyuki, et al. "Ocular Hypotensive Mechanism of Intravitreally Injected Brai Natriuretic Peptide in Rabbit." Investigative Opthalmology & Visual Science, Dec. 1996, vol. 37, No. 13, pp. 2671-2677.

Townsend, Jared B. et al. "Jeffamine Derivatized TentaGel Beads and Poly(dimethylsiloxane) Microbead Cassettes for Ultrahigh-Throughput in Situ Releasable Solution-Phase Cell-Based Screening of One-Bead-One-Compound Combinatorial Small Molecule Libraries." J. Comb. Chem., vol. 12, No. 5, pp. 700-712 (2010).

Unnamalai, Naryanan, et al. "Cationic oligopeptide-mediated delivery of dsRNA for post-transcriptional gene silencing in plant cells." FEBS Letters 566 (2004), pp. 307-310. Published by Elsevier B.V.on behalf of the Federation of European Biochemical Sciences.

Yun et al., "Fibroblast Growth Factors: Biology, Function, and Application for Tissue Regeneration." J. Tissue Engineering, vol. 2010, Article ID 218142, 18 pages (Oct. 2010). doi:10.4061/2010/218142.

Zhang, Chunling, et al. "Sima containing limposomes modified with polyarginine effectively silende the targeted gene." J. Cont. Rel. (2006) 112, pp. 229-239.

International Search Report for PCT/GB2015/050190, dated Apr. 28, 2015.

* cited by examiner

SEQUENCE LISTING

<160> NUMBER OF SEQ ID NOS: 281

<210> SEQ ID NO 1
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 1

Asp Trp Phe Lys Ala Phe Tyr Asp Lys Val Ala Glu Lys Phe Lys Glu
1               5                   10                  15

Ala Phe

<210> SEQ ID NO 2
<211> LENGTH: 35
<212> TYPE: PRT
<213> ORGANISM: Unknown
<220> FEATURE:
<223> OTHER INFORMATION: Description of Unknown:
      Cell penetrating peptide

<400> SEQUENCE: 2

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
                20                  25                  30

Ala Lys Ala
        35

<210> SEQ ID NO 3
<211> LENGTH: 36
<212> TYPE: PRT
<213> ORGANISM: Unknown
<220> FEATURE:
<223> OTHER INFORMATION: Description of Unknown:
      Cell penetrating peptide

<400> SEQUENCE: 3

Cys Gly Gly Gly Ala Arg Lys Lys Ala Ala Lys Ala Ala Arg Lys Lys
1               5                   10                  15

Ala Ala Lys Ala Ala Arg Lys Lys Ala Ala Lys Ala Ala Arg Lys Lys
                20                  25                  30

Ala Ala Lys Ala
        35

<210> SEQ ID NO 4
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 4

Arg Leu Arg Trp Arg
1               5

<210> SEQ ID NO 5
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 5

Arg Arg Leu Ser Tyr Ser Arg Arg Arg Phe
1               5                   10
```

```
<210> SEQ ID NO 6
<211> LENGTH: 11
<212> TYPE: PRT
<213> ORGANISM: Unknown
<220> FEATURE:
<223> OTHER INFORMATION: Description of Unknown:
      Cell penetrating peptide

<400> SEQUENCE: 6

Lys Lys Leu Phe Lys Lys Ile Leu Lys Lys Leu
1               5                   10

<210> SEQ ID NO 7
<211> LENGTH: 14
<212> TYPE: PRT
<213> ORGANISM: Unknown
<220> FEATURE:
<223> OTHER INFORMATION: Description of Unknown:
      Cell penetrating peptide

<400> SEQUENCE: 7

Tyr Lys Gln Cys His Lys Lys Gly Gly Lys Lys Gly Ser Gly
1               5                   10

<210> SEQ ID NO 8
<211> LENGTH: 10
<212> TYPE: PRT
<213> ORGANISM: Crotalus durissus

<400> SEQUENCE: 8

Cys Arg Trp Arg Trp Lys Cys Cys Lys Lys
1               5                   10

<210> SEQ ID NO 9
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 9

Thr Lys Arg Arg Ile Thr Pro Lys Asp Val Ile Asp Val Arg Ser Val
1               5                   10                  15

Thr Thr Arg Ile Asn Thr
            20

<210> SEQ ID NO 10
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 10

Thr Lys Arg Arg Ile Thr Pro Lys Asp Val Ile Asp Val Arg Ser Val
1               5                   10                  15

Thr Thr Lys Ile Asn Thr
            20

<210> SEQ ID NO 11
<211> LENGTH: 22
<212> TYPE: PRT
<213> ORGANISM: Unknown
```

```
<220> FEATURE:
<223> OTHER INFORMATION: Description of Unknown:
      Cell penetrating peptide

<400> SEQUENCE: 11

Thr Lys Arg Arg Ile Thr Pro Lys Arg Val Ile Arg Val Arg Ser Val
1               5                   10                  15

Thr Thr Glu Ile Asn Thr
            20

<210> SEQ ID NO 12
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 12

Thr Lys Arg Arg Ile Thr Pro Lys Lys Val Ile Lys Val Arg Ser Val
1               5                   10                  15

Thr Thr Glu Ile Asn Thr
            20

<210> SEQ ID NO 13
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 13

Thr Lys Arg Arg Ile Thr Pro Lys Arg Val Ile Arg Val Arg Ser Val
1               5                   10                  15

Thr Thr Arg Ile Asn Thr
            20

<210> SEQ ID NO 14
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 14

Thr Lys Arg Arg Ile Thr Pro Lys Lys Val Ile Lys Val Arg Ser Val
1               5                   10                  15

Thr Thr Lys Ile Asn Thr
            20

<210> SEQ ID NO 15
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 15

Gly Gly Ser Gln Pro Lys Lys Lys Arg Lys
1               5                   10

<210> SEQ ID NO 16
```

```
<211> LENGTH: 8
<212> TYPE: PRT
<213> ORGANISM: Unknown
<220> FEATURE:
<223> OTHER INFORMATION: Description of Unknown:
      Cell penetrating peptide

<400> SEQUENCE: 16

Gly Gly Lys Lys Lys Arg Lys Val
1               5

<210> SEQ ID NO 17
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 17

Arg Lys Lys Arg Arg Arg Glu Ser Arg Lys Lys Arg Arg Arg Glu Ser
1               5                   10                  15

<210> SEQ ID NO 18
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 18

Gly Arg Pro Arg Glu Ser Gly Lys Lys Arg Lys Arg Lys Arg Leu Lys
1               5                   10                  15

Pro

<210> SEQ ID NO 19
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 19

Gly Lys Arg Lys Lys Lys Gly Lys Leu Gly Lys Lys Arg Asp Pro
1               5                   10                  15

<210> SEQ ID NO 20
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 20

Gly Lys Arg Lys Lys Lys Gly Lys Leu Gly Lys Lys Arg Pro Arg Ser
1               5                   10                  15

Arg

<210> SEQ ID NO 21
<211> LENGTH: 18
<212> TYPE: PRT
<213> ORGANISM: Unknown
<220> FEATURE:
<223> OTHER INFORMATION: Description of Unknown:
```

```
                      Cell penetrating peptide

<400> SEQUENCE: 21

Arg Lys Lys Arg Arg Arg Glu Ser Arg Ala Arg Arg Ser Pro Arg
1               5                   10                  15

His Leu

<210> SEQ ID NO 22
<211> LENGTH: 19
<212> TYPE: PRT
<213> ORGANISM: Unknown
<220> FEATURE:
<223> OTHER INFORMATION: Description of Unknown:
      Cell penetrating peptide

<400> SEQUENCE: 22

Ser Arg Arg Ala Arg Arg Ser Pro Arg Glu Ser Gly Lys Lys Arg Lys
1               5                   10                  15

Arg Lys Arg

<210> SEQ ID NO 23
<211> LENGTH: 19
<212> TYPE: PRT
<213> ORGANISM: Unknown
<220> FEATURE:
<223> OTHER INFORMATION: Description of Unknown:
      Cell penetrating peptide

<400> SEQUENCE: 23

Val Lys Arg Gly Leu Lys Leu Arg His Val Arg Pro Arg Val Thr Arg
1               5                   10                  15

Met Asp Val

<210> SEQ ID NO 24
<211> LENGTH: 14
<212> TYPE: PRT
<213> ORGANISM: Unknown
<220> FEATURE:
<223> OTHER INFORMATION: Description of Unknown:
      Cell penetrating peptide

<400> SEQUENCE: 24

Ser Arg Arg Ala Arg Arg Ser Pro Arg His Leu Gly Ser Gly
1               5                   10

<210> SEQ ID NO 25
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 25

Leu Arg Arg Glu Arg Gln Ser Arg Leu Arg Arg Glu Arg Gln Ser Arg
1               5                   10                  15

<210> SEQ ID NO 26
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 26
```

```
Gly Ala Tyr Asp Leu Arg Arg Arg Glu Arg Gln Ser Arg Leu Arg Arg
1               5                   10                  15

Arg Glu Arg Gln Ser Arg
            20
```

<210> SEQ ID NO 27
<211> LENGTH: 11
<212> TYPE: PRT
<213> ORGANISM: Human immunodeficiency virus 1

<400> SEQUENCE: 27

```
Tyr Gly Arg Lys Lys Arg Arg Gln Arg Arg Arg
1               5                   10
```

<210> SEQ ID NO 28
<211> LENGTH: 10
<212> TYPE: PRT
<213> ORGANISM: Human immunodeficiency virus 1

<400> SEQUENCE: 28

```
Gly Arg Lys Lys Arg Arg Gln Arg Arg Arg
1               5                   10
```

<210> SEQ ID NO 29
<211> LENGTH: 9
<212> TYPE: PRT
<213> ORGANISM: Human immunodeficiency virus 1

<400> SEQUENCE: 29

```
Arg Lys Lys Arg Arg Gln Arg Arg Arg
1               5
```

<210> SEQ ID NO 30
<211> LENGTH: 13
<212> TYPE: PRT
<213> ORGANISM: Human immunodeficiency virus 1

<400> SEQUENCE: 30

```
Gly Arg Lys Lys Arg Arg Gln Arg Arg Arg Pro Pro Gln
1               5                   10
```

<210> SEQ ID NO 31
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 31

```
Cys Gly Gly Gly Gly Tyr Gly Arg Lys Lys Arg Arg Gln Arg Arg Arg
1               5                   10                  15
```

<210> SEQ ID NO 32
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 32

```
Cys Gly Gly Gly Gly
1               5
```

<210> SEQ ID NO 33
<211> LENGTH: 12
<212> TYPE: PRT
<213> ORGANISM: Unknown
<220> FEATURE:
<223> OTHER INFORMATION: Description of Unknown:
      Cell penetrating peptide

<400> SEQUENCE: 33

Gly Arg Lys Lys Arg Arg Gln Arg Arg Arg Cys Gly
1               5                   10

<210> SEQ ID NO 34
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 34

Arg Lys Lys Arg Arg Gln Arg Arg Arg Cys
1               5                   10

<210> SEQ ID NO 35
<211> LENGTH: 9
<212> TYPE: PRT
<213> ORGANISM: Unknown
<220> FEATURE:
<223> OTHER INFORMATION: Description of Unknown:
      Cell penetrating peptide

<400> SEQUENCE: 35

Arg Lys Lys Arg Arg Ala Arg Arg Arg
1               5

<210> SEQ ID NO 36
<211> LENGTH: 11
<212> TYPE: PRT
<213> ORGANISM: Unknown
<220> FEATURE:
<223> OTHER INFORMATION: Description of Unknown:
      Cell penetrating peptide

<400> SEQUENCE: 36

Tyr Gly Arg Arg Arg Arg Arg Arg Arg Arg Arg
1               5                   10

<210> SEQ ID NO 37
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 37

Gly Arg Lys Lys Arg Arg Gln Arg Arg Arg Pro Trp Gln
1               5                   10

<210> SEQ ID NO 38
<211> LENGTH: 13
<212> TYPE: PRT
<213> ORGANISM: Unknown
<220> FEATURE:
<223> OTHER INFORMATION: Description of Unknown:
      Cell penetrating peptide

```
<400> SEQUENCE: 38

Gly Arg Arg Arg Arg Arg Arg Arg Arg Pro Pro Gln
1               5                   10

<210> SEQ ID NO 39
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 39

Arg Lys Lys Arg Arg Gln Arg Arg Arg Lys Lys Arg Arg Gln Arg
1               5                   10                  15

Arg Arg

<210> SEQ ID NO 40
<211> LENGTH: 49
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (2)..(49)
<223> OTHER INFORMATION: This region may encompass 2-4 "Tyr Gly Arg Lys
      Lys Arg Arg Gln Arg Arg Arg Gly" repeating units

<400> SEQUENCE: 40

Cys Tyr Gly Arg Lys Lys Arg Arg Gln Arg Arg Arg Gly Tyr Gly Arg
1               5                   10                  15

Lys Lys Arg Arg Gln Arg Arg Arg Gly Tyr Gly Arg Lys Lys Arg Arg
            20                  25                  30

Gln Arg Arg Arg Gly Tyr Gly Arg Lys Lys Arg Arg Gln Arg Arg Arg
        35                  40                  45

Gly

<210> SEQ ID NO 41
<211> LENGTH: 25
<212> TYPE: PRT
<213> ORGANISM: Unknown
<220> FEATURE:
<223> OTHER INFORMATION: Description of Unknown:
      Cell penetrating peptide

<400> SEQUENCE: 41

Cys Tyr Gly Arg Lys Glu Arg Arg Gln Glu Arg Arg Gly Tyr Gly Arg
1               5                   10                  15

Lys Glu Arg Arg Gln Glu Arg Arg Gly
            20                  25

<210> SEQ ID NO 42
<211> LENGTH: 11
<212> TYPE: PRT
<213> ORGANISM: Unknown
<220> FEATURE:
<223> OTHER INFORMATION: Description of Unknown:
      Cell penetrating peptide

<400> SEQUENCE: 42

Arg Arg Arg Gln Arg Arg Lys Lys Arg Gly Tyr
1               5                   10
```

<210> SEQ ID NO 43
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 43

Arg Arg Arg Gln Arg Arg Lys Lys Arg Gly
1               5                   10

<210> SEQ ID NO 44
<211> LENGTH: 9
<212> TYPE: PRT
<213> ORGANISM: Unknown
<220> FEATURE:
<223> OTHER INFORMATION: Description of Unknown:
      Cell penetrating peptide

<400> SEQUENCE: 44

Arg Arg Arg Gln Arg Arg Lys Lys Arg
1               5

<210> SEQ ID NO 45
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 45

Gln Pro Pro Arg Arg Arg Gln Arg Arg Lys Lys Arg Gly
1               5                   10

<210> SEQ ID NO 46
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 46

Thr Arg Gln Ala Arg Arg Asn Arg Arg Arg Trp Arg Glu Arg Gln
1               5                   10                  15

Arg

<210> SEQ ID NO 47
<211> LENGTH: 13
<212> TYPE: PRT
<213> ORGANISM: Human T-cell leukemia virus type 2

<400> SEQUENCE: 47

Thr Arg Arg Gln Arg Thr Arg Arg Ala Arg Arg Asn Arg
1               5                   10

<210> SEQ ID NO 48
<211> LENGTH: 10
<212> TYPE: PRT
<213> ORGANISM: Human respiratory syncytial virus

<400> SEQUENCE: 48

Arg Arg Ile Pro Asn Arg Arg Pro Arg Arg
1               5                   10

```
<210> SEQ ID NO 49
<211> LENGTH: 19
<212> TYPE: PRT
<213> ORGANISM: Brome mosaic virus

<400> SEQUENCE: 49

Lys Met Thr Arg Ala Gln Arg Arg Ala Ala Ala Arg Arg Asn Arg Trp
1               5                   10                  15

Thr Ala Arg

<210> SEQ ID NO 50
<211> LENGTH: 19
<212> TYPE: PRT
<213> ORGANISM: Cowpea chlorotic mottle virus

<400> SEQUENCE: 50

Lys Leu Thr Arg Ala Gln Arg Arg Ala Ala Ala Arg Lys Asn Lys Arg
1               5                   10                  15

Asn Thr Arg

<210> SEQ ID NO 51
<211> LENGTH: 15
<212> TYPE: PRT
<213> ORGANISM: Flock house virus

<400> SEQUENCE: 51

Arg Arg Arg Arg Asn Arg Thr Arg Arg Asn Arg Arg Arg Val Arg
1               5                   10                  15

<210> SEQ ID NO 52
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 52

Asn Ala Lys Thr Arg Arg His Glu Arg Arg Arg Lys Leu Ala Ile Glu
1               5                   10                  15

Arg

<210> SEQ ID NO 53
<211> LENGTH: 22
<212> TYPE: PRT
<213> ORGANISM: Saccharomyces cerevisiae

<400> SEQUENCE: 53

Lys Arg Ala Arg Asn Thr Glu Ala Ala Arg Arg Ser Arg Ala Arg Lys
1               5                   10                  15

Leu Gln Arg Met Lys Gln
            20

<210> SEQ ID NO 54
<211> LENGTH: 28
<212> TYPE: PRT
<213> ORGANISM: Homo sapiens

<400> SEQUENCE: 54

Arg Ile Lys Ala Glu Arg Lys Arg Met Arg Asn Arg Ile Ala Ala Ser
1               5                   10                  15
```

```
Lys Ser Arg Lys Arg Lys Leu Glu Arg Ile Ala Arg
            20                  25

<210> SEQ ID NO 55
<211> LENGTH: 26
<212> TYPE: PRT
<213> ORGANISM: Homo sapiens

<400> SEQUENCE: 55

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 56
<211> LENGTH: 14
<212> TYPE: PRT
<213> ORGANISM: Unknown
<220> FEATURE:
<223> OTHER INFORMATION: Description of Unknown:
      Cell penetrating peptide

<400> SEQUENCE: 56

Val Ser Arg Arg Arg Arg Arg Gly Gly Arg Arg Arg Arg
1               5                   10

<210> SEQ ID NO 57
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 57

Arg Arg Trp Arg Arg Trp Asn Arg Phe Asn Arg Arg Arg Cys Arg
1               5                   10                  15

<210> SEQ ID NO 58
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 58

His Trp Ser Tyr Ile Leu Arg Pro Arg Arg Arg Arg Arg Arg Lys
1               5                   10                  15

<210> SEQ ID NO 59
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 59

Arg Cys Gly Arg Ala Ser Arg Cys Arg Val Arg Trp Met Arg Arg
1               5                   10                  15

Arg Ile

<210> SEQ ID NO 60
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 60

Phe Phe Leu Ile Pro Lys Gly
1               5

<210> SEQ ID NO 61
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 61

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 62
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 62

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 63
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 63

Lys Trp Phe Glu Thr Trp Phe Thr Glu Trp Pro Lys Lys Arg Lys
1               5                   10                  15

<210> SEQ ID NO 64
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 64

Lys Ala Thr Trp Phe Glu Thr Trp Phe Thr Glu Trp Ser Gln Pro Lys
1               5                   10                  15

Lys Lys Arg Lys Val
            20

<210> SEQ ID NO 65
<211> LENGTH: 21
<212> TYPE: PRT
```

```
<213> ORGANISM: Unknown
<220> FEATURE:
<223> OTHER INFORMATION: Description of Unknown:
      Cell penetrating peptide

<400> SEQUENCE: 65

Lys Glu Thr Trp Phe Glu Thr Trp Phe Ala Glu Trp Ser Gln Pro Lys
1               5                   10                  15

Lys Lys Arg Lys Val
            20

<210> SEQ ID NO 66
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 66

Lys Glu Thr Trp Phe Glu Thr Trp Phe Thr Ala Trp Ser Gln Pro Lys
1               5                   10                  15

Lys Lys Arg Lys Val
            20

<210> SEQ ID NO 67
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 67

Lys Glu Thr Trp Phe Glu Thr Trp Phe Thr Glu Trp Ala Gln Pro Lys
1               5                   10                  15

Lys Lys Arg Lys Val
            20

<210> SEQ ID NO 68
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 68

Lys Glu Thr Trp Phe Glu Thr Trp Phe Thr Glu Trp Ser Ala Pro Lys
1               5                   10                  15

Lys Lys Arg Lys Val
            20

<210> SEQ ID NO 69
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 69

Lys Glu Thr Trp Phe Glu Thr Trp Phe Thr Glu Trp Ser Gln Pro Lys
1               5                   10                  15

Lys Lys Arg Lys Ala
```

20

<210> SEQ ID NO 70
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 70

Gly Gly Lys Glu Thr Trp Trp Glu Thr Trp
1               5                   10

<210> SEQ ID NO 71
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 71

Gly Gly Trp Trp Glu Thr Trp Trp Thr Glu
1               5                   10

<210> SEQ ID NO 72
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 72

Gly Gly Thr Trp Trp Thr Glu Trp Ser Gln
1               5                   10

<210> SEQ ID NO 73
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 73

Gly Gly Thr Glu Trp Ser Gln Pro Lys Lys
1               5                   10

<210> SEQ ID NO 74
<211> LENGTH: 27
<212> TYPE: PRT
<213> ORGANISM: Unknown
<220> FEATURE:
<223> OTHER INFORMATION: Description of Unknown:
      Cell penetrating peptide

<400> SEQUENCE: 74

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 75
<211> LENGTH: 27
<212> TYPE: PRT

```
<213> ORGANISM: Unknown
<220> FEATURE:
<223> OTHER INFORMATION: Description of Unknown:
      Cell penetrating peptide

<400> SEQUENCE: 75

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 76
<211> LENGTH: 25
<212> TYPE: PRT
<213> ORGANISM: Unknown
<220> FEATURE:
<223> OTHER INFORMATION: Description of Unknown:
      Cell penetrating peptide

<400> SEQUENCE: 76

Arg Arg Arg Arg Arg Arg Arg Arg Gly Ala Leu Phe Leu Ala Phe
1               5                   10                  15

Leu Ala Ala Ala Leu Ser Leu Met Gly
            20                  25

<210> SEQ ID NO 77
<211> LENGTH: 27
<212> TYPE: PRT
<213> ORGANISM: Unknown
<220> FEATURE:
<223> OTHER INFORMATION: Description of Unknown:
      Cell penetrating peptide

<400> SEQUENCE: 77

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 78
<211> LENGTH: 20
<212> TYPE: PRT
<213> ORGANISM: Unknown
<220> FEATURE:
<223> OTHER INFORMATION: Description of Unknown:
      Cell penetrating peptide

<400> SEQUENCE: 78

Gly Leu Trp Arg Ala Leu Trp Arg Leu Leu Arg Ser Leu Trp Arg Leu
1               5                   10                  15

Leu Trp Arg Ala
            20

<210> SEQ ID NO 79
<211> LENGTH: 20
<212> TYPE: PRT
<213> ORGANISM: Unknown
<220> FEATURE:
<223> OTHER INFORMATION: Description of Unknown:
      Cell penetrating peptide

<400> SEQUENCE: 79

Gly Leu Trp Arg Ala Leu Trp Arg Leu Leu Arg Ser Leu Trp Arg Leu
1               5                   10                  15

Leu Trp Lys Ala
```

-continued

```
                20

<210> SEQ ID NO 80
<211> LENGTH: 20
<212> TYPE: PRT
<213> ORGANISM: Unknown
<220> FEATURE:
<223> OTHER INFORMATION: Description of Unknown:
      Cell penetrating peptide

<400> SEQUENCE: 80

Gly Leu Phe Lys Ala Leu Leu Lys Leu Leu Lys Ser Leu Trp Lys Leu
1               5                   10                  15

Leu Leu Lys Ala
            20

<210> SEQ ID NO 81
<211> LENGTH: 20
<212> TYPE: PRT
<213> ORGANISM: Unknown
<220> FEATURE:
<223> OTHER INFORMATION: Description of Unknown:
      Cell penetrating peptide

<400> SEQUENCE: 81

Gly Leu Phe Arg Ala Leu Leu Arg Leu Leu Arg Ser Leu Trp Arg Leu
1               5                   10                  15

Leu Leu Arg Ala
            20

<210> SEQ ID NO 82
<211> LENGTH: 20
<212> TYPE: PRT
<213> ORGANISM: Unknown
<220> FEATURE:
<223> OTHER INFORMATION: Description of Unknown:
      Cell penetrating peptide

<400> SEQUENCE: 82

Gly Leu Phe Glu Ala Leu Leu Glu Leu Leu Glu Ser Leu Trp Glu Leu
1               5                   10                  15

Leu Leu Glu Ala
            20

<210> SEQ ID NO 83
<211> LENGTH: 40
<212> TYPE: PRT
<213> ORGANISM: Unknown
<220> FEATURE:
<223> OTHER INFORMATION: Description of Unknown:
      Cell penetrating peptide

<400> SEQUENCE: 83

Gly Leu Phe Glu Ala Leu Leu Glu Leu Leu Glu Ser Leu Trp Glu Leu
1               5                   10                  15

Leu Leu Glu Ala Cys Cys Tyr Lys Ala Lys Lys Lys Lys Lys
            20                  25                  30

Lys Trp Lys Lys Lys Lys Gln Ser
        35                  40

<210> SEQ ID NO 84
<211> LENGTH: 30
<212> TYPE: PRT
<213> ORGANISM: Unknown
<220> FEATURE:
```

<223> OTHER INFORMATION: Description of Unknown:
    Cell penetrating peptide

<400> SEQUENCE: 84

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 85
<211> LENGTH: 30
<212> TYPE: PRT
<213> ORGANISM: Unknown
<220> FEATURE:
<223> OTHER INFORMATION: Description of Unknown:
    Cell penetrating peptide

<400> SEQUENCE: 85

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 86
<211> LENGTH: 27
<212> TYPE: PRT
<213> ORGANISM: Unknown
<220> FEATURE:
<223> OTHER INFORMATION: Description of Unknown:
    Cell penetrating peptide

<400> SEQUENCE: 86

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 87
<211> LENGTH: 24
<212> TYPE: PRT
<213> ORGANISM: Unknown
<220> FEATURE:
<223> OTHER INFORMATION: Description of Unknown:
    Cell penetrating peptide

<400> SEQUENCE: 87

Leu Asn Ser Ala Gly Tyr Leu Leu Gly Lys Ile Asn Leu Lys Ala Leu
1               5                   10                  15

Ala Ala Leu Ala Lys Lys Ile Leu
            20

<210> SEQ ID NO 88
<211> LENGTH: 25
<212> TYPE: PRT
<213> ORGANISM: Unknown
<220> FEATURE:
<223> OTHER INFORMATION: Description of Unknown:
    Cell penetrating peptide

<400> SEQUENCE: 88

Gly Trp Thr Leu Asn Ser Ala Gly Tyr Leu Leu Gly Lys Leu Lys Ala
1               5                   10                  15

Leu Ala Ala Leu Ala Lys Lys Ile Leu
            20                  25

<210> SEQ ID NO 89
<211> LENGTH: 21
<212> TYPE: PRT
<213> ORGANISM: Unknown
<220> FEATURE:
<223> OTHER INFORMATION: Description of Unknown:
     Cell penetrating peptide

<400> SEQUENCE: 89

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 90
<211> LENGTH: 21
<212> TYPE: PRT
<213> ORGANISM: Unknown
<220> FEATURE:
<223> OTHER INFORMATION: Description of Unknown:
     Cell penetrating peptide

<400> SEQUENCE: 90

Ala Gly Tyr Leu Leu Gly Lys Ile Asn Leu Lys Pro Leu Ala Ala Leu
1               5                   10                  15

Ala Lys Lys Ile Leu
            20

<210> SEQ ID NO 91
<211> LENGTH: 20
<212> TYPE: PRT
<213> ORGANISM: Unknown
<220> FEATURE:
<223> OTHER INFORMATION: Description of Unknown:
     Cell penetrating peptide

<400> SEQUENCE: 91

Leu Asn Ser Ala Gly Tyr Leu Leu Gly Lys Ala Leu Ala Ala Leu Ala
1               5                   10                  15

Lys Lys Ile Leu
            20

<210> SEQ ID NO 92
<211> LENGTH: 21
<212> TYPE: PRT
<213> ORGANISM: Unknown
<220> FEATURE:
<223> OTHER INFORMATION: Description of Unknown:
     Cell penetrating peptide
<220> FEATURE:
<221> NAME/KEY: MOD_RES
<222> LOCATION: (10)..(11)
<223> OTHER INFORMATION: Ornithine
<220> FEATURE:
<221> NAME/KEY: MOD_RES
<222> LOCATION: (18)..(19)
<223> OTHER INFORMATION: Ornithine

<400> SEQUENCE: 92

Ala Gly Tyr Leu Leu Gly Lys Leu Leu Xaa Xaa Leu Ala Ala Ala Ala
1               5                   10                  15

Leu Xaa Xaa Leu Leu
            20

<210> SEQ ID NO 93
<211> LENGTH: 18

```
<212> TYPE: PRT
<213> ORGANISM: Unknown
<220> FEATURE:
<223> OTHER INFORMATION: Description of Unknown:
      Cell penetrating peptide

<400> SEQUENCE: 93

Lys Trp Lys Leu Phe Lys Lys Ile Gly Ala Val Leu Lys Val Leu Thr
1               5                   10                  15

Thr Gly

<210> SEQ ID NO 94
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 94

Lys Leu Ala Leu Lys Leu Ala Leu Lys Ala Leu Lys Ala Ala Leu Lys
1               5                   10                  15

Leu Ala

<210> SEQ ID NO 95
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 95

Gln Leu Ala Leu Gln Leu Ala Leu Gln Ala Leu Gln Ala Ala Leu Gln
1               5                   10                  15

Leu Ala

<210> SEQ ID NO 96
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 96

Leu Lys Thr Leu Thr Glu Thr Leu Lys Glu Leu Thr Lys Thr Leu Thr
1               5                   10                  15

Glu Leu

<210> SEQ ID NO 97
<211> LENGTH: 12
<212> TYPE: PRT
<213> ORGANISM: Unknown
<220> FEATURE:
<223> OTHER INFORMATION: Description of Unknown:
      Cell penetrating peptide

<400> SEQUENCE: 97

Lys Ala Leu Ala Lys Ala Leu Ala Lys Ala Leu Ala
1               5                   10

<210> SEQ ID NO 98
<211> LENGTH: 9
<212> TYPE: PRT
```

<213> ORGANISM: Unknown
<220> FEATURE:
<223> OTHER INFORMATION: Description of Unknown:
      Cell penetrating peptide

<400> SEQUENCE: 98

Arg Arg Trp Trp Arg Arg Trp Arg Arg
1               5

<210> SEQ ID NO 99
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 99

Trp Leu Arg Arg Ile Lys Ala Trp Leu Arg Arg Ile Lys Ala Trp Leu
1               5                   10                  15

Arg Arg Ile Lys Ala
            20

<210> SEQ ID NO 100
<211> LENGTH: 11
<212> TYPE: PRT
<213> ORGANISM: Unknown
<220> FEATURE:
<223> OTHER INFORMATION: Description of Unknown:
      Cell penetrating peptide

<400> SEQUENCE: 100

Tyr Ala Arg Ala Ala Ala Arg Gln Ala Arg Ala
1               5                   10

<210> SEQ ID NO 101
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 101

Val Arg Leu Pro Pro Pro Val Arg Leu Pro Pro Pro Val Arg Leu Pro
1               5                   10                  15

Pro Pro

<210> SEQ ID NO 102
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 102

Val Lys Leu Pro Pro Pro Val Lys Leu Pro Pro Pro Val Lys Leu Pro
1               5                   10                  15

Pro Pro

<210> SEQ ID NO 103
<211> LENGTH: 18
<212> TYPE: PRT
<213> ORGANISM: Unknown
<220> FEATURE:

```
<223> OTHER INFORMATION: Description of Unknown:
      Cell penetrating peptide

<400> SEQUENCE: 103

Val Glu Leu Pro Pro Val Glu Leu Pro Pro Val Glu Leu Pro
1               5                   10                  15

Pro Pro

<210> SEQ ID NO 104
<211> LENGTH: 18
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (1)..(18)
<223> OTHER INFORMATION: This sequence may encompass 3-6 "Pro Pro Arg"
      repeating units

<400> SEQUENCE: 104

Pro Pro Arg Pro Pro Arg Pro Pro Arg Pro Pro Arg Pro Pro Arg
1               5                   10                  15

Pro Arg

<210> SEQ ID NO 105
<211> LENGTH: 18
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (1)..(18)
<223> OTHER INFORMATION: This sequence may encompass 3-6 "Pro Arg Arg"
      repeating units

<400> SEQUENCE: 105

Pro Arg Arg Pro Arg Arg Pro Arg Arg Pro Arg Arg Pro Arg Arg
1               5                   10                  15

Arg Arg

<210> SEQ ID NO 106
<211> LENGTH: 36
<212> TYPE: PRT
<213> ORGANISM: Unknown
<220> FEATURE:
<223> OTHER INFORMATION: Description of Unknown:
      Cell penetrating peptide

<400> SEQUENCE: 106

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Asn Val Val Thr
            20                  25                  30

Arg His Arg Tyr
        35

<210> SEQ ID NO 107
<211> LENGTH: 36
<212> TYPE: PRT
<213> ORGANISM: Unknown
<220> FEATURE:
<223> OTHER INFORMATION: Description of Unknown:
```

Cell penetrating peptide

<400> SEQUENCE: 107

Gly Pro Ser Gln Pro Thr Tyr Pro Gly Asp Asp Ala Pro Val Arg Asp
1               5                   10                  15

Leu Ile Arg Phe Tyr Arg Asp Leu Arg Arg Tyr Leu Asn Val Val Thr
            20                  25                  30

Arg His Arg Tyr
        35

<210> SEQ ID NO 108
<211> LENGTH: 36
<212> TYPE: PRT
<213> ORGANISM: Unknown
<220> FEATURE:
<223> OTHER INFORMATION: Description of Unknown:
      Cell penetrating peptide

<400> SEQUENCE: 108

Gly Pro Ser Gln Pro Thr Tyr Pro Gly Asp Asp Ala Pro Val Arg Asp
1               5                   10                  15

Leu Arg Arg Phe Tyr Arg Asp Leu Arg Arg Tyr Leu Asn Val Val Thr
            20                  25                  30

Arg His Arg Tyr
        35

<210> SEQ ID NO 109
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 109

Gly Ser Pro Trp Gly Leu Gln His His Pro Pro Arg Thr
1               5                   10

<210> SEQ ID NO 110
<211> LENGTH: 14
<212> TYPE: PRT
<213> ORGANISM: Unknown
<220> FEATURE:
<223> OTHER INFORMATION: Description of Unknown:
      Cell penetrating peptide

<400> SEQUENCE: 110

Arg Leu Ser Gly Met Asn Glu Val Leu Ser Phe Arg Trp Leu
1               5                   10

<210> SEQ ID NO 111
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 111

Lys Leu Trp Met Arg Trp Tyr Ser Pro Thr Thr Arg Arg Tyr Gly
1               5                   10                  15

<210> SEQ ID NO 112
<211> LENGTH: 26
<212> TYPE: PRT

<213> ORGANISM: Unknown
<220> FEATURE:
<223> OTHER INFORMATION: Description of Unknown:
      Cell penetrating peptide

<400> SEQUENCE: 112

Pro Tyr Ser Arg Pro His Val Gln Leu Trp Tyr Pro Asn Arg Glu Ser
1               5                   10                  15

Cys Arg Ser Leu Ile Arg Ser Leu Gly Pro
            20                  25

<210> SEQ ID NO 113
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 113

Tyr Thr Ala Ile Ala Trp Val Lys Ala Phe Ile Arg Lys Leu Arg Lys
1               5                   10                  15

<210> SEQ ID NO 114
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 114

Ile Ala Trp Val Lys Ala Phe Ile Arg Lys Leu Arg Lys Gly Pro Leu
1               5                   10                  15

Gly

<210> SEQ ID NO 115
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 115

Phe Lys Ile Tyr Asp Lys Lys Val Arg Thr Arg Val Val Lys His
1               5                   10                  15

<210> SEQ ID NO 116
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 116

Arg Ala Ser Lys Arg Asp Gly Ser Trp Val Lys Lys Leu His Arg Ile
1               5                   10                  15

Leu Glu

<210> SEQ ID NO 117
<211> LENGTH: 16
<212> TYPE: PRT
<213> ORGANISM: Unknown
<220> FEATURE:

<223> OTHER INFORMATION: Description of Unknown:
      Cell penetrating peptide

<400> SEQUENCE: 117

Lys Gly Thr Tyr Lys Lys Lys Leu Met Arg Ile Pro Leu Lys Gly Thr
1               5                   10                  15

<210> SEQ ID NO 118
<211> LENGTH: 19
<212> TYPE: PRT
<213> ORGANISM: Unknown
<220> FEATURE:
<223> OTHER INFORMATION: Description of Unknown:
      Cell penetrating peptide

<400> SEQUENCE: 118

Leu Tyr Lys Lys Gly Pro Ala Lys Lys Gly Arg Pro Pro Leu Arg Gly
1               5                   10                  15

Trp Phe His

<210> SEQ ID NO 119
<211> LENGTH: 34
<212> TYPE: PRT
<213> ORGANISM: Herpes simplex virus type 1

<400> SEQUENCE: 119

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 120
<211> LENGTH: 12
<212> TYPE: PRT
<213> ORGANISM: Hepatitis B virus

<400> SEQUENCE: 120

Pro Leu Ser Ser Ile Phe Ser Arg Ile Gly Asp Pro
1               5                   10

<210> SEQ ID NO 121
<211> LENGTH: 26
<212> TYPE: PRT
<213> ORGANISM: Unknown
<220> FEATURE:
<223> OTHER INFORMATION: Description of Unknown:
      Cell penetrating peptide

<400> SEQUENCE: 121

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 122
<211> LENGTH: 40
<212> TYPE: PRT
<213> ORGANISM: Pestivirus sp.

<400> SEQUENCE: 122

Tyr Leu Leu Asp Gly Met Thr Asn Thr Ile Glu Asn Ala Arg Gln Gly
1               5                   10                  15

```
Ala Ala Arg Val Thr Ser Trp Leu Gly Arg Gln Leu Arg Ile Ala Gly
            20                  25                  30

Lys Arg Leu Glu Gly Arg Ser Lys
            35                  40

<210> SEQ ID NO 123
<211> LENGTH: 40
<212> TYPE: PRT
<213> ORGANISM: Pestivirus sp.

<400> SEQUENCE: 123

Asp Gly Met Thr Asn Thr Ile Glu Asn Ala Arg Gln Gly Ala Ala Arg
1               5                   10                  15

Val Thr Ser Trp Leu Gly Arg Gln Leu Arg Ile Ala Gly Lys Arg Leu
            20                  25                  30

Glu Gly Arg Ser Lys Thr Trp Phe
            35                  40

<210> SEQ ID NO 124
<211> LENGTH: 37
<212> TYPE: PRT
<213> ORGANISM: Pestivirus sp.

```
1               5                   10                  15
Ile Ala Gly Lys Arg Leu Glu Gly Arg Ser Lys
            20                  25

<210> SEQ ID NO 128
<211> LENGTH: 25
<212> TYPE: PRT
<213> ORGANISM: Pestivirus sp.

<400> SEQUENCE: 128

Arg Gln Gly Ala Ala Arg Val Thr Ser Trp Leu Gly Arg Gln Leu Arg
1               5                   10                  15

Ile Ala Gly Lys Arg Leu Glu Gly Arg
            20                  25

<210> SEQ ID NO 129
<211> LENGTH: 32
<212> TYPE: PRT
<213> ORGANISM: Unknown
<220> FEATURE:
<223> OTHER INFORMATION: Description of Unknown:
      Cell penetrating peptide

<400> SEQUENCE: 129

Gly Asn Gly Lys Leu Ile Lys Gly Arg Thr Pro Ile Lys Phe Gly Lys
1               5                   10                  15

Ala Asp Cys Asp Arg Pro Pro Lys His Ser Gln Asn Gly Met Gly Lys
            20                  25                  30

<210> SEQ ID NO 130
<211> LENGTH: 29
<212> TYPE: PRT
<213> ORGANISM: Unknown
<220> FEATURE:
<223> OTHER INFORMATION: Description of Unknown:
      Cell penetrating peptide

<400> SEQUENCE: 130

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 131
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 131

Lys Leu Ile Lys Gly Arg Thr Pro Ile Lys Phe Gly Lys
1               5                   10

<210> SEQ ID NO 132
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 132

Arg Gly Gly Arg Leu Ser Tyr Ser Arg Arg Arg Phe Ser Thr Ser Thr
```

```
1               5                   10                  15

Gly Arg

<210> SEQ ID NO 133
<211> LENGTH: 20
<212> TYPE: PRT
<213> ORGANISM: Unknown
<220> FEATURE:
<223> OTHER INFORMATION: Description of Unknown:
      Cell penetrating peptide

<400> SEQUENCE: 133

Ala Leu Trp Lys Thr Leu Leu Lys Lys Val Leu Lys Ala Pro Lys Lys
1               5                   10                  15

Lys Arg Lys Val
            20

<210> SEQ ID NO 134
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 134

Ala Leu Trp Lys Thr Leu Leu Lys Lys Val Leu Lys Ala
1               5                   10

<210> SEQ ID NO 135
<211> LENGTH: 23
<212> TYPE: PRT
<213> ORGANISM: Unknown
<220> FEATURE:
<223> OTHER INFORMATION: Description of Unknown:
      Cell penetrating peptide

<400> SEQUENCE: 135

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 136
<211> LENGTH: 23
<212> TYPE: PRT
<213> ORGANISM: Unknown
<220> FEATURE:
<223> OTHER INFORMATION: Description of Unknown:
      Cell penetrating peptide

<400> SEQUENCE: 136

Gly Ile Gly Lys Trp Leu His Ser Ala Lys Lys Phe Gly Lys Ala Phe
1               5                   10                  15

Val Gly Glu Ile Met Asn Ser
            20

<210> SEQ ID NO 137
<211> LENGTH: 23
<212> TYPE: PRT
<213> ORGANISM: Unknown
<220> FEATURE:
<223> OTHER INFORMATION: Description of Unknown:
      Cell penetrating peptide

<400> SEQUENCE: 137
```

```
Gly Ile Gly Lys Phe Leu His Ser Ala Lys Lys Trp Gly Lys Ala Phe
1               5                   10                  15

Val Gly Gln Ile Met Asn Cys
                20
```

<210> SEQ ID NO 138
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 138

```
Val Leu Thr Thr Gly Leu Pro Ala Leu Ile Ser Trp Ile Arg Arg
1               5                   10                  15

His Arg Arg His Cys
                20
```

<210> SEQ ID NO 139
<211> LENGTH: 21
<212> TYPE: PRT
<213> ORGANISM: Unknown
<220> FEATURE:
<223> OTHER INFORMATION: Description of Unknown:
      Cell penetrating peptide

<400> SEQUENCE: 139

```
Thr Arg Ser Ser Arg Ala Gly Leu Gln Phe Pro Val Gly Arg Val His
1               5                   10                  15

Arg Leu Leu Arg Lys
                20
```

<210> SEQ ID NO 140
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 140

```
Arg Ala Gly Leu Gln Phe Pro Val Gly Arg Val His Arg Leu Leu Arg
1               5                   10                  15

Lys
```

<210> SEQ ID NO 141
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 141

```
Ala Gly Leu Gln Phe Pro Val Gly Arg Val His Arg Leu Leu Arg Lys
1               5                   10                  15
```

<210> SEQ ID NO 142
<211> LENGTH: 15
<212> TYPE: PRT
<213> ORGANISM: Unknown
<220> FEATURE:
<223> OTHER INFORMATION: Description of Unknown:
      Cell penetrating peptide

```
<400> SEQUENCE: 142

Gly Leu Gln Phe Pro Val Gly Arg Val His Arg Leu Leu Arg Lys
1               5                   10                  15

<210> SEQ ID NO 143
<211> LENGTH: 14
<212> TYPE: PRT
<213> ORGANISM: Unknown
<220> FEATURE:
<223> OTHER INFORMATION: Description of Unknown:
      Cell penetrating peptide

<400> SEQUENCE: 143

Leu Gln Phe Pro Val Gly Arg Val His Arg Leu Leu Arg Lys
1               5                   10

<210> SEQ ID NO 144
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 144

Gln Phe Pro Val Gly Arg Val His Arg Leu Leu Arg Lys
1               5                   10

<210> SEQ ID NO 145
<211> LENGTH: 12
<212> TYPE: PRT
<213> ORGANISM: Unknown
<220> FEATURE:
<223> OTHER INFORMATION: Description of Unknown:
      Cell penetrating peptide

<400> SEQUENCE: 145

Phe Pro Val Gly Arg Val His Arg Leu Leu Arg Lys
1               5                   10

<210> SEQ ID NO 146
<211> LENGTH: 11
<212> TYPE: PRT
<213> ORGANISM: Unknown
<220> FEATURE:
<223> OTHER INFORMATION: Description of Unknown:
      Cell penetrating peptide

<400> SEQUENCE: 146

Pro Val Gly Arg Val His Arg Leu Leu Arg Lys
1               5                   10

<210> SEQ ID NO 147
<211> LENGTH: 37
<212> TYPE: PRT
<213> ORGANISM: Homo sapiens

<400> SEQUENCE: 147

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35
```

<210> SEQ ID NO 148
<211> LENGTH: 22
<212> TYPE: PRT
<213> ORGANISM: Homo sapiens

<400> SEQUENCE: 148

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 149
<211> LENGTH: 19
<212> TYPE: PRT
<213> ORGANISM: Homo sapiens

<400> SEQUENCE: 149

Lys Cys Phe Gln Trp Gln Arg Asn Met Arg Lys Val Arg Gly Pro Pro
1               5                   10                  15

Val Ser Cys

<210> SEQ ID NO 150
<211> LENGTH: 24
<212> TYPE: PRT
<213> ORGANISM: Unknown
<220> FEATURE:
<223> OTHER INFORMATION: Description of Unknown:
      Cell penetrating peptide

<400> SEQUENCE: 150

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 151
<211> LENGTH: 7
<212> TYPE: PRT
<213> ORGANISM: Unknown
<220> FEATURE:
<223> OTHER INFORMATION: Description of Unknown:
      Cell penetrating peptide

<400> SEQUENCE: 151

Arg Arg Ile Arg Pro Arg Pro
1               5

<210> SEQ ID NO 152
<211> LENGTH: 9
<212> TYPE: PRT
<213> ORGANISM: Unknown
<220> FEATURE:
<223> OTHER INFORMATION: Description of Unknown:
      Cell penetrating peptide

<400> SEQUENCE: 152

Pro Arg Pro Leu Pro Phe Pro Arg Pro
1               5

<210> SEQ ID NO 153
<211> LENGTH: 20
<212> TYPE: PRT
<213> ORGANISM: Unknown
<220> FEATURE:
<223> OTHER INFORMATION: Description of Unknown:

Cell penetrating peptide

<400> SEQUENCE: 153

Val Asp Lys Gly Ser Tyr Leu Pro Arg Pro Thr Pro Pro Arg Pro Ile
1               5                   10                  15

Tyr Asn Arg Asn
            20

<210> SEQ ID NO 154
<211> LENGTH: 24
<212> TYPE: PRT
<213> ORGANISM: Homo sapiens

<400> SEQUENCE: 154

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 155
<211> LENGTH: 24
<212> TYPE: PRT
<213> ORGANISM: Unknown
<220> FEATURE:
<223> OTHER INFORMATION: Description of Unknown:
      Cell penetrating peptide

<400> SEQUENCE: 155

Leu Gly Thr Tyr Thr Gln Asp Phe Asn Lys Phe His Thr Phe Ala Gln
1               5                   10                  15

Thr Ala Ile Gly Val Gly Ala Pro
            20

<210> SEQ ID NO 156
<211> LENGTH: 24
<212> TYPE: PRT
<213> ORGANISM: Unknown
<220> FEATURE:
<223> OTHER INFORMATION: Description of Unknown:
      Cell penetrating peptide

<400> SEQUENCE: 156

Leu Gly Thr Tyr Thr Gln Asp Phe Asn Lys Phe His Thr Phe Pro Gln
1               5                   10                  15

Thr Ala Ile Gly Val Trp Ala Pro
            20

<210> SEQ ID NO 157
<211> LENGTH: 15
<212> TYPE: PRT
<213> ORGANISM: Homo sapiens

<400> SEQUENCE: 157

Lys Phe His Thr Phe Pro Gln Thr Ala Ile Gly Val Gly Ala Pro
1               5                   10                  15

<210> SEQ ID NO 158
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 158

```
Met Val Arg Arg Phe Leu Val Thr Leu Arg Ile Arg Arg Ala Cys Gly
1               5                   10                  15

Pro Pro Arg Val Arg Val
            20
```

<210> SEQ ID NO 159
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 159

```
Met Val Thr Val Leu Phe Arg Arg Leu Arg Ile Arg Arg Ala Cys Gly
1               5                   10                  15

Pro Pro Arg Val Arg Val
            20
```

<210> SEQ ID NO 160
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 160

```
Arg Leu Val Ser Tyr Asn Gly Ile Ile Phe Phe Leu Lys
1               5                   10
```

<210> SEQ ID NO 161
<211> LENGTH: 12
<212> TYPE: PRT
<213> ORGANISM: Unknown
<220> FEATURE:
<223> OTHER INFORMATION: Description of Unknown:
      Cell penetrating peptide

<400> SEQUENCE: 161

```
Phe Asn Leu Pro Leu Pro Ser Arg Pro Leu Leu Arg
1               5                   10
```

<210> SEQ ID NO 162
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 162

```
Met Ala Ser Ile Trp Val Gly His Arg Gly
1               5                   10
```

<210> SEQ ID NO 163
<211> LENGTH: 18
<212> TYPE: PRT
<213> ORGANISM: Mus sp.

<400> SEQUENCE: 163

```
Leu Leu Ile Ile Leu Arg Arg Arg Ile Arg Lys Gln Ala His Ala His
1               5                   10                  15

Ser Lys
```

```
<210> SEQ ID NO 164
<211> LENGTH: 18
<212> TYPE: PRT
<213> ORGANISM: Unknown
<220> FEATURE:
<223> OTHER INFORMATION: Description of Unknown:
      Cell penetrating peptide

<400> SEQUENCE: 164

Leu Ser Thr Ala Ala Asp Met Gln Gly Val Val Thr Asp Gly Met Ala
1               5                   10                  15

Ser Gly

<210> SEQ ID NO 165
<211> LENGTH: 16
<212> TYPE: PRT
<213> ORGANISM: Drosophila sp.

<400> SEQUENCE: 165

Arg Gln Ile Lys Ile Trp Phe Gln Asn Arg Arg Met Lys Trp Lys Lys
1               5                   10                  15

<210> SEQ ID NO 166
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 166

Arg Gln Ile Lys Ile Trp Phe Pro Asn Arg Arg Met Lys Trp Lys Lys
1               5                   10                  15

<210> SEQ ID NO 167
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 167

Arg Gln Pro Lys Ile Trp Phe Pro Asn Arg Arg Lys Pro Trp Lys Lys
1               5                   10                  15

<210> SEQ ID NO 168
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 168

Arg Gln Ile Arg Ile Trp Phe Gln Asn Arg Arg Met Arg Trp Arg Arg
1               5                   10                  15

<210> SEQ ID NO 169
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 169
```

```
Arg Gln Ile Lys Ile Trp Phe Gln Lys Asn Arg Arg Met Lys Trp Lys
1               5                   10                  15

Lys

<210> SEQ ID NO 170
<211> LENGTH: 23
<212> TYPE: PRT
<213> ORGANISM: Unknown
<220> FEATURE:
<223> OTHER INFORMATION: Description of Unknown:
      Cell penetrating peptide

<400> SEQUENCE: 170

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 171
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 171

Arg His Ile Lys Ile Trp Phe Gln Asn Arg Arg Met Lys Trp Lys Lys
1               5                   10                  15

<210> SEQ ID NO 172
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 172

Arg Val Ile Arg Val Trp Phe Gln Asn Lys Arg Cys Lys Asp Lys Lys
1               5                   10                  15

<210> SEQ ID NO 173
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 173

Ser Gln Ile Lys Ile Trp Phe Gln Asn Lys Arg Ala Lys Ile Lys Lys
1               5                   10                  15

<210> SEQ ID NO 174
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 174

Arg Gln Val Thr Ile Trp Phe Gln Asn Arg Arg Val Lys Glu Lys Lys
1               5                   10                  15
```

<210> SEQ ID NO 175
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 175

Lys Gln Ile Asn Asn Trp Phe Ile Asn Gln Arg Lys Arg His Trp Lys
1               5                   10                  15

<210> SEQ ID NO 176
<211> LENGTH: 26
<212> TYPE: PRT
<213> ORGANISM: Unknown
<220> FEATURE:
<223> OTHER INFORMATION: Description of Unknown:
      Cell penetrating peptide

<400> SEQUENCE: 176

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 177
<211> LENGTH: 25
<212> TYPE: PRT
<213> ORGANISM: Unknown
<220> FEATURE:
<223> OTHER INFORMATION: Description of Unknown:
      Cell penetrating peptide

<400> SEQUENCE: 177

Ala Ala Val Ala Leu Leu Pro Ala Val Leu Leu Ala Leu Leu Ala Lys
1               5                   10                  15

Asn Asn Leu Lys Asp Cys Gly Leu Phe
            20                  25

<210> SEQ ID NO 178
<211> LENGTH: 25
<212> TYPE: PRT
<213> ORGANISM: Unknown
<220> FEATURE:
<223> OTHER INFORMATION: Description of Unknown:
      Cell penetrating peptide

<400> SEQUENCE: 178

Ala Ala Val Ala Leu Leu Pro Ala Val Leu Leu Ala Leu Leu Ala Lys
1               5                   10                  15

Asn Asn Leu Lys Glu Cys Gly Leu Tyr
            20                  25

<210> SEQ ID NO 179
<211> LENGTH: 23
<212> TYPE: PRT
<213> ORGANISM: Unknown
<220> FEATURE:
<223> OTHER INFORMATION: Description of Unknown:
      Cell penetrating peptide

<400> SEQUENCE: 179

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 180
<211> LENGTH: 30
<212> TYPE: PRT
<213> ORGANISM: Bos sp.

<400> SEQUENCE: 180

Met Val Lys Ser Lys Ile Gly Ser Trp Ile Leu Val Leu Phe Val Ala
1               5                   10                  15

Met Trp Ser Asp Val Gly Leu Cys Lys Arg Pro Lys Pro
            20                  25                  30

<210> SEQ ID NO 181
<211> LENGTH: 28
<212> TYPE: PRT
<213> ORGANISM: Mus sp.

<400> SEQUENCE: 181

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 182
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 182

Gly Ala Leu Phe Leu Gly Phe Leu Gly Ala Ala Gly Ser Thr Met Gly
1               5                   10                  15

Ala

<210> SEQ ID NO 183
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 183

Ala Ala Val Ala Leu Leu Pro Ala Val Leu Leu Ala Leu Leu Ala Pro
1               5                   10                  15

<210> SEQ ID NO 184
<211> LENGTH: 16
<212> TYPE: PRT
<213> ORGANISM: Unknown
<220> FEATURE:
<223> OTHER INFORMATION: Description of Unknown:
      Cell penetrating peptide

<400> SEQUENCE: 184

Ala Ala Val Ala Leu Leu Pro Ala Val Leu Leu Lys Leu Leu Ala Pro
1               5                   10                  15

<210> SEQ ID NO 185
<211> LENGTH: 12
<212> TYPE: PRT

```
<213> ORGANISM: Unknown
<220> FEATURE:
<223> OTHER INFORMATION: Description of Unknown:
      Cell penetrating peptide

<400> SEQUENCE: 185

Ala Ala Val Leu Leu Pro Val Leu Leu Ala Ala Pro
1               5                   10

<210> SEQ ID NO 186
<211> LENGTH: 10
<212> TYPE: PRT
<213> ORGANISM: Unknown
<220> FEATURE:
<223> OTHER INFORMATION: Description of Unknown:
      Cell penetrating peptide

<400> SEQUENCE: 186

Pro Ile Glu Val Cys Met Tyr Arg Glu Pro
1               5                   10

<210> SEQ ID NO 187
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 187

Val Thr Val Leu Ala Leu Gly Ala Leu Ala Gly Val Gly Val Gly
1               5                   10                  15

<210> SEQ ID NO 188
<211> LENGTH: 17
<212> TYPE: PRT
<213> ORGANISM: Unknown
<220> FEATURE:
<223> OTHER INFORMATION: Description of Unknown:
      Cell penetrating peptide

<400> SEQUENCE: 188

Cys Ser Ile Pro Pro Glu Val Lys Phe Asn Lys Pro Phe Val Tyr Leu
1               5                   10                  15

Ile

<210> SEQ ID NO 189
<211> LENGTH: 6
<212> TYPE: PRT
<213> ORGANISM: Unknown
<220> FEATURE:
<223> OTHER INFORMATION: Description of Unknown:
      Cell penetrating peptide

<400> SEQUENCE: 189

Pro Phe Val Tyr Leu Ile
1               5

<210> SEQ ID NO 190
<211> LENGTH: 15
<212> TYPE: PRT
<213> ORGANISM: Unknown
<220> FEATURE:
<223> OTHER INFORMATION: Description of Unknown:
      Cell penetrating peptide

<400> SEQUENCE: 190
```

```
Ser Asp Leu Trp Glu Met Met Val Ser Leu Ala Cys Gln Tyr
1               5                   10                  15
```

<210> SEQ ID NO 191
<211> LENGTH: 13
<212> TYPE: PRT
<213> ORGANISM: Unknown
<220> FEATURE:
<223> OTHER INFORMATION: Description of Unknown:
      Cell penetrating peptide

<400> SEQUENCE: 191

```
Gly Pro Phe His Phe Tyr Gln Phe Leu Phe Pro Pro Val
1               5                   10
```

<210> SEQ ID NO 192
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 192

```
Pro Leu Ile Leu Leu Arg Leu Leu Arg Gly Gln Phe
1               5                   10
```

<210> SEQ ID NO 193
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 193

```
Pro Leu Ile Tyr Leu Arg Leu Leu Arg Gly Gln Phe
1               5                   10
```

<210> SEQ ID NO 194
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 194

```
Pro Leu Ile Leu Leu Phe Lys Leu Leu Gly Gln Phe
1               5                   10
```

<210> SEQ ID NO 195
<211> LENGTH: 12
<212> TYPE: PRT
<213> ORGANISM: Unknown
<220> FEATURE:
<223> OTHER INFORMATION: Description of Unknown:
      Cell penetrating peptide

```
<220> FEATURE:
<221> NAME/KEY: MISC_FEATURE
<222> LOCATION: (10)..(12)
<223> OTHER INFORMATION: May or may not be present

<400> SEQUENCE: 195

Pro Leu Gly Tyr Leu Phe Leu Leu Arg Gly Gln Phe
1               5                   10

<210> SEQ ID NO 196
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 196

Pro Leu Ile Tyr Pro Phe Leu Arg Leu Gly Gln Phe
1               5                   10

<210> SEQ ID NO 197
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 197

Val Pro Thr Leu Lys
1               5

<210> SEQ ID NO 198
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 198

Val Pro Thr Leu Glu
1               5

<210> SEQ ID NO 199
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 199

Val Pro Thr Leu Gln
1               5

<210> SEQ ID NO 200
<211> LENGTH: 5
<212> TYPE: PRT
<213> ORGANISM: Unknown
<220> FEATURE:
<223> OTHER INFORMATION: Description of Unknown:
      Cell penetrating peptide
```

```
<400> SEQUENCE: 200

Val Pro Ala Leu Lys
1               5

<210> SEQ ID NO 201
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 201

Val Pro Ala Leu Arg
1               5

<210> SEQ ID NO 202
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 202

Val Pro Met Ile Lys
1               5

<210> SEQ ID NO 203
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 203

Val Pro Met Leu Lys
1               5

<210> SEQ ID NO 204
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 204

Val Ser Ala Leu Lys
1               5

<210> SEQ ID NO 205
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 205

Ile Pro Ala Leu Lys
1               5

<210> SEQ ID NO 206
<211> LENGTH: 5
<212> TYPE: PRT
```

-continued

<213> ORGANISM: Unknown
<220> FEATURE:
<223> OTHER INFORMATION: Description of Unknown:
      Cell penetrating peptide

<400> SEQUENCE: 206

Ile Pro Met Leu Lys
1               5

<210> SEQ ID NO 207
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 207

Pro Met Leu Lys Glu
1               5

<210> SEQ ID NO 208
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 208

Lys Leu Pro Val Thr
1               5

<210> SEQ ID NO 209
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 209

Lys Leu Gly Val Met
1               5

<210> SEQ ID NO 210
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 210

Glu Leu Pro Val Met
1               5

<210> SEQ ID NO 211
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 211

Gln Leu Pro Val Met
1               5

<210> SEQ ID NO 212
<211> LENGTH: 22
<212> TYPE: PRT
<213> ORGANISM: Unknown
<220> FEATURE:
<223> OTHER INFORMATION: Description of Unknown:
      Cell penetrating peptide

<400> SEQUENCE: 212

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 213
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 213

Arg Leu Ile Tyr Leu Arg Leu Leu Arg Gly Gln Phe
1               5                   10

<210> SEQ ID NO 214
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 214

Pro Leu Arg Leu Leu Arg Leu Leu Arg Gly Gln Phe
1               5                   10

<210> SEQ ID NO 215
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 215

Arg Lys Ile Leu Leu Arg Leu Leu Arg Gly Gln Phe
1               5                   10

<210> SEQ ID NO 216
<211> LENGTH: 12
<212> TYPE: PRT
<213> ORGANISM: Unknown
<220> FEATURE:
<223> OTHER INFORMATION: Description of Unknown:

```
                    Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 216

Pro Leu Arg Leu Arg Phe Leu Leu Arg Gly Gln Phe
1               5                   10

<210> SEQ ID NO 217
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 217

Arg Leu Ile Arg Leu Phe Leu Leu Arg Gly Gln Phe
1               5                   10

<210> SEQ ID NO 218
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 218

Arg Leu Ile Leu Leu Phe Arg Arg Leu Gly Gln Phe
1               5                   10

<210> SEQ ID NO 219
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 219

Arg Arg Ile Leu Leu Gln Leu Leu Arg Gly Gln Phe
1               5                   10

<210> SEQ ID NO 220
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 220
```

```
Pro Leu Gly Arg Pro Gln Leu Arg Arg Gly Gln Phe
1               5                   10
```

<210> SEQ ID NO 221
<211> LENGTH: 12
<212> TYPE: PRT
<213> ORGANISM: Unknown
<220> FEATURE:
<223> OTHER INFORMATION: Description of Unknown:
      Cell penetrating peptide
<220> FEATURE:
<221> NAME/KEY: MISC_FEATURE
<222> LOCATION: (10)..(12)
<223> OTHER INFORMATION: May or may not be present

<400> SEQUENCE: 221

```
Asp Asp Ile Leu Leu Gln Leu Leu Asp Gly Gln Phe
1               5                   10
```

<210> SEQ ID NO 222
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 222

```
Val Ser Leu Lys Lys
1               5
```

<210> SEQ ID NO 223
<211> LENGTH: 5
<212> TYPE: PRT
<213> ORGANISM: Unknown
<220> FEATURE:
<223> OTHER INFORMATION: Description of Unknown:
      Cell penetrating peptide

<400> SEQUENCE: 223

```
Val Ser Gly Lys Lys
1               5
```

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline

<400> SEQUENCE: 224

```
Gly Gly Gly Val Xaa
1               5
```

<210> SEQ ID NO 225
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Phe Leu Gly
1

<210> SEQ ID NO 226
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Leu Ala Leu
1

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MOD_RES
<222> LOCATION: (12)..(12)
<223> OTHER INFORMATION: Citrulline
<220> FEATURE:
<221> NAME/KEY: MISC_FEATURE
<222> LOCATION: (13)..(13)
<223> OTHER INFORMATION: May or may not be present

<400> SEQUENCE: 227

Lys Gly Lys Pro Ile Leu Phe Phe Arg Leu Lys Xaa Glu
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (11)..(11)
<223> OTHER INFORMATION: May or may not be present

<400> SEQUENCE: 228

Lys Pro Ile Leu Phe Phe Arg Leu Gly Lys Glu
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE

```
<222> LOCATION: (13)..(13)
<223> OTHER INFORMATION: May or may not be present

<400> SEQUENCE: 229

Lys Gly Ser Pro Ile Leu Phe Phe Arg Leu Gly Lys Glu
1               5                   10

<210> SEQ ID NO 230
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Cys Gly Val Leu Glu Ser Phe Lys Ala Ser Phe Leu Ser Ala Leu Glu
1               5                   10                  15

Glu Trp Thr Lys Lys Leu Gln
            20

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Trp Leu Lys Ala Phe Tyr Asp Lys Val Ala Glu Lys Leu Lys Glu
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asp Trp Phe Lys Ala Phe Tyr Asp Lys Val Ala Glu Lys Phe Lys Glu
1               5                   10                  15

<210> SEQ ID NO 233
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 234
<211> LENGTH: 37
<212> TYPE: PRT
<213> ORGANISM: Artificial Sequence
<220> FEATURE:
```

<223> OTHER INFORMATION: Description of Artificial Sequence: Synthetic
       polypeptide

<400> SEQUENCE: 234

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
            20                  25                  30

Leu Lys Glu Phe Phe
        35

<210> SEQ ID NO 235
<211> LENGTH: 37
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 235

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
            20                  25                  30

Leu Lys Glu Ala Phe
        35

<210> SEQ ID NO 236
<211> LENGTH: 37
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 236

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
            20                  25                  30

Leu Lys Glu Ala Phe
        35

<210> SEQ ID NO 237
<211> LENGTH: 37
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 237

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
        35

<210> SEQ ID NO 238
<211> LENGTH: 37
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 238

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
        35

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Alpha-aminoisobutyric acid
<220> FEATURE:
<221> NAME/KEY: MOD_RES
<222> LOCATION: (17)..(17)
<223> OTHER INFORMATION: Alpha-aminoisobutyric acid

<400> SEQUENCE: 239

Asp Trp Phe Lys Ala Phe Tyr Asp Lys Val Xaa Glu Lys Phe Lys Glu
1               5                   10                  15

Xaa Phe

<210> SEQ ID NO 240
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Alpha-aminoisobutyric acid
<220> FEATURE:
<221> NAME/KEY: MOD_RES
<222> LOCATION: (17)..(17)
<223> OTHER INFORMATION: Alpha-aminoisobutyric acid

<400> SEQUENCE: 240

Asp Trp Phe Lys Ala Phe Tyr Asp Lys Val Xaa Glu Lys Phe Lys Glu
1               5                   10                  15

Xaa Phe

<210> SEQ ID NO 241
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Tyr Val Ala Asp
1

<210> SEQ ID NO 242
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val Asp Val Ala Asp
1               5

<210> SEQ ID NO 243
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Glu Val Asp
1

<210> SEQ ID NO 244
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Glu Val Asp
1

<210> SEQ ID NO 245
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Gln Met Asp
1

<210> SEQ ID NO 246
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Leu Glu Val Asp
1

<210> SEQ ID NO 247
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247
```

```
Trp Glu His Asp
1

<210> SEQ ID NO 248
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Val Glu Ile Asp
1

<210> SEQ ID NO 249
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ile Glu Thr Asp
1

<210> SEQ ID NO 250
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ile Glu Thr Asp
1

<210> SEQ ID NO 251
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Leu Glu His Asp
1

<210> SEQ ID NO 252
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Leu Glu His Asp
1

<210> SEQ ID NO 253
<211> LENGTH: 4
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 253

Ala Glu Val Asp
1

<210> SEQ ID NO 254
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Glu Val Asp
1

<210> SEQ ID NO 255
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Thr Ala Asp
1

<210> SEQ ID NO 256
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Leu Glu Glu Asp
1

<210> SEQ ID NO 257
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Leu Glu Glu Asp
1

<210> SEQ ID NO 258
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Arg Arg Arg Arg Arg Arg
1               5

```
<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Arg Arg Arg Arg Arg Arg Arg
1               5

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Arg Arg Arg Arg Arg Arg Arg Arg
1               5

<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Arg Arg Arg Arg Arg Arg Arg Arg Arg
1               5

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Arg Arg Arg Arg Arg Arg Arg Arg Arg Arg
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Arg Arg Arg Arg Arg Arg Arg Arg Arg Arg Arg
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264
```

```
Arg Arg Arg Arg Arg Arg Arg Arg Arg Arg Arg
1               5                   10
```

<210> SEQ ID NO 265
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

```
Arg Arg Arg Arg Arg Arg Arg Arg Arg Arg Arg Arg Arg
1               5                   10
```

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

```
Arg Arg Arg Arg Arg Arg Arg Arg Arg Arg Arg Arg Arg Arg
1               5                   10
```

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

```
Arg Arg Arg Arg Arg Arg Arg Arg Arg Arg Arg Arg Arg Arg Arg
1               5                   10                  15
```

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: This sequence may encompass 6-11 residues

<400> SEQUENCE: 268

```
Arg Arg Arg Arg Arg Arg Arg Arg Arg Arg Arg
1               5                   10
```

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

```
Arg Arg Arg Arg Arg Arg Trp
1               5
```

```
<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Arg Arg Arg Arg Arg Arg Arg Trp
1               5

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Arg Arg Arg Arg Arg Arg Arg Arg Trp
1               5

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Arg Arg Arg Arg Arg Arg Arg Arg Arg Trp
1               5                   10

<210> SEQ ID NO 273
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Arg Arg Arg Arg Arg Arg Arg Arg Arg Arg Trp
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Arg Arg Arg Arg Arg Arg Arg Arg Arg Arg Trp
1               5                   10

<210> SEQ ID NO 275
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
```

```
<222> LOCATION: (1)..(6)
<223> OTHER INFORMATION: This sequence may encompass 1-6 residues

<400> SEQUENCE: 275

Pro Pro Pro Pro Pro Pro
1               5

<210> SEQ ID NO 276
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Phe Phe Leu Ile Pro Lys Gly Arg Arg Arg Arg Arg Arg
1               5                   10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Phe Phe Leu Ile Pro Lys Gly Arg Arg Arg Arg Arg Arg Arg
1               5                   10

<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Phe Phe Leu Ile Pro Lys Gly Arg Arg Arg Arg Arg Arg Arg Arg
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Phe Phe Leu Ile Pro Lys Gly Arg Arg Arg Arg Arg Arg Arg Arg Arg
1               5                   10                  15

<210> SEQ ID NO 280
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Phe Phe Leu Ile Pro Lys Gly Arg Arg Arg Arg Arg Arg Arg Arg Arg
1               5                   10                  15

Arg
```

```
<210> SEQ ID NO 281
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Phe Phe Leu Ile Pro Lys Gly Arg Arg Arg Arg Arg Arg Arg Arg
1               5                   10                  15

Arg Arg
```

TOPICAL DELIVERY OF THERAPEUTIC AGENTS USING CELL-PENETRATING PEPTIDES FOR THE TREATMENT OF AGE-RELATED MACULAR DEGENERATION AND OTHER EYE DISEASES

RELATED APPLICATIONS

This application claims priority to and the benefit of U.S. Provisional Patent Application No. 62/533,231 filed on Jul. 17, 2017, which is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Aug. 29, 2018, is named 34984-004US_SL.txt and is 79,537 bytes in size.

BACKGROUND OF THE DISCLOSURE

Age-related macular degeneration (AMD) affects about 14-24% of the people aged 65 to 74 and about 35% of the people over 75, and about 200 million people around the world, and is the leading cause of legal blindness in developed countries. AMD results in vision impairment or loss in the center of the visual field (the macula) because of damage to the retina. The two principal forms of AMD are atrophic (non-exudative or "dry") AMD and neovascular (exudative or "wet") AMD. Atrophic AMD is characterized by geographic atrophy (GA) at the center of the macula in the advanced stage of AMD, and vision can slowly deteriorate over many years due to loss of photoreceptors and development of GA. Neovascular AMD is a more severe form of AMD and is characterized by neovascularization (e.g., choroidal neovascularization) in the advanced stage of AMD, which can rapidly lead to blindness. Neovascular AMD affects about 30 million patients worldwide and is a leading cause of vision loss in people aged 60 years or older—if untreated, patients are likely to lose central vision in the affected eye within 24 months of disease onset. About 85% of AMD patients have the dry form, and about 15% develop neovascular AMD. There is no approved treatment for atrophic AMD in the United States, while approved treatments for neovascular AMD (primarily anti-angiogenic agents) show efficacy in about 50% of neovascular AMD patients.

SUMMARY OF THE DISCLOSURE

The present disclosure provides for the topical delivery of a therapeutic agent using a cell-penetrating peptide (CPP) in the treatment of AMD and other eye disorders. In some embodiments, the therapeutic agent is or includes an anti-dyslipidemic agent, an antioxidant, an anti-inflammatory agent, a complement inhibitor, a neuroprotector or an anti-angiogenic agent, or any combination thereof. In some embodiments, the therapeutic agent is or includes an anti-dyslipidemic agent. In certain embodiments, the anti-dyslipidemic agent is or includes an apolipoprotein (apo) mimetic (e.g., an apoA-I mimetic such as L-4F or D-4F, or an apoE mimetic such as AEM-28-14) or/and a statin (e.g., atorvastatin or simvastatin). The therapeutic agent can be mixed with, non-covalently associated with or covalently bonded to the CPP, or can be encapsulated in CPP-conjugated nanoparticles, micelles or liposomes. In certain embodiments, the therapeutic agent is mixed with the CPP, whether or not non-covalently associated with the CPP. In further embodiments, the therapeutic agent is non-covalently bound to or associated with the CPP, such as by electrostatic interaction, hydrophobic interaction or hydrogen bonding, or any combination thereof. The therapeutic agent-CPP mixture, complex or conjugate, or the therapeutic agent-containing CPP-conjugated nanoparticles, micelles or liposomes, can enter the anterior and posterior segments of the eye for the treatment of AMD and other eye disorders. In certain embodiments, the CPP is a polycationic or arginine-rich CPP [e.g., a polyarginine such as $R_6$-$R_{11}$ (SEQ ID NO: 268) (e.g., $R_6$ (SEQ ID NO: 258) or $R_9$ (SEQ ID NO: 261)) or a TAT-related CPP such as TAT(49-57)], or an amphipathic CPP (e.g., Pep-1 or penetratin). In some embodiments, the therapeutic agent-CPP mixture, complex or conjugate, or the therapeutic agent-containing CPP-modified nanoparticles, micelles or liposomes, is/are applied to the surface of the eye by means of an eye drop or a contact lens (e.g., a corneal lens or a scleral lens). A therapeutic agent (e.g., an anti-dyslipidemic agent) and a CPP can be administered in any stage (including the early, intermediate and advanced stages) of AMD to treat atrophic AMD or neovascular AMD, and can also be administered prior to development of AMD to prevent or delay the onset of AMD.

In some embodiments, one or more of the following therapeutic agents are used to treat AMD or other eye disorders:

1) anti-dyslipidemic agents;
2) PPAR-α agonists, PPAR-δ agonists and PPAR-γ agonists;
3) anti-amyloid agents and inhibitors of other toxic substances (e.g., aldehydes);
4) inhibitors of lipofuscin or components thereof;
5) visual/light cycle modulators and dark adaptation agents;
6) antioxidants;
7) neuroprotectors (neuroprotectants);
8) apoptosis inhibitors and necrosis inhibitors;
9) C-reactive protein inhibitors;
10) inhibitors of the complement system or components (e.g., proteins) thereof;
11) inhibitors of inflammasomes;
12) anti-inflammatory agents;
13) immunosuppressants;
14) modulators (inhibitors and activators) of matrix metalloproteinases and other inhibitors of cell migration;
15) anti-angiogenic agents;
16) low-level light therapies, laser therapies, photodynamic therapies and radiation therapies;
17) agents that preserve or improve the health of the endothelium or/and the blood flow of the vascular system of the eye; and
18) cell (e.g., RPE cell) replacement therapies.

The therapeutic agent(s) can be administered locally or systemically and in any suitable mode, such as topically (e.g., by eye drop or contact lens), orally or parenterally (e.g., intravenously or subcutaneously). In some embodiments, the therapeutic agent(s) are mixed with, non-covalently associated with or covalently bonded to a CPP, or are encapsulated in CPP-modified nanoparticles, micelles or liposomes, and are administered by eye drop or contact lens (e.g., corneal lens or scleral lens).

In some embodiments, an anti-dyslipidemic agent (e.g., an apoA-I mimetic or an apoE mimetic, or/and a statin) is used in conjunction with an additional anti-dyslipidemic agent, an antioxidant, an anti-inflammatory agent, a complement inhibitor, a neuroprotector or an anti-angiogenic agent, or any combination or all thereof, to treat AMD or another eye disorder. In certain embodiments, the additional therapeutic agent is or comprises an anti-angiogenic agent (e.g., an anti-VEGF/VEGFR agent such as aflibercept, bevacizumab, ranibizumab or brolucizumab).

Besides AMD, other eye diseases and disorders that can be treated with one or more of the therapeutic agents described herein (e.g., an anti-dyslipidemic agent such as an apo mimetic, or/and an anti-angiogenic agent such as an anti-VEGF/VEGFR agent) include without limitation maculopathy (e.g., age-related maculopathy and diabetic maculopathy), macular edema (e.g., diabetic macular edema [DME] and macular edema following retinal vein occlusion [RVO]), retinopathy (e.g., diabetic retinopathy [including in patients with DME]), RVO (e.g., central RVO and branch RVO), Coats' disease (exudative retinitis), uveitis, retinal pigment epithelium detachment, and diseases associated with increased intra- or extracellular lipid storage or accumulation in addition to AMD.

BRIEF DESCRIPTION OF THE DRAWINGS

A better understanding of features and advantages of the present disclosure will be obtained by reference to the following detailed description, which sets forth illustrative embodiments of the disclosure, and the accompanying drawings.

Figure 7A:
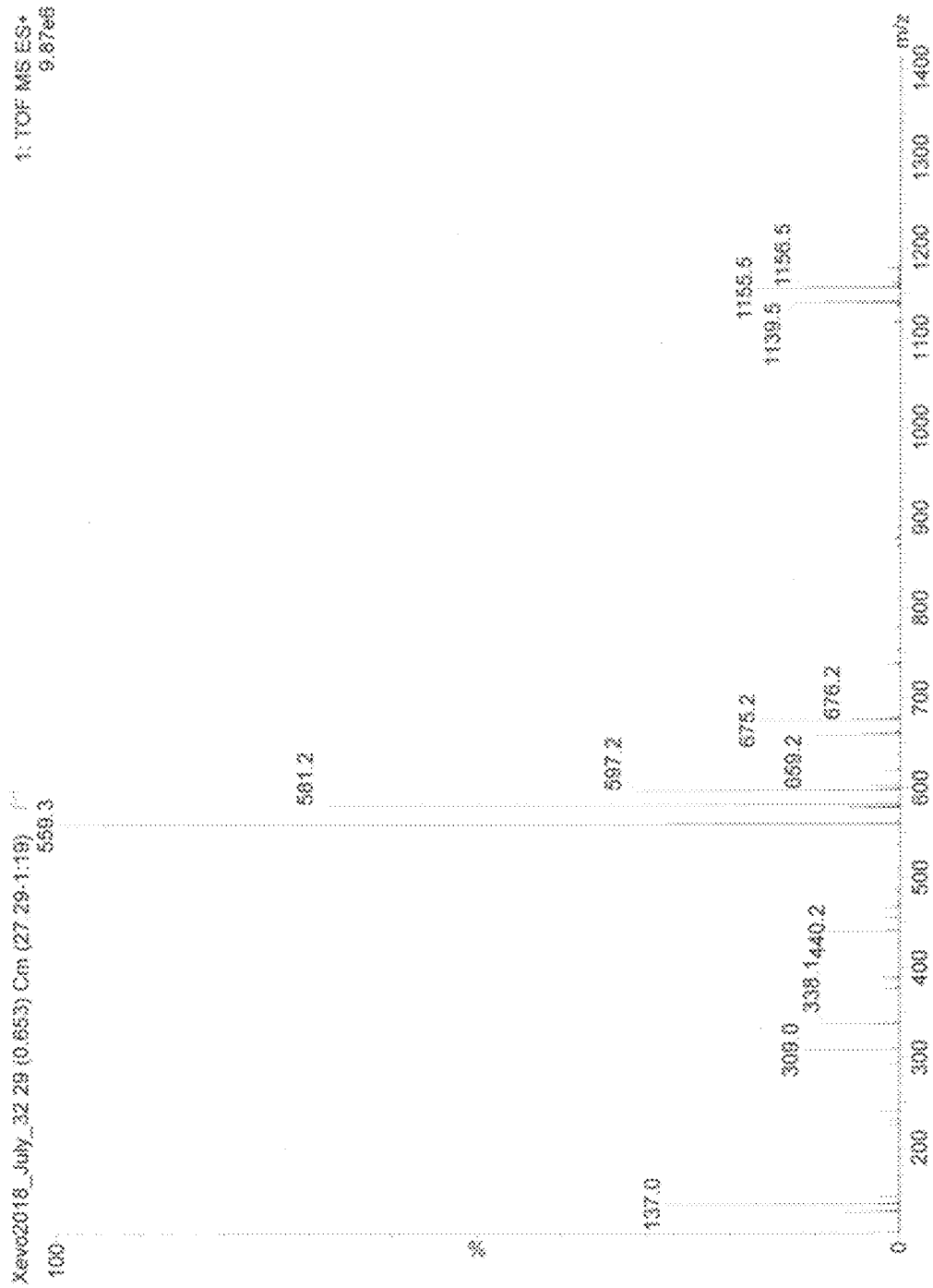
Figure 7B:
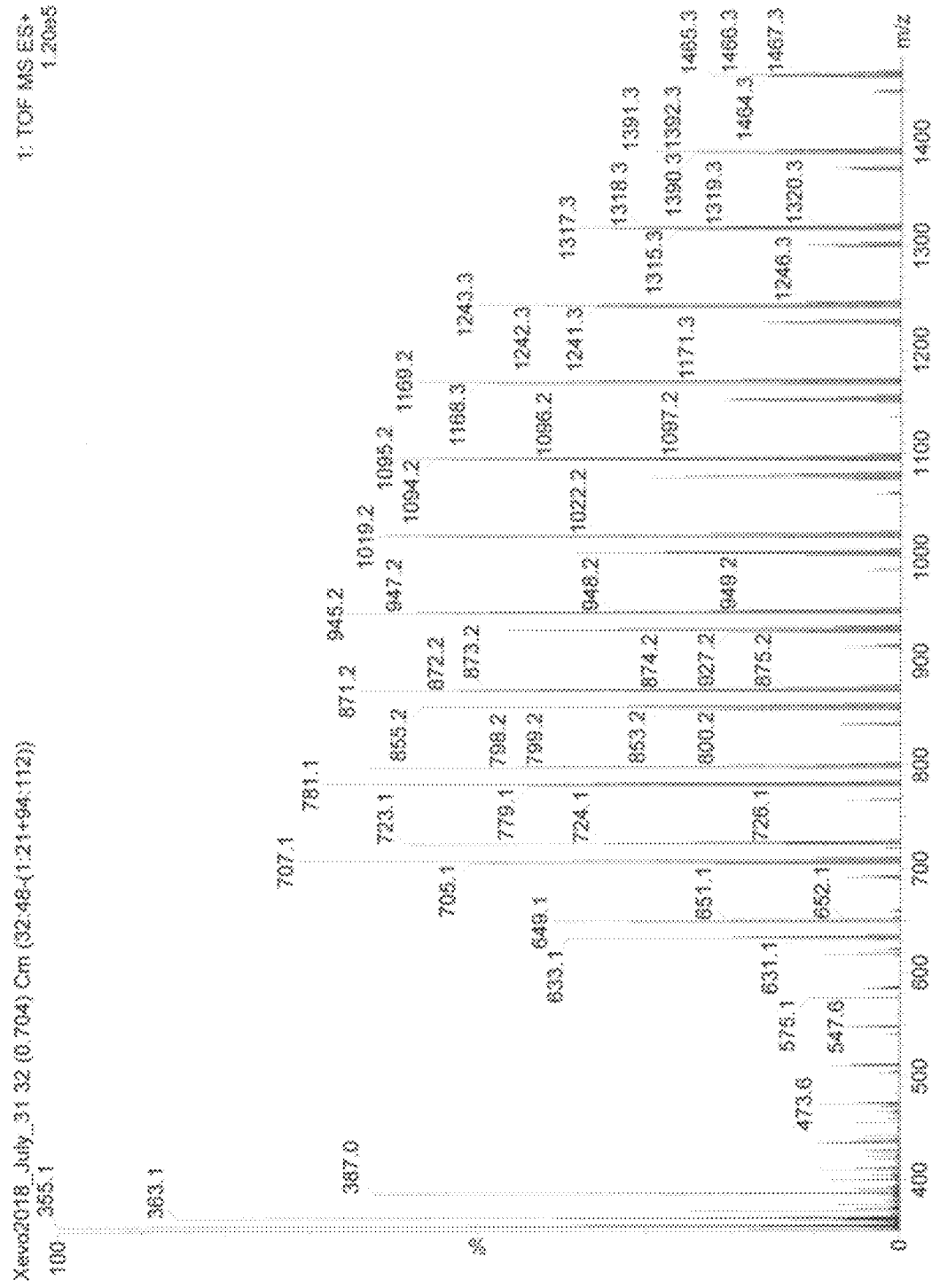

The peak at 559 m/z ($M^+$) in FIG. 7A demonstrates that atorvastatin mixed with the CPP hexa-arginine (SEQ ID NO: 258) crossed the outer shell membrane of a chicken egg, whereas the absence of a peak at 559 m/z in FIG. 7B demonstrates that atorvastatin did not cross the membrane in the absence of hexa-arginine (SEQ ID NO: 258).

Figure 8:
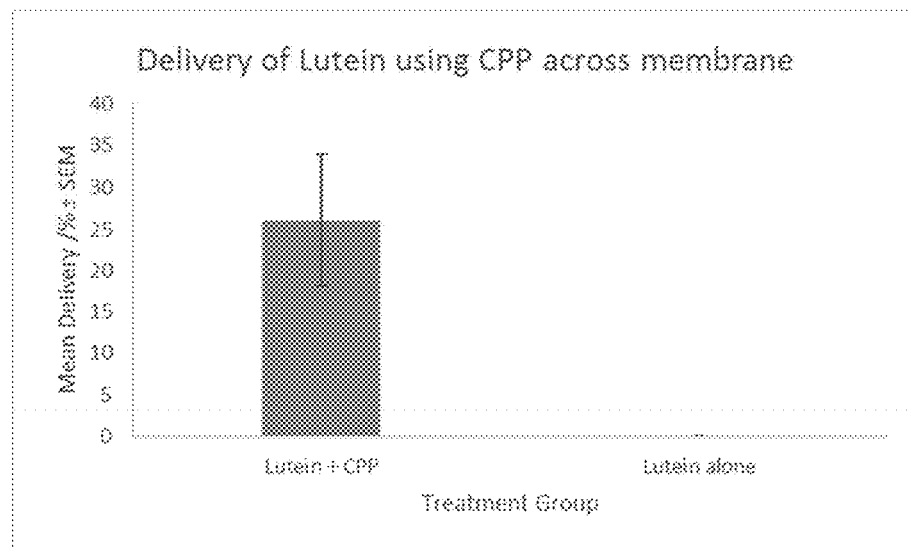

FIG. 8 shows that 26±8% of the applied amount of lutein mixed with the CPP hexa-arginine (SEQ ID NO: 258) crossed the outer shell membrane of a chicken egg, whereas lutein did not cross the membrane in the absence of hexa-arginine (SEQ ID NO: 258).

Figure 9:
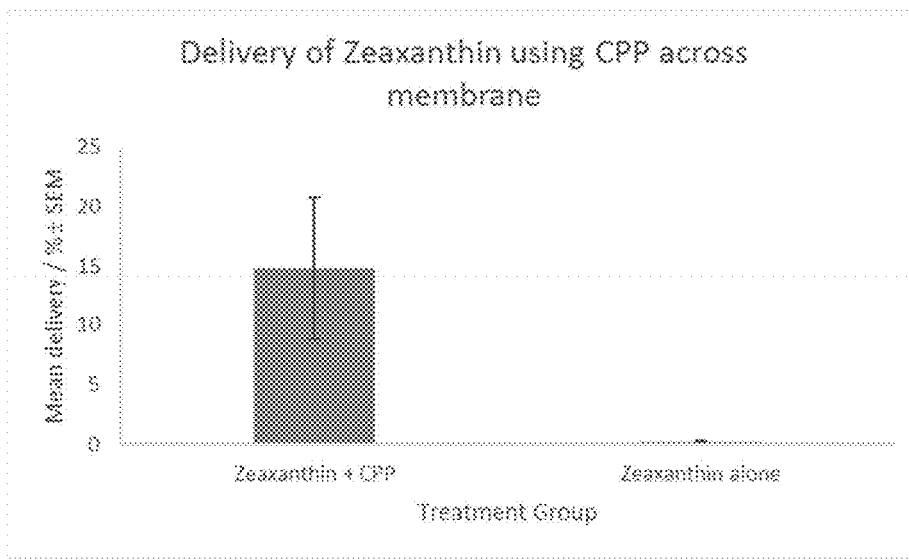

FIG. 9 shows that 15±5% of the applied amount of zeaxanthin mixed with the CPP hexa-arginine (SEQ ID NO: 258) crossed the outer shell membrane of a chicken egg, whereas a very small amount of zeaxanthin crossed the membrane in the absence of hexa-arginine (SEQ ID NO: 258).

Figure 10:
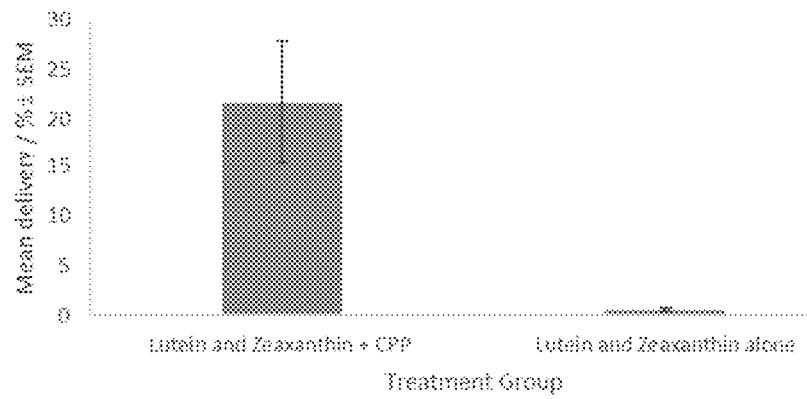

FIG. 10 shows that 21±6% of the applied amount of lutein and zeaxanthin mixed with the CPP hexa-arginine (SEQ ID NO: 258) crossed the outer shell membrane of a chicken egg, whereas a very small amount of lutein and zeaxanthin crossed the membrane in the absence of hexa-arginine (SEQ ID NO: 258).

Figure 11A:
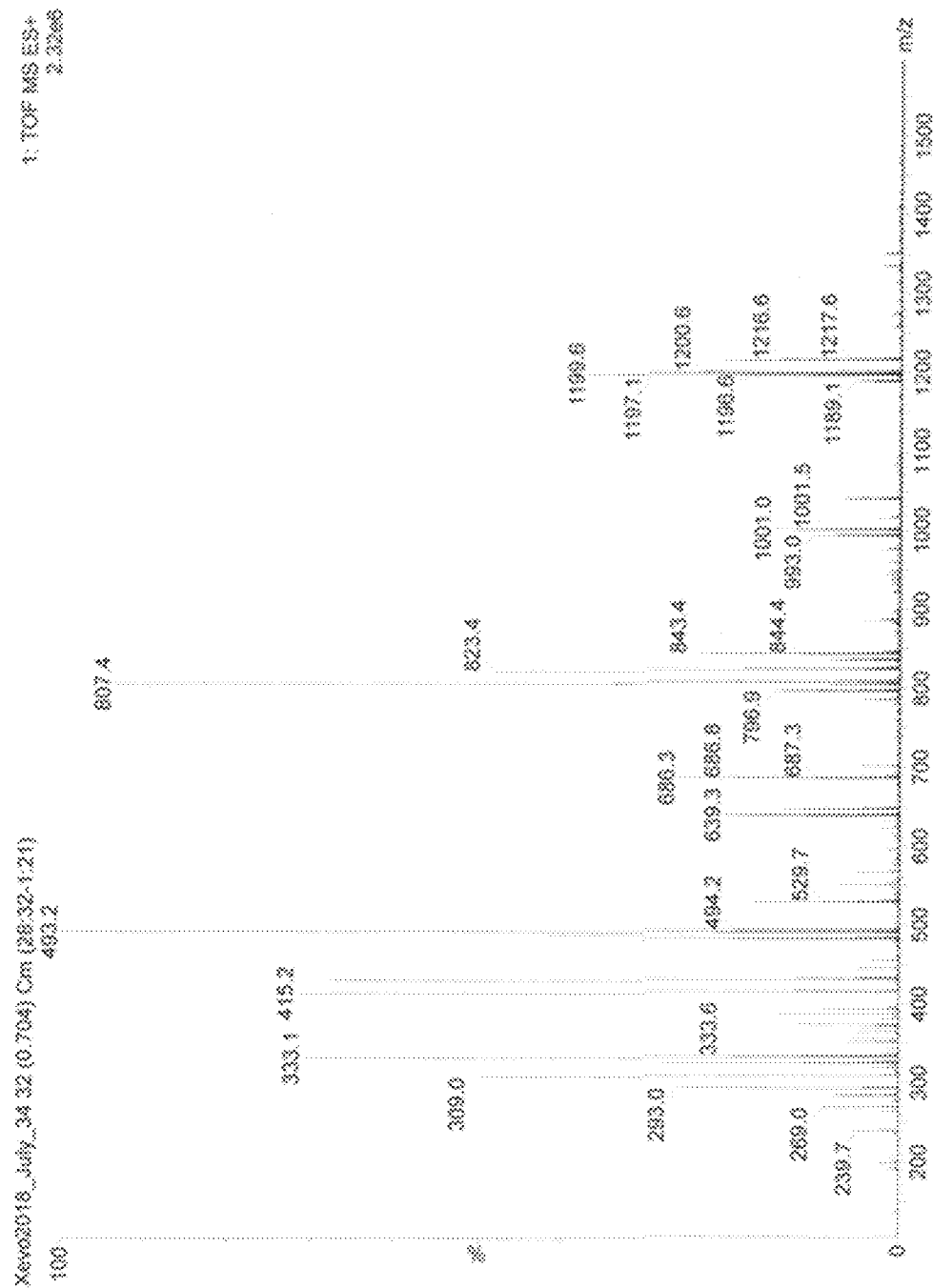
Figure 11B:
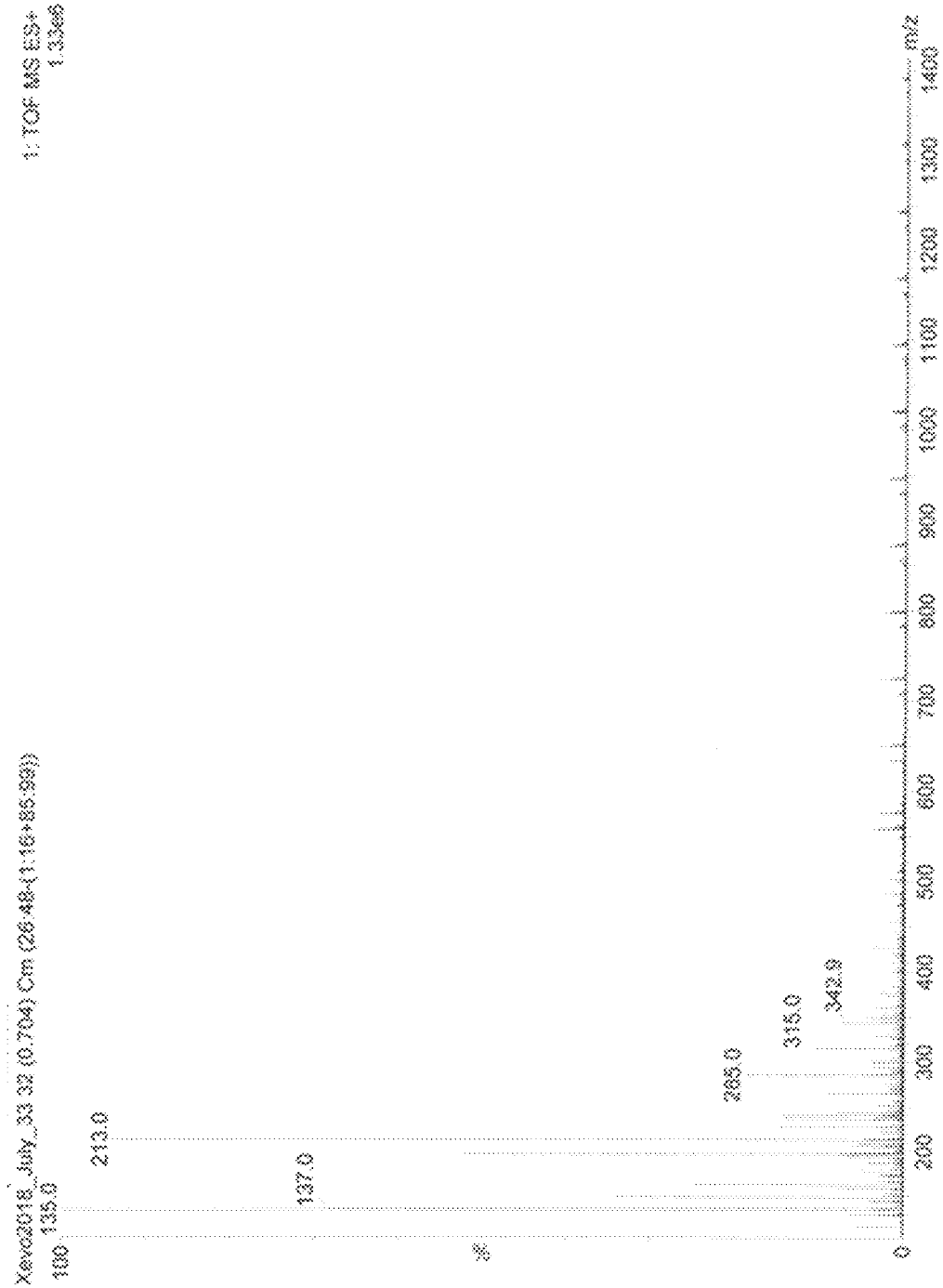

The peaks at 415 m/z (M+Na), 807 m/z (2M+Na) and 1199 m/z (3M+Na) in FIG. 11A demonstrate that dexamethasone mixed with the CPP hexa-arginine (SEQ ID NO: 258) crossed the outer shell membrane of a chicken egg, whereas the absence of a peak at 415 m/z, 807 m/z or 1199 m/z in FIG. 11B demonstrates that dexamethasone did not cross the membrane in the absence of hexa-arginine (SEQ ID NO: 258).

Figure 12A:
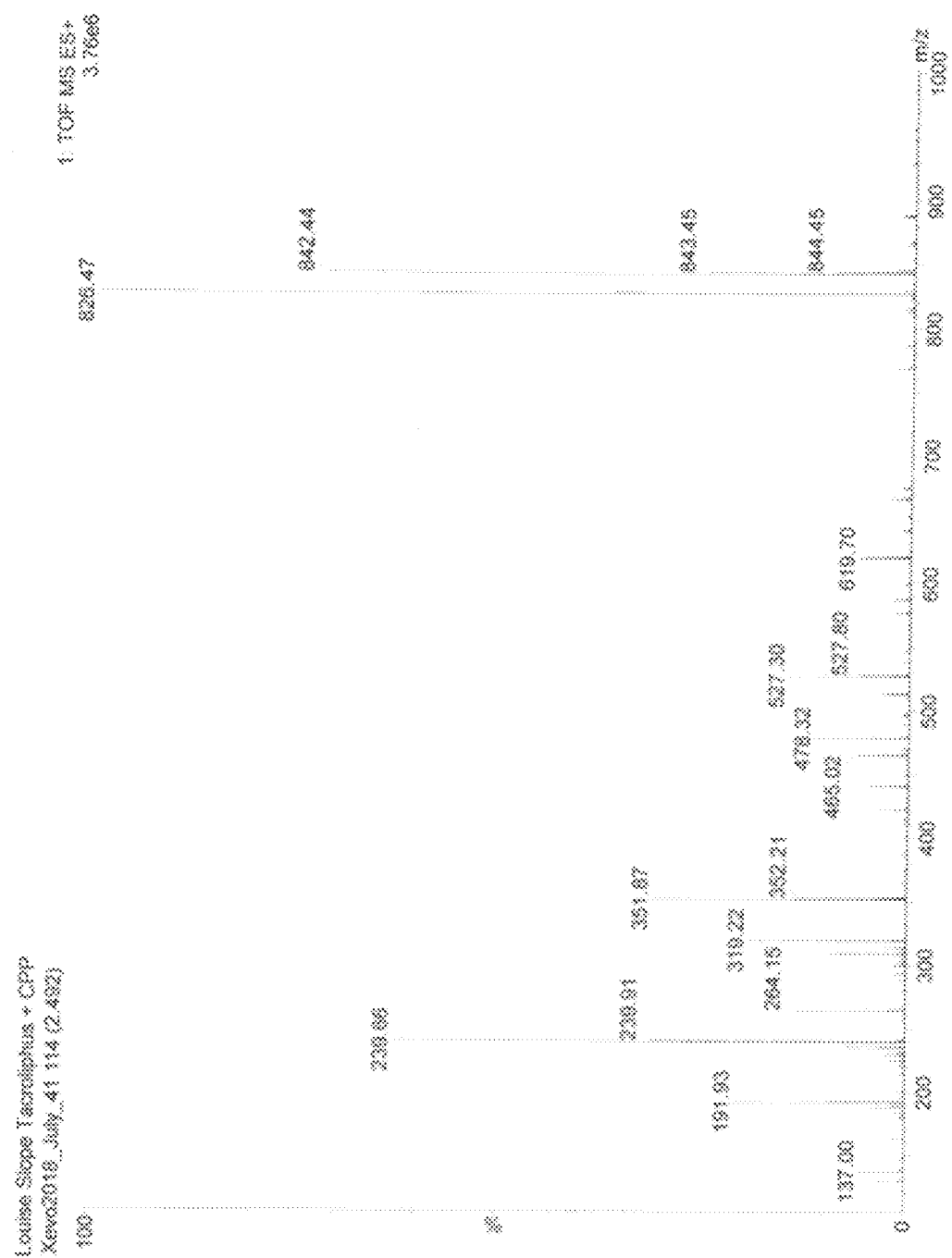
Figure 12B:
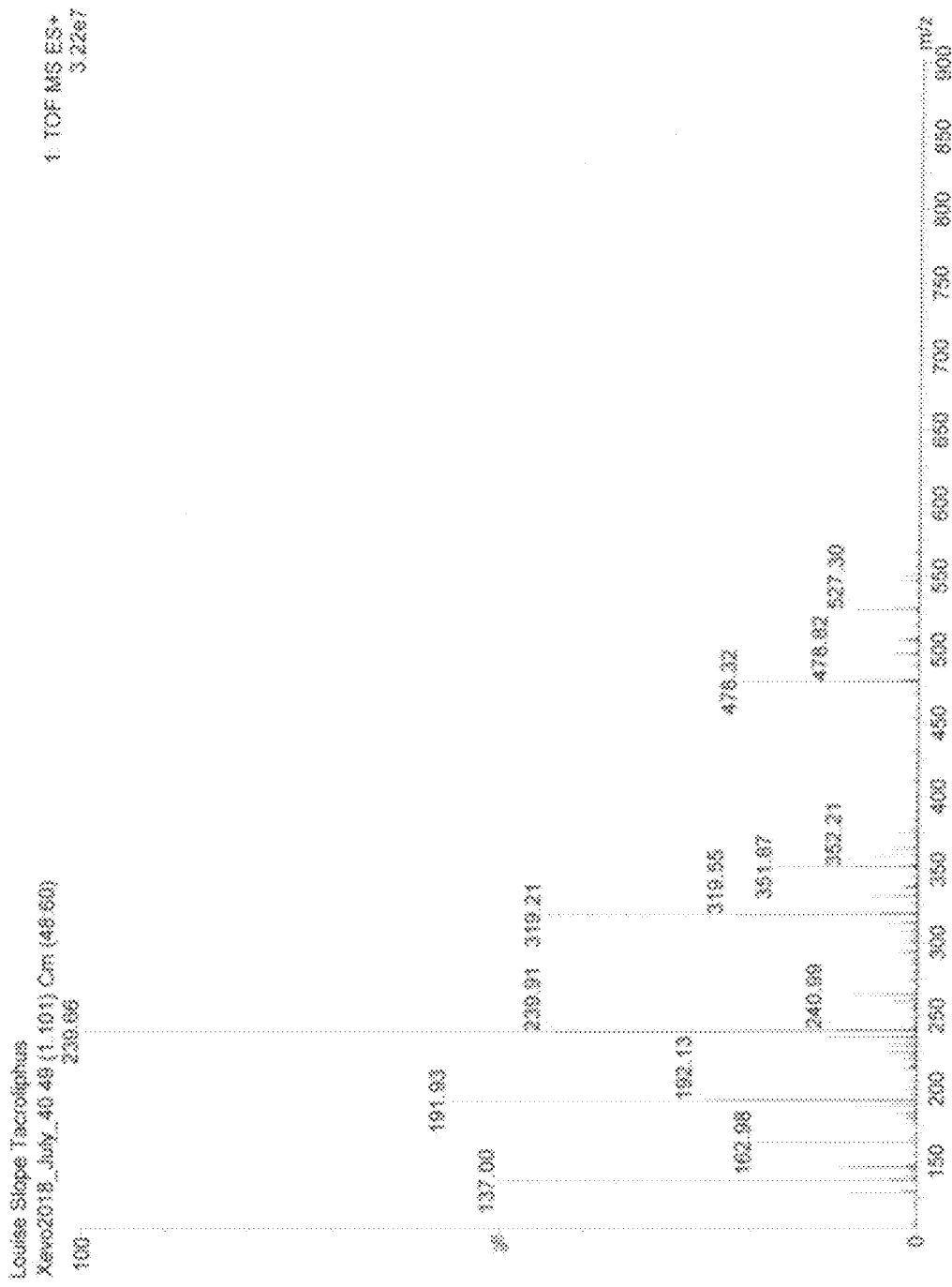

The peaks at 826 m/z (M+Na) and 842 m/z (M+K) in FIG. 12A demonstrate that tacrolimus mixed with the CPP hexa-arginine (SEQ ID NO: 258) crossed the outer shell membrane of a chicken egg, whereas the absence of a peak at 826 m/z or 842 m/z in FIG. 12B demonstrates that tacrolimus did not cross the membrane in the absence of hexa-arginine (SEQ ID NO: 258).

Figure 13:
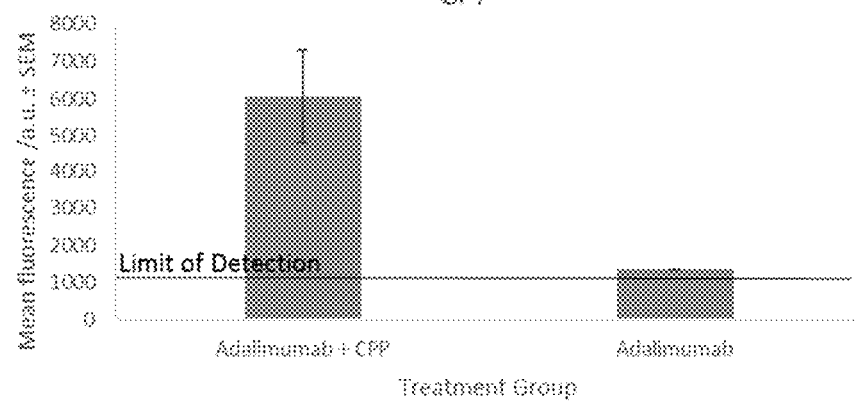

FIG. 13 shows that when mixed with the CPP hexa-arginine (SEQ ID NO: 258), the amount of adalimumab which crossed the outer shell membrane of a chicken egg was markedly greater than the amount of adalimumab which crossed the membrane in the absence of hexa-arginine (SEQ ID NO: 258).

Figure 14:
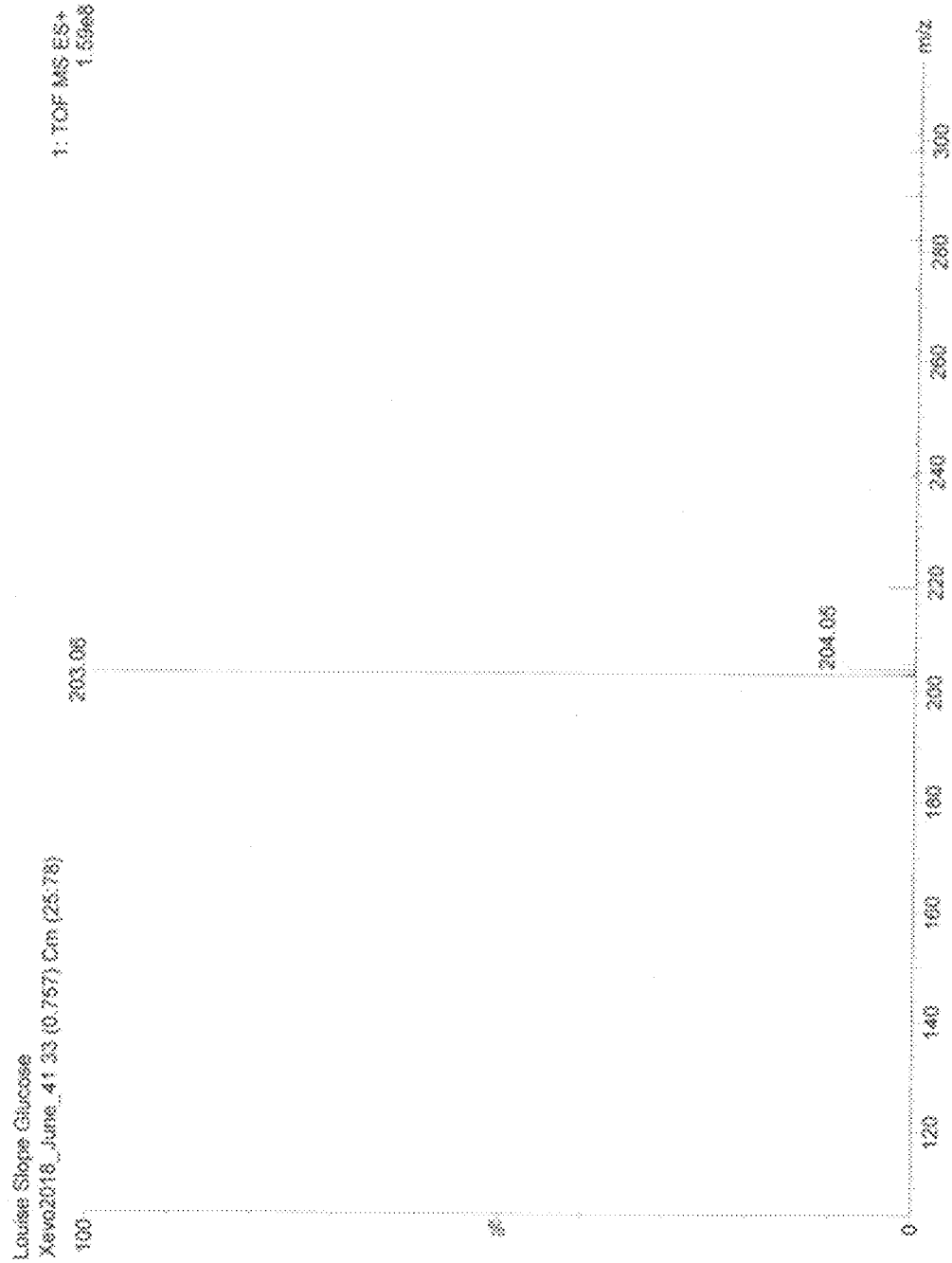

FIG. 14 demonstrates that glucose mixed with the CPP hexa-arginine (SEQ ID NO: 258) crossed the outer shell membrane of a chicken egg (203 m/z for glucose+Na).

Figure 15:
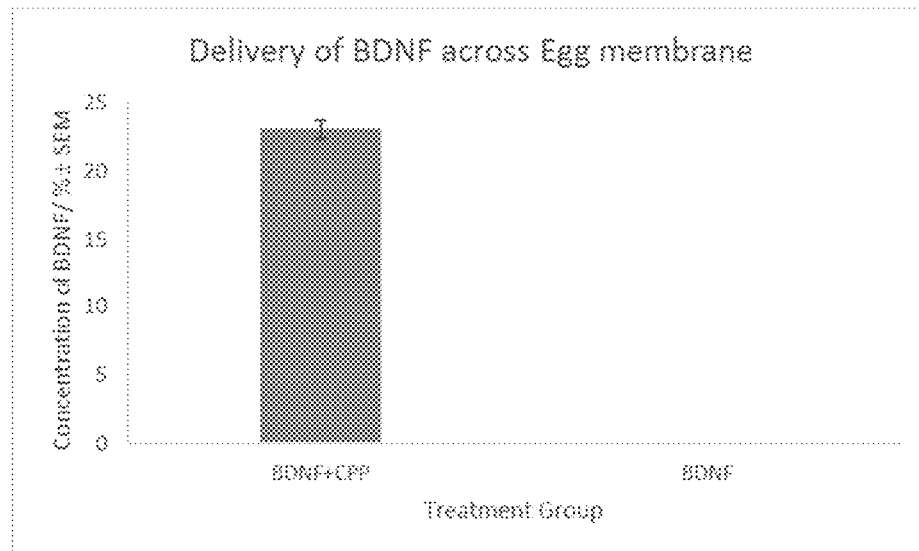

FIG. 15 shows that 23±1% of the applied amount of brain-derived neurotrophic factor (BDNF) mixed with the CPP hexa-arginine (SEQ ID NO: 258) crossed the outer shell membrane of a chicken egg, whereas BDNF did not cross the membrane in the absence of hexa-arginine (SEQ ID NO: 258).

Figure 16:
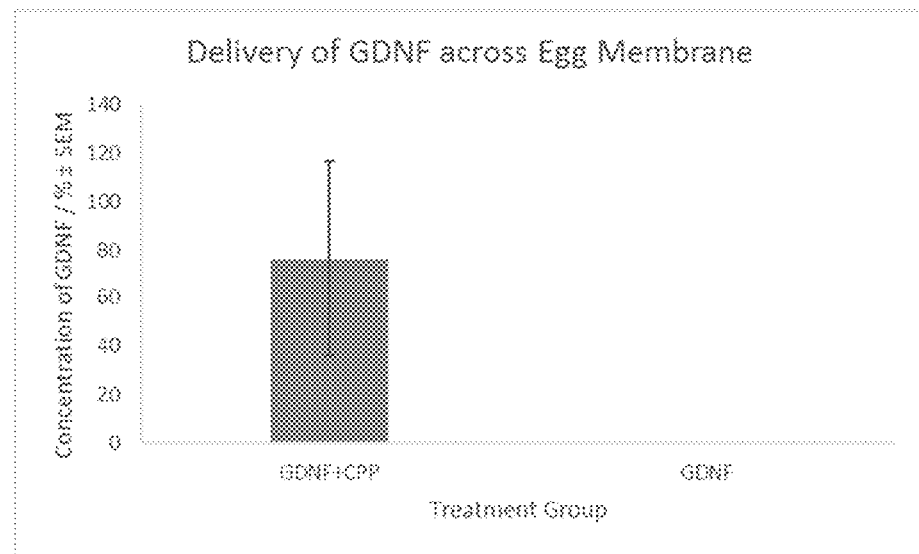

FIG. 16 shows that 76±40% of the applied amount of glial cell-derived neurotrophic factor (GDNF) mixed with the CPP hexa-arginine (SEQ ID NO: 258) crossed the outer shell membrane of a chicken egg, whereas GDNF did not cross the membrane in the absence of hexa-arginine (SEQ ID NO: 258).

Figure 17:
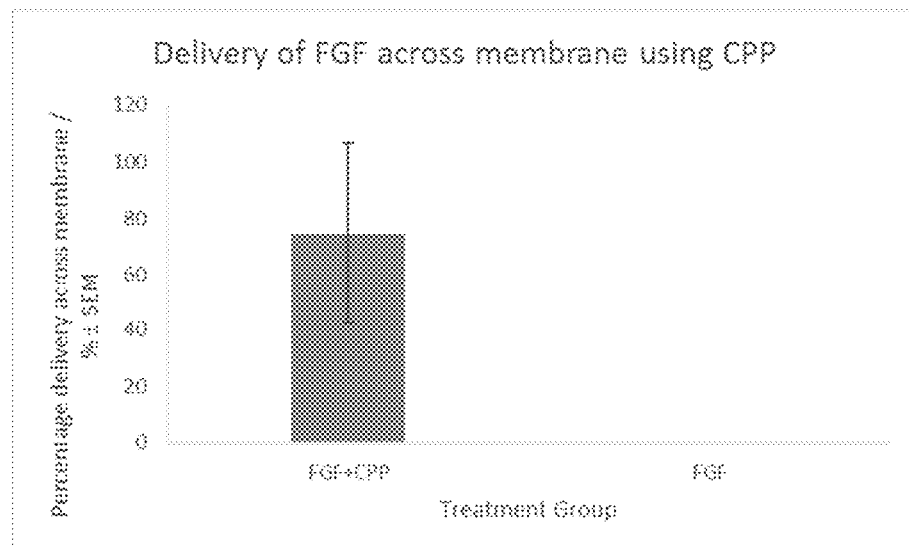

FIG. 17 shows that 74±32% of the applied amount of fibroblast growth factor (FGF) mixed with the CPP hexa-arginine (SEQ ID NO: 258) crossed the outer shell membrane of a chicken egg, whereas FGF did not cross the membrane in the absence of hexa-arginine (SEQ ID NO: 258).

Figure 18:
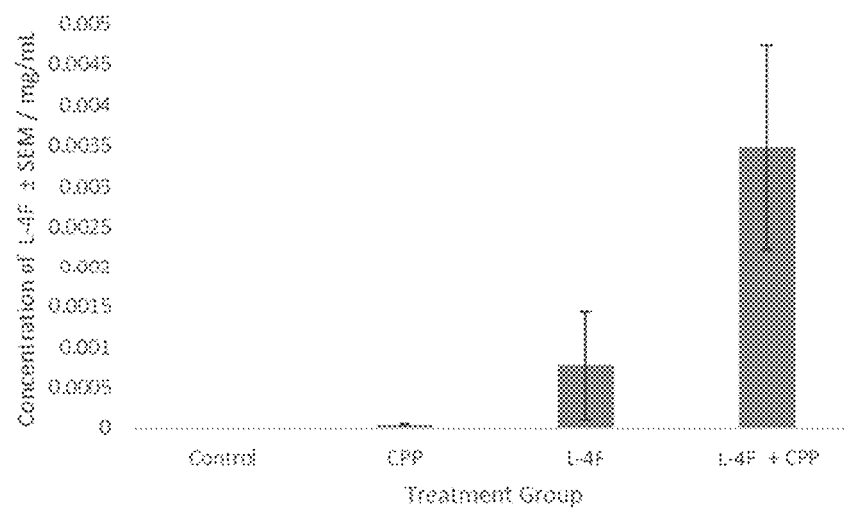

FIG. 18 shows that a significantly greater amount of L-4F was delivered into the posterior segment (the vitreous and the retina) of the porcine eye ex vivo when mixed with the CPP hexa-arginine (SEQ ID NO: 258).

Figure 19:
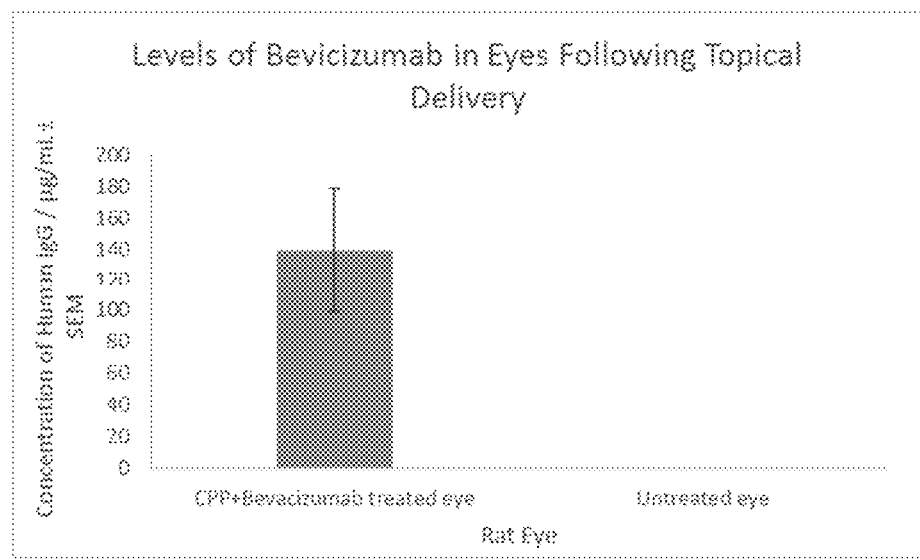

FIG. 19 shows that bevacizumab mixed with the CPP hexa-arginine (SEQ ID NO: 258) entered into the posterior segment (the vitreous and the retina) of the treated rat eye in vivo. Bevacizumab was not detected in the fellow untreated eye or in the bloodstream.

DETAILED DESCRIPTION OF THE DISCLOSURE

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein can be employed in practicing the disclosure. It is also understood that every embodiment of the disclosure can optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act, the order of the acts of the method is not necessarily limited to the order in which the acts of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

It is further understood that the present disclosure encompasses analogs, derivatives, prodrugs, fragments, salts, solvates, hydrates, clathrates and polymorphs of all of the compounds/substances disclosed herein, as appropriate. The specific recitation of "analogs", "derivatives", "prodrugs", "fragments", "salts", "solvates", "hydrates", "clathrates" or "polymorphs" with respect to a compound/substance or a group of compounds/substances in certain instances of the disclosure shall not be interpreted as an intended omission of any of these forms in other instances of the disclosure where the compound/substance or the group of compounds/substances is mentioned without recitation of any of these forms.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

I. DEFINITIONS

Unless defined otherwise or clearly indicated otherwise by their use herein, all technical and scientific terms used herein have the same meaning as commonly understood by those of ordinary skill in the art to which this application belongs.

As used in the specification and the appended claims, the indefinite articles "a" and "an" and the definite article "the" can include plural referents as well as singular referents unless specifically stated otherwise or the context clearly indicates otherwise.

The abbreviation "aka" denotes also known as.

The term "exemplary" as used herein means "serving as an example, instance or illustration". Any embodiment or feature characterized herein as "exemplary" is not necessarily to be construed as preferred or advantageous over other embodiments or features.

The term "about" or "approximately" means an acceptable error for a particular value as determined by one of ordinary skill in the art, which depends in part on how the value is measured or determined. In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within ±20%, 15%, 10% or 5% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The symbols "ug" and "µg" are used interchangeably herein to denote microgram(s). Similarly, the symbols "uL" and "µL" are used interchangeably herein to denote microliter(s).

The term "antioxidants" includes without limitation substances that inhibit the oxidation of other substances, substances that retard the deterioration of other substances by oxidation, and scavengers of free radical species, reactive oxygen species, hydroxyl radical species, and oxidized lipids and lipid peroxidation products.

The term "apolipoprotein mimetics" encompasses apolipoprotein peptide mimetics and apolipoprotein mimetic peptides.

The term "polypeptides" encompasses peptides and proteins. The term "proteins" typically refers to larger polypeptides, and the term "peptides" typically refers to shorter polypeptides. In certain embodiments, a peptide contains no more than about 50, 40 or 30 amino acid residues. Conventional notation is used herein to portray polypeptide sequences: the left-hand end of a polypeptide sequence is the amino (N)-terminus, and the right-hand end of the sequence is the carboxyl (C)-terminus.

The term "conservative substitution" refers to substitution of an amino acid in a polypeptide with a functionally, structurally or chemically similar natural or unnatural amino acid. In certain embodiments, the following groups each contain natural amino acids that are conservative substitutions for one another:

1) Glycine (Gly/G), Alanine (Ala/A);
2) Isoleucine (Ile/I), Leucine (Leu/L), Methionine (Met/M), Valine (Val/V);
3) Phenylalanine (Phe/F), Tyrosine (Tyr/Y), Tryptophan (Trp/W);
4) Serine (Ser/S), Threonine (Thr/T), Cysteine (Cys/C);
5) Asparagine (Asn/N), Glutamine (Gln/Q);
6) Aspartic acid (Asp/D), Glutamic acid (Glu/E); and
7) Arginine (Arg/R), Lysine (Lys/K), Histidine (His/H).

In further embodiments, the following groups each contain natural amino acids that are conservative substitutions for one another:

1) non-polar: Ala, Val, Leu, Ile, Met, Pro (proline/P), Phe, Trp;
2) hydrophobic: Val, Leu, Ile, Phe, Trp;
3) aliphatic: Ala, Val, Leu, Ile;
4) aromatic: Phe, Tyr, Trp, His;
5) uncharged polar or hydrophilic: Gly, Ala, Ser, Thr, Cys, Asn, Gln, Tyr;
6) aliphatic hydroxyl- or sulfhydryl-containing: Ser, Thr, Cys;
7) amide-containing: Asn, Gln;
8) acidic: Asp, Glu;
9) basic: Lys, Arg, His; and
10) small: Gly, Ala, Ser, Cys.

In other embodiments, amino acids may be grouped as set out below:

1) hydrophobic: Val, Leu, Ile, Met, Phe, Trp;
2) aromatic: Phe, Tyr, Trp, His;
3) neutral hydrophilic: Gly, Ala, Ser, Thr, Cys, Asn, Gln;
4) acidic: Asp, Glu;
5) basic: Lys, Arg, His; and
6) residues that influence backbone orientation: Pro, Gly.

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" carrier or excipient of a pharmaceutical composition is also compatible with the other ingredients of the composition.

The term "therapeutically effective amount" refers to an amount of a substance that, when administered to a subject, is sufficient to prevent, reduce the risk of developing, delay the onset of, slow the progression of or cause regression of the medical condition being treated, or to alleviate to some extent the medical condition or one or more symptoms or complications of that condition, at least in some fraction of the subjects taking that substance. The term "therapeutically effective amount" also refers to an amount of a substance that is sufficient to elicit the biological or medical response of a cell, tissue, organ, system, animal or human which is sought by a researcher, veterinarian, medical doctor or clinician.

The terms "treat", "treating" and "treatment" include alleviating, ameliorating, inhibiting the progress of, reversing or abrogating a medical condition or one or more symptoms or complications associated with the condition, and alleviating, ameliorating or eradicating one or more causes of the condition. Reference to "treatment" of a medical condition includes prevention of the condition. The terms "prevent", "preventing" and "prevention" include precluding, reducing the risk of developing and delaying the onset of a medical condition or one or more symptoms or complications associated with the condition.

The term "medical conditions" includes diseases and disorders. The terms "diseases" and "disorders" are used interchangeably herein.

The term "subject" refers to an animal, including but not limited to a mammal, such as a primate (e.g., a human, a chimpanzee or a monkey), a rodent (e.g., a rat, a mouse, a guinea pig, a gerbil or a hamster), a lagomorph (e.g., a rabbit), a bovine (e.g., a cattle), a suid (e.g., a pig), a caprine (e.g., a sheep), an equine (e.g., a horse), a canine (e.g., a dog) or a feline (e.g., a cat). The terms "subject" and "patient" are used interchangeably herein in reference, e.g., to a mammalian subject, such as a human subject.

II. PATHOGENESIS AND PATHOPHYSIOLOGY OF AMD

Age-related changes to the retina and the choroid of the eye which contribute to the development of age-related macular degeneration (AMD) include the loss of rod photoreceptors, the thinning of the choroid, and the accumulation of lipofuscin and reportedly components thereof (e.g., A2E [N-retinylidene-N-retinyl-ethanolamine]) in the retinal pigment epithelium (RPE) as well as lipids in the sub-RPE basal lamina (sub-RPE-BL) space and the Bruch's membrane (BrM, which is the inner wall of the choroid). Lipoprotein particles and reportedly beta-amyloid (Aβ) accumulate to form basal linear deposits (BLinD) on the BrM. The RPE secretes apolipoprotein B (apoB)-lipoprotein particles of abnormal composition into the BrM, where they accumulate with age and eventually form a lipid wall on the BrM. BLinD and drusen are believed to develop from such a lipid wall. The lipid wall, and accumulation of abnormal deposits resulting in part from abnormalities in proteolytic processes in regulating the BrM, stimulate chronic inflammation. The abnormal aggregates of material, combined with the loss of normal extracellular matrix (ECM) maintenance function (partially mediated by altered ratios of matrix metalloproteinases [MMPs] and tissue inhibitors of MMPs [TIMPs]), result in alterations in the BrM, with consequent formation of BLinD and drusen.

Drusen are extracellular deposits rich in lipids (e.g., esterified cholesterol [EC] and phospholipids) and lipoprotein components (e.g., apoB or/and apoE) and form in the sub-RPE-BL space between the RPE-BL and the inner collagenous layer of the BrM, possibly as a result of RPE secretion of EC-rich very low-density lipoproteins (VLDLs) basolaterally. "Hard" drusen are small, distinct and far away from one another, and may not cause vision problem for a long time, if at all. In contrast, "soft" drusen are large, have poorly defined edges, and cluster closer together. Soft drusen are more fragile than hard drusen, are oily upon dissection due to a high lipid constitution, and are a major risk factor for the development of advanced atrophic or neovascular AMD Esterified cholesterol and phospholipids (in the form of lipoprotein particles of 60-80 nm diameter) accumulate in the BrM and the sub-RPE-BL space throughout adulthood and eventually aggregate as BLinD on the BrM or soft drusen in the sub-RPE-BL space of older eyes. Soft drusen and BLinD are two forms (a lump and a thin layer, respectively) of the same lipid-rich extracellular lesion containing lipoprotein-derived debris and specific to AMD. Lipid constituents of soft drusen and BLinD interact with reactive oxygen species to form pro-inflammatory peroxidized lipids (or lipid peroxides), which inhibit paraoxonase 1 activity, activate the complement system and elicit choroidal neovascularization. Furthermore, drusen contain immunogenic complement components. EC-rich, apoB/apoE-containing lipoproteins (e.g., VLDLs) secreted by RPE cells are retained by a BrM that progressively thickens with age, until an oily layer forms on the BrM, with oxidation of lipids or other modifications followed by fusion of individual lipoproteins over time to form BLinD. An inflammatory response to the accumulated material ensues with activation of the complement system and other components of the immune system. Moreover, by altering the BrM with subsequent calcification and fracture, the accumulation of lipid-containing material leads to neovascularization in the sub-RPE-BL space and breakthrough to the subretinal space, the potential space between the photoreceptors and the RPE. Furthermore, the lipid-rich drusen in the sub-RPE-BL space and BLinD overlying the BrM block oxygen and nutrients (including vitamin A) from reaching the RPE cells and the photoreceptors (rods and cones) in the retina, which results in their atrophy/degeneration and eventually death.

Other extracellular lesions associated with AMD include subretinal drusenoid deposits (SDD), which are compositionally distinct from drusen, contain unesterified (free) cholesterol (UC) and form between the RPE and photoreceptors, possibly as a result of RPE secretion of UC-rich lipoproteins apically. The formation of SDD in the subretinal space may also lead to sequelae such as inflammation and neovascularization (e.g., type 2 or 3).

Figure 1:
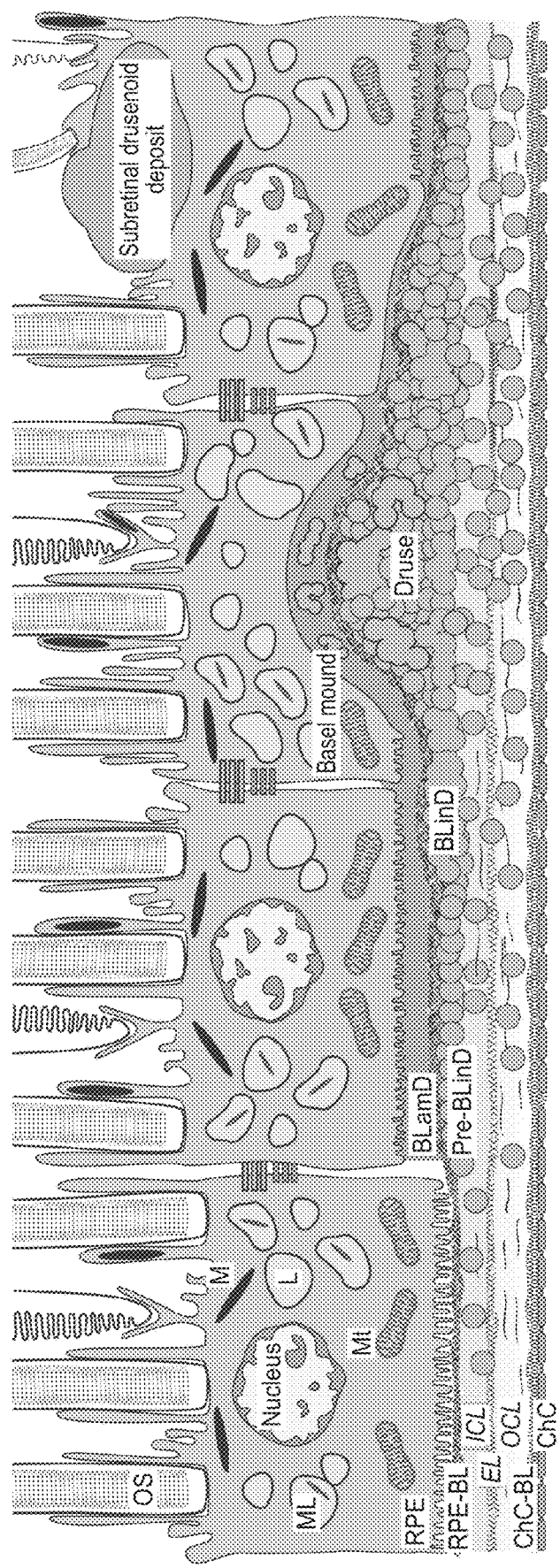
FIG. 1 illustrates tissue layers involved in AMD pathology and the role of lipid accumulation in AMD pathogenesis. OS: outer segment of photoreceptors; RPE: retinal pigment epithelium; RPE-BL: RPE basal lamina; ICL: inner collagenous layer; EL: elastic layer; OCL: outer collagenous layer; ChC-BL: ChC basal lamina; ChC: choriocapillaris endothelium; BLamD: basal laminar deposit; BLinD: basal linear deposit; pre-BLinD: pre-basal linear deposit; L: lipofuscin; M: melanosome; ML: melanolipofuscin; Mt: mitochondria; circles: lipoprotein particles. The Bruch's membrane (BrM) consists of the ICL, EL and OCL. BlamD is a thickening of the RPE-BL. Basal mound is soft druse material within BLamD. RPE cells contain melanosome, lipofuscin and melanolipofuscin, which provide signals for, e.g., color fundus photography, fundus autofluorescence and optical coherence tomography.

FIG. 1 illustrates tissue layers involved in AMD pathology and the role of lipid accumulation in AMD pathogenesis. The BrM consists of three layers: the inner collagenous layer (ICL), the elastic layer (EL) and the outer collagenous layer (OCL). In healthy eyes, the RPE basal lamina (RPE-BL) is attached to the ICL of the BrM, and there is no space between the RPE-BL and the ICL (the sub-RPE-BL space is a "potential" space). Throughout adulthood RPE cells secrete lipoprotein particles (circles in FIG. 1) basally, which are dispersed in the ICL and the OCL of the BrM (the left-most panel in FIG. 1). As more lipoprotein particles are secreted and accumulate over the years, they form pre-BLinD on the tightly packed ICL of the BrM (the second-from-left panel in FIG. 1). Secretion and accumulation of more lipoprotein particles over the years result in aggregation of the lipoprotein particles to form BLinD (a layer) on the BrM ICL and soft drusen (lumps) (the two middle panels in FIG. 1). The formation of pre-BLinD creates a space between the RPE-BL and the BrM ICL (sub-RPE-BL space), which increases with the formation of BLinD and soft drusen and with a greater amount of them. The accumulation of lipid deposits, BLinD and soft drusen, elevates the RPE off the BrM ICL (the second-from-right panel in FIG. 1), and if the elevation (the sub-RPE-BL space) is sufficiently large, the RPE-BL can become detached from the BrM ICL. For instance, drusenoid pigment epithelial detachment (PED) can occur as a result of formation of soft drusen with a diameter of about 350 microns or more. As drusen grow over time, RPE cells become increasingly removed from their source of nutrients and oxygen in the choriocapillaris. Some RPE cells on the top of drusen migrate anteriorly into the neurosensory retina to seek retinal vasculature, and the RPE layer breaks up as RPE cells die, resulting in atrophy of the RPE layer. Migration or death of RPE cells can result in collapse of drusen because migrated or dead RPE cells no longer secrete lipids that feed drusen. Furthermore, the lipid barrier created by BLinD and soft drusen blocks the exchange of incoming oxygen and nutrients (including vitamin A) and outgoing waste between the choriocapillaris and the RPE cells, which leads to RPE cell atrophy and then death. RPE cell atrophy and death also result in the atrophy and death of photoreceptors as the RPE cells can no longer shuttle nutrients to the photoreceptors. In addition, BLinD on the BrM and soft drusen in the sub-RPE-BL space are rich sources of lipids that can be oxidized to form highly anti-inflammatory, and thus pro-angiogenic, oxidized lipids such as oxidized phospholipids. The biomechanically fragile cleavage plane created by BLinD and soft drusen are vulnerable to ramification by new blood vessels emanating from the choroid, crossing the BrM, and infiltrating the sub-RPE-BL space in type 1 neovascularization (NV) and breaking through to the subretinal space in type 2 NV, which are described below. Leakage of fluid from the neovessels into the sub-RPE-BL space in types 1 and 2 NV further contributes to the volume of the sub-RPE-BL space and the elevation of the RPE off the BrM, and thereby can cause PED.

Chronic inflammatory responses to the changes described above include complement-mediated pathways, infiltration by circulating macrophages, and activation of inflammasomes and microglia. Activation of the complement cascade leads to activation of the central component 3 (C3) and initiation of the terminal pathway with the cleavage of component 5 (C5) into C5a and C5b. The terminal pathway results in the assembly of a membrane attack complex (MAC), e.g., in the basal RPE membrane, the BrM or the choriocapillary endothelial cell membrane, by stepwise binding of C5b, C6, C7, C8 and polymerized C9 to form a pore in the lipid bilayer of the membrane. The MAC can lead to the dysfunction and death of the RPE, the BrM or/and the choriocapillary endothelium, with outer retinal atrophy ensuing. In addition, C5a elicits pro-angiogenic effects, and combined with calcification and fracture of the BrM, can contribute to NV, including choroidal NV (CNV).

The early stage of AMD (which is atrophic AMD) is characterized by the presence of a few medium-size drusen and pigmentary abnormalities such as hyperpigmentation or hypopigmentation of the RPE. The intermediate stage of AMD (which is atrophic AMD) is characterized by the presence of at least one large druse, numerous medium-size drusen, hyperpigmentation or hypopigmentation of the RPE, and geographic atrophy (GA) that does not extend to the center of the macula (non-central [or para-central] GA). GA represents the absence of a continuous pigmented layer and the death of at least some portion of RPE cells. Non-central GA spares the fovea and thus preserves central vision. However, patients with non-central GA can experience visual disturbances such as paracentral scotomas, which can impair vision in dim light, decrease contrast sensitivity and impair reading ability. Sub-RPE-BL drusen elevate the RPE off the BrM and thereby can cause mild vision loss, including metamorphopsia (a vision defect in which objects appear to be distorted) through disturbance of overlying photoreceptors and slowing of rod-mediated dark adaptation.

The advanced stage of AMD that remains atrophic AMD is characterized by the presence of drusen and GA that extends to the center of the macula (central GA). Central GA includes macular atrophy. Central GA involves the fovea and thus results in significant loss of central vision and visual acuity. RPE below the retina atrophies, which causes vision loss through the death of photoreceptors. RPE atrophy can result from a large accumulation of drusen or/and BLinD that contributes to the death of the overlying RPE, when the drusen become thick and the RPE is far removed from the choriocapillaris. Drusen may include calcification in the form of hydroxyapatite, and may progress to complete calcification, at which stage RPE cells have died. The RPE-BL thickens in a stereotypic manner to form basal laminar deposits (BLamD); RPE cells hence reside on a thick layer of BLamD. Junctions between the normally hexagonal-shaped RPE cells may be perturbed, and individual RPE cells may round up, stack and migrate anteriorly into the neurosensory retina, where the RPE cells are farther from their supply of nutrients and oxygen in the choriocapillaris. Once RPE cells begin the anterior migration, the overall RPE layer begins to atrophy.

The advanced stage of AMD that becomes neovascular AMD is characterized by neovascularization and any of its potential sequelae, including leakage (e.g., of plasma), plasma lipid and lipoprotein deposition, sub-RPE-BL, subretinal and intraretinal fluid, hemorrhage, fibrin, fibrovascular scars and RPE detachment. In CNV, new blood vessels grow up from the choriocapillaris and through the BrM, which causes vision loss via the aforementioned sequelae. There are three types of neovascularization (NV). Type 1 NV occurs in the sub-RPE-BL space, and new blood vessels emanate from the choroid under the macular region. Type 2 NV occurs in the subretinal space above the RPE, and new blood vessels emanate from the choroid and break through to the subretinal space. In types 1 and 2 NV, new blood vessels cross the BrM and may ramify in the pro-angiogenic cleavage plane created by soft drusen and BLinD. Type 3 NV (retinal angiomatous proliferation) occurs predominantly within the retina (intraretinal), but can also occur in the subretinal space, and new blood vessels emanate from the retina with possible anastomoses to the choroidal circulation. Type 3 NV is the most difficult subtype of NV to diagnose and has the most devastating consequences in terms of photoreceptor damage, but type 3 NV responds well to treatment with an anti-VEGF agent. A neovascular AMD patient can also have a mixture of subtypes of NV, including type 1 plus type 2, type 1 plus type 3, and type 2 plus type 3. The approximate occurrence of the different subtypes of NV among newly presenting neovascular AMD patients is: 40% type 1, 9% type 2, 34% type 3, and 17% mixed (of the mixed, 80% type 1 plus type 2, 16% type 1 plus type 3, and 4% type 2 plus type 3). Another form of NV is polypoidal vasculopathy, which is of choroidal origin and is the most common form of NV among Asians, whose eyes generally have few drusen but may have BLinD. The RPE can become detached from the BrM in each subtype of NV. For instance, leakage of fluid from neovessels into the sub-RPE-BL space in type 1 NV can result in pigment epithelium detachment. The new blood vessels generated by NV are fragile, leading to leakage of fluid, blood and proteins below the macula. Leakage of blood into the subretinal space is particularly toxic to photoreceptors, and intraretinal fluid signifies a poor prognosis for vision. Bleeding and leaking from the new blood vessels, with subsequent fibrosis, can cause irreversible damage to the retina and rapid vision loss if left untreated.

Modified lipids, including peroxidized lipids, can be strongly pro-inflammatory and thus can be pro-angiogenic. Therefore, modification (including oxidation) of lipids can be an important step leading to the development of NV, including type 1 NV. For example, the modified lipids linoleate hydroperoxide and 7-ketocholesterol can be present in and on the BrM and can stimulate NV. NV can be regarded as a wound-healing process following inflammation.

Both eyes of a patient with AMD, whether atrophic or neovascular, typically are in a diseased state. However, one of the eyes typically is in a more diseased condition than the other eye.

For a description of the different stages of AMD, see, e.g., R. Jager et al., *N. Engl. J. Med.*, 358:2606-2617 (2008). The Age-Related Eye Disease Study (AREDS) Research Group has also developed a fundus photographic severity scale for AMD. See, e.g., M. Davis et al., *Arch. Ophthalmol.*, 123: 1484-1498 (2005).

For discussions of the pathogenesis and pathophysiology of AMD, see, e.g., C. A. Curcio et al., The oil spill in ageing Bruch membrane, *Br. J. Ophthalmol.*, 95(12):1638-1645 (2011); J. W. Miller, Age-Related Macular Degeneration Revisited—Piecing the Puzzle, *Am. J. Ophthalmol.*, 155(1): 1-35 (2013); R. Spaide et al., Choroidal neovascularization in age-related macular degeneration—what is the cause?, *Retina*, 23:595-614 (2003); and S. Bressler et al., Age-Related Macular Degeneration: Non-neovascular Early AMD, Intermediate AMD, and Geographic Atrophy, in Retina, S. Ryan et al., Eds., pp. 1150-1182, Elsevier (London 2013).

III. TRANSEPITHELIAL DRUG-DELIVERY SYSTEMS COMPRISING A CELL-PENETRATING PEPTIDE

The present disclosure provides transepithelial, transmembrane and transmucosal drug-delivery systems (TDSs) comprising a therapeutic agent and a cell-penetrating peptide (CPP). Examples of therapeutic agents include without limitation those described herein. In some embodiments, the therapeutic agent is or includes an anti-dyslipidemic agent, an antioxidant, an anti-inflammatory agent, a complement inhibitor, a neuroprotector or an anti-angiogenic agent, or any combination thereof. In certain embodiments, the therapeutic agent is or includes an anti-dyslipidemic agent. In some embodiments, a TDS comprises a therapeutic agent mixed with, non-covalently associated with or covalently bonded to a CPP, or encapsulated in CPP-conjugated nanoparticles, micelles or liposomes. When applied topically to the surface of the eye, the TDS can enter the anterior segment and the posterior segment (including the vitreous and the retina) of the eye, including by crossing the tear film (pre-corneal film), the corneal and conjunctival epithelia, the spherical layer of the suprachoroidal space, and tissue barriers such as the blood-retinal barrier. Non-covalent or covalent bonding to a CPP, or encapsulation in CPP-modified nanoparticles, micelles or liposomes, may also enhance the stability (e.g., resistance to proteases) or/and the aqueous solubility of the therapeutic agent.

Various mechanisms of translocation of a CPP across a biological membrane or tissue barrier have been proposed, which can depend in part on the type of CPP. Such mechanisms include without limitation direct translocation, endocytosis (including macropinocytosis, clathrin-mediated endocytosis, caveolin-mediated endocytosis, and clathrin-/caveolin-independent endocytosis), formation of inverted micelles, and formation of transient pores. Without intending to be bound by theory, a therapeutic agent mixed with a CPP can traverse a biological membrane or tissue barrier through transitory perturbation/disruption of the membrane or barrier by the CPP. CPPs are reviewed in, e.g., F. Milletti, Drug Disc. Today, 17:850-860 (2012); F. Heitz et al., Br. J. Pharmacol., 157:195-206 (2009); K. Wagstaff and D. Jans, Curr. Med. Chem., 13:1371-1387 (2006); and S. Deshayes et al., Cell. Mol. Life Sci., 62:1839-1849 (2005).

In some embodiments, the anti-dyslipidemic agent is or includes an apolipoprotein (apo) mimetic. In certain embodiments, the apo mimetic has at least one amphipathic α-helical domain. In some embodiments, the apo mimetic is an apoA-I mimetic. In some embodiments, the apoA-I mimetic is 4F or a variant or salt thereof. In certain embodiments, the apoA-I mimetic is L-4F or D-4F or a salt (e.g., acetate salt) thereof, each optionally having a protecting group at the N-terminus or/and the C-terminus (e.g., Ac-DWFKAFYDKVAEKFKEAF-NH$_2$ (SEQ ID NO: 1)). In other embodiments, the apo mimetic is an apoE mimetic. In certain embodiments, the apoE mimetic is AEM-28-14 or a variant or salt thereof.

In further embodiments, the anti-dyslipidemic agent is or includes a statin. Examples of statins include without limitation atorvastatin, cerivastatin, fluvastatin, mevastatin, monacolins (e.g., monacolin K [lovastatin]), pitavastatin, pravastatin, rosuvastatin, simvastatin, and analogs, derivatives and salts thereof. In some embodiments, the statin is a substantially hydrophobic/lipophilic statin or a salt thereof. Examples of substantially hydrophobic/lipophilic statins include, but are not limited to, atorvastatin, lovastatin, mevastatin, simvastatin, and salts thereof. In certain embodiments, the statin is atorvastatin or a salt (e.g., calcium salt) thereof, or simvastatin.

In some embodiments, the therapeutic agent is a polypeptide (e.g., a peptide or protein). In other embodiments, the therapeutic agent is a small molecule. In still other embodiments, the therapeutic agent is a polynucleotide (e.g., a plasmid DNA, a microRNA, an anti-sense polynucleotide or an siRNA) or an anti-sense peptide-nucleic acid (PNA).

Positive charges can increase the membrane-translocating ability of a peptide. Accordingly, in some embodiments the CPP comprises at least 2, 3, 4, 5 or 6 basic natural or/and non-natural amino acid residues. In certain embodiments, the CPP comprises at least 6 basic natural or/and non-natural amino acid residues. A peptide having a stretch of cationic residues can have better membrane-translocating ability than a peptide having the same number of cationic residues interspersed. Accordingly, in some embodiments the CPP comprises at least 2, 3, 4, 5 or 6 consecutive basic natural or/and non-natural amino acid residues.

In some embodiments, the CPP comprises basic natural or/and non-natural amino acid residues selected from the L- and D-isomers of arginine, homoarginine, lysine, ornithine, histidine,

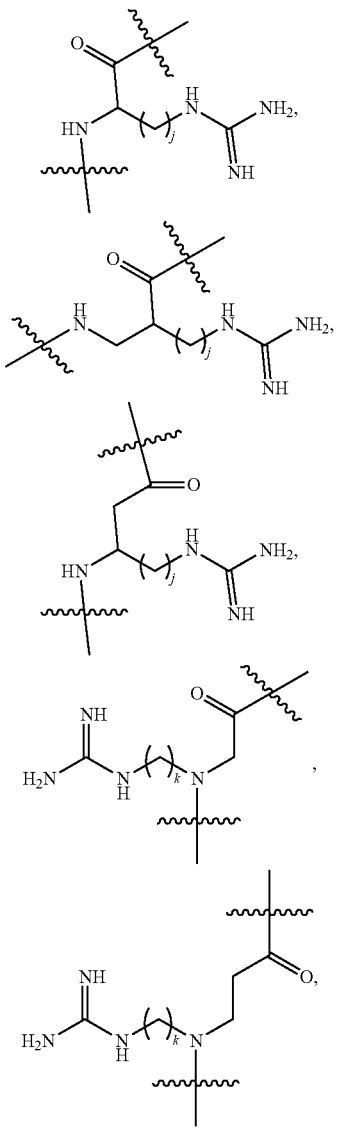

and combinations thereof, wherein:

j is 1, 2, 3, 4, 5 or 6; and k is 2, 3, 4, 5 or 6.

In certain embodiments, the CPP comprises 1, 2, 3 or more arginine residues, or/and 1, 2, 3 or more lysine residues.

In some embodiments, the CPP is a polycationic CPP having a net positive charge of at least +3, +4, +5 or +6 at a pH of about 7.4. In certain embodiments, the CPP is a polycationic CPP having a net positive charge of at least +5 or +6 at a pH of about 7.4. A polycationic CPP can also have a plurality of cationic residues other than protonated basic amino acid residues, such as sulfonium cation residues or phosphonium cation residues. See, e.g., J. Kramer et al., ACS Cent. Sci., 1:83-88 (2015); and C. Ornelas-Megiatto et al., J. Am. Chem. Soc., 134:1902-1905 (2012). Some polycationic CPPs can also be amphipathic CPPs.

Examples of polycationic CPPs include without limitation:

1) GGG(ARKKAAKA)$_4$ (SEQ ID NO: 2) (peptide for ocular delivery [POD]), which is capable of nuclear targeting;

2) CGGG(ARKKAAKA)$_4$ (SEQ ID NO: 3) (cysteine added to the N-terminus of POD), which is capable of nuclear targeting;
3) RLRWR (AIP6) (SEQ ID NO: 4);
4) RRLSYSRRRF (SynB3) (SEQ ID NO: 5);
5) KKLFKKILKKL (BP16) (SEQ ID NO: 6);
6) YKQCHKKGGKKGSG (NrTP1 derived from crotamine) (SEQ ID NO: 7), which is capable of nuclear targeting;
7) CRWRWKCCKK [crotamine(30-39)] (SEQ ID NO: 8), which is not capable of nuclear targeting;
8) TKRRITPKDVIDVRSVTTRINT {[E148R]Mce1A (130-151)} (SEQ ID NO: 9);
9) TKRRITPKDVIDVRSVTTKINT {[E148K]Mce1A (130-151)} (SEQ ID NO: 10);
10) TKRRITPKRVIRVRSVTTEINT {[D138R, D141R] Mce1A(130-151)} (SEQ ID NO: 11);
11) TKRRITPKKVIKVRSVTTEINT {[D138K, D141K] Mce1A(130-151)} (SEQ ID NO: 12);
12) TKRRITPKRVIRVRSVTTRINT {[D138R, D141R, E148R]Mce1A(130-151)} (SEQ ID NO: 13);
13) TKRRITPKKVIKVRSVTTKINT {[D138K, D141K, E148K]Mce1A(130-151)} (SEQ ID NO: 14);
14) GGSQPKKKRK (Ostacolo pep-6) (SEQ ID NO: 15);
15) GGKKKRKV (Ostacolo pep-7) (SEQ ID NO: 16);
16) RKKRRRESRKKRRRES (Diatos peptide vector 3 [DPV3]) (SEQ ID NO: 17);
17) GRPRESGKKRKRKRLKP (DPV6) (SEQ ID NO: 18);
18) GKRKKKGKLGKKRDP (DPV7) (SEQ ID NO: 19);
19) GKRKKKGKLGKKRPRSR (DPV7b) (SEQ ID NO: 20);
20) RKKRRRESRRARRSPRHL (DPV3/10) (SEQ ID NO: 21);
21) SRRARRSPRESGKKRKRKR (DPV10/6) (SEQ ID NO: 22);
22) VKRGLKLRHVRPRVTRMDV (DPV1047) (SEQ ID NO: 23), which is capable of nuclear targeting;
23) SRRARRSPRHLGSG (DPV10) (SEQ ID NO: 24), which is capable of nuclear targeting;
24) LRRERQSRLRRERQSR (DPV15) (SEQ ID NO: 25), which is capable of nuclear targeting;
25) GAYDLRRRERQSRLRRRERQSR (DPV15b) (SEQ ID NO: 26), which is capable of nuclear targeting;
the corresponding peptides having all D-amino acid residues; and
the corresponding peptides (L- and D-isomers) having the reverse order of amino acid sequence;
wherein:
each peptide can optionally have one or more, or all, D-amino acid residues;
each peptide can optionally have a protecting group at the N-terminus or/and the C-terminus (e.g., acetyl at the N-terminus or/and —NH$_2$ at the C-terminus);
each peptide can optionally have a cysteamide group at the C-terminus; and
each peptide can optionally have one, two or more hydrophobic/lipophilic groups (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and polyethylene glycol (PEG) moieties (those comprising, e.g., about 2-20 or 2-10 PEG units) attached to the N-terminus, the C-terminus or/and side chain(s).
In some embodiments, the CPP comprises 6, 7, 8, 9, 10, 11, 12, 13, 14, 15 or more consecutive residues of

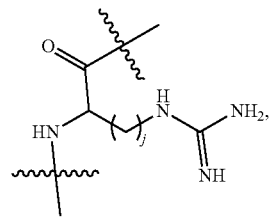

wherein:
j is 1, 2, 3, 4, 5 or 6;
the CPP can optionally have one or more, or all, D-amino acid residues;
the CPP can optionally have a protecting group at the N-terminus or/and the C-terminus (e.g., acetyl at the N-terminus or/and —NH$_2$ at the C-terminus);
the CPP can optionally have a cysteamide group at the C-terminus; and the CPP can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.
In certain embodiments, j is 3 (arginine), 4 (homoarginine), 5 or 6. In some embodiments, the CPP comprises 6, 7, 8, 9, 10 or 11 consecutive residues of

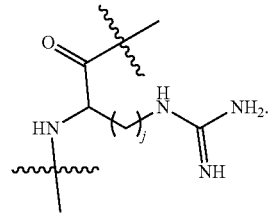

In further embodiments, the CPP has all D-amino acid residues. In certain embodiments, the CPP has a hydrophobic group (e.g., stearyl or stearoyl) attached to the N-terminus. In some embodiments, the CPP is a homopolymer.
In further embodiments, the CPP comprises 6, 7, 8, 9, 10, 11, 12, 13, 14, 15 or more consecutive residues of

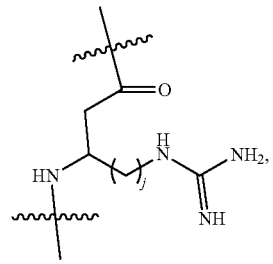

wherein:
j is 1, 2, 3, 4, 5 or 6;
the CPP can optionally have one or more, or all, D-amino acid residues;
the CPP can optionally have a protecting group at the N-terminus or/and the C-terminus (e.g., acetyl at the N-terminus or/and —NH$_2$ at the C-terminus);

the CPP can optionally have a cysteamide group at the C-terminus; and the CPP can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.

In certain embodiments, j is 3, 4, 5 or 6 (e.g., 3). In some embodiments, the CPP comprises 6, 7, 8, 9, 10 or 11 consecutive residues of

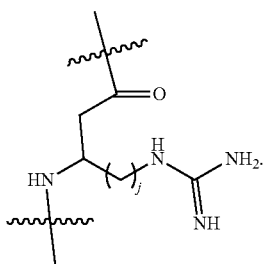

In certain embodiments, the CPP has a hydrophobic group (e.g., stearyl or stearoyl) attached to the N-terminus. In some embodiments, the CPP is a homopolymer.

In other embodiments, the CPP comprises 6, 7, 8, 9, 10, 11, 12, 13, 14, 15 or more consecutive residues of

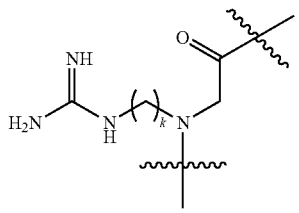

wherein:

k is 2, 3, 4, 5 or 6;

the CPP can optionally have a protecting group at the N-terminus or/and the C-terminus (e.g., acetyl at the N-terminus or/and —$NH_2$ at the C-terminus);

the CPP can optionally have a cysteamide group at the C-terminus; and the CPP can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.

In certain embodiments, k is 3, 4, 5 or 6 (e.g., 6). In some embodiments, the CPP comprises 6, 7, 8, 9, 10 or 11 (e.g., 9) consecutive residues of

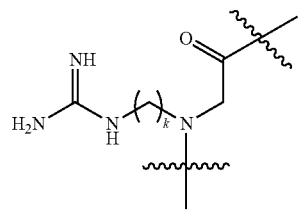

In certain embodiments, k is 6 and the CPP comprises 9 consecutive residues of

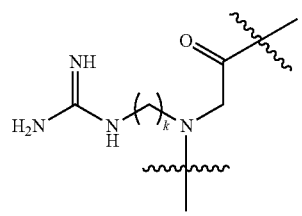

In some embodiments, the CPP is a homopolymer.

In additional embodiments, the CPP is an arginine-rich CPP comprising 5, 6, 7, 8 or more arginine residues. Arginine-rich CPPs can be a subset of polycationic CPPs. Some arginine-rich CPPs can also be amphipathic CPPs.

Examples of arginine-rich CPPs include, but are not limited to:

1) YGRKKRRQRRR [HIV-1 TAT(47-57)] (SEQ ID NO: 27) and the corresponding isomer having all D-amino acids, both of which are capable of nuclear targeting;
2) GRKKRRQRRR [TAT(48-57)] (SEQ ID NO: 28) and the corresponding isomer having all D-amino acids, both of which are capable of nuclear targeting;
3) RKKRRQRRR [TAT(49-57)] (SEQ ID NO: 29) and the corresponding isomer having all D-amino acids, both of which are capable of nuclear targeting;
4) GRKKRRQRRRPPQ [TAT(48-60)] (SEQ ID NO: 30) and the corresponding isomer having all D-amino acids, both of which are capable of nuclear targeting;
5) CGGGGYGRKKRRQRRR (SEQ ID NO: 31) [CGGGG (SEQ ID NO: 32) added to the N-terminus of TAT(47-57)], which is capable of nuclear targeting;
6) GRKKRRQRRRCG (SEQ ID NO: 33) [CG added to the C-terminus of TAT(48-57)], which is capable of nuclear targeting;
7) RKKRRQRRRC (SEQ ID NO: 34) [Cys added to C-terminus of TAT(49-57)], which is capable of nuclear targeting;
8) RKKRRARRR {[Q54A]TAT(49-57)} (SEQ ID NO: 35);
9) YGRRRRRRRRR {[K50R, K51R, Q54R]TAT(47-57)} (SEQ ID NO: 36);
10) GRKKRRQRRRPWQ {[P59W]TAT(48-60)} (SEQ ID NO: 37);
11) GRRRRRRRRRPPQ {[K50R, K51R, Q54R]TAT(48-60)} (SEQ ID NO: 38);
12) RKKRRQRRRRKKRRQRRR [dimer of TAT(49-57)] (SEQ ID NO: 39);
13) C(YGRKKRRQRRRG)$_{2-4}$ (Rosenecker TAT$_{2-4}$) (SEQ ID NO: 40), wherein the Cys sulfhydryl group is optionally modified by dithiodipyridine reaction, and each oligomer is capable of nuclear targeting;

14) C(YGRKERRQERRG)$_2$ (Rosenecker TAT$_2$-M1) (SEQ ID NO: 41), wherein the Cys sulfhydryl group is optionally modified by dithiodipyridine reaction, and the dimer is not capable of nuclear targeting;
15) RRRQRRKKRGY {TAT(47-57) in reverse order [Rev-TAT(47-57)]} (SEQ ID NO: 42) and the corresponding isomer having all D-amino acids;
16) RRRQRRKKRG {TAT(48-57) in reverse order [Rev-TAT(48-57)]} (SEQ ID NO: 43) and the corresponding isomer having all D-amino acids;
17) RRRQRRKKR {TAT(49-57) in reverse order [Rev-TAT(49-57)]} (SEQ ID NO: 44) and the corresponding isomer having all D-amino acids;
18) QPPRRRQRRKKRG {TAT(48-60) in reverse order [Rev-TAT(48-60)]} (SEQ ID NO: 45) and the corresponding isomer having all D-amino acids;
19) TRQARRNRRRRWRERQR [HIV-1 Rev(34-50)] (SEQ ID NO: 46);
20) TRRQRTRRARRNR [HTLV-2 Rex(4-16)] (SEQ ID NO: 47);
21) RRIPNRRPRR (an HRSV-derived peptide) (SEQ ID NO: 48);
22) KMTRAQRRAAARRNRWTAR [BMV Gag(7-25)] (SEQ ID NO: 49);
23) KLTRAQRRAAARKNKRNTR [CCMV Gag(7-25)] (SEQ ID NO: 50);
24) RRRRNRTRRNRRRVR [FHV Coat(35-49)] (SEQ ID NO: 51);
25) NAKTRRHERRRKLAIER [P22 N(14-30)] (SEQ ID NO: 52);
26) KRARNTEAARRSRARKLQRMKQ [yeast GCN4 (231-252)] (SEQ ID NO: 53), which is capable of nuclear targeting;
27) RIKAERKRMRNRIAASKSRKRKLERIAR [human cJun(252-279)] (SEQ ID NO: 54);
28) KRRIRRERNKMAAAKSRNRRRELTDT [human cFos(139-164)] (SEQ ID NO: 55);
29) VSRRRRRRGGRRRR (low molecular weight protamine [LMWP]) (SEQ ID NO: 56);
30) RRWRRWNRFNRRRCR (IMT-P8) (SEQ ID NO: 57);
31) HWSYILRPRRRRRRK (SEQ ID NO: 58);
32) RCGRASRCRVRWMRRRRI (BEN_1079) (SEQ ID NO: 59);
the corresponding peptides having all D-amino acid residues; and
the corresponding peptides (L- and D-isomers) having the reverse order of amino acid sequence;
wherein:
each peptide can optionally have one or more, or all, D-amino acid residues;
each peptide can optionally have a protecting group at the N-terminus or/and the C-terminus (e.g., acetyl at the N-terminus or/and —NH$_2$ at the C-terminus);
each peptide can optionally have a cysteamide group at the C-terminus; and
each peptide can optionally have one, two or more hydrophobic/lipophilic groups (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and PEG moieties (those comprising, e.g., about 2-20 or 2-10 PEG units) attached to the N-terminus, the C-terminus or/and side chain(s).

In some embodiments, the CPP is a polyarginine comprising 6, 7, 8, 9, 10, 11, 12, 13, 14, 15 or more consecutive arginine residues, wherein:

the polyarginine can optionally have one or more, or all, D-arginine residues;
the polyarginine can optionally have a protecting group at the N-terminus or/and the C-terminus (e.g., acetyl at the N-terminus or/and —NH$_2$ at the C-terminus);
the polyarginine can optionally have a cysteamide group at the C-terminus; and
the polyarginine can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.

In some embodiments, the polyarginine is a homopolymer, such as RRRRRR ($R_6$) (SEQ ID NO: 258), $R_7$ (SEQ ID NO: 259), $R_8$ (SEQ ID NO: 260), $R_9$ (SEQ ID NO: 261), $R_{10}$ (SEQ ID NO: 262), $R_{11}$ (SEQ ID NO: 263), $R_{12}$ (SEQ ID NO: 264), $R_{13}$ (SEQ ID NO: 265), $R_{14}$ (SEQ ID NO: 266) or $R_{15}$ (SEQ ID NO: 267). In certain embodiments, the polyarginine is $R_6$ (SEQ ID NO: 258), $R_7$ (SEQ ID NO: 259), $R_8$ (SEQ ID NO: 260), $R_9$ (SEQ ID NO: 261), $R_{10}$ (SEQ ID NO: 262) or $R_{11}$ (SEQ ID NO: 263) (e.g., $R_6$ (SEQ ID NO: 258) or $R_9$ (SEQ ID NO: 261)). In some embodiments, the polyarginine has all D-arginine residues (e.g., D-$R_6$, D-$R_7$, D-$R_8$, D-$R_9$, D-$R_{10}$ or D-$R_{11}$). In further embodiments, the polyarginine has a hydrophobic group (e.g., stearyl or stearoyl) attached to the N-terminus (e.g., the L- or D-isomer of $R_6$ (SEQ ID NO: 258), $R_7$ (SEQ ID NO: 259), $R_8$ (SEQ ID NO: 260), $R_9$ (SEQ ID NO: 261), $R_{10}$ (SEQ ID NO: 262) or $R_{11}$ (SEQ ID NO: 263) stearylated or stearoylated at the N-terminus). In some embodiments, the polyarginine has one, two or more tryptophan residues at the N-terminus or/and the C-terminus, such as $R_6W$ (SEQ ID NO: 269), $R_7W$ (SEQ ID NO: 270), $R_8W$ (SEQ ID NO: 271), $R_9W$ (SEQ ID NO: 272), $R_{10}W$ (SEQ ID NO: 273) or $R_{11}W$ (SEQ ID NO: 274). In further embodiments, the polyarginine has a hydrophobic sequence at the N-terminus or/and the C-terminus. In certain embodiments, the hydrophobic sequence is FFLIPKG (SEQ ID NO: 60) (penetration-accelerating sequence [Pas]), such as in Pas$R_6$ (SEQ ID NO: 276), Pas$R_7$ (SEQ ID NO: 277), Pas$R_8$ (SEQ ID NO: 278), Pas$R_9$ (SEQ ID NO: 279), Pas$R_{10}$ (SEQ ID NO: 280) or Pas$R_{11}$ (SEQ ID NO: 281). A hydrophobic sequence can also be added to other polycationic or arginine-rich CPPs, which can enhance the membrane-translocating ability of the CPPs and can generate amphipathic CPPs.

In additional embodiments, the CPP is an amphipathic CPP comprising polar or/and charged (e.g., basic or/and acidic) amino acid residues, and non-polar or hydrophobic amino acid residues. For example, an amphipathic CPP can comprise hydrophilic residues alternating or interspersed with hydrophobic residues, or one or more hydrophilic regions and one or more hydrophobic regions. An amphipathic CPP can be, e.g., a primary amphipathic CPP having a sequential assembly of hydrophilic region(s) and hydrophobic region(s), or a secondary amphipathic CPP whose conformation (e.g., an α-helix or a β-sheet/strand) allows positioning of hydrophilic residues and hydrophobic residues on opposite sides of the molecule. A conventional right-handed α-helix averages 3.6 residues per turn. A proline-rich peptide can form a left-handed polyproline II (PPII) helix, which averages 3.0 residues per turn. Some amphipathic CPPs can also be polycationic or/and arginine-rich CPPs.

Examples of amphipathic CPPs include without limitation:

1) KETWWETWWTEWSQPKKKRKV (Pep-1) (SEQ ID NO: 61), optionally having acetyl at the N-terminus or/and cysteamide at the C-terminus, which is capable of nuclear targeting;
2) KETWFETWFTEWSQPKKKRKV (Pep-2) (SEQ ID NO: 62), optionally having acetyl at the N-terminus or/and cysteamide at the C-terminus, which is capable of nuclear targeting;
3) KWFETWFTEWPKKRK (Pep-3) (SEQ ID NO: 63), optionally acetylated or PEGylated at the N-terminus or/and having cysteamide at the C-terminus;
4) KATWFETWFTEWSQPKKKRKV (Pep-21) (SEQ ID NO: 64), optionally having acetyl at the N-terminus or/and cysteamide at the C-terminus, which is capable of nuclear targeting;
5) KETWFETWFAEWSQPKKKRKV (Pep-29) (SEQ ID NO: 65), optionally having acetyl at the N-terminus or/and cysteamide at the C-terminus, which is capable of nuclear targeting;
6) KETWFETWFTAWSQPKKKRKV (Pep-30) (SEQ ID NO: 66), optionally having acetyl at the N-terminus or/and cysteamide at the C-terminus, which is capable of nuclear targeting;
7) KETWFETWFTEWAQPKKKRKV (Pep-32) (SEQ ID NO: 67), optionally having acetyl at the N-terminus or/and cysteamide at the C-terminus, which is capable of nuclear targeting;
8) KETWFETWFTEWSAPKKKRKV (Pep-33) (SEQ ID NO: 68), optionally having acetyl at the N-terminus or/and cysteamide at the C-terminus, which is capable of nuclear targeting;
9) KETWFETWFTEWSQPKKKRKA (Pep-40) (SEQ ID NO: 69), optionally having acetyl at the N-terminus or/and cysteamide at the C-terminus;
10) KETWFETWFTEWSQPKKKRKV (Pep-43) (SEQ ID NO: 62), optionally having acetyl at the N-terminus or/and cysteamide at the C-terminus, which is capable of nuclear targeting;
11) GGKETWWETW (Ostacolo pep-2) (SEQ ID NO: 70);
12) GGWWETWWTE (Ostacolo pep-3) (SEQ ID NO: 71);
13) GGTWWTEWSQ (Ostacolo pep-4) (SEQ ID NO: 72);
14) GGTEWSQPKK (Ostacolo pep-5) (SEQ ID NO: 73);
15) GALFLGFLGAAGSTMGAWSQPKKKRKV (aka MPG) (SEQ ID NO: 74), optionally having acetyl at the N-terminus or/and cysteamide at the C-terminus, which is capable of nuclear targeting;
16) GALFLGFLGAAGSTMGAWSQPKSKRKV {aka MPGΔ$^{NLS}$ (MPG having a mutation in the nuclear localization sequence [NLS])} (SEQ ID NO: 75), optionally having acetyl at the N-terminus or/and cysteamide at the C-terminus, which is not capable of nuclear targeting;
17) RRRRRRRRRGALFLAFLAAALSLMG (R9-ΔMPG [R$_9$ (SEQ ID NO: 261) attached to an MPG variant]) (SEQ ID NO: 76);
18) MGLGLHLLVLAAALQGAWSQPKKKRKV (P1) (SEQ ID NO: 77), which is capable of nuclear targeting;
19) GLWRALWRLLRSLWRLLWRA (aka CADY-R) (SEQ ID NO: 78), optionally having acetyl at the N-terminus or/and cysteamide at the C-terminus;
20) GLWRALWRLLRSLWRLLWKA (aka CADY-K) (SEQ ID NO: 79), optionally having acetyl at the N-terminus or/and cysteamide at the C-terminus;
21) GLFKALLKLLKSLWKLLLKA (ppTG1) (SEQ ID NO: 80);
22) GLFRALLRLLRSLWRLLLRA (ppTG20) (SEQ ID NO: 81);
23) GLFEALLELLESLWELLLEA (JTS1) (SEQ ID NO: 82);
24) GLFEALLELLESLWELLLEACCYKAKKKKKKKKWKKKKQS (JTS1-K13) (SEQ ID NO: 83);
25) WEAKLAKALAKALAKHLAKALAKALKACEA (aka KALA) (SEQ ID NO: 84);
26) WEAALAEALAEALAEHLAEALAEALEALAA (aka GALA) (SEQ ID NO: 85);
27) GWTLNSAGYLLGKINLKALAALAKKIL (transportan [TP]) (SEQ ID NO: 86);
28) LNSAGYLLGKINLKALAALAKKIL (TP7) (SEQ ID NO: 87);
29) GWTLNSAGYLLGKLKALAALAKKIL (TP9) (SEQ ID NO: 88);
30) AGYLLGKINLKALAALAKKIL (TP10) (SEQ ID NO: 89), optionally having stearyl or stearoyl at the N-terminus;
31) AGYLLGKINLKPLAALAKKIL (TP10-2) (SEQ ID NO: 90);
32) LNSAGYLLGKALAALAKKIL (TP13) (SEQ ID NO: 91);
33) AGYLLGKLLOOLAAAALOOLL (PepFect 14 [PF14]) (SEQ ID NO: 92), optionally having stearyl or stearoyl at the N-terminus, wherein "O" is ornithine;
34) KWKLFKKIGAVLKVLTTG (CM$_{18}$-Tat$_{11}$) (SEQ ID NO: 93);
35) KLALKLALKALKAALKLA (model amphipathic peptide [MAP]) (SEQ ID NO: 94);
36) QLALQLALQALQAALQLA [MAP17 or MAP(Q)] (SEQ ID NO: 95);
37) LKTLTETLKELTKTLTEL (MAP12) (SEQ ID NO: 96);
38) KALAKALAKALA (a MAP analog) (SEQ ID NO: 97);
39) RRWWRRWRR (aka W/R) (SEQ ID NO: 98);
40) WLRRIKAWLRRIKAWLRRIKA (aka WLR or W3) (SEQ ID NO: 99);
41) YARAAARQARA (aka YARA or PTD4) (SEQ ID NO: 100);
42) VRLPPPVRLPPPVRLPPP (sweet arrow peptide [SAP]) (SEQ ID NO: 101);
43) VKLPPPVKLPPPVKLPPP [SAP(K)] (SEQ ID NO: 102);
44) VELPPPVELPPPVELPPP [SAP(E)] (SEQ ID NO: 103);
45) (PPR)$_{3-6}$ (SEQ ID NO: 104);
46) (PRR)$_{3-6}$ (SEQ ID NO: 105);
47) GPSQPTYPGDDAPVRDLIRFYRDLQRYLNVVTRHRY (aPP4R1) (SEQ ID NO: 106);
48) GPSQPTYPGDDAPVRDLIRFYRDLRRYLNVVTRHRY (aPP5R1) (SEQ ID NO: 107);
49) GPSQPTYPGDDAPVRDLRRFYRDLRRYLNVVTRHRY (aPP6R1) (SEQ ID NO: 108);
50) GSPWGLQHHPPRT (439A) (SEQ ID NO: 109);
51) RLSGMNEVLSFRWL (SG3) (SEQ ID NO: 110);
52) KLWMRWYSPTTRRYG (IVV-14) (SEQ ID NO: 111);
53) PYSRPHVQLWYPNRESCRSLIRSLGP (BEN_0805) (SEQ ID NO: 112);
54) YTAIAWVKAFIRKLRK (YTA2) (SEQ ID NO: 113);

55) IAWVKAFIRKLRKGPLG (YTA4) (SEQ ID NO: 114);
56) FKIYDKKVRTRVVKH (SVM1, a CPP predicted by support vector machine model and shown to be a CPP) (SEQ ID NO: 115);
57) RASKRDGSWVKKLHRILE (SVM2) (SEQ ID NO: 116);
58) KGTYKKKLMRIPLKGT (SVM3) (SEQ ID NO: 117);
59) LYKKGPAKKGRPPLRGWFH (SVM4) (SEQ ID NO: 118);
60) the helical polyarginine mimic (HPRM) designated P11 [H. Tang et al., Chem. Sci., 4:3839-3844 (2013)];
61) the HPRM designated P13 [Tang (supra)];
62) the HPRM designated P14 [Tang (supra)];
63) DAATATRGRSAASRPTERPRAPARSASR-PRRPVE [HSV-1 VP22(267-301)] (SEQ ID NO: 119), which is capable of nuclear targeting;
64) PLSSIFSRIGDP [HBV PreS2(41-52)] (SEQ ID NO: 120);
65) DPKGDPKGVTVTVTVTGKGDPKPD (VT5) (SEQ ID NO: 121);
66) YLLDGMTNTIENARQGAARVTSWLGRQL-RIAGKRLEGRSK [pestivirus envelope glycoprotein $E^{rns}$(181-220)] (SEQ ID NO: 122), which is capable of nuclear targeting;
67) DGMTNTIENARQGAARVTSWLGRQLRIAGKR-LEGRSKTWF [$E^{rns}$(184-223)] (SEQ ID NO: 123), which is capable of nuclear targeting;
68) ENARQGAARVTSWLGRQLRIAGKRLEGR-SKTWFGAYA [$E^{rns}$(191-227)] (SEQ ID NO: 124), which is capable of nuclear targeting;
69) ENARQGAARVTSWLGRQLRIAGKRLEGR-SKTWF [$E^{rns}$(191-223)] (SEQ ID NO: 125), which is capable of nuclear targeting;
70) ENARQGAARVTSWLGRQLRIAGKRLEGRSK [$E^{rns}$(191-220)] (SEQ ID NO: 126), which is capable of nuclear targeting;
71) RQGAARVTSWLGRQLRIAGKRLEGRSK [$E^{rns}$(194-220)] (SEQ ID NO: 127), which is capable of nuclear targeting;
72) RQGAARVTSWLGRQLRIAGKRLEGR [$E^{rns}$(194-218)] (SEQ ID NO: 128), which is capable of nuclear targeting;
73) GNGKLIKGRTPIKFGKADCDRPPKHSQNGMGK {ribotoxin 2 L3 loop(57-89) [R2L3(57-89)]} (SEQ ID NO: 129), which is capable of nuclear targeting;
74) KLIKGRTPIKFGKADCDRPPKHSQNGMGK [R2L3(60-89)] (SEQ ID NO: 130), which is capable of nuclear targeting;
75) KLIKGRTPIKFGK [R2L3(60-73)] (SEQ ID NO: 131);
76) RGGRLSYSRRRFSTSTGR (SynBI) (SEQ ID NO: 132);
77) ALWKTLLKKVLKAPKKKRKV ($S4_{13}$-$PV_{rev}$) (SEQ ID NO: 133), optionally having acetyl at the N-terminus or/and —NH$_2$ at the C-terminus, which is capable of nuclear targeting;
78) ALWKTLLKKVLKA {[M4K]dermaseptin S4(1-13) without NLS} (SEQ ID NO: 134);
79) GIGKFLHSAKKFGKAFVGEIMNS (magainin 2) (SEQ ID NO: 135);
80) GIGKWLHSAKKFGKAFVGEIMNS ([F5W]magainin 2) (SEQ ID NO: 136);
81) GIGKFLHSAKKWGKAFVGQIMNC ([F12W, E19Q, S23C]magainin 2) (SEQ ID NO: 137);
82) VLTTGLPALISWIRRRHRRHC (p5RHH, a melittin variant) (SEQ ID NO: 138);
83) TRSSRAGLQFPVGRVHRLLRK [buforin 2 (BUF2)] (SEQ ID NO: 139), which is capable of nuclear targeting;
84) RAGLQFPVGRVHRLLRK [BUF2(5-21)] (SEQ ID NO: 140);
85) AGLQFPVGRVHRLLRK [BUF2(6-21)] (SEQ ID NO: 141);
86) GLQFPVGRVHRLLRK [BUF2(7-21)] (SEQ ID NO: 142);
87) LQFPVGRVHRLLRK [BUF2(8-21)] (SEQ ID NO: 143);
88) QFPVGRVHRLLRK [BUF2(9-21)] (SEQ ID NO: 144);
89) FPVGRVHRLLRK [BUF2(10-21)] (SEQ ID NO: 145);
90) PVGRVHRLLRK [BUF2(11-21)] (SEQ ID NO: 146);
91) LLGDFFRKSKEKIGKEFKRIVQRIKD-FLRNLVPRTES (human cathelicidin LL-37) (SEQ ID NO: 147);
92) KCFQWQRNMRKVRGPPVSCIKR {human lactoferrin(38-59) [hLF(38-59)]} (SEQ ID NO: 148), optionally having an intramolecular disulfide bridge between the two terminal cysteine residues, which is capable of nuclear targeting;
93) KCFQWQRNMRKVRGPPVSC [hLF(38-56)] (SEQ ID NO: 149), optionally having an intramolecular disulfide bridge between the two terminal cysteine residues;
94) RRIRPRPPRLPRPRPRPLPFPRPG (bactenecin 7 [Bac7]) (SEQ ID NO: 150);
95) RRIRPRP [Bac7(1-7)] (SEQ ID NO: 151);
96) PRPLPFPRP [Bac7(15-24)] (SEQ ID NO: 152);
97) VDKGSYLPRPTPPRPIYNRN (pyrrhocoricin) (SEQ ID NO: 153);
98) LGTYTQDFNKFHTFPQTAIGVGAP {human calcitonin(9-32) [hCT(9-32)]} (SEQ ID NO: 154);
99) LGTYTQDFNKFHTFAQTAIGVGAP {[P23A]hCT(9-32)} (SEQ ID NO: 155);
100) LGTYTQDFNKFHTFPQTAIGVWAP {[G30W]hCT(9-32)} (SEQ ID NO: 156);
101) KFHTFPQTAIGVGAP [hCT(18-32)] (SEQ ID NO: 157);
102) MVRRFLVTLRIRRACGPPRVRV [p14ARF(1-22)] (SEQ ID NO: 158);
103) MVTVLFRRLRIRRACGPPRVRV [M918 inverting positions 3-8 of p14ARF(1-22)] (SEQ ID NO: 159);
104) RLVSYNGIIFFLK (CD44 binding peptide [CD44BP]) (SEQ ID NO: 160);
105) FNLPLPSRPLLR (a peptide binding to CD44 found by phage display) (SEQ ID NO: 161);
106) MASIWVGHRG (AA3H [the N-terminus of an annexin A isoform]) (SEQ ID NO: 162);
107) LLIILRRRIRKQAHAHSK (murine peptide vascular endothelial cadherin [pVEC]) (SEQ ID NO: 163), which is capable of nuclear targeting;
108) LSTAADMQGVVTDGMASG [azurin(50-67)], aka p18] (SEQ ID NO: 164);
109) RQIKIWFQNRRMKWKK [penetratin or Antennapedia homeodomain-/AntpHD-(43-58)](SEQ ID NO: 165) and the corresponding isomer having all D-amino acids, both of which are capable of nuclear targeting;
110) RQIKIWFPNRRMKWKK {[Q50P]AntpHD(43-58)} (SEQ ID NO: 166);

111) RQPKIWFPNRRKPWKK {[I45P, Q50P, M54K, K55P]AntpHD(43-58)} (SEQ ID NO: 167);
112) RQIRIWFQNRRMRWRR (penetratin-Arg in which all Lys residues are replaced with Arg) (SEQ ID NO: 168);
113) RQIKIWFQKNRRMKWKK (Lys inserted at position 9 of penetratin) (SEQ ID NO: 169);
114) LIRLWSHLIHIWFQNRRLKWKKK (EB1, a penetratin variant) (SEQ ID NO: 170);
115) RHIKIWFQNRRMKWKK (PDX-1, which is [Q2H] penetratin) (SEQ ID NO: 171), which is capable of nuclear targeting;
116) RVIRVWFQNKRCKDKK (Islet-1 homeodomain third helix) (SEQ ID NO: 172), which is capable of nuclear targeting;
117) SQIKIWFQNKRAKIKK (Engrailed-2 homeodomain third helix) (SEQ ID NO: 173), which is capable of nuclear targeting;
118) RQVTIWFQNRRVKEKK (HoxA-13 homeodomain third helix) (SEQ ID NO: 174), which is capable of nuclear targeting;
119) KQINNWFINQRKRHWK (Knotted-1 homeodomain third helix) (SEQ ID NO: 175), which is capable of nuclear targeting;
120) AAVALLPAVLLALLAPVQRKRQKLMP (MTS signal peptide plus NLS of NF-icB p50) (SEQ ID NO: 176), which is capable of nuclear targeting;
121) AAVALLPAVLLALLAKNNLKDCGLF (SEQ ID NO: 177);
122) AAVALLPAVLLALLAKNNLKECGLY (SEQ ID NO: 178);
123) MGLGLHLLVLAAALQGAKKKRKV [Ig(v)] (SEQ ID NO: 179), which is capable of nuclear targeting;
124) MVKSKIGSWILVLFVAMWSDVGLCKKRPKP {bovine prion protein(1-30) [bPrPp(1-30)]} (SEQ ID NO: 180), which is capable of nuclear targeting;
125) MANLGYWLLALFVTMWTDVGLCKKRPKP {murine prion protein(1-28) [mPrPp(1-28)]} (SEQ ID NO: 181), which is capable of nuclear targeting;
the corresponding peptides having all D-amino acid residues; and the corresponding peptides (L- and D-isomers) having the reverse order of amino acid sequence;
wherein:
each peptide can optionally have one or more, or all, D-amino acid residues;
each peptide can optionally have a protecting group at the N-terminus or/and the C-terminus (e.g., acetyl at the N-terminus or/and —NH$_2$ at the C-terminus);
each peptide can optionally have a cysteamide group at the C-terminus; and each peptide can optionally have one, two or more hydrophobic/lipophilic groups (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and PEG moieties (those comprising, e.g., about 2-20 or 2-10 PEG units) attached to the N-terminus, the C-terminus or/and side chain(s).

In other embodiments, the CPP is a hydrophobic CPP rich in non-polar or hydrophobic amino acid residues, wherein the hydrophobic CPP can optionally have a low net charge (e.g., a net charge of +/−1 or +/−2 at a pH of about 7.4). A positive net charge can increase the membrane-translocating ability of a CPP.

Examples of hydrophobic CPPs include, but are not limited to:

1) GALFLGFLGAAGSTMGA (MPG without the NLS and linker) (SEQ ID NO: 182);
2) AAVALLPAVLLALLAP (membrane-translocating sequence peptide [MTS] derived from the hydrophobic H-region of the signal peptide of Kaposi fibroblast growth factor [K-FGF]) (SEQ ID NO: 183);
3) AAVALLPAVLLKLLAP ([A12K]MTS) (SEQ ID NO: 184);
4) AAVLLPVLLAAP (an MTS variant) (SEQ ID NO: 185);
5) PIEVCMYREP (FGF12) (SEQ ID NO: 186);
6) VTVLALGALAGVGVG (integrin (33 signal peptide) (SEQ ID NO: 187);
7) CSIPPEVKFNKPFVYLI (C105Y) (SEQ ID NO: 188);
8) PFVYLI (the mimimal cell-penetrating sequence of C105Y) (SEQ ID NO: 189);
9) SDLWEMMMVSLACQY (Janda pep7) (SEQ ID NO: 190);
10) GPFHFYQFLFPPV (435B) (SEQ ID NO: 191);
11) PLILLRLLR (SEQ ID NO: 192), optionally having GQF added to the C-terminus;
12) PLIYLRLLR (SEQ ID NO: 193), optionally having GQF added to the C-terminus;
13) PLILLFKLL (SEQ ID NO: 194), optionally having GQF added to the C-terminus;
14) PLGYLFLLR (SEQ ID NO: 195), optionally having GQF added to the C-terminus;
15) PLIYPFLRL (SEQ ID NO: 196), optionally having GQF added to the C-terminus;
16) VPTLK (a Bax-inhibiting peptide [BIP]) (SEQ ID NO: 197);
17) VPTLE (a BIP) (SEQ ID NO: 198);
18) VPTLQ (a BIP) (SEQ ID NO: 199);
19) VPALK (a BIP) (SEQ ID NO: 200);
20) VPALR (a BIP) (SEQ ID NO: 201);
21) VPMIK (a BIP) (SEQ ID NO: 202);
22) VPMLK (a BIP) (SEQ ID NO: 203);
23) VSALK (a BIP) (SEQ ID NO: 204);
24) IPALK (a BIP) (SEQ ID NO: 205);
25) IPMLK (a BIP) (SEQ ID NO: 206);
26) PMLKE (a BIP) (SEQ ID NO: 207);
27) KLPVT (a BIP) (SEQ ID NO: 208);
28) KLGVM (a BIP) (SEQ ID NO: 209);
29) ELPVM (a BIP) (SEQ ID NO: 210);
30) QLPVM (a BIP) (SEQ ID NO: 211);
the corresponding peptides having all D-amino acid residues; and
the corresponding peptides (L- and D-isomers) having the reverse order of amino acid sequence;
wherein:
each peptide can optionally have one or more, or all, D-amino acid residues;
each peptide can optionally have a protecting group at the N-terminus or/and the C-terminus (e.g., acetyl at the N-terminus or/and —NH$_2$ at the C-terminus);
each peptide can optionally have a cysteamide group at the C-terminus; and
each peptide can optionally have one, two or more PEG moieties (those comprising, e.g., about 2-20 or 2-10 PEG units) attached to the N-terminus, the C-terminus or/and side chain(s).

A CPP might not fit neatly into the category of polycationic CPPs, arginine-rich CPPs, amphipathic CPPs or hydrophobic CPPs. In some embodiments, the CPP is selected from:
1) TKRRITPKDVIDVRSVTTEINT [Mce1A(130-151), aka Inv3] (SEQ ID NO: 212);

2) RLIYLRLLR (SEQ ID NO: 213), optionally having GQF added to the C-terminus;
3) PLRLLRLLR (SEQ ID NO: 214), optionally having GQF added to the C-terminus;
4) RKILLRLLR (SEQ ID NO: 215), optionally having GQF added to the C-terminus;
5) PLRLRFLLR (SEQ ID NO: 216), optionally having GQF added to the C-terminus;
6) RLIRLFLLR (SEQ ID NO: 217), optionally having GQF added to the C-terminus;
7) RLILLFRRL (SEQ ID NO: 218), optionally having GQF added to the C-terminus;
8) RRILLQLLR (SEQ ID NO: 219), optionally having GQF added to the C-terminus;
9) PLGRPQLRR (SEQ ID NO: 220), optionally having GQF added to the C-terminus;
10) DDILLQLLD (SEQ ID NO: 221), optionally having GQF added to the C-terminus;
11) VSLKK (a BIP) (SEQ ID NO: 222);
12) VSGKK (a BIP) (SEQ ID NO: 223);
13) 50% $M^{Gal}_{10}$ [J. Kramer et al., *ACS Cent. Sci.*, 1:83-88 (2015)];
14) 50% $M^{Glc}_{10}$ [Kramer (supra)];
15) CC12 [C. Chen et al., *Biomaterials*, 112:218-233 (2017)];

the corresponding peptides having all D-amino acid residues; and
the corresponding peptides (L- and D-isomers) having the reverse order of amino acid sequence;

wherein:
each peptide can optionally have one or more, or all, D-amino acid residues;
each peptide can optionally have a protecting group at the N-terminus or/and the C-terminus (e.g., acetyl at the N-terminus or/and —$NH_2$ at the C-terminus);
each peptide can optionally have a cysteamide group at the C-terminus; and
each peptide can optionally have one, two or more hydrophobic/lipophilic groups (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and PEG moieties (those comprising, e.g., about 2-20 or 2-10 PEG units) attached to the N-terminus, the C-terminus or/and side chain(s).

In some embodiments, a CPP, whether a polycationic CPP, an arginine-rich CPP, an amphipathic CPP, a hydrophobic CPP or some other type of CPP, contains no more than about 50, 45, 40, 35, 30, 25, 20, 15 or 10 natural or/and non-natural amino acid residues. In certain embodiments, a CPP has no more than about 30, 25, 20, 15 or 10 natural or/and non-natural amino acid residues. In further embodiments, a CPP contains at least about 5 natural or/and non-natural amino acid residues. In certain embodiments, a CPP has about 5-30, 5-25, 5-20, 5-15 or 5-10 natural or/and non-natural amino acid residues.

In some embodiments, the therapeutic agent (e.g., an anti-dyslipidemic agent such as an apo mimetic [e.g., L-4F or AEM-28-14] or a statin [e.g., atorvastatin or simvastatin]) is mixed with the CPP, whether or not the therapeutic agent is non-covalently associated with the CPP.

In further embodiments, the therapeutic agent (e.g., an anti-dyslipidemic agent such as an apo mimetic [e.g., L-4F or AEM-28-14] or a statin [e.g., atorvastatin or simvastatin]) is non-covalently bound to or associated with the CPP. In certain embodiments, the therapeutic agent and the CPP form a complex (e.g., a stable complex) with each other. An advantage of non-covalent association over covalent bonding is that the former does not require cleavage of the therapeutic agent from the CPP and is not concerned with the issue of whether a therapeutic agent attached to a CPP retains full pharmacological activity.

In some embodiments, the therapeutic agent and the CPP form a charged complex having a net charge, or the therapeutic agent agent and the CPP form a complex, or are non-covalently associated with each other, via charge-based or electrostatic interaction or/and hydrogen bonding between the therapeutic agent agent and the CPP. In certain embodiments, the CPP is a polycationic CPP, an arginine-rich CPP [e.g., a polyarginine such as $R_6$-$R_{11}$ (SEQ ID NO: 268) (e.g., $R_6$ (SEQ ID NO: 258) or $R_9$ (SEQ ID NO: 261)) or a TAT-related CPP such as TAT(49-57)], or an amphipathic CPP (e.g., Pep-1 or penetratin).

In further embodiments, the therapeutic agent and the CPP form a complex, or are non-covalently associated with each other, via hydrophobic interaction or/and hydrogen bonding between the therapeutic agent agent and the CPP. In certain embodiments, the CPP is an amphipathic CPP (e.g., Pep-1 or penetratin) or a hydrophobic CPP.

In additional embodiments, the therapeutic agent and the CPP form a complex, or are non-covalently associated with each other, via both electrostatic interaction and hydrophobic interaction, and optionally hydrogen bonding, between the therapeutic agent and the CPP. In certain embodiments, the CPP is an amphipathic CPP (e.g., Pep-1 or penetratin).

In some embodiments, the CPP-therapeutic agent (e.g., anti-dyslipidemic agent) complex is formed in a molar ratio of the CPP to the therapeutic agent from about 1:1 to about 20:1, 30:1, 40:1, 50:1 or 100:1. In certain embodiments, the complex is formed in a molar ratio of the CPP to the therapeutic agent from about 1:1 to about 10:1 (e.g., from about 1:1 to about 5:1 or from about 5:1 to about 10:1) or from about 10:1 to about 20:1 (e.g., from about 10:1 to about 15:1 or from about 15:1 to about 20:1). In certain embodiments, the complex is formed in a molar ratio of the CPP to the therapeutic agent from about 1:1 to about 5:1, such as about 1:1, 2:1 or 3:1.

Where the therapeutic agent is mixed with or non-covalently associated with the CPP and the therapeutic agent is a polypeptide, polynucleotide or peptide-nucleic acid, in some embodiments the CPP is a polycationic CPP, an arginine-rich CPP [e.g., a polyarginine such as $R_6$-$R_{11}$ (SEQ ID NO: 268) (e.g., $R_6$ (SEQ ID NO: 258) or $R_9$ (SEQ ID NO: 261)) or a TAT-related CPP such as TAT(49-57)], or an amphipathic CPP (e.g., Pep-1 or penetratin). Where the therapeutic agent is a substantially hydrophobic polypeptide or small molecule, in some embodiments the CPP is an amphipathic CPP (e.g., Pep-1 or penetratin) or a hydrophobic CPP. A small-molecule therapeutic agent can also be mixed with or non-covalently associated with another type of CPP, such as a polycationic CPP or an arginine-rich CPP (e.g., a polyarginine such as $R_6$-$R_{11}$ (SEQ ID NO: 268) [e.g., $R_6$ (SEQ ID NO: 258) or $R_9$ (SEQ ID NO: 261)]).

In some embodiments, the CPP and the therapeutic agent (e.g., an anti-dyslipidemic agent) form nanoparticles (e.g., stable nanoparticles) comprising molecules of the CPP surrounding or encapsulating one or more molecules of the therapeutic agent. In certain embodiments, the nanoparticles have an average diameter of no more than about 500 nm, 400 nm, 300 nm, 200 nm or 100 nm (e.g., no more than about 200 nm, 150 nm or 100 nm). In some embodiments, the nanoparticles are formed in a molar ratio of the CPP to the therapeutic agent from about 10:1 to about 20:1, 30:1, 40:1, 50:1 or 100:1. In certain embodiments, the nanoparticles are formed in a molar ratio of the CPP to the therapeutic agent from about 10:1 to about 20:1 (e.g., from about 10:1 to about 15:1, or from about 15:1 to about 20:1).

In certain embodiments, the CPP forming the nanoparticles containing the therapeutic agent is an amphipathic CPP (e.g., Pep-1), a polycationic CPP (e.g., POD) or an arginine-rich CPP (e.g., a polyarginine such as $R_6$-$R_{11}$ (SEQ ID NO: 268) [e.g., $R_6$ (SEQ ID NO: 258) or $R_9$ (SEQ ID NO: 261)]). As an example, Pep-1 molecules form stable nanoparticles around peptides and proteins. A cysteamide group at the C-terminus of the CPP promotes formation of stable nanoparticles as well as translocation across cell membranes. Stabilization of nanoparticles reduces any toxicity of the CPP. As another example, POD conjugated to PEG can form nanoparticles containing a plasmid DNA that, when delivered into RPE cells, expresses a neurotrophic factor such as glial cell-derived neutrophic factor (GDNF).

In other embodiments, the therapeutic agent (e.g., an anti-dyslipidemic agent such as an apo mimetic [e.g., L-4F or AEM-28-14] or a statin [e.g., atorvastatin or simvastatin]) is covalently bonded to the CPP, wherein:
the therapeutic agent can be bonded to the CPP at the N-terminus, the C-terminus or a side chain of the therapeutic agent if the therapeutic agent is a polypeptide; and
the CPP can be bonded to the therapeutic agent at the N-terminus, the C-terminus or a side chain of the CPP.
In some embodiments, the bond between the therapeutic agent and the CPP, whether a direct bond or an indirect bond (e.g., via a linker), is cleavable (e.g., chemically or enzymatically cleavable).

In some embodiments, the therapeutic agent is directly or indirectly bonded to the CPP via a disulfide bond, an amide bond, an ester bond, a hydrazone bond (e.g., 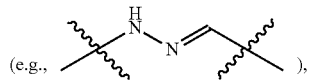 ), an oxime bond (e.g., 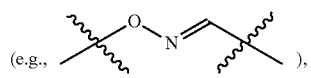 ), a thiazolidine bond (e.g., 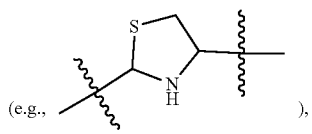 [SMILES: *C1CSC(*)N1] ), a thioether bond, or a succinimide-thioether bond ( 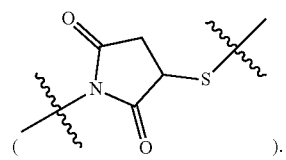 [SMILES: *SC1CC(=O)N(*)C1=O] ).

In certain embodiments, the therapeutic agent is directly or indirectly bonded to the CPP via a disulfide bond. Disulfide bonds, hydrazone bonds, oxime bonds and thiazolidine bonds are, e.g., chemically cleavable. Amide bonds and ester bonds are, e.g., enzymatically cleavable.

In crossing an epithelium (e.g., the corneal or conjunctival epithelium) or a tissue barrier (e.g., the blood-retinal barrier), a therapeutic agent-CPP conjugate may enter cells of the epithelium or the tissue barrier, whether by direct translocation, endocytosis or another mechanism. A disulfide bond can be cleaved in the reducing environment of the cytosol in the presence of disulfide isomerase and a thiol cofactor (e.g., glutathione). An amide bond can be cleaved by, e.g., an amidase in the cytoplasm, and an ester bond can be cleaved by, e.g., an esterase. If the therapeutic agent-CPP conjugate enters cells by endocytosis, it may end up in an endosome (pH about 5.0-6.5) or a lysosome (pH about 4.5-5.0), where an acid-labile bond such as a hydrazone bond, an oxime bond or a thiazolidine bond can be cleaved. The carboxylic acid group of a cis-aconityl linker (infra) facilitates hydrolysis of a nearby amide or ester bond under acidic condition. A peptide linker (infra) can be designed to be cleaved by a selective or non-selective protease present in, e.g., lysosomes or the cytoplasm. A peptide linker containing a PAB moiety (infra) can be designed to be cleaved by a selective or non-selective peptidase present in, e.g., lysosomes or the cytoplasm, followed by self-immolation of the resulting para-aminobenzyl (PAB) carbonate or carbamate moiety to release the therapeutic agent. Similarly, the glycosidic bond of a β-glucuronide-MAB linker (infra) can be cleaved by β-glucuronidase present in, e.g., lysosomes, followed by self-immolation of the resulting meta-amide-para-hydroxybenzyl (MAB) carbonate or carbamate moiety to release the therapeutic agent. If the therapeutic agent is directly or indirectly conjugated to the CPP via a bond that is nominally or substantially non-cleavable, such as a thioether bond (e.g., a succinimide-thioether bond), the therapeutic agent can still be released from the CPP. For example, if the CPP is conjugated to the therapeutic agent via a thioether bond at one end of a linker and the other end of the linker is coupled to the therapeutic agent via, e.g., an ester or amide bond, cleavage of the ester or amide bond releases the therapeutic agent.

In certain embodiments, the therapeutic agent is directly bonded to the CPP. In other embodiments, the therapeutic agent is indirectly bonded to the CPP via a cleavable or non-cleavable linker. In certain embodiments, the linker is cleavable (e.g., chemically or enzymatically cleavable). A linker, whether a non-peptidic linker or a peptide linker, can be coupled to a polypeptide drug or a non-peptidic (e.g., a small-molecule) drug.

In some embodiments, the linker is a non-peptidic linker. Examples of non-peptidic linkers include without limitation

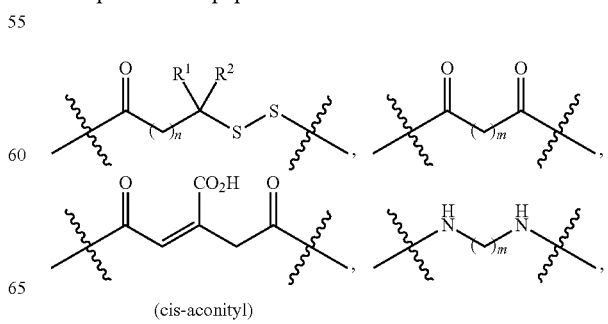

(cis-aconityl)

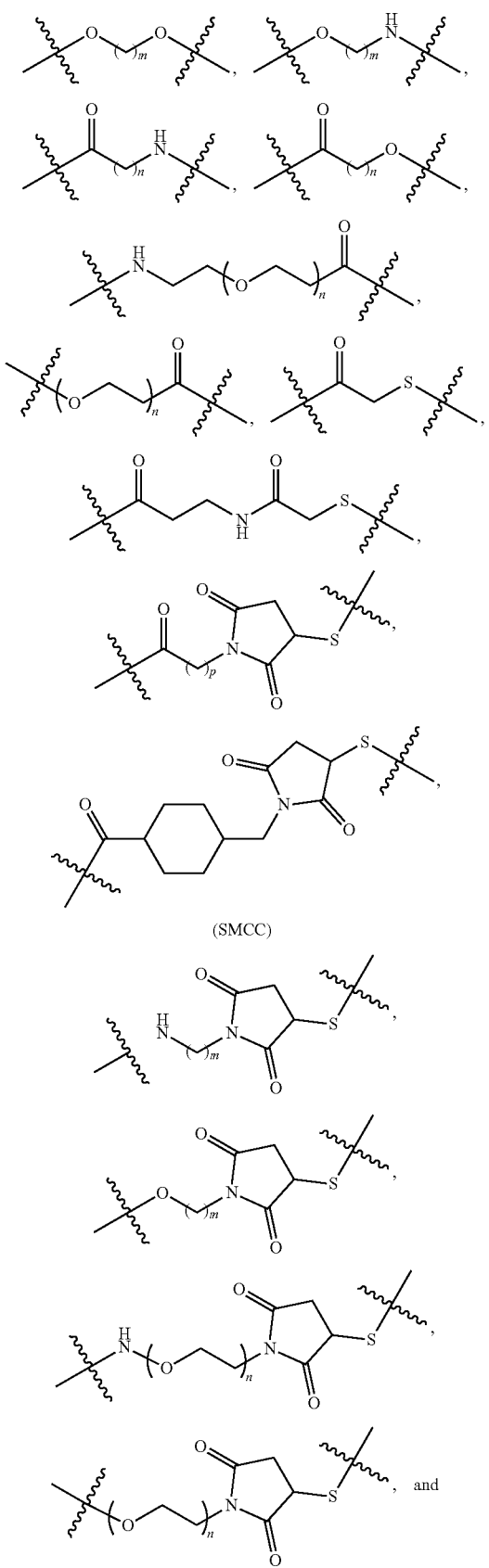

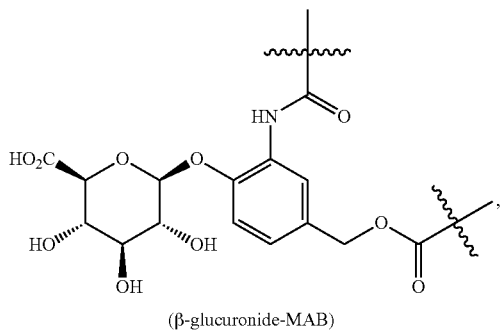

(β-glucuronide-MAB)

wherein:

m is 2, 3, 4, 5 or 6 (e.g., 2);

n is 1, 2, 3, 4, 5 or 6 (e.g., 1 or 2);

p is 2, 3, 4, 5 or 6 (e.g., 3 or 5);

S next to a squiggly line can be the sulfur atom of, e.g., a cysteine, —SCH$_2$CH$_2$NHC(═O)-(cysteamide) or —SCH$_2$CH$_2$C(═O)— group; and $R^1$ and $R^2$ independently are hydrogen or —CH$_3$ (i.e., $R^1$═$R^2$═H, or $R^1$═H and $R^2$═—CH$_3$, or $R^1$═$R^2$═—CH$_3$).

In other embodiments, the linker is a peptide linker comprising at least 2, 3, 4, 5 or 6 natural or/and non-natural amino acid residues, and optionally one or more non-peptidic moieties. In some embodiments, the peptide linker is cleavable. In certain embodiments, the peptide linker is chemically cleavable. US 2016/0158375 discloses numerous self-cleaving dipeptides that can be coupled to a therapeutic agent via an amide bond and can be spontaneously cleaved after a predetermined time of exposure to physiological conditions to release the therapeutic agent in a controlled manner. A dipeptide-therapeutic agent conjugate has the general formula A-B-Q, wherein A is an amino acid or a hydroxyl acid, B is an N-alkylated amino acid, and Q is a primary or secondary amine-bearing therapeutic agent that can be, e.g., a polypeptide or a small molecule. A moiety, such as a CPP, can be directly or indirectly attached to the side chain of A or B. Depending on the chemical instability of the A-B dipeptide, exposure to physiological conditions for a predetermined period of time leads to an intramolecular chemical reaction that cleaves the A-B dipeptide from the therapeutic agent, generating a diketopiperazine or diketomorpholine and releasing the therapeutic agent. A or/and B can be a non-coding or unnatural amino acid, such as a D-amino acid, to inhibit enzymatic cleavage of the dipeptide.

U.S. Pat. No. 9,315,543 describes tyrosine-based linkers that can be spontaneously cleaved after exposure to physiological conditions at pH about 7.4 over a period of time to generate a cyclic urea derivative and release the polypeptide therapeutic in a controlled manner. The tyrosine residue can be a native residue of the polypeptide therapeutic or can be introduced into the polypeptide therapeutic (e.g., at the N-terminus or the C-terminus), and the polypeptide therapeutic is attached to the linker via the side-chain hydroxyl group of the tyrosine residue. A general example of a polypeptide therapeutic coupled to a CPP via a chemically cleavable tyrosine-based linker is:

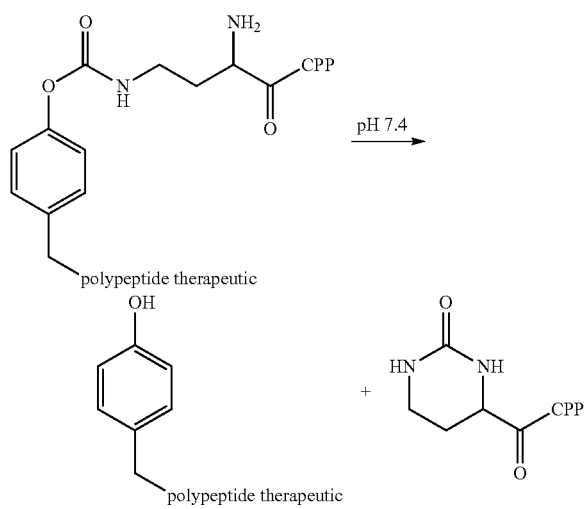

The CPP can be directly attached to 2,4-diaminobutanoic acid (as shown in the example above) or can be attached to it via a spacer group. A tyrosine residue can also be introduced into a small-molecule drug so that self-cleavage of the tyrosine-based linker under physiological conditions releases the small-molecule drug. For example, a tyrosine residue can be coupled to the carboxyl group of atorvastatin via an amide bond so that atorvastatin can be conjugated to a CPP via a self-cleaving tyrosine-based linker.

In further embodiments, the peptide linker is enzymatically cleavable. Non-limiting examples of enzymatically cleavable peptide linkers include:

1) Val-Cit, wherein Cit is citrulline;

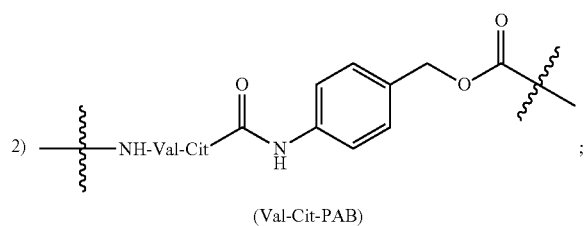

(Val-Cit-PAB)

3) Gly-Gly-Gly-Val-Cit-PAB (SEQ ID NO: 224);
4) Phe-Lys;
5) Phe-Lys-PAB;
6) Ala-Ala-Asn-PAB;
7) GFLG (SEQ ID NO: 225);
8) ALAL (SEQ ID NO: 226);
9) GKPILFFRLKr, optionally having Lys added to the N-terminus or/and Glu added to the C-terminus, wherein the lower case "r" denotes D-Arg;
10) GKPILFFRLK-Cit (SEQ ID NO: 227), optionally having Lys added to the N-terminus or/and Glu added to the C-terminus, wherein Cit is citrulline;
11) GSKPILFFRLKr, optionally having Lys added to the N-terminus or/and Glu added to the C-terminus, wherein the lower case "r" denotes D-Arg;
12) PILFFRLGK (SEQ ID NO: 228), optionally having Lys added to the N-terminus or/and Glu added to the C-terminus; and
13) GSPILFFRLGK (SEQ ID NO: 229), optionally having Lys added to the N-terminus or/and Glu added to the C-terminus.

In some embodiments, the therapeutic agent is covalently bonded to a polyarginine CPP (e.g., $R_6$ (SEQ ID NO: 258), $R_7$ (SEQ ID NO: 259), $R_8$ (SEQ ID NO: 260) or $R_9$ (SEQ ID NO: 261)). In some embodiments, the therapeutic agent is a polypeptide and the polyarginine CPP is directly or indirectly (e.g., via a linker) bonded to the N-terminus, the C-terminus or a side chain of the therapeutic agent. In certain embodiments, the polyarginine CPP is directly bonded to the N-terminus of the therapeutic agent. In some embodiments, the therapeutic polypeptide is an anti-dyslipidemic agent, such as an apo mimetic (e.g., an apoA-I mimetic such as L-4F or D-4F, or an apoE mimetic such as AEM-28-14).

A CPP can be directly or indirectly (e.g., via a linker) attached to the the N-terminus, the C-terminus or a side chain of a therapeutic polypeptide (including a peptide or protein) by any suitable method of recombinant fusion or chemical conjugation known in the art. In some embodiments, a CPP is recombinantly fused to the the N-terminus, the C-terminus or a side chain of a therapeutic polypeptide via a cleavable (e.g., chemically or enzymatically cleavable) peptide linker. Similarly, a CPP can be directly or indirectly (e.g., via a linker) attached to a non-peptidic (e.g., small-molecule) drug by any suitable method of chemical conjugation known in the art.

Instead of being conjugated to a CPP, a therapeutic agent (e.g., an anti-dyslipidemic agent such as an apo mimetic [e.g., L-4F or AEM-28-14] or a statin [e.g., atorvastatin or simvastatin]) can be attached to a small-molecule α-helix mimic. M. Okuyama et al., *Nature Methods*, 4:153-159 (2007) disclose small-molecule mimics of an α-helical protein transduction domain that can be coupled directly or indirectly via a cleavable or non-cleavable linker to a biomolecule (e.g., a peptide or protein) or a small-molecule drug, including di-guanidine 2G-SMoC and tetra-guanidine 4G-SMoC, where the term "SMoC" denotes small-molecule carrier.

In some embodiments, the TDS is a nanoparticle, micelle or liposome encapsulating a plurality of molecules of the therapeutic agent (e.g., an anti-dyslipidemic agent such as an apo mimetic [e.g., L-4F or AEM-28-14] or a statin [e.g., atorvastatin or simvastatin]), wherein a plurality of molecules of the CPP are directly or indirectly (e.g., via a linker) conjugated to the surface of the nanoparticle, micelle or liposome. In certain embodiments, a plurality of poly(ethylene glycol) moieties are directly or indirectly (e.g., via a linker) conjugated to the surface of the nanoparticle, micelle or liposome. PEGylation of the surface of, e.g., liposomes can increase the stability and half-life of the liposomes. In some embodiments, the CPP-modified nanoparticles, micelles or liposomes have an average diameter of no more than about 500 nm, 400 nm, 300 nm, 200 nm or 100 nm (e.g., no more than about 200 nm, 150 nm or 100 nm). The CPP-conjugated nanoparticles, micelles or liposomes can provide controlled- and sustained-release of the therapeutic agent.

The CPP-conjugated nanoparticles, micelles or liposomes can be composed of one substance or material, or can be mixed nanoparticles, micelles or liposomes composed of two or more substances or materials. In some embodiments, the CPP-modified nanoparticles, micelles or liposomes are composed of one or more biodegradable polymers, one or more polysaccharides (e.g., chitosan), or one or more lipids (e.g., a solid lipid such as glycerol behenate, glycerol palmitostearate or wax cetyl palmitate, and optionally a liquid lipid such as a medium-chain triglyceride [e.g., Miglyol® 812]), and optionally a surfactant (e.g., for stabilization of lipid nanoparticles). In certain embodiments, the CPP-modified nanoparticles or micelles are composed of a biodegradable polymer (e.g., a natural homopolymer, a synthetic homopolymer, a natural copolymer or a synthetic copolymer, or any combination or blend thereof). Examples of biodegradable polymers are described elsewhere herein. In some embodiments, the CPP-modified nanoparticles are composed of poly(lactic acid) (PLA), poly(glycolic acid) (PGA) or poly(ε-caprolactone) (PCL), or a copolymer thereof [e.g., poly(lactic-co-glycolic acid) (PLGA)], or a copolymer thereof with poly(ethylene glycol) (e.g., PLGA-PEG). In certain embodiments, the CPP-modified nanoparticles are composed of PLGA or PLGA-PEG. In further embodiments, the CPP-modified micelles are composed of an amphiphilic block copolymer, such as lactosomes composed of, e.g., three poly(sarcosine) blocks and a poly(lactic acid) block. Lactic acid can be L-lactic acid, D-lactic acid or D,L-lactic acid. In other embodiments, the CPP-modified micelles are composed of one or more surfactants or phospholipids. In additional embodiments, the CPP-modified liposomes are composed of one or more phospholipids. Examples of phospholipids are described elsewhere herein. In certain embodiments, the CPP-modified liposomes are composed of one or more phosphatidylcholines (e.g., Phospholipon® 90 G).

In certain embodiments, the CPP conjugated to the surface of nanoparticles, micelles or liposomes is or comprises a polycationic CPP (e.g., POD), an arginine-rich CPP [e.g., a polyarginine such as $R_6$-$R_{11}$ (SEQ ID NO: 268) (e.g., $R_6$ (SEQ ID NO: 258), $R_9$ (SEQ ID NO: 261) or $R_{11}$ (SEQ ID NO: 263)), or a TAT-related CPP such as TAT(49-57) or TAT(47-57)], or an amphipathic CPP (e.g., Pep-1, penetratin or EB1), or any combination thereof.

Alternative to non-covalently or covalently bonding a therapeutic polypeptide (e.g., an anti-dyslipidemic polypeptide such as an apo mimetic [e.g., L-4F or AEM-28-14]) to a CPP, the therapeutic polypeptide itself can be modified to acquire membrane-translocating ability. For example, the polypeptide can be a stapled polypeptide formed by, e.g., ring-closing olefin metathesis. Stapling of a polypeptide can confer membrane-translocating ability and increase α-helicity of the polypeptide by rigidifying the polypeptide structure and stabilizing the helical structure. Moreover, a stapled polypeptide can have increased resistance to proteases and stability in blood. A stapled polypeptide can be made, e.g., by incorporating non-natural amino acids containing olefin-bearing tethers and generating a hydrocarbon staple by ruthenium-catalyzed olefin metathesis. Without intending to be bound by theory, a hydrocarbon-stapled polypeptide with increased lipophilicity and α-helicity can have enhanced affinity to and interaction with cell membranes, and thereby be able to translocate across cell membranes. Stapled peptides generally are membrane-translocating regardless of their peptide sequence. A stapled polypeptide can retain full biological activity, or may have enhanced biological activity.

Another modification that can confer membrane-translocating ability to a therapeutic agent (e.g., an anti-dyslipidemic agent such as an apo mimetic [e.g., L-4F or AEM-28-14] or a statin [e.g., atorvastatin or simvastatin]) is prenylation. Peptides and proteins bearing a prenyl group-containing moiety (e.g., geranyl, farnesyl or geranylgeranyl) can cross cell membranes in an energy-independent, non-endocytic manner. A prenyl group-containing moiety directs the peptide or protein bearing it to cell membranes. In some embodiments, a peptide or protein is prenylated at a cysteine residue near or at the C-terminus. If a peptide or protein does not have a cysteine residue near or at the C-terminus, a cysteine residue can be incorporated near or at the C-terminus for prenylation. Prenylated peptides generally are membrane-translocating regardless of their peptide sequence, and prenylated peptides as short as two amino acids can translocate across cell membranes. Prenylated polypeptides can have a membrane-translocation efficiency comparable to or greater than that of polypeptides conjugated to a CPP such as penetratin. Small molecules can also be prenylated by being attached to a prenyl group-containing moiety or by being modified to have a prenyl group [—$CH_2$(H)C=C($CH_3$)$_2$].

Similar to prenylation, lipidation of a therapeutic agent (e.g., an anti-dyslipidemic agent such as an apo mimetic [e.g., L-4F or AEM-28-14] or a statin) can confer membrane-translocating ability. A polypeptide can be attached to one, two or more lipophilic groups (e.g., $C_8$-$C_{20}$ alkyl or/and $C_8$-$C_{20}$ acyl) at the N-terminus, the C-terminus or/and side chain(s). Examples of $C_8$-$C_{20}$ alkyl groups include without limitation octyl, decyl, lauryl, myristyl, palmityl, stearyl and arachidyl, and examples of $C_8$-$C_{20}$ acyl groups include without limitation octanoyl, decanoyl, lauroyl, myristoyl, palmitoyl, stearoyl and arachidoyl. In some embodiments, a polypeptide is lipidated with a fatty acid (e.g., a $C_{10}$-$C_{20}$ fatty acid such as decanoyl, lauroyl, myristoyl, palmitoyl, stearoyl or arachidoyl) at the N-terminus. A lipidated polypeptide (or small molecule) can have enhanced affinity to cell membranes.

Besides anti-dyslipidemic agents, any of the other kinds of therapeutic agents described herein, whether peptides, proteins, polynucleotides or small molecules, can be mixed with, non-covalently associated with or covalently attached to a CPP, encapsulated in CPP-conjugated nanoparticles, micelles or liposomes, coupled to a small-molecule α-helix mimic (e.g., 2G-SMoC or 4G-SMoC), or modified (e.g., stapled, prenylated or lipidated) to acquire the ability to cross epithelia, tissue barriers or cell membranes. Such therapeutic agents include, but are not limited to, antioxidants, anti-inflammatory agents, complement inhibitors, neuroprotectors and anti-angiogenic agents. In some embodiments, an anti-angiogenic agent (e.g., an anti-VEGF/VEGFR agent such as aflibercept, brolucizumab, bevacizumab or ranibizumab) is mixed with or non-covalently associated with a CPP {e.g., a polycationic CPP, an arginine-rich CPP (e.g., a polyarginine such as $R_6$-$R_{11}$ (SEQ ID NO: 268) [e.g., $R_6$ (SEQ ID NO: 258) or $R_9$ (SEQ ID NO: 261)]), or an amphipathic CPP (e.g., Pep-1)}.

A transepithelial, transmembrane or transmucosal drug-delivery system (TDS) comprising a therapeutic agent and a CPP (e.g., an anti-dyslipidemic agent mixed with, non-covalently associated with or covalently bonded to a CPP, or encapsulated in CPP-conjugated nanoparticles, micelles or liposomes), or a modified (e.g., stapled, prenylated, lipidated or coupled to a small-molecule α-helix mimic) therapeutic agent (e.g., anti-dyslipidemic agent), can be administered to a subject for the treatment of an eye disease (e.g., atrophic or neovascular AMD) by any suitable route. In some embodiments, the TDS or the modified therapeutic agent is applied to the surface of the eye by means of an eye drop or a contact lens (e.g., a corneal lens or a scleral lens). Topical administration by eye drop or contact lens is non-invasive or minimally invasive, increases patient compliance and avoids potential side effects of alternative procedures for local administration such as intravitreal injections, including elevated intraocular pressure, bacterial and sterile endophthalmitis, cataract formation, vitreal hemorrhage and retinal detachment, as well as retinal thinning and geographic atrophy potentially caused by repeated intravitreal injections. Furthermore, administration of a TDS or a modified therapeutic agent by eye drop or contact lens can deliver a therapeutically effective amount of the therapeutic agent to target site(s) in the eye (e.g., in the anterior or/and posterior segments of the eye) in a much smaller dose than systemic (e.g., oral or parenteral) administration of the therapeutic agent without the use of a CPP or a membrane translocation-conferring modification, and hence can avoid or reduce potential side effects of a high dose of the therapeutic agent.

In some embodiments, the therapeutic agent (if a polypeptide) or/and the CPP of a TDS, or a modified polypeptide therapeutic, administered by eye drop or contact lens has one or more, or all, D-amino acid residues for enhanced resistance to proteolysis. The ocular surface contains peptidases/proteases. Moreover, in crossing an epithelium (e.g., the corneal or conjunctival epithelium) or a tissue barrier (e.g., the blood-retinal barrier), a TDS or a modified polypeptide therapeutic may enter the cytoplasm, endosomes or lysosomes of cells of the epithelium or the tissue barrier, where proteases are present.

IV. PHARMACEUTICAL COMPOSITIONS COMPRISING A CELL-PENETRATING PEPTIDE

The disclosure further provides pharmaceutical compositions comprising a therapeutic agent and a cell-penetrating peptide (CPP), or a modified (e.g., stapled, prenylated, lipidated or coupled to a small-molecule α-helix mimic) therapeutic agent, and one or more pharmaceutically acceptable carriers or excipients. Examples of therapeutic agents and CPPs include without limitation those described herein. In some embodiments, the therapeutic agent is or includes an anti-dyslipidemic agent, an antioxidant, an anti-inflammatory agent, a complement inhibitor, a neuroprotector or an anti-angiogenic agent, or any combination thereof. In certain embodiments, the therapeutic agent is or includes an anti-dyslipidemic agent. In some embodiments, the anti-dyslipidemic agent is or includes an apolipoprotein (apo) mimetic (e.g., an apoA-I mimetic such as L-4F or D-4F, or an apoE mimetic such as AEM-28-14) or/and a statin (e.g., atorvastatin or simvastatin). The use of both an apo mimetic and a statin can have synergistic effect. In additional embodiments, the therapeutic agent is or includes an anti-angiogenic agent (e.g., an anti-VEGF/VEGFR agent such as aflibercept, brolucizumab, bevacizumab or ranibizumab).

Examples of pharmaceutically acceptable carriers and excipients include without limitation those described elsewhere herein. In certain embodiments, the one or more pharmaceutically acceptable carriers or excipients are or include phosphate-buffered saline (PBS). In further embodiments, a pharmaceutical composition containing a polypeptide therapeutic and a CPP, or a modified (e.g., stapled, prenylated, lipidated or coupled to a small-molecule α-helix mimic) polypeptide therapeutic, comprises one or more excipients that increase peptide/protein solubility, inhibit peptide/protein aggregation, reduce solution viscosity or increase peptide/protein stability, or any combination or all thereof. Examples of such excipients include without limitation those described elsewhere herein.

Alternative to or in addition to a CPP, a pharmaceutical composition can comprise one or more chemical penetration enhancers (CPEs) that enhance penetration of a macromolecule (e.g., a polypeptide) or a small molecule across epithelia, tissue barriers or cell membranes. Non-limiting examples of CPEs include hydrocarbons (e.g., alkanes and alkenes [e.g., squalene]); terpenes and terpenoids (e.g., D-limonene, carvone, eucalyptol, menthol, menthone and nerolidol); essential/volatile oils (e.g., anise oil, caraway oil, cardamom oil, *chenopodium* oil, *eucalyptus* oil and lemon oil); ethers and fatty ethers (e.g., 2-n-nonyl-1,3-dioxolane); phenols (e.g., eugenol); alcohols and fatty alcohols (e.g., methanol, ethanol, isopropyl alcohol, pentanol, lauryl alcohol, oleyl alcohol, benzyl alcohol, diethylene glycol monoethyl ether, propylene glycol, dipropylene glycol, polyethylene glycol and glycerol); benzoic acids (e.g., salicylic acid and acetylsalicylic acid); fatty acids (e.g., capric acid, lauric acid, myristic acid, oleic acid, linoleic acid and linolenic acid); esters, fatty alcohol esters and fatty acid esters (e.g., ethyl acetate, methyl laurate, isopropyl myristate, isopropyl palmitate, methyl oleate, ethyl oleate, propylene glycol mono-oleate, glycerol mono-oleate, triacetin and pentadecalactone); hydroxyl-containing esters, fatty alcohol esters and fatty acid esters (e.g., lauryl lactate, glyceryl/glycerol monolaurate, glycerol monoleate [mono-olein], sorbitan oleate and octyl salicylate); amines (e.g., diethanolamine and triethanolamine); amides, fatty amine amides and fatty acid amides (e.g., urea, dimethylformamide, dimethylacetamide, diethylacetamide, diethyltoluamide, N-lauroyl sarcosine, 1-dodecylazacycloheptane-2-one [laurocapram or Azone®], Azone-related compounds, and pyrrolidone compounds [e.g., 2-pyrrolidone and N-methyl-2-pyrrolidone]); ionic and non-ionic surfactants (e.g., cetyltrimethylammonium bromide, sodium laurate, sodium laureth sulfate [sodium lauryl ether sulfate], sodium cholate, sodium lauroyl sarcosinate, N-lauroyl sarcosine, sorbitan monolaurate, Brij® surfactants, Pluronic® surfactants, Tween® surfactants, saponins, alkyl glycosides, and fatty ether and fatty ester saccharides); phospholipids (e.g., lecithin); organic sulfoxides (e.g., dimethyl sulfoxide and decylmethyl sulfoxide); and ginsenoside.

US 2007/0269379 provides an extensive list of CPEs. In certain embodiments, the CPE is or includes a saponin, an alkyl glycoside (e.g., a 1-O or S—$C_8$-$C_{20}$ alkyl glycoside such as the corresponding glucoside, galactoside, mannoside, lactoside, maltoside [e.g., dodecyl, tridecyl or tetradecyl maltoside], melibioside or sucroside [e.g., dodecyl sucrose]), or a fatty ether or fatty ester saccharide (e.g., a $C_8$-$C_{20}$ alkyl ether or $C_8$-$C_{20}$ fatty acid ester saccharide such as the corresponding glucoside, galactoside, mannoside, lactoside, maltoside, melibioside, sucroside [e.g., sucrose monododecanoate] or trehaloside), or any combination thereof.

In some embodiments, a pharmaceutical composition comprises a CPP and a therapeutic agent (e.g., an anti-dyslipidemic agent) in a molar ratio from about 1:1 to about 20:1, 30:1, 40:1, 50:1 or 100:1. In certain embodiments, the molar ratio of the CPP to the therapeutic agent is from about 1:1 to about 20:1, from about 1:1 to about 10:1 (e.g., from about 1:1 to about 5:1 or from about 5:1 to about 10:1), or from about 10:1 to about 20:1 (e.g., from about 10:1 to about 15:1 or from about 15:1 to about 20:1). In certain embodiments, the molar ratio of the CPP to the therapeutic agent is from about 1:1 to about 3:1 or 5:1, such as about 1:1, 2:1 or 3:1. Most CPPs containing 30 or fewer amino acids are non-toxic to cells and tissues in the eye or other parts of the body at concentrations relevant for membrane translocation, so a large molar excess of a CPP does not present a toxicity issue.

In some embodiments, a pharmaceutical composition comprises a therapeutic agent mixed with a CPP, whether or not the therapeutic agent is non-covalently associated with the CPP. In further embodiments, a pharmaceutical composition comprises a therapeutic agent non-covalently associated with a CPP. In other embodiments, a pharmaceutical composition comprises a therapeutic agent covalently bonded to a CPP. In still other embodiments, a pharmaceutical composition comprises a therapeutic agent encapsulated in CPP-conjugated nanoparticles, micelles or liposomes. In additional embodiments, a pharmaceutical composition contains any transepithelial, transmembrane or transmucosal drug-delivery system comprising a therapeutic agent and a CPP described herein.

A pharmaceutical composition can be formulated for any suitable mode of administration. In some embodiments, the pharmaceutical composition is formulated as an eye drop. In other embodiments, the pharmaceutical composition is formulated for delivery by a contact lens (e.g., a corneal lens or a scleral lens).

V. APOLIPOPROTEIN MIMETICS

As described above, age-related macular degeneration (AMD) is a disorder that has a variety of underlying factors. Three of the major factors of AMD are formation of lipid-rich deposits, inflammation and neovascularization in the retina, the subretinal space, the sub-RPE-BL space and the BrM. Formation of lipid-containing deposits is one of the initial major factors that leads to sequelae such as chronic inflammation, non-central or/and central geographic atrophy (GA) of the retina, neovascularization (including CNV) and ultimately central vision loss or legal blindness. Lipid-scavenging apolipoprotein mimetics, which also possess other beneficial properties such as antioxidant, anti-inflammatory and anti-angiogenic properties, can be used to treat AMD and complications thereof.

Apolipoprotein (apo) mimetic peptides can effectively reduce the accumulation of lipid-rich deposits in the eye. Apo mimetics can modulate (e.g., inhibit) the production of lipoproteins (e.g., VLDLs), modulate (e.g., inhibit) cellular uptake of plasma lipids (e.g., cholesterol) and lipoproteins (e.g., VLDLs), mediate the clearance or scavenging of lipids (e.g., cholesterol and oxidized lipids, such as oxysterols) and lipoproteins (e.g., VLDLs) and remnants thereof (e.g., low-density lipoproteins [LDLs] and chylomicron remnants), and inhibit the formation of lipid-containing lesions. For example, apoE mimetics enhance the secretion of pre-β HDL-like, apoA-I-containing particles, improve HDL function, induce lipid (e.g., cholesterol) efflux (e.g., via ATP-binding cassette transporters such as ABCA1) and reverse cholesterol transport, mediate the clearance of lipids (e.g., triglycerides and cholesterol) and pro-inflammatory, apoB-containing lipoproteins (e.g., VLDLs, LDLs and chylomicrons) via hepatic uptake of VLDL-triglyceride (TG) and LDL-cholesterol, decrease the formation of lipid-containing lesions, have antioxidant properties (e.g., increase the activity of paraoxonase 1 [PON-1], which inter alia prevents LDL oxidation and catalyzes the hydrolysis of oxidized phospholipids and lipid hydroperoxides, and decrease the activity of myeloperoxidase, which generates reactive oxygen species and hypochlorous acid and whose oxidation of apoA-I reduces HDL-mediated inhibition of inflammation and apoptosis), have anti-inflammatory properties (e.g., decrease the expression of pro-inflammatory cytokines such as TNF-α and IL-6), and have anti-angiogenic properties (e.g., inhibit the proliferation of vascular smooth muscle cells). As another example, apoA-I mimetics induce the formation of nascent pre-3 HDL particles, enhance the functions of HDLs, promote lipid (e.g., cholesterol) efflux (e.g., via ABC transporters such as ABCA1) and reverse cholesterol transport, reduce the formation of lipid-containing lesions (in the eye and arterial intima), have antioxidant properties (e.g., stimulate PON-1 activity and inhibit LDL oxidation), and have anti-inflammatory properties (e.g., inhibit the expression of pro-inflammatory cytokines such as TNF-α and IL-1β and that of cell adhesion molecules such as CD11b and VCAM-1). As a further example, apoA-V mimetics decrease VLDL-TG production and stimulate lipoprotein lipase-mediated lipolysis of VLDL-TG. As an additional example, apoC-II mimetics increase lipid (e.g., cholesterol) efflux and activate lipoprotein lipase-mediated lipolysis of lipoproteins. A beneficial effect of increased lipoprotein lipase-mediated lipolysis of lipoproteins can be, e.g., reduced tissue availability of dietary-derived lipids, which may affect the upstream sources to RPE-derived lipoproteins that are secreted into the BrM, the sub-RPE-BL space and the subretinal space.

As an illustrative example, apoA-I mimetics such as those described herein (e.g., L-4F and D-4F) can dissolve, mobilize and remove accumulated extracellular, and potentially intracellular, lipid deposits in the eye. For instance, L-4F and D-4F may be able to remove intracellular lipids via the LDL-receptor by forming pre-β HDL particles. Lipid deposits on the BrM form a lipid wall that acts as a diffusion barrier between the RPE and the choriocapillaris, promotes the formation of basal linear deposits (BLinD) and soft drusen, and is implicated in local inflammation and oxidative stress. ApoA-I mimetics (e.g., L-4F and D-4F) can clear lipid deposits from the BrM, thereby remodeling the BrM structure to a normal or healthier state and restoring the BrM function, including reduced hydraulic resistivity and increased metabolite and micronutrient exchange between the choriocapillaris and the RPE, which improves RPE health. Moreover, apoA-I mimetics (e.g., L-4F and D-4F) can facilitate the efflux and clearance of lipids (e.g., cholesterol and phospholipids), lipoproteins and lipoprotein components via the BrM into the choriocapillaris and systemic circulation and ultimately to the liver for their metabolism and excretion into the bile.

In addition, apoA-I mimetics (e.g., L-4F and D-4F) possess antioxidant and anti-inflammatory properties related to and independent of their lipid-clearing ability. For example, apoA-I mimetics (e.g., L-4F and D-4F) can reduce local inflammation and oxidative stress by clearing lipid deposits from the BrM, BLinD and soft drusen. Furthermore, apoA-I mimetics (e.g., L-4F and D-4F) inhibit the oxidation of lipids and LDLs and hence the formation of pro-inflammatory oxidized lipids and LDLs, scavenge lipid hydroperoxides from LDLs, and promote the destruction of existing oxidized lipids (e.g., by enhancing PON-1 activity). For instance, apoA-I mimetics (e.g., L-4F and D-4F) can protect phospholipids from oxidation by, e.g., binding seeding molecules required for formation of pro-inflammatory oxidized phospholipids, such as Ox-PAPC (PAPC is L-α-1-palmitoyl-2-arachidonoyl-sn-glycero-3-phosphocholine), POVPC (1-palmitoyl-2-[5-oxovaleryl]-sn-glycero-3-phosphocholine), PGPC (1-palmitoyl-2-glutaryl-sn-glycero-3-phosphocholine), and PEIPC (1-palmitoyl-2-[5,6-epoxyisoprostane $E_2$]-sn-glycero-3-phosphocholine). ApoA-I mimetics (e.g., L-4F and D-4F) also have high affinity for pro-inflammatory oxidized lipids (e.g., phospholipids, sterols and fatty acids) as well as for unmodified lipids and mediate the removal of oxidized lipids and unmodified lipids. Moreover, apoA-I mimetics (e.g., L-4F and D-4F) have potent anti-inflammatory effects by, e.g., decreasing the production of pro-inflammatory cytokines such as IL-1β and TNF-α, and increasing the expression of heme oxygenase 1 (HMOX1) and thereby upregulating the expression of anti-inflammatory IL-10 and IL-1 receptor antagonist (IL-1RA). Furthermore, apoA-I mimetics (e.g., L-4F and D-4F) increase the expression of the antioxidant enzyme superoxide dismutase and stimulate the activity of paraoxonases (e.g., PON-1), which have anti-dyslipidemic, antioxidant and anti-inflammatory properties. In addition, apoA-I mimetics (e.g., L-4F and D-4F) have anti-angiogenic properties (e.g., inhibit the proliferation of vascular smooth muscle cells) and anti-apoptotic properties (e.g., inhibit the expression of caspases).

The majority of AMD-associated lipid deposits are extracellular and accessible to lipid-clearing apoA-I mimetics. In addition, intracellular lipid deposits can be accessible to apo mimetics mixed with, non-covalently associated with or covalently bonded to a CPP or encapsulated in CPP-conjugated nanoparticles, micelles or liposomes, or accessible to modified (e.g., stapled, prenylated, lipidated or coupled to a small-molecule α-helix mimic) apo mimetics. Therefore, apoA-I mimetics (e.g., L-4F and D-4F) can be used at any stage of AMD, including from early- to advanced-stage AMD, to treat an important upstream factor of AMD—accumulation of lipid deposits such as BlinD on the BrM and soft drusen in the sub-RPE-BL space—and, through the removal of such deposits, to inhibit or curtail downstream factors of AMD, such as local inflammation and oxidative stress. In addition, lipid-clearing apoA-I mimetics (e.g., L-4F and D-4F) can be used prior to development of AMD to prevent or delay the onset of AMD.

In some embodiments, apolipoprotein mimetics include amphipathic α-helical domains of apolipoproteins which bind to/associate with lipids (e.g., cholesterol) or lipid complexes (e.g., VLDL-cholesterol and LDL-cholesterol) and are capable of removing/clearing lipids or lipid complexes. In certain embodiments, lipid-binding, amphipathic α-helical domains of apolipoproteins include:

1) sequences from about amino acid (aa) 209 to about aa 219, sequences from about aa 220 to about aa 241, and sequences from about aa 209 to about aa 241 of wild-type (wt) human apoA-I (hApoA-I), sequences overlapping, encompassing or within those ranges, and variants thereof;

2) sequences from about aa 39 or 40 to about aa 50, sequences from about aa 51 to about aa 71 or 77, sequences from about aa 39 or 40 to about aa 71, and sequences from about aa 39 or 40 to about aa 77 of wt human apoA-II (hApoA-II), sequences overlapping, encompassing or within those ranges, and variants thereof;

3) sequences from about aa 7 to about aa 32, sequences from about aa 33 to about aa 53, and sequences from about aa 7 to about aa 53 of wt human apoC-I (hApoC-I), sequences overlapping, encompassing or within those ranges, and variants thereof;

4) sequences from about aa 43 to about aa 55 of wt human apoC-II (hApoC-II), sequences overlapping, encompassing or within that range, and variants thereof;

5) sequences from about aa 40 to about aa 67 of wt human apoC-III (hApoC-III), sequences overlapping, encompassing or within that range, and variants thereof; and 6) sequences from about aa 203 to about aa 266 and sequences from about aa 244 to about aa 272 of wt human apoE (hApoE), sequences overlapping, encompassing or within those ranges (e.g., residues about 234-254), and variants thereof.

In some embodiments, an apo mimetic comprises two, three or more lipid-binding, amphipathic α-helical domains linearly (or tandem-wise) or non-linearly attached to one another directly or indirectly via a linker or spacer group containing one or more amino acid residues or a group having multiple (e.g., two, three or more) points of attachment, such as in a tristar configuration. Such an apo mimetic may have increased lipid affinity and ability to induce cholesterol efflux, for example, compared to the corresponding apo mimetic having only one lipid-binding, amphipathic α-helical domain. To promote clearance of lipids (e.g., via hepatic uptake of lipid-containing lipoproteins such as VLDLs and LDLs), in some embodiments an apo mimetic comprises one or more lipid-binding, amphipathic α-helical domains directly or indirectly (e.g., via a linker) connected to a lipoprotein receptor-binding region, such as an LDL receptor-binding region (e.g., residues about 130-169 of wt hApoE, a sequence overlapping, encompassing or within that range [e.g., residues about 131-162 or about 141-150], or a variant thereof). In further embodiments, apo mimetics include polypeptides (including fusion proteins and chimeras) that comprise such lipid-binding, amphipathic α-helical domains of apolipoproteins or variants thereof, optionally connected to an LDL receptor-binding region.

Non-limiting examples of apoA-I mimetics include 2F, 3F, 3F-1, 3F-2, 3F-14, 4F (e.g., L-4F and D-4F), 4F-P-4F, 4F-IHS-4F, 4F2, 5F, 6F, 7F, 18F, 5A, 5A-C1, 5A-CH1, 5A-CH2, 5A-H1, 18A, 37 pA (18A-P-18A), ELK (name), ELK-1A, ELK-1F, ELK-1K1A1E, ELK-1L1K, ELK-1W, ELK-2A, ELK-2A2K2E (or ELK-2K2A2E), ELK-2E2K, ELK-2F, ELK-3E3EK, ELK-3E3K3A, ELK-3E3LK, ELK-PA, ELK-P2A, ELKA (name), ELKA-CH2, ATI-5261, CS-6253, ETC-642, FAMP (Fukuoka University apoA-I mimetic peptide), FREL, KRES, ApoJ(113-122), ApoA-I Milano ([R173C]hApoA-I), ApoA-I Paris ([R151C]hApoA-I), CGVLESFKASFLSALEEWTKKLQ (monomer, dimers and trimers) (SEQ ID NO: 230), DWLKAFYDKVAEKLKE (monomer, dimers and trimers) (SEQ ID NO: 231), DWFKAFYDKVAEKFKE (monomer, dimers and trimers) (SEQ ID NO: 232), DWFKAFYDKVAEKFKEAF (4F) (monomer, dimers and trimers) (SEQ ID NO: 1), DWLKAFYDKVAEKLKEAFPDWLKAFYDK-VAEKLKEAF (SEQ ID NO: 233), DWLKAFYDK-VAEKLKEFFPDWLKAFYDKVAEKLKEFF (SEQ ID NO: 234), DWFKAFYDKVAEKLKEAFPDWFKAFYDK-VAEKLKEAF (SEQ ID NO: 235), DKLKAFYDKVFE-WAKEAFPDKLKAFYDKVFEWLKEAF (SEQ ID NO: 236), DKWKAVYDKFAEAFKEFLPDKWKAVYDK-FAEAFKEFL (SEQ ID NO: 237), DWFKAFYDK-VAEKFKEAFPDWFKAFYDKVAEKFKEAF (4F-P-4F) (SEQ ID NO: 238), and the corresponding apoA-I mimetics having one or more, or all, D-amino acids (e.g., D-4F having all D-amino acids) or/and the reverse order of amino acid sequence (e.g., Rev-L-4F and Rev-D-4F).

Non-limiting examples of apoE mimetics include Ac-hE18A-NH$_2$ (AEM-28, which contains an LDL receptor-/heparin-binding domain [apoE mimic] and a lipid-binding domain [apoA-I mimic]), Ac-[R]hE18A-NH$_2$, AEM-28-14, EpK, hEp, mR18L, COG-112, COG-133, COG-1410, hApoE(130-149) monomer and dimers (including N-acetylated dimers), hApoE(130-159) monomer and dimers (including N-acetylated dimers), hApoE(141-155) monomer and dimers (including N-acetylated dimers), Ac-Y-hApoE(141-155)$_2$-C, hApoE(202-223), hApoE(239-252), hApoE(245-266), hApoE(263-286) and hApoE(268-289). Examples of apoC-II mimetics include without limitation C-II-a.

The present disclosure encompasses the following apolipoprotein mimetic peptides:

1) apo mimetics in which all of the amino acid residues have the L-stereochemistry;

2) apo mimetics in which one or more, or all, of the amino acid residues have the D-stereochemistry;

3) apo mimetics which have the reverse order of amino acid sequence and in which all of the amino acid residues have the L-stereochemistry;

4) apo mimetics which have the reverse order of amino acid sequence and in which one or more, or all, of the amino acid residues have the D-stereochemistry; and 5) multimers (including dimers and trimers) of an apo mimetic in which two, three or more units of an apo mimetic are linearly or non-linearly attached to one another directly or indirectly, including tandem repeats and multimers in which two, three or more units of an apo mimetic are linearly or non-linearly attached to one another indirectly via a linker or spacer group containing one or more amino acid residues or a group having multiple (e.g., two, three or more) points of attachment such as in a tristar configuration, and including dimers and trimers in which two or three units of an apo mimetic are linearly attached to one another via a linker or spacer group containing 1-3 or 1-6 (e.g., one) proline residue(s) (SEQ ID NO: 275);

6) apo mimetics comprising two, three or more different wild-type domains/regions or variants thereof of the same apolipoprotein (e.g., apoA-I or apoE) or different apolipoproteins (e.g., apoA-I and apoE), wherein the two or more different domains/regions may mediate two or more different functions of the apolipoprotein(s) (e.g., apoA-I or/and apoE) and can be attached to one another in a similar manner as described above for multimers of an apo mimetic; and 7) apo mimetics comprising in one compound two, three or more different apo mimetics of the same category (e.g., apoA-I mimetics or apoE mimetics) or different categories [e.g., apoA-I mimetic(s) and apoE mimetic(s)], wherein the two or more different apo mimetics may mimic different functional or/and structural aspects of the apolipoprotein(s) (e.g., apoA-I or/and apoE) and can be attached to one another in a similar manner as described above for multimers of an apo mimetic.

The apolipoprotein mimetics described herein can have a protecting group at the N-terminus or/and the C-terminus. In some embodiments, the apo mimetics have an N-terminal protecting group that is an unsubstituted or substituted $C_2$-$C_{20}$ or $C_2$-$C_{10}$ acyl group (e.g., acetyl, propionyl, butanoyl, pentanoyl, hexanoyl, octanoyl, decanoyl, lauroyl, myristoyl, palmitoyl, stearoyl or arachidoyl), an unsubstituted or substituted benzoyl group, a carbobenzoxy group, an N-protected (e.g., N-methyl) anthranilyl group, or one or two unsubstituted or substituted $C_1$-$C_{20}$ or $C_1$-$C_{10}$ alkyl groups (e.g., one or two methyl, ethyl, propyl, butyl, pentyl, hexyl, octyl, decyl, lauryl, myristyl, palmityl, stearyl or arachidyl groups). Such groups can also be attached to the C-terminus or/and one or more side chains. Furthermore, the apo mimetics can have a functional group other than —$CO_2H$ at the C-terminus, such as a —$C(O)NH_2$ or —$C(O)NR^1R^2$ amide group, wherein $R^1$ and $R^2$ independently are hydrogen, alkyl, cycloalkyl, heterocyclyl, aryl or heteroaryl, or $R^1$ and $R^2$ and the nitrogen atom to which they are connected form a heterocyclic or heteroaryl ring. An amide group at the C-terminus can be regarded as a protecting group at the C-terminus. Therefore, the disclosure encompasses apo mimetics having, e.g., both an acetyl group at the N-terminus and a —$C(O)NH_2$ group at the C-terminus. However, apo mimetics (e.g., L-6F) that do not require protection of the N-terminus or/and the C-terminus for their stability or activity can be produced by living organisms (e.g., transgenic tomatoes), which can significantly decrease the cost of their production in large scale.

The disclosure also encompasses variants of the apolipoprotein mimetics described herein, wherein the variants of the apo mimetics can comprise one or more amino acid additions/insertions, deletions or/and substitutions. In other words, the disclosure encompasses variants in which one or more natural or/and unnatural amino acids are added to or inserted in, one or more amino acid residues are deleted from, or one or more natural or/and unnatural amino acids are substituted (conservative or/and non-conservative substitutions) for one or more amino acid residues of, any of the apo mimetics described herein, or any combination or all thereof. An unnatural amino acid can have the same chemical structure as the counterpart natural amino acid but have the D-stereochemistry, or it can have a different chemical structure and the D- or L-stereochemistry. Unnatural amino acids can be utilized, e.g., to promote α-helix formation or/and to increase the stability of the peptide (e.g., resist proteolytic degradation). For example, D-4F is resistant to intestinal peptidases and thus is suitable for oral use. Examples of unnatural amino acids include without limitation alanine analogs (e.g., α-ethylGly [α-aminobutyric acid or Abu], α-n-propylGly [α-aminovaleric acid, norvaline or Nva], α-tert-butylGly [Tbg], α-vinylGly [Vg or Vlg], α-allylGly [Alg], α-propargylGly [Prg], 3-cyclopropylAla [Cpa], and α-aminoisobutyric acid [Aib]), leucine analogs (e.g., norleucine [Nle]), proline analogs (e.g., CMePro [α-MePro]), phenylalanine analogs {e.g., 2FPhe [Phe(2-F)], 2MePhe [Phe(2-Me)], (2,4,6-trimethylphenyl)alanine [Tmp], biphenylalanine [Bip], Bip2EtMeO [Bip(2'-Et-4'-OMe)], 1-naphthylalanine [Nal(1)], 2-naphthylalanine [Nal(2)], 1,2,3,4-tetrahydroisoquinoline-3-carboxylic acid [Tic], CMePhe [α-MePhe], CMe2FPhe [α-MePhe(2-F)], and CMe2MePhe [α-MePhe(2-Me)]}, tyrosine analogs (e.g., Tyr(2,6-diMe) [Dmt] and CMeTyr [α-MeTyr]), serine analogs (e.g., homoserine [isothreonine or hSer]), glutamine analogs (e.g., citrulline [Cit]), arginine analogs (e.g., homoarginine [hArg]), lysine analogs (e.g., homolysine [hLys], ornithine [Orn] and CMeLys [α-MeLys]), α,α-disubstituted amino acids (e.g., Aib, α,α-diethylGly [Deg], α-cyclohexylAla [2-Cha], 1-aminocyclopropane-1-carboxylic acid [Acp, Acpr or Ac3c], 1-aminocyclobutane-1-carboxylic acid [Acb or Ac4c], 1-aminocyclopentane-1-carboxylic acid [Acpe or Ac5c], and 1-aminocyclohexane-1-carboxylic acid [Ach, Acx or Ac6c]), and other unnatural amino acids disclosed in WO 2015/184177 A1 and A. Santoprete et al., J. Pept. Sci., 17:270-280 (2011). One or more peptidomimetic moieties can also be used in additions or/and substitutions. The variants can have a protecting group at the N-terminus or/and the C-terminus, such as an acyl (e.g., acetyl) group at the N-terminus or/and an amide group [e.g., —$C(O)NH_2$] at the C-terminus. In some embodiments, a biological or pharmacological activity of a variant of an apo mimetic is enhanced relative to, or substantially similar to (e.g., not diminished by more than about 10%, 20% or 30% relative to), that of the apo mimetic with a native amino acid sequence. As a non-limiting example, the disclosure encompasses a variant of 4F called 4F2, which has the sequence DWFKAFYDKV-Aib-EKFKE-Aib-F (SEQ ID NO: 239) in which $A^{11}$ and $A^7$ are substituted with α-aminoisobutyric acid (Aib). In certain embodiments, 4F2 has the structure Ac-DWFKAFYDKV-Aib-EKFKE-Aib-F-$NH_2$ (SEQ ID NO: 240), where all the amino acid residues have the L-form (L-4F2), or one or more, or all, of the amino acid residues have the D-form (e.g., D-4F2 having all D-amino acid residues).

Variants of the apoliprotein mimetics described herein also include analogs and derivatives of the apo mimetics that have one or more other kinds of modification alternative to or in addition to one or more amino acid additions/insertions, deletions or/and substitutions. As an example, variants of apo mimetics include fusion proteins and chimeras comprising a lipid-binding, amphipathic helical domain of an apolipoprotein or a variant thereof (e.g., 4F) which is directly or indirectly (e.g., via a linker) attached to a heterologous polypeptide. The heterologous polypeptide can impart a beneficial property, such as increased half-life. For instance, the heterologous polypeptide can be an Fc domain of an immunoglobulin (e.g., IgG1, IgG2 or IgG4), or a modified Fc domain of an immunoglobulin which has, e.g., one or more amino acid substitutions or mutations that alter (e.g., reduce) the effector functions of the Fc domain. An Fc domain can be modified to have reduced ability, e.g., to bind to an Fc receptor, activate the complement system, stimulate an attack by phagocytic cells, or interfere with the physiological metabolism or functioning of retinal cells, or any combination or all thereof. Inclusion of an Fc domain in a fusion protein or chimera can permit dimerization of the fusion protein or chimera (e.g., via formation of an intermolecular disulfide bond between two Fc domains), which may enhance the biological or pharmacological activity of the fusion protein or chimera. Alternatively, a longevity-enhancing heterologous polypeptide can be, e.g., human serum albumin (HSA) or a carboxy-terminal peptide (CTP) derived from the beta chain of human chorionic gonadotropin, such as CTP-001, CTP-002 or CTP-003 as disclosed in WO 2014/159813. As another example, an apo mimetic, such as an apoA-I mimetic (e.g., L-4F) or an apoE mimetic (e.g., AEM-28-14), can be directly or indirectly (e.g., via a linker) attached to a natural or synthetic polymer (e.g., polyethylene glycol [PEG]) at the N-terminus, the C-terminus or/and one or more side chains. PEGylation of an apo mimetic with one or more PEG moieties totaling, e.g., about 1-5 kDa, 5-10 kDa or 10-20 kDa may increase the protease resistance, stability and half-life, reduce the aggregation and increase the solubility of the apo mimetic. As a further example, an apo mimetic can be glycosylated with, e.g., an oligosaccharide or polysaccharide at one or more positions, such as an apoC-III mimetic containing one or more sialic acid residues. As a still further example, an apo mimetic can be phosphorylated. As an additional example, an apo mimetic can be complexed to a phospholipid (e.g., L-4F complexed to DMPC [1,2-dimyristoyl-sn-glycero-3-phosphocholine] or POPC [1-palmitoyl-2-oleoyl-sn-glycero-3-phosphocholine]).

Anti-dyslipidemic agents also include reconstituted high-density lipoprotein (rHDL) mimetics comprising hApoA-I or a variant thereof (e.g., a mutant or/and shortened construct thereof), or an apoA-I mimetic, complexed with one or more phospholipids. ApoA-I is the main protein component of HDL particles. Such reconstituted HDL mimetics can mimic nascent pre-β HDL and perform the biological functions of HDL, including promoting efflux of cholesterol from cells (e.g., via ATP-binding cassette transporters such as ABCA1, ABCG1 and ABCG4), incorporation of cholesterol into HDL particles, and reverse transport of cholesterol from peripheral tissues to the liver for metabolism and biliary excretion of cholesterol. HDL also promotes the clearance and destruction of oxidized lipids (e.g., by transporting them to the liver for metabolism and excretion and by enhancing PON-1 activity), and possesses other antioxidant, anti-inflammatory and anti-apoptotic properties. Therefore, reconstituted HDL mimetics can clear and destroy oxidized lipids and inhibit, e.g., the production of reactive oxygen species, the oxidation of LDL, the expression of pro-inflammatory cytokines and cell adhesion molecules, and apoptosis. Reconstituted HDL mimetics can also comprise hApoA-II or a variant thereof (e.g., a mutant or/and shortened construct thereof), or an apoA-II mimetic, alternative to or in addition to hApoA-I or a variant thereof, or an apoA-I mimetic. ApoA-II is the second most abundant protein in HDL particles. In certain embodiments, reconstituted HDL mimetics are discoidal or disc-shaped. Mature HDL particles destined for the liver are spherical and develop through the formation of intermediate discoidal HDL particles or lipid-poor pre-β HDL particles, which are particularly effective in inducing cholesterol efflux via interaction of apoA-I with ABC transporters such as ABCA1 and are the main acceptors of cholesterol from peripheral cells. Non-limiting examples of phospholipids include those described elsewhere herein. In certain embodiments, the one or more phospholipids are or include one or more phosphatidylcholines, such as DMPC (1,2-dimyristoyl-sn-glycero-3-phosphocholine), PLPC (1-palmitoyl-2-linoleoyl-sn-glycero-3-phosphocholine) or POPC (1-palmitoyl-2-oleoyl-sn-glycero-3-phosphocholine), or any combination or all thereof. Examples of reconstituted HDL mimetics include without limitation 4F/phospholipid(s) complexes (e.g., 4F/DMPC complex, 4F/PLPC complex, and 4F/POPC complex), 5A/phospholipid(s) complexes [e.g., 5A/DMPC complex, 5A/PLPC complex, 5AP (5A/POPC complex), and 5A/sphingomyelin-containing phospholipid(s) complexes], 5A-CH1/POPC complex, 37 pA/phospholipid(s) complexes, ELK-2A/DMPC complex, ELK-2A/POPC complex, ELK-2A2K2E/POPC complex, ELKA-CH2/POPC complex, ETC-642 (ESP-2418 complexed with sphingomyelin [SM] and 1,2-dipalmitoyl-sn-glycero-3-phosphocholine [DPPC]), hApoA-I/phospholipid(s) complexes, hApoA-I/POPC disc complex, CER-001 (recombinant hApoA-I complexed with sphingomyelin and dipalmitoyl phosphatidylglycerol [DPPG]), CSL-111 (hApoA-I/soybean phosphatidylcholine complex), CSL-112 (hApoA-I/phosphatidylcholine complex), ApoA-I Milano/phospholipid(s) complexes (e.g., ETC-216 [MDCO-216, ApoA-I Milano/POPC complex]), and ApoA-I Paris/phospholipid(s) complexes (e.g., ApoA-I Paris/POPC complex). In certain embodiments, the reconstituted HDL mimetic is CSL-112.

In addition to or alternative to the use of an apolipoprotein mimetic, an agent that increases the level of an apolipoprotein (e.g., apoE, apoA-I, apoA-V or apoC-II), e.g., by stimulating its production, can be used. For example, an agent that increases the level of apoA-I (e.g., 1,2-dimyristoyl-α-glycero-3-phosphocholine [DMPC]) can be administered in addition to or alternative to the use of an apoA-I mimetic.

For discussions of apolipoprotein mimetic peptides, including their biological properties, functions and actions, see, e.g., G. Anantharamaiah et al., *Protein Pept. Lett.*, 23:1024-1031 (2016); W. D'Souza et al., *Circ. Res.*, 107: 217-227 (2010); Y. Ikenaga et al., *J. Atheroscler. Thromb.*, 23:385-394 (2016); C. Recio et al., *Front. Pharmacol.*, 7:526 (2017); S. Reddy et al., *Curr. Opin. Lipidol.*, 25:304-308 (2014); O. Sharifov et al., *Am. J. Cardiovasc. Drugs*, 11:371-381 (2011); R. Stoekenbroek et al., *Handb. Exp. Pharmacol.*, 224:631-648 (2015); Y. Uehara et al., *Circ. J.*, 79:2523-2528 (2015); and C. White et al., *J. Lipid Res.*, 55:2007-2021 (2014).

Apolipoprotein mimetic peptides and the other peptides described herein (including cell-penetrating peptides) can be prepared according to procedures known to those of skill in the art. As a non-limiting example, apo mimetics and salts thereof can be prepared by sequentially condensing protected amino acids on a suitable resin support and removing the protecting groups, removing the resin support, and purifying the products by methods known in the art. Solid-phase synthesis of peptides and salts thereof can be facilitated through the use of, e.g., microwave, and can be automated through the use of commercially available peptide synthesizers. Solid-phase synthesis of peptides and salts thereof is described in, e.g., J. M. Palomo, *RSCAdv.*, 4:32658-32672 (2014); M. Amblard et al., *Mol. Biotechnol.*, 33(3):239-254 (2006); and M. Stawikowski and G. B. Fields, *Curr. Protoc. Protein Sci.*, Unit 18.1: Introduction to Peptide Synthesis (2012). Protecting groups suitable for the synthesis of peptides and salts thereof are described in, e.g., P. Wuts and T. Greene, Greene's Protective Groups in Organic Synthesis, $4^{th}$ Ed., John Wiley and Sons (New York 2006). Methods for purifying peptides and salts thereof include without limitation crystallization, column (e.g., silica gel) chromatography, high-pressure liquid chromatograpy (including reverse-phase HPLC), hydrophobic adsorption chromatography, silica gel adsorption chromatography, partition chromatography, supercritical fluid chromatography, counter-current distribution, ion-exchange chromatography, and ion exchange using basic and acidic resins.

Apo mimetics and the other peptides described herein (including CPPs), or salts thereof, are used in substantially pure form. In certain embodiments, a peptide or a salt thereof has a purity of at least about 90%, 95%, 96%, 97%, 98% or 99% (e.g., at least about 95% or 98%). The peptide or salt thereof can be purified—that is, substantially free from undesired chemical or biochemical components resulting from its preparation or isolation that are unsuitable for use in a pharmaceutical formulation, or having a level of such undesired chemical or biochemical components sufficiently low so as not to prevent use of the peptide or salt thereof in a pharmaceutical formulation.

VI. APOA-I MIMETIC 4F

The apoA-I mimetic 4F, including L-4F and D-4F, possesses anti-dyslipidemic properties. For example, L-4F is capable of binding both oxidized lipids and unoxidized lipids with a greater affinity than apoA-I itself and reduces lipid deposits, e.g., in the sub-RPE-BL space and on the Bruch's membrane (BrM). L-4F is a potent lipid acceptor and scavenger that removes extracellular lipids (and potentially intracellular lipids), including neutral lipids, esterified cholesterol and phospholipids, from, e.g., the BrM and the sub-RPE-BL space, thereby improving, e.g., the BrM structure (e.g., reducing the thickness and normalizing the layer arrangement of the BrM) and the BrM function (e.g., decreasing hydraulic resistivity of the BrM and increasing metabolite and micronutrient exchange between the RPE and the choriocapillaris, including facilitating multimolecular complexes carrying such nutrients). Extracellular age-related lipid deposits at, e.g., the BrM form a hydrophobic diffusion barrier that causes oxidative stress and inflammation in, e.g., the RPE and the retina, and removal of such lipid deposits by L-4F curtails such oxidative stress and inflammation.

L-4F possesses additional beneficial properties. For instance, L-4F exhibits a strong anti-inflammatory property, due in part to its high-affinity binding to pro-inflammatory oxidized lipids (e.g., oxidized phospholipids) and fatty acid hydroperoxides and its clearance of such oxidized lipids. L-4F can also enhance the ability of HDL-cholesterol to protect LDL-cholesterol from oxidation, thereby curtailing the formation of pro-inflammatory oxidized lipids. Furthermore, L-4F inhibits complement activation and reduces the levels of complement factor D and the membrane attack complex, which can be additional reasons for its antioxidant and anti-inflammatory properties and can result from its inhibition of downstream effects of lipid deposition. In addition, L-4F has anti-angiogenic property. Extracellular lipid-rich deposits in the sub-RPE-BL space provide a biomechanically fragile, pro-inflammatory milieu into which new blood vessels can enter and propagate, unimpeded by RPE basal lamina connections to the rest of the BrM. Removal of such lipid deposits by L-4F can close up or substantially reduce this pro-angiogenic cleavage plane.

In a study conducted on a macaque model of human early AMD and described below, L-4F demonstrated an effective ability to scavenge neutral lipids and esterified cholesterol, to rejuvenate/normalize the BrM, and to curtail downstream effects of lipid deposition such as complement activation and local inflammation. L-4F also appeared to effectively scavenge phospholipids, a major source of pro-inflammatory oxidized lipids, although staining for phospholipids was not done in the study. The results of the macaque study are expected to be translatable to all stages and forms of AMD in humans in which extracellular lipid deposits play a pathological role, including early AMD, intermediate AMD and advanced AMD, and including atrophic AMD and neovascular AMD. In humans, oil red O-binding neutral lipids greatly accumulate in the macular BrM and the sub-RPE-BL space throughout adulthood and are components of drusen, and esterified cholesterol and phospholipids (in the form of lipoprotein particles of 60-80 nm diameter) also greatly accumulate in the macular BrM and the sub-RPE-BL space throughout adulthood and eventually aggregate as BLinD on the BrM or soft drusen in the sub-RPE-BL space of older eyes. Drusen are rich in esterified cholesterol and phospholipids, attributed to the core and the surface, respectively, of RPE-secreted lipoproteins. Furthermore, because lipoproteins (both native and modified) in drusen are not bound to structural collagen and elastin fibrils, unlike lipoproteins in the BrM, the former are more loosely bound than the latter and hence are easier to remove. Therefore, the great reduction of filipin-binding esterified cholesterol and oil red O-binding neutral lipids from the BrM in the macaque study demonstrates the ability of L-4F to effectively reduce soft drusen and scavenge lipids, including neutral lipids and esterified cholesterol, from eye tissues, including the BrM. Although the RPE has active proteases, intravitreally injected L-4F readily crossed the RPE and reached the BrM, and effectively removed lipid deposits from the BrM in the macaque study. Removal of lipid deposits from the BrM by L-4F normalizes the structure and function of the BrM. In addition, reduction of drusen volume by L-4F can decrease elevation of the RPE layer off the BrM and thereby can reduce metamorphopsia, and can prevent, delay the onset of or slow the progression of non-central or central geographic atrophy (GA) and thereby can improve vision. Reduction of drusen volume in humans can be readily quantified using spectral domain optical coherence tomography (SDOCT) and commercially available software.

By reducing lipid deposits, L-4F can maintain or improve the health of the RPE and thereby can prevent or forestall RPE atrophy, including in non-central and central GA. Soft drusen and drusenoid pigment epithelial detachments (PED) grow over time because RPE cells continue to secrete lipoproteins. The RPE layer over the drusen and drusenoid PED roughens over time, and RPE cells migrate out of the RPE layer and anteriorly into the neurosensory retina, preferentially over the apices, where the RPE cells are farther from the choriocapillaris and thus seek oxygen from the retinal circulation. By removing native and modified lipids from drusen, L-4F can prevent the anterior migration of RPE cells and thereby can keep RPE cells sufficiently close to the choriocapillaris so that RPE cells are not energetically and metabolically decompensated and hence do not atrophy. Furthermore, removal of lipid deposits from the BrM improves the transport of incoming oxygen and micronutrients (including vitamin A) and outgoing waste between the choriocapillaris and the RPE. By reducing drusen and removing lipid deposits from the BrM, L-4F can maintain RPE health and forestall RPE atrophy, and thereby can preserve photoreceptors and vision. Health of the RPE overlying drusen can be monitored by SDOCT of the macula.

Reduction of lipid deposits had downstream benefits in the macaque study, including a great decrease in the number of membrane attack complexes (MAC) present in the BrM and the choriocapillaris. The MAC (C5b-9) is the final product of activation of the complement system, and builds up in the BrM-choriocapillaris complex during a person's lifespan, starting in childhood. By decreasing the level of MAC, L-4F can improve the health of the BrM and the choriocapillaris endothelium, and thereby can improve the blood supply to the outer retina and oxygen and micronutrient exchange between the choriocapillaris and the RPE and can promote the clearing of lipoprotein particles secreted by the RPE into the systemic circulation.

In addition, by removing lipids L-4F can prevent or forestall neovascularization (NV). Basal linear deposits and soft drusen are major sources of potentially pro-inflammatory lipids in the sub-RPE-BL space where type 1 NV, the most common type of NV, occurs. Removal of native lipids, including esterified cholesterol in lipoprotein deposits, from eye tissues by L-4F, as demonstrated in the macaque study, reduces the amount of native lipids available for modifications such as peroxidation. Modified lipids, including peroxidized lipids, can be strongly pro-inflammatory and thus can stimulate NV. L-4F can also scavenge any peroxidized lipids and other modified lipids formed. Furthermore, by reducing the bulk size of drusen, L-4F can prevent the migration of RPE cells away from the oxygen- and nutrient-transporting choriocapillaris and hence their secretion of distress-induced VEGF, a potent stimulus of NV. Moreover, normalization of the BrM as a result of removal of lipid deposits from the BrM by L-4F suppresses choroidal NV by reinforcing the natural barrier between the choriocapillaris and the sub-RPE-BL space. Therefore, through its ability to scavenge native lipids and modified (e.g., oxidized) lipids, L-4F can prevent or curtail NV, including type 1 NV, and can improve the treatment of neovascular AMD, and reduce the treatment burden, with anti-angiogenic agents, including intravitreally injected anti-VEGF agents.

The disclosure provides for the use of 4F or a variant or a pharmaceutically acceptable salt (e.g., acetate salt) thereof in the prevention or treatment of AMD, including pre-AMD, the early, intermediate and advance stages of AMD, and atrophic AMD and neovascular AMD. In some embodiments, all the amino acid residues of 4F have the L-stereochemistry (L-4F). In other embodiments, one or more, or all, of the amino acid residues of 4F have the D-stereochemistry (e.g., D-4F having all D-amino acids). In yet other embodiments, a 4F variant has the reverse order of amino acid sequence of 4F (e.g., Rev-L-4F or Rev-D-4F). 4F or a variant thereof can have a protecting group at the N-terminus or/and the C-terminus, such as an acyl (e.g., acetyl) group at the N-terminus or/and an amide group (e.g., —C(O)NH$_2$) at the C-terminus. In certain embodiments, L-4F or D-4F has the structure Ac-DWFKAFYDKVAEKFKEAF-NH$_2$ (SEQ ID NO: 1). When folded into the appropriate secondary structure, L-4F is an amphipathic α-helix that has opposing polar and hydrophobic faces and mimics apoA-I, the predominant apolipoprotein of HDL.

In some embodiments, 4F (e.g., L-4F or D-4F) or a variant or salt thereof is mixed with, non-covalently associated with or covalently bonded to a cell-penetrating peptide, is encapsulated in CPP-conjugated nanoparticles, micelles or liposomes, or is coupled to a small-molecule α-helix mimic (e.g., 2G-SMoC or 4G-SMoC). In other embodiments, 4F (e.g., L-4F or D-4F) or a variant or salt thereof has a membrane translocation-conferring modification (e.g., stapling, prenylation or lipidation).

VII. STATINS

Like apolipoprotein mimetics, statins are anti-dyslipidemic agents. Statins inhibit HMG-CoA reductase, the enzyme that catalyzes the rate-limiting step in cholesterol biosynthesis, and thereby inhibit cholesterol biosynthesis in eye tissues (e.g., the RPE) and other tissues (e.g., the liver) that are potential sources of cholesterol in the eye. In addition, statins reduce apoB synthesis and secretion, decrease the production of apoB-containing VLDLs and LDLs, increase the level of liver LDL receptors, and lower the plasma level of lipids (e.g., LDL-cholesterol) available for uptake into the eye. Since drusen are extracellular deposits rich in lipids (including esterified cholesterol [EC]) and lipoprotein components (including apoB) and form in the sub-RPE-BL space possibly as a result of RPE secretion of EC-rich VLDLs basolaterally, statins can reduce drusen (including large soft drusen) deposits and thereby can prevent or resolve drusenoid pigment epithelial detachments (PEDs). Drusen are rich sources of lipids that are susceptible to oxidation, and oxidized lipids can be highly pro-inflammatory and thus pro-angiogenic. Furthermore, confluent soft drusen form a hydrophobic diffusion barrier that impedes the exchange of incoming oxygen and nutrients and outgoing waste between the choriocapillaris and RPE cells, which can lead to the atrophy and death of RPE cells and photoreceptors. In addition, cholesterol crystals and oxidized LDLs impair the phagocytic function of RPE cells and induce the secretion of pro-inflammatory IL-6 and IL-8 from RPE cells. Therefore, by tackling an important upstream cause of AMD, lipid accumulation, statins can prevent or curtail sequelae such as inflammation, geographic atrophy and neovascularization, and thereby can improve vision (e.g., visual acuity). Independent of or perhaps in part due to their lipid-lowering properties, statins increase the phagocytic function of RPE cells (e.g., by increasing the cell membrane fluidity of RPE cells) and possess antioxidant properties (e.g., reduce oxidative stress-induced injury to RPE cells), anti-inflammatory properties (e.g., decrease the levels of pro-inflammatory IL-6 and IL-8), and anti-angiogenic properties (e.g., downregulate VEGF expression and reduce laser-induced choroidal neovascularization).

The disclosure provides for the use of a statin or a pharmaceutically acceptable salt thereof in the prevention or treatment of AMD, including pre-AMD, the early, intermediate and advance stages of AMD, and atrophic AMD and neovascular AMD. Like treatment with an apo mimetic (e.g., an apoA-I mimetic such as L-4F or D-4F, or an apoE mimetic such as AEM-28-14), beneficial effects of treatment with a statin include, but are not limited to:

1) reduction of drusen (including soft drusen) size (e.g., diameter or volume), number or amount (e.g., by at least about 50%, 60%, 70%, 80%, 90%, 95% or 99%);

2) prevention or resolution of drusenoid PEDs (e.g., promotion of re-attachment of the RPE-BL to the BrM ICL, or flattening of a PED or decrease in the separation/distance between the detached RPE-BL and the BrM ICL by at least about 50%, 60%, 70%, 80%, 90%, 95% or 99%);

3) enhancement of the phagocytic function (e.g., phagocytosis of drusen and other undesired matter) of RPE cells (e.g., increase in the percentage of phagocytic RPE cells by at least about 33%, 50%, 66%, 80% or 100%);

4) prevention or curtailment of atrophy and death of RPE cells and photoreceptors (e.g., reduction of the area of non-central or/and central geographic atrophy by at least about 30%, 40%, 50%, 60%, 70%, 80% or 90%);

5) prevention or forestalling of progression to or development of intermediate atrophic AMD, advanced atrophic AMD or neovascular AMD;

6) prevention or curtailment of vision loss [e.g., reduction of loss of visual acuity to no more than about 5, 4, 3, 2 or 1 letter(s)]; and 7) improvement of visual acuity (e.g., by at least about 3, 6, 9 or 12 letters).

Examples of statins include without limitation atorvastatin, cerivastatin, fluvastatin, mevastatin, monacolins (e.g., monacolin K [lovastatin]), pitavastatin, pravastatin, rosuvastatin, simvastatin, and analogs, derivatives and salts thereof. In some embodiments, the statin is a substantially hydrophobic/lipophilic statin or a salt thereof. Examples of substantially hydrophobic/lipophilic statins include, but are not limited to, atorvastatin, lovastatin, mevastatin and simvastatin. In certain embodiments, the statin is atorvastatin or a salt (e.g., calcium salt) thereof, or simvastatin.

In some embodiments, a statin is mixed with, non-covalently associated with or covalently bonded to a cell-penetrating peptide, is encapsulated in CPP-modified nanoparticles, micelles or liposomes, or is conjugated to a small-molecule α-helix mimic (e.g., 2G-SMoC or 4G-SMoC). In other embodiments, a statin has a membrane translocation-conferring modification (e.g., prenylation or lipidation).

VIII. THERAPEUTIC AGENTS

As described above, AMD has a variety of underlying factors, including formation of lipid-rich deposits, formation of toxic byproducts, oxidation, inflammation, neovascularization and cell death. One or more therapeutic agents targeting one or more underlying factors of AMD, or having different mechanisms of action, can be utilized for the treatment of AMD. Therapeutic agents that can be used, optionally in combination with an apolipoprotein mimetic or/and a statin, to treat AMD include without limitation:

1) anti-dyslipidemic agents;
2) PPAR-α agonists, PPAR-δ agonists and PPAR-γ agonists;
3) anti-amyloid agents and inhibitors of other toxic substances (e.g., aldehydes);
4) inhibitors of lipofuscin or components thereof;
5) visual/light cycle modulators and dark adaptation agents;
6) antioxidants;
7) neuroprotectors (neuroprotectants);
8) apoptosis inhibitors and necrosis inhibitors;
9) C-reactive protein (CRP) inhibitors;
10) inhibitors of the complement system or components (e.g., proteins) thereof;
11) inhibitors of inflammasomes;
12) anti-inflammatory agents;
13) immunosuppressants;
14) modulators (inhibitors and activators) of matrix metalloproteinases (MMPs) and other inhibitors of cell migration;
15) anti-angiogenic agents;
16) low-level light therapies, laser therapies, photodynamic therapies and radiation therapies;
17) agents that preserve or improve the health of the endothelium or/and the blood flow of the vascular system of the eye; and
18) cell (e.g., RPE cell) replacement therapies.

A particular therapeutic agent may exert more than one biological or pharmacological effect and may be classified in more than one category.

A therapeutic agent is used in a therapeutically effective amount. When used in combination with another therapeutic agent (e.g., an apolipoprotein mimetic or a statin), a therapeutic agent can be administered substantially concurrently with the other therapeutic agent (such as during the same doctor's visit, or within about 30 or 60 minutes of each other), or prior to or subsequent to administration of the other therapeutic agent. When administered concurrently with another therapeutic agent, a therapeutic agent can be administered in the same formulation or in separate formulations as the other therapeutic agent.

Formation of lipid-rich deposits is an important upstream cause of AMD that leads to complications such as non-central and central geographic atrophy and neovascularization. One multi-pronged approach to preventing or minimizing the accumulation of lipid-rich material is to inhibit the production of lipids (e.g., cholesterol and fatty acids) and lipoproteins (e.g., VLDLs) by RPE cells, to inhibit the uptake of plasma lipids (e.g., cholesterol and fatty acids) and lipoproteins (e.g., VLDLs) by RPE cells, to inhibit the secretion of lipids (e.g., cholesterol and fatty acids) and lipoproteins (e.g., VLDLs) and components thereof (e.g., apoB and apoE) by RPE cells into the BrM, the sub-RPE-BL space and the subretinal space, and to clear lipids (e.g., cholesterol and oxidized lipids) and lipoproteins (e.g., VLDLs) and components thereof (e.g., apoB and apoE) from the BrM, the sub-RPE-BL space and the subretinal space. For example, apoB is involved in the formation of at least hepatic VLDL, which is the parent of at least plasma LDL. Inhibition of apoB production by RPE cells and inhibition of the uptake by RPE cells of fatty acids available to lipidate apoB could curtail the production of VLDLs, and hence possibly LDLs, by RPE cells.

Anti-dyslipidemic agents modulate inter alia the production, uptake and clearance of lipids, lipoproteins and other substances that play a role in the formation of lipid-containing deposits in the retina, the subretinal space, the sub-RPE-BL space, and the choroid (e.g., the BrM). Anti-dyslipidemic apolipoprotein mimetics and statins are described above. Another class of anti-dyslipidemic agents is fibrates, which activate peroxisome proliferator-activated receptor-alpha (PPAR-α). Fibrates are hypolipidemic agents that reduce fatty acid and triglyceride production, induce lipoprotein lipolysis but stimulate the production of high-density lipoprotein (HDL, which mediates reverse cholesterol transport), increase VLDL and LDL removal from plasma, and stimulate reverse cholesterol transport from peripheral cells or tissues to the circulation and ultimately the liver, where cholesterol is metabolized and excreted into the bile. Examples of fibrates include without limitation bezafibrate, ciprofibrate, clinofibrate, clofibric acid, clofibrate, aluminum clofibrate (alfibrate), clofibride, etofibrate, fenofibric acid, fenofibrate, gemfibrozil, ronifibrate, simfibrate, and analogs, derivatives and salts thereof. Other hypotriglyceridemic agents include omega-3 fatty acids (e.g., docosahexaenoic acid [DHA], docosapentaenoic acid [DPA], eicosapentaenoic acid [EPA], α-linolenic acid [ALA], and fish oil [which contains, e.g., DHA and EPA]) and esters (e.g., glyceryl and ethyl esters) thereof. Omega-3 fatty acids and esters thereof are also anti-inflammatory (e.g., they inhibit cyclooxygenase and 5-lipoxygenase and hence the synthesis of prostanglandins and leukotrienes, respectively, and they inhibit the activation of NF-κB and hence the expression of pro-inflammatory cytokines such as IL-6 and TNF-α).

Lipid-lowering agents further include pro-protein convertase subtilisin/kexin type 9 (PCSK9) inhibitors. PCSK9 inhibitors increase expression of the LDL receptor on hepatocytes by enhancing LDL receptor recycling to the cell membrane surface of hepatocytes, where the LDL receptor binds to and initiates ingestion of LDL particles transporting lipids such as cholesterol. Examples of PCSK9 inhibitors include without limitation berberine (which decreases PCSK9 level), annexin A2 (which inhibits PCSK9 activity), anti-PCSK9 monoclonal antibodies (e.g., alirocumab, bococizumab, evolocumab, LGT-209, LY3015014 and RG7652), peptides that mimic the epidermal growth factor-A (EGF-A) domain of the LDL receptor which binds to PCSK9, PCSK9-binding adnectins (e.g., BMS-962476), anti-sense polynucleotides and anti-sense peptide-nucleic acids (PNAs) that target mRNA for PCSK9, and PCSK9-targeting siRNAs (e.g., inclisiran [ALN-PCS] and ALN-PCS02).

Anti-sense polynucleotides and anti-sense PNAs are single-stranded, highly specific, complementary sequences that bind to the target mRNA and thereby promote degradation of the mRNA by an RNase H. Small interfering RNAs (siRNAs) are relatively short stretches of of double-stranded RNA that are incorporated into the RNA-induced silencing complex (RISC) present in the cytoplasm of cells and bind to the target mRNA, thereby resulting in degradation of the mRNA by a RISC-dependent mechanism. The greater the length of complementarity between the siRNA and the target mRNA, the greater the specificity of the siRNA for the target mRNA.

Cholesterol can also be cleared through, e.g., the removal of HDL-cholesteryl ester by the gut. Lecithin-cholesterol acyltransferase (LCAT), a plasma enzyme that is activated by, e.g., apolipoprotein A-I, converts free cholesterol into cholesteryl ester, which is then sequestered into the core of HDL particles. Therefore, LCAT activators increase HDL-cholesteryl ester level and are anti-dyslipidemic. Apolipoproteins A-I and E are major physiological activators of LCAT. Hence, LCAT activators include without limitation apoA-I and apoE and derivatives, fragments and analogs thereof, including apoA-I mimetics and apoE mimetics.

Acetyl-CoA carboxylase (ACC) inhibitors can also be used as anti-dyslipidemic agents. ACC inhibitors inhibit fatty acid and triglyceride (TG) synthesis and decrease VLDL-TG secretion. Non-limiting examples of ACC inhibitors include anthocyanins, avenaciolides, benzodioxepines {e.g., 7-(4-propyloxy-phenylethynyl)-3,3-dimethyl-3,4 dihydro-2H-benzo[b][1,4]dioxepine}, benzothiophenes [e.g., N-ethyl-N'-(3-{[4-(3,3-dimethyl-1-oxo-2-oxa-7-azaspiro[4.5]dec-7-yl)piperidin-1-yl]-carbonyl}-1-benzothien-2-yl)urea], bis-piperidinylcarboxamides (e.g., CP-640186), chloroacetylated biotin, cyclodim, diclofop, haloxyfop, biphenyl- and 3-phenyl pyridines, phenoxythiazoles {e.g., 5-(3-acetamidobut-1-ynyl)-2-(4-propyloxyphenoxy)thiazole}, piperazine oxadiazoles, (4-piperidinyl)-piperazines, soraphens (e.g., soraphen $A_{1\alpha}$), spiro-piperidines, spiro-pyrazolidinediones, spiro[chroman-2,4'-piperidin]-4-ones, 5-(tetradecyloxy)-2-furancarboxylic acid (TOFA), thiazolyl phenyl ethers, thiophenes [e.g., 1-(3-{[4-(3,3-dimethyl-1-oxo-2-oxa-7-azaspiro[4.5]dec-7-yl)piperidin-1-yl]-carbonyl}-5-(pyridin-2-yl)-2-thienyl)-3-ethylurea], and analogs, derivatives and salts thereof.

Anti-dyslipidemic agents also include inhibitors of acyl-CoA cholesterol acyltransferase (ACAT) (also called sterol O-acyltransferase [SOAT]), including ACAT1 (SOAT1) and ACAT2 (SOAT2). ACAT inhibitors inhibit cholesterol esterification, decrease the production and secretion of VLDL and LDL apoB (or the production and secretion of apoB-containing VLDLs and LDLs), and stimulate HDL-mediated cholesterol efflux from cells. Examples of ACAT inhibitors include without limitation avasimibe, octimibate, pactimibe, pellitorine, terpendole C, and analogs, derivatives and salts thereof.

Other anti-dyslipidemic agents include inhibitors of stearoyl-CoA desaturase-1 (SCD-1) (also called stearoyl-CoA delta-9 desaturase). SCD-1 is an endoplasmic reticulum enzyme that catalyzes the formation of a double bond in stearoyl-CoA and palmitoyl-CoA, the rate-limiting step in the formation of the mono-unsaturated fatty acids oleate and palmitoleate from stearoyl-CoA and palmitoyl-CoA, respectively. Oleate and palmitoleate are major components of cholesterol esters, alkyl-diacylglycerol and phospholipids. Examples of inhibitors of SCD-1 activity or expression include CAY-10566, CVT-11127, benzimidazole-carboxamides (e.g., SAR-224), hexahydro-pyrrolopyrroles (e.g., SAR-707), 3-(2-hydroxyethoxy)-N-(5-benzylthiazol-2-yl)-benzamides {e.g., 3-(2-hydroxyethoxy)-4-methoxy-N-[5-(3-trifluoromethylbenzyl)thiazol-2-yl]benzamide and 4-ethylamino-3-(2-hydroxyethoxy)-N-[5-(3-trifluoromethylbenzyl)thiazol-2-yl]benzamide}, piperazin-1-ylpyridazine-based compounds (e.g., XEN-103), spiropiperidine-based compounds {e.g., 1'-{6-[5-(pyridin-3-ylmethyl)-1,3,4-oxadiazol-2-yl]pyridazin-3-yl}-5-(trifluoromethyl)-3,4-dihydrospiro[chromene-2,4'-piperidine] and 5-fluoro-1'-{6-[5-(pyridin-3-ylmethyl)-1,3,4-oxadiazol-2-yl]pyridazin-3-yl}-3,4-dihydrospiro[chromene-2,4'-piperidine]}, 5-alkyl-4,5-dihydro-3H-spiro[1,5-benzoxazepine-2,4'-piperidine]-based compounds {e.g., 6-[5-(cyclopropylmethyl)-4,5-dihydro-1'H,3H-spiro[1,5-benzoxazepine-2,4'-piperidin]-1'-yl]-N-(2-hydroxy-2-pyridin-3-ylethyl)pyridazine-3-carboxamide}, benzoylpiperidine-based compounds {e.g., 6-[4-(2-methylbenzoyl)piperidin-1-yl]pyridazine-3-carboxylic acid (2-hydroxy-2-pyridin-3-ylethyl)amide}, piperidine-aryl urea-based compounds {e.g., 4-(2-chlorophenoxy)-N-[3-(methyl carbamoyl)phenyl]piperidine-1-carboxamide}, 1-(4-phenoxypiperidin-1-yl)-2-arylaminoethanone-based compounds, the cis-9,trans-11 isomer and the trans-10,cis-12 isomer of conjugated linoleic acid, substituted heteroaromatic compounds disclosed in WO 2009/129625 A1, SCD-1-targeting anti-sense polynucleotides and peptide-nucleic acids, SCD-1-targeting siRNAs, and analogs, derivatives and salts thereof.

Another class of anti-dyslipidemic agents is glucagon-like peptide-1 (GLP-1) receptor agonists. GLP-1 receptor agonists reduce the production of apoB and VLDL particles and hence VLDL-apoB and VLDL-TG, decrease the cellular content of cholesterol and triglycerides, and reduce or reverse hepatic steatosis (fatty liver) by decreasing hepatic lipogenesis. Non-limiting examples of GLP-1 receptor agonists include exendin-4, albiglutide, dulaglutide, exenatide, liraglutide, lixisenatide, semaglutide, taspoglutide, CNTO736, CNTO3649, HM11260C (LAPS-Exendin), NN9926 (OG9S7GT), TT401, ZY0G1, and analogs, derivatives and salts thereof. Because GLP-1, the endogenous ligand of the GLP-1 receptor, is rapidly degraded by dipeptidyl peptidase 4 (DPP-4), anti-dyslipidemic effects similar to those of GLP-1 receptor agonists can be achieved with the use of a DPP-4 inhibitor, albeit with potentially lower potency. Non-limiting examples of DPP-4 inhibitors include alogliptin, anagliptin, dutogliptin, evogliptin, gemigliptin, gosogliptin, linagliptin, omarigliptin, saxagliptin, septagliptin, sitagliptin, teneligliptin, trelagliptin, vildagliptin, berberine, lupeol, and analogs, derivatives and salts thereof.

Additional anti-dyslipidemic agents include inhibitors of the microsomal triglyceride transfer protein (MTTP), which is expressed predominantly in hepatocytes and enterocytes but also in RPE cells. MTTP catalyzes the assembly of cholesterol, triglycerides and apoB to chylomicrons and VLDLs. MTTP inhibitors inhibit the synthesis and secretion of apoB-containing chylomicrons and VLDLs. Examples of MTTP inhibitors include, but are not limited to, microRNAs (e.g., miRNA-30c), MTTP-targeting anti-sense polynucleotides and anti-sense PNAs, implitapide, lomitapide, dirlotapide, mitratapide, CP-346086, JTT-130, SLx-4090, and analogs, derivatives and salts thereof. Systemic administration of an MTTP inhibitor may result in hepatic steatosis (e.g., accumulation of triglycerides in the liver), which can be averted by, e.g., local administration of the MTTP inhibitor, use of an MTTP inhibitor that is not systemically absorbed (e.g., SLx-4090), or co-administration of a GLP-1 receptor agonist, or any combination or all thereof. Another option for avoiding hepatic steatosis is the use of miRNA-30c. One region of the sequence of miRNA-30c decreases MTTP expression and apoB secretion, and another region decreases fatty acid synthesis, with no deleterious effect to the liver.

MicroRNAs are relatively short non-coding RNAs that target one or more mRNAs in the same pathway or different biological pathways and silence the mRNA(s). MicroRNAs resemble siRNAs of the RNA interference (RNAi) pathway, except that miRNAs derive from regions of RNA transcripts that fold back on themselves to form short hairpins, whereas siRNAs derive from longer regions of double-stranded RNA. Although either strand of the miRNA duplex formed by the RNase III enzyme Dicer may potentially act as a functional miRNA, only one strand is usually incorporated into the RISC. The mature miRNA becomes part of an active RISC containing Dicer and many associated proteins including Argonaute proteins (e.g., Ago1/2). Argonaute proteins are important for miRNA-induced silencing and bind the mature miRNA and orient it for interaction with the target mRNA(s). Certain Argonaute proteins (e.g., Ago2) cleave mRNAs directly. The mature miRNA binds to the target mRNA(s), resulting in silencing of the mRNA(s) via cleavage of the mRNA(s), destabilization of the mRNA(s) through shortening of their poly(A) tail, or/and less efficient translation of the mRNA(s) into proteins by ribosomes.

Other kinds of anti-dyslipidemic agents include anti-sense polynucleotides and anti-sense peptide-nucleic acids (PNAs) that target mRNA for apoB, including apoB48 and apoB100. ApoB is important in the formation of VLDLs and subsequently LDLs. Use of an anti-sense polynucleotide or PNA wholly or partially (e.g., at least about 50%, 60%, 70%, 80%, 90% or 95%) complementary to mRNA for apoB blocks translational expression of apoB and hence the production of VLDLs and LDLs. Examples of anti-sense polynucleotides targeting mRNA for apoB include without limitation mipomersen. Anti-sense polynucleotides and anti-sense PNAs can also target mRNA for apoC-III. ApoC-III is a component of VLDLs, inhibits lipoprotein lipase and hepatic lipase, and acts to reduce hepatic uptake of triglycerides, thereby causing hypertriglyceridemia.

Anti-sense polynucleotides and anti-sense PNAs can regulate gene expression by targeting miRNAs as wells as mRNAs. For example, miRNA-33a and miRNA-33b repress the expression of the ATP-binding cassette transporter ABCA1 (cholesterol efflux regulatory protein [CERP]), which mediates the efflux of cholesterol and phospholipids. Use of an anti-sense polynucleotide or PNA wholly or partially (e.g., at least about 50%, 60%, 70%, 80%, 90% or 95%) complementary to miRNA-33a or/and miRNA-33b increases reverse cholesterol transport and HDL production and decreases VLDL-TG production, fatty acid production and oxidation. Increased expression of ABCA1 is also protective against angiogenesis in AMD. As another example, overexpression of miRNA-122 increases cholesterol synthesis, and hence use of an anti-sense polynucleotide or PNA targeting miRNA-122 decreases cholesterol synthesis, including in the liver.

Peptide-nucleic acids present advantages as anti-sense DNA or RNA mimics. In addition to binding to RNA or DNA targets in a sequence-specific manner with high affinity, PNAs can possess high stability and resistance to nucleases and proteases.

Furthermore, cholesterylester transfer protein (CETP) inhibitors can be used as anti-dyslipidemic agents. CETP transfers cholesterol from HDLs to VLDLs and LDLs. CETP inhibitors increase HDL-cholesterol level, decrease VLDL-cholesterol and LDL-cholesterol levels, and increase reverse cholesterol transport from peripheral cells or tissues to the circulation and ultimately the liver, where cholesterol is metabolized and excreted into the bile. Examples of CETP inhibitors include, but are not limited to, anacetrapib, dalcetrapib, evacetrapib, torcetrapib, AMG 899 (TA-8995) and analogs, derivatives and salts thereof.

Other anti-dyslipidemic agents that increase cellular lipid (e.g., cholesterol) efflux include liver X receptor (LXR) agonists and retinoid X receptor (RXR) agonists. LXR heterodimerizes with the obligate partner RXR. The LXR/RXR heterodimer can be activated with either an LXR agonist or an RXR agonist. Activation of the LXR/RXR heterodimer decreases fatty acid synthesis, increases HDL-cholesterol level and increases lipid (e.g., cholesterol) efflux from cells to the circulation and ultimately the liver, where lipids are metabolized and excreted into the bile. Non-limiting examples of LXR agonists include endogenous ligands such as oxysterols {e.g., 22(R)-hydroxycholesterol, 24(S)-hydroxycholesterol, 27-hydroxycholesterol and cholestenoic acid}, synthetic agonists such as acetyl-podocarpic dimer, hypocholamide, N,N-dimethyl-3β-hydroxy-cholenamide (DMHCA), GW3965, T0901317, and analogs, derivatives and salts thereof. Non-limiting examples of RXR agonists include endogenous ligands such as 9-cis-retinoic acid, and synthetic agonists such as bexarotene, AGN 191659, AGN 191701, AGN 192849, BMS649, LG100268, LG100754, LGD346, and analogs, derivatives and salts thereof.

PPAR-α agonists and PPAR-γ agonists can also be used to treat AMD. The hypolipidemic effects of the PPAR-α-activating fibrates are described above. Fibrates also decrease the expression of vascular endothelial growth factor (VEGF) and VEGF receptor 2 (VEGFR2), which play an important role in the development of neovascularization, including CNV. Examples of PPAR-α agonists include, but are not limited to, fibrates and perfluoroalkanoic acids (e.g., perfluorooctanoic acid and perfluorononanoic acid). PPAR-γ-activating thiazolidinediones also have anti-dyslipidemic effects. Like LXR, PPAR-γ heterodimerizes with RXR. Thiazolidinediones decrease the level of lipids (e.g., fatty acids and triglycerides), increase the level of HDLs (which mediate reverse cholesterol transport), and increase the efflux of lipids (e.g., cholesterol) from cells to the circulation and ultimately the liver, where lipids are metabolized and excreted into the bile. Like fibrates, thiazolidinediones also inhibit VEGF-induced angiogenesis. Examples of PPAR-γ agonists include without limitation thiazolidinediones (e.g., balaglitazone, ciglitazone, darglitazone, englitazone, lobeglitazone, netoglitazone, pioglitazone, rivoglitazone, rosiglitazone and troglitazone), rhodanine, berberine, honokiol, perfluorononanoic acid, and analogs, derivatives and salts thereof.

Other anti-dyslipidemic PPAR modulators include PPAR-δ agonists. PPAR-δ agonists increase HDL level, reduce VLDL level, and increase the expression of cholesterol efflux transporters (e.g., ABCA1). Non-limiting examples of PPAR-δ agonists include GFT505 (a dual PPAR-α/δ agonist), GW0742, GW501516, sodelglitazar (GW677954), MBX-8025, and analogs, derivatives and salts thereof.

Anti-dyslipidemic agents also include inhibitors of bromodomain and extra-terminal domain (BET) proteins such as BRD2, BRD3, BRD4 and BRDT. A non-limiting example of a BET (viz., BRD4) inhibitor is apabetalone (RVX-208), which increases HDL and HDL-cholesterol levels, increases cholesterol efflux and reverse cholesterol transport, stimulates the production of apoA-I (the main protein component of HDL), and is also anti-inflammatory.

Another way to increase cholesterol efflux from cells is to increase the level of cardiolipin in the inner mitochondrial membrane. Increased cardiolipin content may also prevent or curtail mitochondrial dysfunction. A non-limiting example of agents that increase the level of cardiolipin in the inner mitochondrial membrane is elamipretide (MTP-131), a cardiolipin peroxidase inhibitor and a mitochondria-targeting peptide.

If systemic administration of an inhibitor of a lipid-modulating enzyme or an anti-dyslipidemic agent that increases lipid efflux (e.g., reverse cholesterol transport) results in hepatic steatosis or abnormal levels of lipids in the blood, or risks doing so, hepatic steatosis or abnormal levels of lipids in the blood can be averted or treated by, e.g., local administration of the enzyme inhibitor or the anti-dyslipidemic agent to the eye, co-use of an agent that reduces or reverses hepatic steatosis, or co-use of an agent that decreases lipid levels in the blood, or any combination or all thereof. Examples of agents that reduce or reverse hepatic steatosis include without limitation agents that reduce hepatic lipogenesis, such as GLP-1 receptor agonists, which can be administered, e.g., systemically for this purpose. A non-limiting example of agents that decrease lipid levels in the blood is statins, which can be administered systemically for this purpose.

Other compounds that bind to and neutralize or/and facilitate clearance of lipids and toxic lipid byproducts (e.g., oxidized lipids) can also be used. For example, cyclodextrins have a hydrophilic exterior but a hydrophobic interior, and hence can form water-soluble complexes with hydrophobic molecules. Therefore, cyclodextrins, including α-cyclodextrins (6-membered sugar ring molecules), β-cyclodextrins (7-membered sugar ring molecules), γ-cyclodextrins (8-membered sugar ring molecules) and derivatives thereof (e.g., methyl-β-cyclodextrin), can form water-soluble inclusion complexes with lipids (e.g., cholesterol) and toxic lipid byproducts (e.g., oxidized lipids) and thereby can neutralize their effect or/and facilitate their removal.

Another kind of anti-dyslipidemic agents is endoplasmic reticulum (ER) modulators that restore proper ER function, including without limitation azoramide. The ER plays an important role in lipid metabolism. ER dysfunction and chronic ER stress are associated with many pathologies, including obesity and inflammation. Azoramide improves ER protein-folding ability and activates ER chaperone capacity to protect cells against ER stress.

AMD reportedly is associated with extracellular deposits of apoE and amyloid-beta (Aβ), including in drusen. Aβ deposits reportedly are involved in inflammatory events. For instance, amyloid-β reportedly induces the production of the pro-inflammatory cytokines IL-1β and TNF-α by macrophages and microglia, which can increase the expression of complement factor B in RPE cells and may contribute to AMD progression. Accordingly, anti-amyloid agents (e.g., inhibitors of Aβ formation or aggregation into plaques/ deposits, and promoters of Aβ clearance) can potentially be useful for treating AMD. Examples of anti-amyloid agents (e.g., anti-Aβ agents) include without limitation anti-Aβ antibodies (e.g., bapineuzumab, solanezumab. GSK-933776 [it also reduces complement C3a deposition in the BrM], RN6G [PF4382923], AN-1792, 2H6 and deglycosylated 2H6), anti-apoE antibodies (e.g., HJ6.3), apoE mimetics (e.g., AEM-28), cystatin C, berberine, L-3-n-butylphthalide, T0901317, and analogs, derivatives, fragments and salts thereof.

Elevated levels of other toxic byproducts are also associated with AMD. For example, elevated levels of toxic aldehydes such as 4-hydroxynonenal (HNE) and malondialdehyde (MDA) are present in patients with AMD, particularly atrophic AMD. An agent that inhibits the formation of toxic aldehydes, binds to them and lowers their level, or promotes their breakdown or clearance, such as the aldehyde trap NS2, can be used to treat AMD.

In addition, with age lipofuscin and components thereof (e.g., A2E) reportedly accumulate in the RPE as a byproduct of visual cycling. Lipofuscin is pro-inflammatory, and the lipofuscin bisretinoid A2E reportedly inhibits lysosomal degradative function and cholesterol metabolism in the RPE, induces the complement system and mediates blue light-induced apoptosis, and thus has been implicated in the atrophy and cell death of RPE cells. Accordingly, inhibitors of lipofuscin or components thereof (e.g., A2E), including inhibitors of their formation or accumulation and promoters of their breakdown or clearance, can potentially be useful for treating AMD. Examples of inhibitors of lipofuscin or components thereof (e.g., A2E) include without limitation isotretinoin, which inhibits the formation of lipofuscin and A2E and accumulation of lipofuscin pigments; soraprazan, which promotes the release of lipofuscin from RPE cells; and retinol-binding protein 4 (RBP4) antagonists (e.g., A1120, LBS-008 and compound 43 [a cyclopentyl-fused pyrrolidine]), which inhibit the formation of lipofuscin bisretinoids such as A2E.

Another potential way to prevent or curtail the accumulation of lipofuscin bisretinoids (e.g., A2E) is to interfere with the visual/light cycle in photoreceptors. For example, the visual/light cycle modulator fenretinide reduces serum levels of retinol and RBP4 and inhibits retinol binding to RBP4, which decreases the level of light cycle retinoids and halts the accumulation of lipofuscin bisretinoids (e.g., A2E). Other visual/light cycle modulators include without limitation inhibitors of the trans-to-cis-retinol isomerase RPE65 (e.g., emixustat [ACU-4429] and retinylamine), which, by inhibiting the conversion of all-trans retinol to 11-cis retinol in the RPE, reduce the amount of retinol available and its downstream byproduct A2E. Like fenretinide, emixustat reduces the accumulation of lipofuscin and A2E in the RPE. Treatment with a light cycle modulator may slow the rate of the patient's rod-mediated dark adaptation. To speed up the rate of dark adaptation, a dark adaptation agent can be administered. Non-limiting examples of dark adaptation agents include carotenoids (e.g., carotenes such as β-carotene), retinoids (e.g., all-trans retinol [vitamin A], 11-cis retinol, all-trans retinal [vitamin A aldehyde], 11-cis retinal, all-trans retinoic acid [tretinoin] and esters thereof, 9-cis-retinoic acid [alitretinoin] and esters thereof, 11-cis retinoic acid and esters thereof, 13-cis-retinoic acid [isotretinoin] and esters thereof, etretinate, acitretin, adapalene, bexarotene and tazarotene), and analogs, derivatives and salts thereof.

Oxidative events play a significant role in the pathogenesis of AMD. For instance, accumulation of peroxidized lipids can lead to inflammation and neovascularization. Furthermore, oxidative stress can compromise the regulation of the complement system by RPE cells (the complement system is discussed below). To prevent, delay the onset of or slow the progression of AMD, antioxidants can be administered. In addition, antioxidants can be neuroprotective by preventing or curtailing toxicity in the retina and interfering with cell-death pathways. For example, the mitochondria-targeting electron scavenger XJB-5-131 inhibits oxidation of cardiolipin, a mitochondria-specific polyunsaturated phospholipid, thereby curtailing cell death, including in the brain. As another example, crocin and crocetin, carotenoids found in saffron, can protect cells from apoptosis. As yet another example, xanthophylls (e.g., lutein and zeaxanthin) can protect against development of drusen-like lesions at the RPE, loss of macular pigment and light-induced photoreceptor apoptosis. As still another example, carnosic acid, a benzenediol abietane diterpene found in rosemary and sage, can upregulate antioxidant enzymes, protect retinal cells from hydrogen peroxide toxicity, and increase the thickness of the outer nuclear layer. As a further example, curcuminoids (e.g., curcumin) found in turmeric can upregulate hemeoxygenase-1, thereby protecting RPE cells from hydrogen peroxide-induced apoptosis. As a yet further example, zinc increases catalase and glutathione peroxidase activity, thereby protecting RPE cells and photoreceptors from hydrogen peroxide and tert-butyl hydroperoxide, and protects photoreceptors and other retinal cells from caspase-mediated cell death. As a still further example, cyclopentenone prostaglandins (e.g., cyclopentenone 15-deoxy-A-prostaglandin $J_2$ [15d-$PGJ_2$], a ligand for PPAR-γ) can protect RPE cells from oxidative injury by, e.g., upregulating the synthesis of glutathione, an antioxidant. Cyclopentenone prostaglandins also possess anti-inflammatory property. As an additional example, N-acetylcarnosine scavenges lipid peroxyl radicals in the eye, thereby reducing cell damage.

Antioxidants include without limitation:

vitamins and analogs thereof, including vitamin A, vitamin $B_1$ (thiamine), vitamin $B_2$ (riboflavin), vitamin $B_3$ (e.g., niacin [nicotinic acid] and nicotinamide), vitamin $B_6$ (e.g., pyridoxal, pyridoxamine, 4-pyridoxic acid and pyridoxine), vitamin $B_9$ (folic acid), vitamin $B_{12}$ (cobalamin), vitamin C (ascorbic acid), vitamin E (including tocopherols [e.g., α-tocopherol] and tocotrienols), and vitamin E analogs (e.g., trolox [water-soluble]);

carotenoids, including carotenes (e.g., 3-carotene), xanthophylls (e.g., lutein, zeaxanthin and meso-zeaxanthin), and carotenoids in saffron (e.g., crocin and crocetin);

sulfur-containing antioxidants, including glutathione (GSH), N-acetyl-L-cysteine (NAC), bucillamine, S-nitroso-N-acetyl-L-cysteine (SNAC), S-allyl-L-cysteine (SAC), S-adenosyl-L-methionine (SAM), α-lipoic acid and taurine;

scavengers of radicals, reactive oxygen species (ROS) and reactive nitrogen species (RNS), including carnosine, N-acetylcarnosine, curcuminoids (e.g., curcumin, demethoxycurcumin and tetrahydrocurcumin), ebselen, glutathione, hydroxycinnamic acids and derivatives (e.g., esters and amides) thereof (e.g., caffeic acid, rosmarinic acid and tranilast), melatonin and metabolites thereof, nitrones (e.g., disufenton sodium [NXY-059]), nitroxides (e.g., XJB-5-131), polyphenols (e.g., flavonoids [e.g., apigenin, genistein, luteolin, naringenin and quercetin]), superoxide dismutase mimetics (infra), tirilazad, vitamin C, and vitamin E and analogs thereof (e.g., α-tocopherol and trolox);

inhibitors of enzymes that produce ROS, including NADPH oxidase (NOX) inhibitors (e.g., apocynin, decursin and decursinol angelate [both inhibit NOX-1, -2 and -4 activity and expression], diphenylene iodonium, and GKT-831 [formerly GKT-137831, a dual NOX1/4 inhibitor]), NADH: ubiquinone oxidoreductase (complex I) inhibitors (e.g., metformin and rotenone), and myeloperoxidase inhibitors (e.g., azide, 4-aminobenzoic acid hydrazide and apoE mimetics [e.g., AEM-28 and AEM-28-14]);

substances that mimic or increase the activity or production of antioxidant enzymes, including superoxide dismutase (SOD) {e.g., SOD mimetics such as manganese (III)- and zinc (III)-porphyrin complexes (e.g., MnTBAP, MnTMPyP and ZnTBAP), manganese (II) penta-azamacrocyclic complexes (e.g., M40401 and M40403), manganese (III)-salen complexes (e.g., those disclosed in U.S. Pat. No. 7,122,537) and OT-551 (a cyclopropyl ester prodrug of tempol hydroxylamine), and resveratrol and apoA-I mimetics such as 4F (both increase expression)}, catalase (e.g., catalase mimetics such as manganese (III)-salen complexes (e.g., those disclosed in U.S. Pat. No. 7,122,537), and zinc [increases activity]), glutathione peroxidase (GPx) (e.g., apomorphine and zinc [both increase activity], and beta-catenin, etoposide and resveratrol [all three increase expression]), glutathione reductase (e.g., 4-tert-butylcatechol and redox cofactors such as flavin adenine dinucleotide [FAD] and NADPH [all three enhance activity]), glutathione S-transferase (GST) (e.g., phenylalkyl isothiocyanate-cysteine conjugates {e.g., S—[N-benzyl(thiocarbamoyl)]-L-cysteine}, phenobarbital, rosemary extract and carnosol [all enhance activity]), thioredoxin (Trx) (e.g., geranylgeranylacetone, prostaglandin $E_1$ and sulforaphane [all increase expression]), NADPH-quinone oxidoreductase 1 (NQO1) {e.g., flavones [e.g., β-naphthoflavone (5,6-benzoflavone)] and triterpenoids [e.g., oleanolic acid analogs such as TP-151 (CDDO), TP-155 (CDDO methyl ester), TP-190, TP-218, TP-222, TP-223 (CDDO carboxamide), TP-224 (CDDO monomethylamide), TP-225, TP-226 (CDDO dimethylamide), TP-230, TP-235 (CDDO imidazolide), TP-241, CDDO monoethylamide, CDDO mono(trifluoroethyl)amide, and (+)-TBE-B disclosed in A. Dinkova-Kostova et al., *Proc. Natl. Acad. Sci. USA*, 102:4584-4589 (2005)], all of which increase expression by activating Nrf2}, heme oxygenase 1 (HO-1) {e.g., curcuminoids (e.g., curcumin), triterpenoids (e.g., oleanolic acid analogs [supra, such as TP-225]), and apoA-I mimetics (supra, such as 4F), all of which increase expression), and paraoxonase 1 (PON-1) (e.g., apoE mimetics [supra, such as AEM-28 and AEM-28-14] and apoA-I mimetics [supra, such as 4F], both types increasing activity);

activators of transcription factors that upregulate expression of antioxidant enzymes, including activators of nuclear factor (erythroid-derived 2)-like 2 (NFE2L2 or Nrf2) {e.g., bardoxolone methyl, OT-551, fumarates (e.g., dimethyl and monomethyl fumarate), dithiolethiones (e.g., oltipraz), flavones (e.g., β-naphthoflavone), isoflavones (e.g., genistein), sulforaphane, trichostatin A, triterpenoids (e.g., oleanolic acid analogs [supra, such as TP-225]), and melatonin (increases Nrf2 expression)};

mitochondria-targeted antioxidants, including MitoE, MitoQ and cardiolipin peroxidation inhibitors (e.g., elamipretide, SkQ1 and XJB-5-131);

other kinds of antioxidants, including anthocyanins, benzenediol abietane diterpenes (e.g., carnosic acid), cyclopentenone prostaglandins (e.g., 15d-PGJ$_2$ [increases GSH synthesis]), flavonoids {e.g., flavonoids in *Ginkgo biloba* (e.g., myricetin and quercetin [increases levels of GSH, SOD, catalase, GPx and GST]), prenylflavonoids (e.g., isoxanthohumol), flavones (e.g., apigenin), isoflavones (e.g., genistein), flavanones (e.g., naringenin) and flavanols (e.g., catechin and epigallocatechin-3-gallate)}, omega-3 fatty acids and esters thereof (supra), phenylethanoids (e.g., tyrosol and hydroxytyrosol), retinoids (e.g., all-trans retinol [vitamin A]), stilbenoids (e.g., resveratrol), uric acid, apoA-I mimetics (e.g., 4F), apoE mimetics (e.g., AEM-28 and AEM-28-14), and minerals (e.g., selenium and zinc [e.g., zinc monocysteine]); and analogs, derivatives and salts thereof.

Antioxidants can be provided by way of, e.g., a dietary supplement, such as an AREDS or AREDS2 formulation, an ICAPS® formulation, an Ocuvite® formulation, Saffron 2020™ or Phototrop®. If a supplement contains a relatively high amount of zinc (e.g., zinc acetate, zinc oxide or zinc sulfate), copper (e.g., cupric oxide or cupric sulfate) can optionally be co-administered with zinc to prevent copper-deficiency anemia associated with high zinc intake. Saffron 2020™ contains saffron, resveratrol, lutein, zeaxanthin, vitamins A, B$_2$, C and E, zinc and copper. Phototrop® comprises acetyl-L-carnitine, omega-3 fatty acids and coenzyme Q$_{10}$. An exemplary Age-Related Eye Disease Study (AREDS) formulation includes β-carotene, vitamin C, vitamin E, zinc (e.g., zinc oxide) and copper (e.g., cupric oxide). Exemplary AREDS2 formulations contain:

1) β-carotene, vitamin C, vitamin E and zinc; or
2) vitamin C, vitamin E, zinc and copper; or
3) vitamin C, vitamin E and zinc; or
4) β-carotene, vitamin C, vitamin E, omega-3 fatty acids (DHA and EPA), zinc and copper; or
5) β-carotene, vitamin C, vitamin E, lutein, zeaxanthin, zinc and copper; or
6) β-carotene, vitamin C, vitamin E, lutein, zeaxanthin, omega-3 fatty acids (DHA and EPA), zinc and copper.

Exemplary ICAPS® formulations include:
1) vitamin A, vitamin C, vitamin E, zinc and copper; or
2) vitamin A, vitamin B$_2$, vitamin C, vitamin E, lutein, zeaxanthin, zinc, copper and selenium.

Exemplary Ocuvite® formulations contain:
1) vitamin C, vitamin E, lutein, zeaxanthin, zinc and copper; or
2) vitamin C, vitamin E, lutein, omega-3 fatty acids, zinc and copper; or
3) vitamin A, vitamin C, vitamin E, lutein, zeaxanthin, zinc, copper and selenium.

Alternative to or in addition to antioxidants, other neuroprotectors (neuroprotectants) can be administered to treat AMD. Neuroprotectors can be used, e.g., to promote the health or/and growth of cells in the retina, or/and to prevent cell death regardless of the initiating event. For instance, ciliary neurotrophic factor (CNTF) rescues photoreceptors from degeneration. Likewise, brimonidine protects retinal ganglion cells, bipolar cells and photoreceptors from degeneration. As another example, glatiramer acetate reduces retinal microglial cytotoxicity (and inflammation and drusen size). Examples of neuroprotectors include without limitation berberine, glatiramer acetate, glucose, apoE mimetics (e.g., CN-105), α$_2$-adrenergic receptor agonists (e.g., apraclonidine and brimonidine), serotonin 5-HT$_{1A}$ receptor agonists (e.g., AL-8309B and azapirones [e.g., buspirone, gepirone and tandospirone]), neuroprotectins (e.g., neuroprotectins A, B and D1), endogenous neuroprotectors {e.g., carnosine, FGF, CNTF, glial cell-derived neurotrophic factor (GDNF) family (e.g., GDNF, artemin, neurturin and persephin), and neurotrophins (e.g., brain-derived neurotrophic factor [BDNF], nerve growth factor [NGF], neurotrophin-3 [NT-3] and neurotrophin-4 [NT-4])}, prostaglandin analogs (e.g., unoprostone isopropyl [UF-021]), and analogs, derivatives, fragments and salts thereof.

Furthermore, other neuroprotectors that can be used to treat AMD include agents that prevent the death of retina-associated cells (e.g., RPE cells and photoreceptors) by apoptosis (programmed cell death) or/and necrosis (characterized by cell swelling and rupture). For example, nucleoside reverse transcriptase inhibitors (NRTIs) block the death of RPE cells via inhibition of P2X7-mediated NLRP3 inflammasome activation of caspase-1, and reduce geographic atrophy and CNV. As another example, the first apoptosis signal (Fas) receptor inhibitor ONL-1204 protects retinal cells, including photoreceptors, from apoptosis. If apoptosis is reduced (e.g., through inhibition of caspases), necrosis may increase to compensate for the reduction in apoptosis, so an effective strategy for preventing or curtailing the death of retina-associated cells can involve inhibition of both apoptosis and necrosis.

Examples of apoptosis inhibitors include without limitation first apoptosis signal (Fas) receptor inhibitors (e.g., ONL-1204), cardiolipin peroxidation inhibitors (e.g., elamipretide, SkQ1 and XJB-5-131), tissue factor (TF) inhibitors (e.g., anti-TF antibodies and fragments thereof and fusion proteins thereof [e.g., ICON-1]), inhibitors of inflammasomes, inhibitors of P2X7-mediated NLRP3 activation of caspase-1 (e.g., NRTIs, such as abacavir [ABC], lamivudine [3TC], stavudine [d4T], me-d4T and zidovudine [AZT]), inhibitors of ATP purinoceptor P2X7 (e.g., AZD9056, CE-224535 and GSK1482169), inhibitors of apoptosis-associated speck-like protein containing caspase-recruitment domain (ASC) {e.g., cysteinyl leukotriene receptor antagonists such as cysLTR1 antagonists (e.g., cinalukast, gemilukast [dual cysLTR1/cysLTR2 antagonist], iralukast, montelukast, pranlukast, tomelukast, verlukast, zafirlukast, CP-195494, CP-199330, ICI-198615, MK-571 and lipoxins [e.g., LXA4 and 15-epi-LXA4]) and cysLTR2 antagonists (e.g., HAMI-3379)}, other inhibitors of NLRP3 activation of caspase-1 (e.g., myxoma virus M013 protein), neuroprotectins, members of the Bcl-2 family (e.g., Bcl-2, Bcl-XL and Bcl-w), members of the inhibitor of apoptosis protein (IAP) family (e.g., cellular IAP 1 [cIAP1], cIAP2, X-linked IAP [XIAP], NLR family apoptosis inhibitory protein [NAIP], and survivin), and analogs, derivatives, fragments and salts thereof.

Apoptosis inhibitors also include inhibitors of caspases, including but not limited to:

inhibitors of the caspase family (pan caspase inhibitors), such as quinoline-2-carbonyl-Val-Asp(OMe)-2,6-difluorophenoxymethylketone (also called Q-VD(OMe)-OPh by BioVision, Inc. of Milpitas, Calif.), tert-butyloxycarbonyl-Asp(OMe)-fluoromethylketone (aka Boc-D-FMK), benzyloxycarbonyl-Val-Ala-Asp(OMe)-NH$_2$ (aka Z-VAD), and benzyloxycarbonyl-Val-Ala-Asp(OMe)-fluoromethylketone (aka Z-VAD-FMK);

inhibitors of caspase-1, such as belnacasan (VX-765), pralnacasan (VX-740), parthenolide, cytokine response modifier A (crmA), and benzyloxycarbonyl-Tyr-Val-Ala-Asp(OMe)-fluoromethylketone (aka Z-YVAD-FMK) (SEQ ID NO: 241);

inhibitors of caspase-2, such as benzyloxycarbonyl-Val-Asp(OMe)-Val-Ala-Asp(OMe)-fluoromethylketone (aka Z-VDVAD-FMK) (SEQ ID NO: 242);

inhibitors of caspase-3, such as XIAP, survivin, quinoline-2-carbonyl-Asp(OMe)-Glu(OMe)-Val-Asp(OMe)-2,6-difluorophenoxymethylketone (aka Q-DEVD-OPh) (SEQ ID NO: 243), benzyloxycarbonyl-Asp(OMe)-Glu(OMe)-Val-Asp(OMe)-fluoromethylketone (aka Z-DEVD-FMK) (SEQ ID NO: 244), and benzyloxycarbonyl-Asp(OMe)-Gln-Met-Asp(OMe)-fluoromethylketone (aka Z-DQMD-FMK) (SEQ ID NO: 245);

inhibitors of caspase-4, such as benzyloxycarbonyl-Leu-Glu(OMe)-Val-Asp(OMe)-fluoromethylketone (aka Z-LEVD-FMK) (SEQ ID NO: 246);

inhibitors of caspase-5, such as benzyloxycarbonyl-Trp-Glu(OMe)-His-Asp(OMe)-fluoromethylketone (aka Z-WEHD-FMK) (SEQ ID NO: 247);

inhibitors of caspase-6, such as crmA and benzyloxycarbonyl-Val-Glu(OMe)-Ile-Asp(OMe)-fluoromethylketone (aka Z-VEID-FMK) (SEQ ID NO: 248);

inhibitors of caspase-7, such as XIAP and survivin;

inhibitors of caspase-8, such as crmA, quinoline-2-carbonyl-Ile-Glu(OMe)-Thr-Asp(OMe)-2,6-difluorophenoxymethylketone (aka Q-IETD-OPh) (SEQ ID NO: 249), and benzyloxycarbonyl-Ile-Glu(OMe)-Thr-Asp(OMe)-fluoromethylketone (aka Z-IETD-FMK) (SEQ ID NO: 250);

inhibitors of caspase-9, such as cIAP2., XIAP, quinoline-2-carbonyl-Leu-Glu(OMe)-His-Asp(OMe)-2,6-difluorophenoxymethylketone (aka Q-LEHD-OPh) (SEQ ID NO: 251), and benzyloxycarbonyl-Leu-Glu(OMe)-His-Asp(OMe)-fluoromethylketone (aka Z-LEHD-FMK) (SEQ ID NO: 252);

inhibitors of caspase-10, such as benzyloxycarbonyl-Ala-Glu(OMe)-Val-Asp(OMe)-fluoromethylketone (aka AEVD-FMK (SEQ ID NO: 253) or Z-AEVD-FMK (SEQ ID NO: 254));

inhibitors of caspase-12, such as benzyloxycarbonyl-Ala-Thr-Ala-Asp(OMe)-fluoromethylketone (aka Z-ATAD-FMK) (SEQ ID NO: 255);

inhibitors of caspase-13, such as benzyloxycarbonyl-Leu-Glu(OMe)-Glu(OMe)-Asp(OMe)-fluoromethylketone (aka LEED-FMK (SEQ ID NO: 256) or Z-LEED-FMK (SEQ ID NO: 257)); and analogs, derivatives, fragments and salts thereof.

Examples of necrosis inhibitors include without limitation caspase inhibitors, inhibitors of receptor-interacting protein (RIP) kinases (e.g., necrostatins such as necrostatins 1, 5 and 7), Necrox compounds (e.g., Necrox-2 and Necrox-5), Nec-1s, and analogs, derivatives and salts thereof.

Elevated levels of C-reactive protein (CRP) are found in the blood and eyes of patients with AMD. Elevated CRP levels can increase VEGF production and thereby lead to neovascularization. In addition, CRP is implicated in the pathogenesis of inflammation, and inhibits cholesterol efflux through down-regulation of the cholesterol efflux proteins ABCA1 and ABCG1. Moreover, monomeric CRP can bind to the complement protein C1q and subsequently activate the classical complement pathway, which in tandem with the alternative complement pathway can result in the formation of the membrane attack complex (MAC) and eventually cell lysis. Accordingly, CRP inhibitors that curtail the level (e.g., via decreased production or increased breakdown or clearance) or the activity of CRP can be used to treat AMD. Examples of CRP inhibitors include without limitation DPP-4 inhibitors, thiazolidinediones, stilbenoids, statins, epigallocatechin-3-gallate (EGCG), CRP-i2, CRP-targeting anti-sense polynucleotides and anti-sense PNAs, and analogs, derivatives and salts thereof.

The complement system of the innate immune system is implicated in the pathogenesis of AMD. For example, variants of the CFH gene resulting in defective or deficient complement factor H (CFH) are strongly associated with risk for AMD. Further, the alternative complement pathway may be activated by the accumulation of apolipoproteins (e.g., apoE) and lipofuscin or components thereof (e.g., A2E). In addition, the membrane attack complex (MAC, C5b-9) has been documented on choroidal blood vessels, the Bruch's membrane (BrM) and the RPE and is associated with abnormal RPE cells, suggesting that complement-mediated cell lysis may accelerate RPE dysfunction and death in AMD. Moreover, there is a marked accumulation of the MAC in the BrM and the choriocapillaris endothelium of the aging macula. The complement system also plays a significant role in inflammatory and oxidative events. As an example, the anaphylatoxins C3a, C4a and C5a promote inflammation and generation of cytotoxic oxygen radicals and increase vascular permeability. For instance, binding of C3a and C5a to the C3a and C5a receptors, respectively, leads to an inflammatory response, e.g., by stimulating mast cell-mediated inflammation via histamine release. Activation of the complement cascade and local inflammation are implicated in, e.g., drusen formation, a hallmark of atrophic AMD that can lead to neovascular AMD. In addition, the complement system is implicated in neovascularization, including CNV. For instance, activation of the complement system may result in formation of the MAC in the choriocapillary endothelium, whose breakdown by the MAC can lead to hypoxia and thus CNV. Furthermore, some complement components (e.g., C5a) exhibit pro-angiogenic properties—e.g., the C5a receptor mediates increased VEGF secretion in RPE cells. Moreover, the MAC releases pro-angiogenic molecules (e.g., PDGF and VEGF).

Alternative to or in addition to inhibition of the alternative complement pathway, inhibition of the lectin complement pathway (or/and the classic complement pathway) can be beneficial in the treatment of atrophic AMD or/and neovascular AMD. For example, inhibition of a mannan-binding lectin serine protease (or mannose-associated serine protease [MASP]) (e.g., MASP-1, -2 or -3) using, e.g., an antibody or a fragment thereof (e.g., OMS721, an anti-MASP-2 antibody), can dampen amplification of complement activation and sequelae thereof, such as inflammation. In the lectin pathway, MASPs cleave C2 and C4 to form C2aC4b, a C3-convertase. At the border of the lectin and alternative pathways, the C3-convertase cleaves C3 into C3a and C3b. C3b binds to C2aC4b to form a C5-convertase, which cleaves C5 into C5a and C5b. C5b, C6, C7, C8 and C9 together form the membrane attack complex (MAC), which may result in cell lysis via cell swelling and bursting.

Complement factors H and I inactivate C3b and downregulate the alternative pathway, thereby suppressing inflammation, for example. By inhibiting the formation of the C3-convertase C2aC4b, a MASP inhibitor can be useful for treating atrophic AMD or/and neovascular AMD.

Accordingly, AMD can be treated using inhibitors of the complement system or components (e.g., proteins and factors) thereof {e.g., CFB, CFD, C2, C2a, C2b, C3, C3a, C3b, C3[$H_2O$], C3a receptor, C4, C4a, C4b, C3-convertases (e.g., C2aC4b, C3[$H_2O$]Bb and C3bBb), C5-convertases (e.g., C2aC4bC3b and C3bBbC3b), C5, C5a, C5b, C5a receptor, C6, C7, C8, C9 and MAC (C5b-9)}. As an illustrative example, compstatin inhibits activation of the complement system by binding to C3, the converging protein of all three complement activation pathways, and inhibiting the cleavage of C3 to C3a and C3b by C3-convertases.

Complement factor D (CFD) is the rate-limiting enzyme involved in the activation of the alternative complement pathway (ACP). Hyperactivity of the ACP is implicated in the development of AMD, including geographic atrophy (GA). CFD cleaves CFB bound to C3b deposited on the surface of cells into Ba and Bb. Bb remains associated with C3b to form the C3-convertase of the ACP, C3bBb. If cleavage of molecules of C3 by the Bb subunit of C3bBb into C3a and C3b results in a cluster of C3b molecules on the cell surface, the C5-convertase of the ACP, C3bBbC3b, is formed. The C5-convertase cleaves C5 into the the potent anaphylatoxin C5a and C5b. C5b assembles with C6 through C9 to form the MAC (C5b-C9) on the cell surface. Depending on the number of MACs on the surface of a cell, the formation of MACs can result in sublytic injury or lysis of the cell.

Lampalizumab is an antigen-binding fragment ($F_{ab}$) of a humanized monoclonal antibody targeting CFD. Lampalizumab inhibits complement activation and inflammation and can be used to treat or slow the progression of AMD, including GA. Atrophic AMD patients with a mutation in complement factor I (CFI) appear to exhibit a more positive response to lampalizumab treatment. In the MAHALO Phase II trial, patients receiving monthly intravitreal injections of 10 mg lampalizumab in one eye for 18 months exhibited a reduction in the rate of GA enlargement, and hence the area of GA, in the injected eye by about 20% according to fundus autofluorescence compared to patients receiving a placebo. A subgroup of patients positive for CFI mutations and receiving monthly intravitreal injections of 10 mg lampalizumab for 18 months exhibited an enhanced reduction in the GA growth rate, and hence the area of GA, by about 44% compared to placebo. CFI, a C3b/C4b inactivator, regulates complement activation by cleaving cell-bound or fluid-phase C3b and C4b.

Non-limiting examples of inhibitors of the complement system or components thereof include anti-C1s antibodies and fragments thereof (e.g., TNT-009), other C1s inhibitors (e.g., BCX-1470, nafamostat and serpin 1 [aka C1 inhibitor, such as conestat alfa]), anti-complement factor B (CFB) antibodies and fragments thereof (e.g., bikaciomab and TA106), anti-CFD antibodies and fragments thereof (e.g., lampalizumab), other CFD inhibitors (e.g., ACH-4471, BCX-1470 and nafamostat), CFP (properdin) inhibitors (e.g., CLG561 and anti-CFP antibodies and fragments thereof [e.g., NM9401]), C3bBb and C2aC4b C3-convertase dissociation promoters or formation inhibitors {e.g., CFH and fragments thereof (e.g., Mini-FH and AMY-201), soluble complement receptor 1 (sCR1 such as CDX-1135 and TP10) and fragments thereof (e.g., mirococept), C4b-binding protein (C4BP), soluble decay-accelerating factor (sDAF), and compstatin and analogs and derivatives thereof (e.g., POT-4 [AL-78898A] and Peptides I through IX disclosed in R. Gorham et al., Exp. Eye Res., 116:96-108 [2013])}, C3bBb C3-convertase inhibitors (e.g., TT30), anti-C3 antibodies and fragments thereof, other C3 inhibitors (e.g., CB-2782, compstatin and analogs and derivatives thereof [e.g., AMY-101, APL-1, APL-2, Cp40 and POT-4], mycophenolic acid-glucosamine conjugates [downregulate C3] and neurotropin), anti-C3a antibodies and fragments thereof (e.g., H453 and H454), anti-C3b/iC3b antibodies and fragments thereof (e.g., 3E7), other C3b inhibitors (e.g., TT30), promoters of C3b and C4b cleavage (e.g., CFI, CFH, C4BP, sCR1 and soluble membrane cofactor protein [sMCP]), C5-convertase inhibitors (e.g., CFH-related protein 1 [CFHR1]), anti-C5 antibodies and fragments thereof (e.g., eculizumab, pexelizumab, tesidolumrab [LFG316], Ergidina, Mubodina, ABP959, ALXN1210, MEDI-7814 and RO7112689 [SKY59]), anti-C5 aptamers (e.g., ARC1905 [avacincaptad pegol or ZIMURA®]), other C5 inhibitors (e.g., RA101495, Coversin and C5-targeting siRNAs [e.g., ALN-CC5]), anti-C5a antibodies and fragments thereof (e.g., IFX-1 [CaCP-29] and MEDI-7814), anti-C5a aptamers (e.g., NOX-D19), C5a receptor antagonists {e.g., ADC-1004, CCX-168, JPE-1375, JSM-7717, PMX-025, Ac-F [OPdChaWR](PMX-53) and PMX-205, and anti-C5aR antibodies and fragments thereof (e.g., neutrazimab, NN8209, NN8210 and S5/1)}, other inhibitors of the alternative complement pathway (e.g., KSI-401 and zinc), other inhibitors of the classic complement pathway (e.g., serpin 1 and elastase-resistant serpin 1 mutants [inhibit C1r and C1s]), inhibitors of the lectin complement pathway {e.g., inhibitors of mannose-associated serine proteases (MASPs), such as anti-MASP antibodies and fragments thereof (e.g., anti-MASP-2 antibodies [e.g., OMS721]) and serpin 1 (inhibits MASP-1 and MASP-2)}, other inhibitors of MAC formation (e.g., zinc, soluble CD59 [protectin] and modified CD59 having a glycolipid anchor), and analogs, derivatives, fragments and salts thereof.

Inflammation is also an important contributor to the pathogenesis of AMD, and AMD is associated with chronic inflammation in the region of the RPE, the BrM and the choroid. For example, inflammatory responses may be involved in drusen formation, and can upregulate the expression of VEGF and other pro-angiogenic factors that cause neovascularization, including CNV. Inflammation can be mediated by the cellular immune system (e.g., dendritic cells) or/and the humoral immune system (e.g., the complement system). Inflammation can also be mediated by inflammasomes, which are components of the innate immune system. For example, accumulation of material (e.g., lipoprotein-like particles, lipids and possibly lipofuscin or components thereof [e.g., A2E]) in the BrM may activate the NLRP3 inflammasome, leading to a chronic inflammatory response. In addition, assembly of inflammasomes (e.g., NLRP3) in response to cell-stress signals activates caspases (e.g., caspase-1), which results in inflammation (e.g., via production of pro-inflammatory IL-1β) and ultimately cell death (e.g., of RPE cells).

Many of the substances mentioned in this disclosure possess anti-inflammatory property in addition to the property or properties described for them. Other anti-inflammatory agents include without limitation hydroxychloroquine, corticosteroids (e.g., fluocinolone acetonide and triamcinolone acetonide), steroids having little glucocorticoid activity (e.g., anecortave [anecortave acetate]), non-steroidal anti-inflammatory drugs (e.g., non-selective cyclooxygenase [COX] 1/COX-2 inhibitors [e.g., aspirin and bromfenac] and selective COX-2 inhibitors [e.g., coxibs]), mast cell stabilizers and inflammasome inhibitors.

Examples of inhibitors of inflammasomes (e.g., inhibitors of their assembly or function) include without limitation NLRP3 (NALP3) inhibitors {e.g., IL-4, myxoma virus M013 protein, omega-3 fatty acids, anthraquinones [e.g., chrysophanol], sesquiterpene lactones [e.g., parthenolide], triterpenoids [e.g., asiatic acid], sulfonamides [e.g., CAS No. 16673-34-0], sulfonylureas [e.g., glyburide], and vinyl sulfones [e.g., Bay 11-7082]}, NLRP3/AIM2 inhibitors (e.g. diarylsulfonylureas [e.g., CP-456,773]), NLRP1 inhibitors (e.g., Bcl-2, the loop region of Bcl-2, and Bcl-X[L]), NLRP1B inhibitors (e.g., auranofin), and analogs, derivatives, fragments and salts thereof. Peptide5 (Peptagon™) is derived from the second extracellular loop of human Connexin43 (Cx43). Peptide5 blocks pathological Cx43 hemichannels, thereby inhibiting the release of ATP and activation of the inflammasome pathway of inflammation. Inhibition of the inflammasome pathway of inflammation reduces the release of inflammatory cytokines and reduces tissue/cell damage, and hence Peptide5 also serves as a neuroprotector of retinal cells.

Non-limiting examples of corticosteroids (including glucocorticoids but not mineralocorticoids) include hydrocortisone types (e.g., cortisone, hydrocortisone [cortisol], prednisolone, methylprednisolone, prednisone and tixocortol), betamethasone types (e.g., betamethasone, dexamethasone and fluocortolone), halogenated steroids (e.g., alclometasone, beclometasone, beclometasone dipropionate [e.g., AGN-208397], clobetasol, clobetasone, desoximetasone, diflorasone, diflucortolone, fluprednidene, fluticasone, halobetasol [ulobetasol], halometasone and mometasone), acetonides and related substances (e.g., amcinonide, budesonide, ciclesonide, desonide, fluocinonide, fluocinolone acetonide, flurandrenolide [fludroxycortide], halcinonide, triamcinolone acetonide and triamcinolone), carbonates (e.g., prednicarbate), and analogs, derivatives and salts thereof.

A major mechanism of glucocorticoids' anti-inflammatory effects is stimulation of the synthesis and function of annexins (lipocortins), including annexin A1. Annexins, including annexin A1, suppress leukocyte inflammatory events (including epithelial adhesion, emigration, chemotaxis, phagocytosis and respiratory burst), and inhibit phospholipase A2, which produces the potent pro-inflammatory mediators prostaglandins and leukotrienes. Therefore, anti-inflammatory agents include annexins (e.g., annexin A1), annexin mimetic peptides (e.g., annexin A1 mimetics, such as Ac2-26 and CGEN-855A), and analogs, derivatives, fragments and salts thereof. Glucocorticoids also inhibit the synthesis of prostaglandins by COX-1 and COX-2, akin to NSAIDs.

Examples of non-steroidal anti-inflammatory drugs (NSAIDs) include without limitation:

acetic acid derivatives, such as aceclofenac, bromfenac, diclofenac, etodolac, indomethacin, ketorolac, nabumetone, sulindac, sulindac sulfide, sulindac sulfone and tolmetin;

anthranilic acid derivatives (fenamates), such as flufenamic acid, meclofenamic acid, mefenamic acid and tolfenamic acid;

enolic acid derivatives (oxicams), such as droxicam, isoxicam, lornoxicam, meloxicam, piroxicam and tenoxicam;

propionic acid derivatives, such as fenoprofen, flurbiprofen, ibuprofen, dexibuprofen, ketoprofen, dexketoprofen, loxoprofen, naproxen and oxaprozin;

salicylates, such as diflunisal, salicylic acid, acetylsalicylic acid (aspirin), choline magnesium trisalicylate, salsalate and mesalazine;

selective COX-2 inhibitors, such as apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, niflumic acid, DuP-697, CG100649, GW406381, NS-398, SC-58125, benzothieno[3,2-d]pyrimidin-4-one sulfonamide thio-derivatives, and COX-2 inhibitors derived from *Tribulus terrestris;* other kinds of NSAIDs, such as monoterpenoids (e.g., eucalyptol and phenols [e.g., carvacrol]), anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) (e.g., chebulagic acid, licofelone, 2-(3,4,5-trimethoxyphenyl)-4-(N-methylindol-3-yl)thiophene, and di-tert-butylphenol-based compounds [e.g., DTPBHZ, DTPINH, DTPNHZ and DTPSAL]); and analogs, derivatives and salts thereof.

In non-central and central geographic atrophy, mast cells degranulate in the choroid, releasing histamine and other mediators of inflammation. Mast cell stabilizers block a calcium channel essential for mast cell degranulation, stabilizing the mast cell and thereby preventing the release of histamine and other inflammation mediators. Examples of mast cell stabilizers include without limitation $\beta_2$-adrenergic receptor agonists, cromoglicic acid, ketotifen, methylxanthines, nedocromil, olopatadine, omalizumab, pemirolast, quercetin, tranilast, and analogs, derivatives and salts thereof. Examples of short-acting $\beta_2$-adrenergic agonists include without limitation bitolterol, fenoterol, isoprenaline (isoproterenol), levosalbutamol (levalbuterol), orciprenaline (metaproterenol), pirbuterol, procaterol, ritodrine, salbutamol (albuterol), terbutaline, and analogs, derivatives and salts thereof. Non-limiting examples of long-acting $\beta_2$-adrenergic agonists include arformoterol, bambuterol, clenbuterol, formoterol, salmeterol, and analogs, derivatives and salts thereof. Examples of ultralong-acting $\beta_2$-adrenergic agonists include without limitation carmoterol, indacaterol, milveterol, olodaterol, vilanterol, and analogs, derivatives and salts thereof.

In summary, examples of anti-inflammatory agents include without limitation hydroxychloroquine, anti-amyloid agents, antioxidants, apolipoprotein mimetics (e.g., apoA-I mimetics and apoE mimetics), C-reactive protein inhibitors, complement inhibitors, inflammasome inhibitors, neuroprotectors (e.g., glatiramer acetate), corticosteroids/glucocorticoids, steroids having little glucocorticoid activity (e.g., anecortave), annexins (e.g., annexin A1) and mimetic peptides thereof, non-steroidal anti-inflammatory drugs (NSAIDs), tetracyclines (e.g., doxycycline and minocycline), mast cell stabilizers, omega-3 fatty acids and esters thereof, cyclopentenone prostaglandins, anti-angiogenic agents (e.g., anti-VEGF/VEGFR agents, tissue factor inhibitors and kallikrein inhibitors), inhibitors of pro-inflammatory cytokines (e.g., IL-2, IL-6, IL-8 and TNF-α), inhibitors of signal transducer and activator of transcription (STAT) proteins or their activation {e.g., suppressor of cytokine signaling (SOCS) mimetic peptides (e.g., SOCS1 mimetics [e.g., SOCS1-KIR, NewSOCS1-KIR, PS-5 and Tkip] and SOCS3 mimetics}, and immunosuppressants.

Pro-inflammatory cytokines associated with the development and progression of AMD include without limitation IL-6 and IL-8. Therefore, inhibitors of the signaling, production or secretion of IL-6 and IL-8 can be used to treat atrophic AMD or/and neovascular AMD. Inhibitors of IL-6 include without limitation clazakizumab, elsilimomab, olokizumab, siltuximab and sirukumab, and inhibitors of the IL-6 receptor (IL-6R) include without limitation sarilumab and tocilizumab. Inhibitors of the production of IL-6 include without limitation nafamostat, parthenolide, tranilast, L-carnitine, taurine, flavonoids (e.g., epigallocatechin-3-gallate [EGCG], naringenin and quercetin), M013 protein, apoE mimetics (e.g., AEM-28 and hEp), omega-3 fatty acids and esters thereof, glucocorticoids, immunomodulatory imides (e.g., thalidomide, lenalidomide, pomalidomide and apremilast), prostacyclin and analogs thereof (e.g., ataprost, beraprost [e.g., esuberaprost], carbacyclin, isocarbacyclin, ciprostene, eptaloprost, cicaprost, iloprost, taprostene, treprostinil and 5,6,7-trinor-4,8-inter-m-phenylene-9-fluoro-PGI2), and TNF-α inhibitors (infra). Inhibitors of the production of IL-8 include without limitation alefacept, glucocorticoids and tetracyclines (e.g., doxycycline, minocycline and tetracycline). In addition, statins inhibit the secretion of IL-6 and IL-8 from, e.g., RPE cells.

Other therapeutic agents that can be used to treat atrophic AMD or/and neovascular AMD include immunosuppressants. Immunosuppressants can have anti-inflammatory property. Examples of immunosuppressants include, but are not limited to, glatiramer acetate, inhibitors of interleukin-2 (IL-2) signaling, production or secretion (e.g., antagonists of the IL-2 receptor alpha subunit [e.g., basiliximab and daclizumab], glucocorticoids, mTOR inhibitors [e.g., rapamycin (sirolimus), deforolimus (ridaforolimus), everolimus, temsirolimus, umirolimus (biolimus A9) and zotarolimus], and calcineurin inhibitors [e.g., cyclosporine, pimecrolimus and tacrolimus]), and inhibitors of tumour necrosis factors (e.g., TNF-α) (e.g., adalimumab, certolizumab pegol, golimumab, infliximab, etanercept, bupropion, ART-621, imides [e.g., thalidomide, lenalidomide, pomalidomide and apremilast], and xanthine derivatives [e.g., lisofylline, pentoxifylline and propentofylline]). Immunosuppressants also include agents that suppress gene transcription related to inflammatory M1 macrophages, such as TMi-018.

Inflammation is a stimulus of NV, and hence an anti-inflammatory agent or an immunosuppressant can suppress NV. Among other beneficial uses, an anti-inflammatory agent (e.g., an NSAID such as bromfenac, or a corticosteroid such as triamcinolone acetonide) or an immunosuppressant (e.g., an IL-2 inhibitor such as daclizumab or rapamycin, or a TNF-α inhibitor such as infliximab) can be used to prevent or treat neovascular AMD, or/and to reduce the number or frequency of administration (e.g., injections) of an anti-angiogenic agent (e.g., an anti-VEGF/VEGFR agent) in the treatment of neovascular AMD.

Matrix metalloproteinases (MMPs) degrade extracellular matrix (ECM) proteins and play an important role in cell migration (dispersion and adhesion), cell proliferation, cell differentiation, angiogenesis and apoptosis. For example, as AMD progresses to the advanced stage, elevated levels of MMPs can degrade the Bruch's membrane (BrM), an ECM and part of the choroid. Endothelial cells migrate along the ECM to the site of injury, proliferate, form endothelial tubes, and mature into new blood vessels that arise from capillaries in the choroid and grow through the fractured BrM. Furthermore, breakage in the BrM may allow endothelial cells to migrate into the sub-RPE-BL space and form immature blood vessels that are leaky and tortuous and may extend into the subretinal space. The net result is neovascularization (including CNV) and development of neovascular AMD. MMPs can also cleave peptide bonds of cell-surface receptors, releasing pro-apoptotic ligands such as FAS. MMP inhibitors can be used, e.g., to inhibit angiogenesis and apoptosis, and to treat neovascular AMD (including types 1, 2 or/and 3 neovascularization) or atrophic AMD (including non-central or/and central geographic atrophy). For example, doxycycline curtails loss of photoreceptors. Non-limiting examples of MMP inhibitors include tissue inhibitors of metalloproteinases (e.g., TIMPs 1, 2, 3 and 4), tetracyclines (e.g., doxycycline, incyclinide and minocycline [e.g., NM108]), dichloromethylenediphosphonic acid, batimastat, cipemastat, ilomastat, marimastat, prinomastat, rebimastat, tanomastat, ABT-770, MMI-166, MMI-270, Ro 28-2653, RS-130830, CAS Reg. No. (CRN) 239796-97-5, CRN 420121-84-2, CRN 544678-85-5, CRN 556052-30-3, CRN 582311-81-7, CRN 848773-43-3, CRN 868368-30-3, and analogs, derivatives, fragments and salts thereof.

Alternative to or in addition to MMP inhibitors, other kinds of inhibitors of cell migration can be utilized. For example, rho kinase (ROCK) inhibitors, including ROCK1 and ROCK2 inhibitors, block cell migration, including endothelial cell migration in the early stages of neovascularization. Examples of ROCK inhibitors include without limitation fasudil, netarsudil, ripasudil, AMA-0428, GSK-429286A, RKI-1447, Y-27632 and Y-30141.

In some circumstances, the use of an MMP activator rather than an MMP inhibitor may be desired. The BrM undergoes constant turnover, mediated by MMPs and TIMPs. The BrM thickens progressively with age, partly because of increased levels of TIMPs and a resulting reduction in ECM turnover. Thickening of ECM in the BrM with age may result in the BrM's retention of lipoproteins secreted by the RPE, eventually leading to the formation of BLinD and drusen. The accumulation of lipid-rich BLinD and basal laminar deposits (BLamD, which are excess extracellular matrix in thickened RPE-BL) lengthen the diffusion distance between the choriocapillaris and the RPE. An MMP activator can be used to achieve greater BrM turnover and less thickening of the BrM, but not to the point where the BrM becomes so degraded that new blood vessels can grow through the BrM. Examples of MMP activators include without limitation basigin (extracellular matrix metalloproteinase inducer [EMMPRIN] or CD147), concanavalin A, cytochalasin D, and analogs, derivatives, fragments and salts thereof. Similarly, an MMP activator, or a matrix metalloproteinase, can be employed to reduce the thickness of BLamD persisting over the BrM.

Angiogenesis is the underlying mechanism of neovascularization (including types 1, 2 and 3), which can occur in the advanced stage of AMD to lead to neovascular AMD and severe vision loss if left untreated. Neovascular AMD is characterized by vascular growth and fluid leakage in the choroid, the sub-RPE-BL space, the subretinal space and the neural retina. Leakage from blood vessels can be more responsible for vision loss associated with neovascular AMD than growth of new blood vessels. Vascular endothelial growth factors (VEGFs) are pivotal in the pathogenesis of neovascular AMD. VEGFs are potent, secreted endothelial-cell mitogens that stimulate the migration and proliferation of endothelial cells, and increase the permeability of new blood vessels, resulting in leakage of fluid, blood and proteins from them. In addition, VEGFs increase the level of MMPs, which degrade the ECM further. Moreover, VEGFs enhance the inflammatory response. However, VEGFs or receptors therefor are not the only potential targets for anti-angiogenic agents. For example, targeting integrins associated with receptor tyrosine kinases using an integrin inhibitor (e.g., ALG-1001 [LUMINATE®]) inhibits the production and growth of new blood vessels and reduces the permeability (leakage) of blood vessels. Angiogenesis can also be inhibited through inhibition of other targets, including without limitation kinases (e.g., tyrosine kinases, such as receptor tyrosine kinases) and phosphatases (e.g., tyrosine phosphatases, such as receptor tyrosine phosphatases).

Anti-angiogenic agents can be used to prevent or curtail neovascularization (including types 1, 2 and 3), and to reduce the permeability/leakage of blood vessels. For example, IL-18 eliminates VEGFs from the eye, thereby inhibiting the formation of damaging blood vessels behind the retina. Non-limiting examples of anti-angiogenic agents include inhibitors of VEGFs {e.g., squalamine, ACU-6151, LHA-510, PAN-90806, decorin, anti-VEGF antibodies and fragments thereof (e.g., bevacizumab [AVASTIN®], ranibizumab [LUCENTIS®], brolucizumab [RTH258], ENV1305, ESBA903 and ESBA1008), anti-VEGF irnrmunoconjugates (e.g., KSI-301), anti-VEGF aptamers (e.g., pegaptanib [MACUGEN®]), anti-VEGF designed ankyrin repeat proteins (DARPins) (e.g., abicipar pegol [AGN-150998 or MP0112]), soluble VEGFRs (e.g., sVEGFR1), and soluble fusion proteins containing one or more extracellular domains of one or more VEGFRs (e.g., VEGFR1, VEGFR2 and VEGFR3) (e.g., aflibercept [EYLEA®], conbercept and OPT-302)}, inhibitors of receptors for VEGFs (e.g., VEGFR1 and VEGFR2) (e.g., axitinib, fruquintinib, pazopanib, regorafenib, sorafenib, sunitinib [e.g., GB-102], tivozanib, isoxanthohumol, pristimerin, KPI-285, PF-337210, PP1, TG100572, X-82, D-(LPR), decorin and anti-VEGFR antibodies and fragments thereof [eog., ranucirumab]), inhibitors of platelet-derived growth factors (PDGFs) {e.g., squalamine, PP1, decorin, anti-PDGF aptamers (e.g., E10030 [FOVISTA®] and pegpleranib), ant-PDGF antibodies and fragments thereof (e.g., rinucumab), and soluble PDGFRs} or receptors therefor (PDGFRs) (e.g., axitinib, pazopanib, sorafenib, sunitinib, X-82, and anti-PDGFR antibodies and fragments thereof [e.g., REGN2176-3]), inhibitors of fibroblast growth factors (FGFs) (e.g., squalamine, decorin, anti-FGF antibodies and fragments thereof, anti-FGF aptamers and soluble FGFRs) or receptors therefor (FGFRs) (e.g., pazopanib and anti-FGFR antibodies and fragments thereof), inhibitors of angiopoietins (e.g., decorin, anti-angiopoietin antibodies and fragments thereof such as nesvacumab [REGN910] and REGN910-3, and soluble angiopoietin receptors) or receptors therefor (e.g., antibodies and fragments thereof against angiopoietin receptors), bispecific anti-VEGF/anti-angiopoietin antibodies and fragments thereof (e.g., anti-VEGF/anti-angiopoietin-2 antibodies such as ABP-201 and RG7716), inhibitors of integrins (e.g., ALG-1001 [LUMINATE®], JSM-6427, SF0166, and anti-integrin antibodies and fragments thereof), tissue factor (TF) inhibitors (e.g., anti-TF antibodies and fragments thereof and fusion proteins thereof [e.g., ICON-1]), kallikrein inhibitors (e.g., avoralstat [BCX4161], BCX7353, ecallantide [DX-88], KVD001, and anti-kallikrein antibodies and fragments thereof [e.g., DX-2930]), serine/arginine-protein kinase 1 (SRPK1) inhibitors (e.g., SPHINX31), Src kinase inhibitors (e.g., SKI-606 and TG100572), anecortave (anecortave acetate), angiostatin (e.g., angiostatin K1-3), $\alpha v \beta_3$ inhibitors (e.g., etaracizumab), apoA-I mimetics (e.g., L-4F and L-5F), apoE mimetics (e.g., apoEdp), azurin(50-77) (p28), berberine, bleomycins, borrelidin, carboxyamidotriazole, cartilage-derived angiogenesis inhibitors (e.g., chondromodulin I and troponin I), castanospermine, CM101, inhibitors of the complement system, corticosteroids (including glucocorticoids), cyclopropene fatty acids (e.g., sterculic acid), α-difluoromethylornithine, endostatin, everolimus, fumagillin, genistein, heparin, interferon-α, interleukin-12, interleukin-18, itraconazole, KV11, linomide, MMP inhibitors, 2-methoxyestradiol, pigment epithelium-derived factor (PEDF), platelet factor-4, PPAR-α agonists (e.g., fibrates), PPAR-γ agonists (e.g., thiazolidinediones), prolactin, rapamycin (sirolimus), anti-angiogenic siRNA, sphingosine-1-phosphate inhibitors (e.g., sonepcizumab), squalene, staurosporine, angiostatic steroids (e.g., tetrahydrocortisol) plus heparin, stilbenoids, suramin, SU5416, tasquinimod, tecogalan, tetrathiomolybdate, thalidomide and derivatives thereof (e.g., lenalidomide and pomalidomide), thiabendazole, thrombospondins (e.g., thrombospondin 1), TNP-470, tranilast, triterpenoids (e.g., oleanolic acid analogs [supra, such as TP-225]), tumstatin and fusion proteins thereof (e.g., OCU200), vasostatin, vasostatin 48, Withaferin A, and analogs, derivatives, fragments and salts thereof.

One or more anti-angiogenic agents can be administered at an appropriate time to prevent or reduce the risk of developing pathologies that can lead to severe vision loss. In certain embodiments, one or more anti-angiogenic agents are administered prior to occurrence of scar formation (fibrosis) or a substantial amount thereof.

The anti-angiogenic agents described herein may have additional beneficial properties. For example, the anti-PDGF aptamer E10030 may also have an antifibrotic effect by reducing subretinal fibrosis, which can lead to central vision loss in about 10-15% of people with neovascular AMD. As another example, decorin has antiscarring and antifibrotic properties (e.g., by inhibiting transforming growth factor-beta [TGF-β] and connective tissue growth factor [CTGF]) and anti-inflammatory properties (e.g., by inhibiting complement component C1q) in addition to its anti-angiogenic properties (e.g., by inhibiting VEGF, VEGFR, PDGF and FGF and downregulating the expression of VEGF, angiopoietin and monocyte chemoattractant protein 1 [MCP-1]).

In some embodiments, two or more anti-angiogenic agents targeting different mechanisms of angiogenesis are used to inhibit neovascularization (including types 1, 2 and 3), decrease the permeability/leakage of blood vessels and treat neovascular AMD. In certain embodiments, the two or more anti-angiogenic agents comprise an anti-VEGF/VEGFR agent (e.g., aflibercept, brolucizumab, bevacizumab or ranibizumab) and an agent targeting a different mechanism of angiogenesis. In some embodiments, the two or more anti-angiogenic agents comprise an anti-VEGF/VEGFR agent and an anti-PDGF/PDGFR agent, such as bevacizumab or ranibizumab and E10030, or aflibercept and REGN2176-3. E10030 blocks PDGF-B from binding to its natural receptor on pericytes, causing pericytes to be stripped from newly formed abnormal blood vessels. Left unprotected, the endothelial cells are highly vulnerable to the effects of an anti-VEGF agent. Because of this ability to strip pericytes, E10030 may have an effect on both immature blood vessels and more mature blood vessels slightly later in the disease process. In further embodiments, the two or more anti-angiogenic agents comprise an anti-VEGF/VEGFR agent and an anti-angiopoietin/angiopoietin receptor agent, such as aflibercept and nesvacumab or REGN910-3.

Alternatively, an anti-angiogenic agent targeting different mechanisms of angiogenesis can be employed to treat, e.g., neovascular AMD. For example, a bispecific antibody or DARPin targeting VEGF/VEGFR and PDGF/PDGFR, or a bispecific antibody or DARPin targeting VEGF/VEGFR and angiopoietin/angiopoietin receptor (e.g., a bispecific anti-VEGF/anti-angiopoietin-2 antibody such as ABP-201 or RG7716), can be used.

AMD can also be treated with other kinds of therapy, including low-level light therapy (LLLT), laser photocoagulation therapy (LPT), photodynamic therapy (PDT) and radiation therapy (RT). LLLT, also called photobiomodulation, uses low-level visible or near-infrared light produced by a laser or a non-coherent light source (e.g., a light-emitting diode [LED]) to stimulate cellular functions and processes through photoacceptors for treatment of atrophic and neovascular AMD, diabetic retinopathy and other eye diseases. LPT employs, e.g., an argon (Ar) laser, a micropulse laser or a nanosecond laser, or any combination thereof, and can reduce or eliminate drusen in patients with atrophic AMD or neovascular AMD. Laser surgery can also be employed to destroy abnormal blood vessels in the eye and generally is suitable if the growth of abnormal blood vessels is not too extensive and the abnormal blood vessels are not close to the fovea. PDT utilizes a laser in combination with a compound (e.g., verteporfin) that, upon activation by light of a particular wavelength, injures target cells and not normal cells. A steroid can optionally be administered in PDT. PDT is often employed to treat polypoidal neovasculopathy, the most common form of neovascularization in Asian populations. Examples of RT include without limitation external beam irradiation, focal radiation (e.g., via intravitreal, transvitreal or transpupillary delivery) (e.g., transvitreal delivery of strontium 90 [$^{90}$Sr] X-ray at 15 Gy or 24 Gy doses), and radiation in combination with an anti-VEGF/VEGFR agent (e.g., transvitreal delivery of $^{90}$Sr X-ray at a single 24 Gy dose combined with bevacizumab, or 16 Gy X-ray combined with ranibizumab). PDT or RT can be provided to reduce neovascularization (e.g., CNV) and limit vision loss or improve visual acuity in patients with neovascular AMD. In some embodiments, LLLT, LPT, PDT or RT, or any combination or all thereof, is provided to a patient with neovascular AMD who does not respond adequately to treatment with an anti-angiogenic agent (e.g., an anti-VEGF/VEGFR agent).

Stem cell-derived retinal pigment epithelium (RPE) cells and photoreceptors can rescue the retina, replace lost retinal neurons, and restore or improve vision. Stem cell-derived RPE cells produce neurotrophic factors that promote the survival of photoreceptors. Therefore, cell replacement therapies and stem cell-based therapies, such as stem cell-derived RPE cells and photoreceptors, can be employed to treat AMD. As an illustrative example, an apolipoprotein mimetic [e.g., an apoA-I mimetic (e.g., L-4F) or/and an apoE mimetic (e.g., AEM-28-14)] can be used in combination with RPE cell replacement to treat, e.g., advanced-stage AMD, including central geographic atrophy and neovascular AMD. RPE cells may atrophy and die as a result of rampant lipid deposition in the sub-RPE-BL space and over the BrM. Removal of lipid deposits from the sub-RPE-BL space and the BrM normalizes the BrM structure and function and improves the transport of incoming oxygen and micronutrients (including vitamin A) and outgoing waste between the choriocapillaris and the RPE and thereby improves the health of RPE cells. Therefore, an advanced-stage AMD patient can first be treated with a lipid-clearing apo mimetic [e.g., an apoA-I mimetic (e.g., L-4F) or/and an apoE mimetic (e.g., AEM-28-14)] and then receive RPE cell replacement (e.g., via one or more injections into or implantations in, e.g., the space below the retina). The new RPE cells can prevent disease progression by replacing dead and dying RPE cells. The RPE cells can be, e.g., RPE cells derived from stem cells (e.g., human embryonic stem cells [hESC], human neural stem cells [hNSC], human central nervous system stem cells [hCNS-SC], bone marrow stem cells [BMSC], mesenchymal stem cells [MSC, such as ischemic tolerant MSCs that are allogeneic RPE progenitors] and induced pluripotent stem cells [iPSC], including autologous stem cells and stem cells derived from donor cells) or RPE cells obtained from the translocation of full-thickness retina. In certain embodiments, the RPE cells are derived from human embryonic stem cells (e.g., CPCB-RPE1 cells, MA09-hRPE cells or OPREGEN® cells) or induced pluripotent stem cells. Human retinal progenitor cells (e.g., jCell cells) can also be implanted or injected (e.g., intravitreally) to rescue and reactivate diseased photoreceptors, or to replace dead photoreceptors, for treatment of AMD (and retinitis pigmentosa). Removal of lipid deposits in the eye by the apo mimetic can lead to beneficial effects such as curtailment of local inflammation, oxidative stress and complement activation, which can aid in preventing or forestalling RPE cell atrophy and death.

As an example of an RPE cell replacement therapy, RPE cells can be introduced as a sheet on a polymer or other suitable carrier material that allows the cells to interdigitate with remaining photoreceptors and to resume vital phagocytosis and vitamin A transfer functions, among other functions. A lipid-clearing apo mimetic [e.g., an apoA-I mimetic (e.g., L-4F) or/and an apoE mimetic (e.g., AEM-28-14)] improves traffic of incoming oxygen and nutrients and outgoing waste across the BrM and thereby improves the health of cells in the surrounding area. Optionally in combination with an agent (e.g., an MMP activator or a matrix metalloproteinase) that reduces the thickness of basal laminar deposits (BLamD) persisting over the BrM, the apo mimetic aids in the preparation of a suitable transplant bed for the sheet of RPE cells, which benefit from a clear path from the choriocapillaris to the transplant scaffolding.

As another example of an RPE cell replacement therapy, cells can be introduced into the eye by a non-surgical method. Bone marrow cells can be re-programmed to home in on the RPE layer and to take up residence among the native RPE cells. An apo mimetic [e.g., an apoA-I mimetic (e.g., L-4F) or/and an apoE mimetic (e.g., AEM-28-14)], optionally in combination with an agent (e.g., an MMP activator or a matrix metalloproteinase) that reduces the thickness of BLamD persisting over the BrM, increases the transport of incoming oxygen and nutrients and outgoing waste across the BrM and thereby improves the health of cells in the RPE layer.

RPE rejuvenation can also be practiced. For example, free-floating cells (e.g., umbilical cells) can be injected to provide trophic support to existing cells (e.g., neuronal and RPE cells). A lipid-clearing apo mimetic [e.g., an apoA-I mimetic (e.g., L-4F) or/and an apoE mimetic (e.g., AEM-28-14)] improves traffic of incoming oxygen and nutrients and outgoing waste across the BrM and thereby improves the health of cells in the area of the choroidal watershed. Optionally in combination with an agent (e.g., an MMP activator or a matrix metalloproteinase) that reduces the thickness of BLamD persisting over the BrM, the apo mimetic aids in the preparation of a suitable dispersion bed for the injected cells.

In addition, AMD can be treated by cell replacement therapies for the choriocapillaris. For example, the choriocapillaris endothelium can be replaced with stem cell-derived choriocapillaris endothelial cells.

Furthermore, AMD can be treated by gene therapy. For instance, a gene therapy (e.g., RST-001) can employ the photosensitivity gene channel rhodopsin 2 to create new photoreceptors in retinal ganglion cells. A lipid-clearing apo mimetic [e.g., an apoA-I mimetic (e.g., L-4F) or/and an apoE mimetic (e.g., AEM-28-14)] increases the transport of incoming oxygen and nutrients and outgoing waste across the BrM and thereby improves the health of RPE and photoreceptor cells.

Choroidal blood flow (CBF) decreases with age, possibly due to a decrease in choriocapillaris diameter and density. Choriocapillaris vascular dropout/loss and reduced CBF can occur early in the pathogenesis of AMD. In early AMD, the vascular density of the choriocapillaris is inversely correlated with the density of sub-RPE-BL deposits (e.g., drusen and BLinD), and the number of "ghost" vessels (remnants of previously healthy capillaries) is positively correlated with sub-RPE-BL deposit density. Moreover, decreased CBF is positively correlated with fundus findings associated with an increased risk of choroidal neovascularization (e.g., drusen and pigmentary changes). Vascular endothelial-cell loss may result from activation of the complement system and formation of MACs in the choriocapillaris, which can be inhibited by the use of a complement inhibitor (e.g., an inhibitor of MAC formation, deposition or function). Endothelial dysfunction may also be caused by: 1) a diminished amount of nitric oxide, which can be due to a high level of dimethylarginine (which interferes with L-arginine-stimulated nitric oxide synthesis) and can be corrected by the use of an agent that increases the level of nitric oxide (e.g., a stimulator of nitric oxide synthesis or an inhibitor of dimethylarginine formation; 2) an increase in reactive oxygen species, which can impair nitric oxide synthesis and activity and can be inhibited by the use of an antioxidant (e.g., a scavenger of reactive oxygen species); and 3) inflammatory events, which can be inhibited by an agent that inhibits endothelial inflammatory events (e.g., an apoA-I mimetic such as Rev-D-4F). Low CBF can be increased by using a vasodilator, such as a prostacyclin analog (supra), an activator of soluble guanylate cyclase (e.g., cinaciguat or riociguat), an organic nitrate (e.g., isosorbide mononitrate, isosorbide dinitrate or nitroglycerin, each of which is converted to nitric oxide in the body), MC-1101 (which increases the generation of nitric oxide and also has anti-inflammatory and antioxidant properties), a phosphodiesterase type 5 (PDE5) inhibitor (e.g., avanafil, benzamidenafil, dasantafil, dynafil, lodenafil, mirodenafil, sildenafil, tadalafil, udenafil or vardenafil), a calcium channel blocker (e.g., amlodipine, levamlodipine, cilnidipine, clevidipine, felodipine, isradipine, lercanidipine, nicardipine, nifedipine, nimodipine, nisoldipine or nitrendipine), a selective endothelin receptor A ($ET_A$) antagonist (e.g., ambrisentan, atrasentan, edonentan, sitaxentan or zibotentan), a dual $ET_A/ET_B$ receptor antagonist (e.g., bosentan, macitentan or tezosentan), an $\alpha_1$-adrenoreceptor antagonist (e.g., doxazosin, indoramin, nicergoline, phenoxybenzamine, phentolamine, prazosin, terazosin or tolazoline), or an inhibitor of a complement component that causes smooth muscle contraction (e.g., C3a, C4a or C5a), or any combination thereof. Increasing CBF can prevent rupture of the BrM. To treat vascular loss or/and decreased CBF, one or more therapeutic agents that preserve or improve the health of the endothelium or/and the blood flow of the vascular system of the eye, including the therapeutic agents described herein, can be administered at least in early AMD.

One or more therapeutic agents can be administered in the early stage, the intermediate stage or the advanced stage (atrophic or/and neovascular) of AMD, or prior to development of AMD, or any combination or all thereof, to treat or slow the progression of AMD, or to prevent or delay the onset of the next stage of AMD, or to prevent or delay the onset of AMD.

IX. TREATMENT OF AMD USING THERAPEUTIC AGENTS AND CELL-PENETRATING PEPTIDES

The disclosure provides for the treatment of an eye disorder using a transepithelial, transmembrane or transmucosal drug-delivery system (TDS) comprising a therapeutic agent and a cell-penetrating peptide (CPP). Examples of therapeutic agents and CPPs include without limitation those described herein. In some embodiments, the therapeutic agent is or includes an anti-dyslipidemic agent, an antioxidant, an anti-inflammatory agent, a complement inhibitor, a neuroprotector or an anti-angiogenic agent, or any combination thereof. Where the therapeutic agent is a polypeptide, polynucleotide or peptide-nucleic acid, in some embodiments the CPP is a polycationic CPP, an arginine-rich CPP [e.g., a polyarginine such as $R_6$-$R_{11}$ (SEQ ID NO: 268) (e.g., $R_6$ (SEQ ID NO: 258) or $R_9$ (SEQ ID NO: 261)) or a TAT-related CPP such as TAT(49-57)], or an amphipathic CPP (e.g., Pep-1 or penetratin). Where the therapeutic agent is a substantially hydrophobic polypeptide or small molecule, in some embodiments the CPP is an amphipathic CPP (e.g., Pep-1 or penetratin) or a hydrophobic CPP. A small-molecule therapeutic agent can also be delivered into the eye using another type of CPP, such as a polycationic CPP or an arginine-rich CPP (e.g., a polyarginine such as $R_6$-$R_{11}$ (SEQ ID NO: 268) [e.g., $R_6$ (SEQ ID NO: 258) or $R_9$ (SEQ ID NO: 261)]).

The TDS can be any CPP-containing TDS described herein, including ones where the therapeutic agent is mixed with, non-covalently associated with or covalently bonded to the CPP, or encapsulated in CPP-conjugated nanoparticles, micelles or liposomes. Alternatively, the therapeutic agent can be coupled to a small-molecule α-helix mimic (e.g., 2G-SMoC or 4G-SMoC) or modified (e.g., stapled, prenylated or lipidated) to acquire membrane-translocating ability.

Examples of eye disorders include without limitation those described herein. In certain embodiments, the eye disorder is age-related macular degeneration (AMD), including atrophic (dry) AMD (including geographic atrophy [GA]) and neovascular (wet) AMD.

Accumulation of lipid-containing material (e.g., lipids, lipoproteins and apolipoproteins) occurs early in the pathogenesis of AMD (in particular, atrophic AMD) and leads to sequelae such as inflammation and neovascularization. Accordingly, in some embodiments the therapeutic agent is or includes an anti-dyslipidemic agent. Examples of anti-dyslipidemic agents include without limitation those described herein. In certain embodiments, the anti-dyslipidemic agent is or includes an apolipoprotein (apo) mimetic (e.g., an apoA-I mimetic such as L-4F or D-4F, or an apoE mimetic such as AEM-28-14). In some embodiments, a single apo mimetic is used to treat dry or wet AMD. The single apo mimetic may mediate two or more different functions, such as reduce lipid deposits and inhibit oxidation and inflammation. In other embodiments, a combination of two, three or more different apo mimetics of the same category (e.g., apoA-I mimetics or apoE mimetics) or different categories [e.g., apoA-I mimetic(s) and apoE mimetic(s)] is used to treat dry or wet AMD. The two or more different apo mimetics may mediate two or more different functions, such as reduce lipid deposits and inhibit oxidation and inflammation.

In further embodiments, the anti-dyslipidemic agent is or includes a statin (e.g., atorvastatin or simvastatin). In certain embodiments, a statin is used in a subject with the at-risk complement factor H genotype CC (Y402H). In additional embodiments, the anti-dyslipidemic agent includes both an apo mimetic (e.g., an apoA-I mimetic such as L-4F or D-4F, or an apoE mimetic such as AEM-28-14) and a statin (e.g., atorvastatin or simvastatin). An apo mimetic such as 4F can enhance the activity of a statin or vice versa, or the use of both can have a synergistic effect.

In some embodiments, a TDS comprising an anti-dyslipidemic agent and a CPP is administered prior to development or signs of AMD (e.g., atrophic AMD) to prevent or delay the onset of AMD (e.g., atrophic AMD). In further embodiments, the TDS is administered at least in the early stage of AMD (e.g., to prevent or delay the onset of non-central GA). In still further embodiments, the TDS is administered at least in the intermediate stage of AMD (e.g., to treat non-central GA, or/and to prevent or delay the onset of central GA or/and neovascular AMD). In yet further embodiments, the TDS is administered at least in the advanced stage of atrophic AMD (e.g., to treat central GA, or/and to prevent or delay the onset of neovascular AMD). In additional embodiments, the TDS is administered at least in neovascular AMD to treat neovascular AMD, including types 1, 2 or/and 3 neovascularization (NV). Such embodiments also apply to the use of other kinds of therapeutic agents, with or without the aid of a CPP (or a membrane translocation-conferring modification) or/and a chemical penetration enhancer, to prevent or treat AMD.

Intermediate AMD is characterized by a substantial amount of confluent soft drusen, which can mainly comprise esterified cholesterol and phospholipids. Reduction of confluent soft drusen in intermediate AMD using an anti-dyslipidemic agent can result in decrease in the thickness ("thinning") and normalization of the Bruch's membrane, as well as renewal of the overlying RPE cell layer due to improved exchange of oxygen, micronutrients and metabolites between the choriocapillaris and the RPE. Reduction of confluent soft drusen can be observed by non-invasive techniques such as SDOCT.

An anti-dyslipidemic agent does not need to eliminate or remove all or most of the abnormal lipid deposits from the eye to have a therapeutic or prophylactic effect in AMD. If a threshold amount of abnormal lipids is cleared from the eye, natural transport mechanisms, including traffic between the choriocapillaris endothelium and the RPE layer, can properly work again and can clear remaining abnormal lipids from the eye. Furthermore, lipids accumulate in the eye slowly over a period of years (although fluctuations in druse volume in a shorter time frame are detectable).

Oxidative events contribute to the pathogenesis of AMD, including cell damage and inflammation. Thus, in some embodiments the therapeutic agent is or includes an antioxidant. In addition to their ability to reduce oxidative stress, antioxidants can have other beneficial properties. For instance, saffron carotenoids have anti-inflammatory and cell-protective, as well as antioxidant, effects. Examples of antioxidants include without limitation those described herein. In certain embodiments, the antioxidant is selected from melatonin, vitamins (e.g., vitamin $B_6$, vitamin C and vitamin E [e.g., α-tocopherol]), carotenoids (e.g., xanthophylls [e.g., lutein, zeaxanthin and meso-zeaxanthin] and carotenoids in saffron [e.g., crocin and crocetin]), minerals (e.g., zinc and selenium), and combinations thereof. In some embodiments, the antioxidant is administered prior to development of AMD (e.g., atrophic AMD). In further embodiments, the antioxidant is administered at least in the early stage of AMD. In still further embodiments, the antioxidant is administered at least in the intermediate stage of AMD. In yet further embodiments, the antioxidant is administered at least in the advanced stage of atrophic AMD. In additional embodiments, the antioxidant is administered at least in neovascular AMD. Use of an antioxidant can inhibit the formation of oxidized lipids, which can be strongly pro-inflammatory and hence pro-angiogenic.

Inflammatory events also contribute to the pathogenesis of AMD, including atrophic AMD and neovascular AMD. Therefore, in some embodiments the therapeutic agent is or includes an anti-inflammatory agent. Examples of anti-inflammatory agents include without limitation those described herein. In some embodiments, the anti-inflammatory agent is selected from NSAIDs (e.g., bromfenac and coxibs), immunosuppressants (e.g., glatiramer acetate, IL-2 or IL-2R inhibitors, and TNF-α inhibitors), glucocorticoids (e.g., dexamethasone, fluocinolone acetonide and triamcinolone acetonide), CRP inhibitors, inflammasome inhibitors, complement inhibitors, apo mimetics (e.g., apoA-I mimetics such as L-4F and D-4F), and combinations thereof. In certain embodiments, the anti-inflammatory agent is or includes an NSAID (e.g., bromfenac or a salt [e.g., sodium salt] thereof, or a coxib) or/and an immunosuppressant (e.g., glatiramer acetate). In some embodiments, the anti-inflammatory agent is administered prior to development of AMD (e.g., atrophic AMD). In further embodiments, the anti-inflammatory agent is administered at least in the early stage of AMD. In still further embodiments, the anti-inflammatory agent is administered at least in the intermediate stage of AMD. In yet further embodiments, the anti-inflammatory agent is administered at least in the advanced stage of atrophic AMD. In additional embodiments, the anti-inflammatory agent is administered at least in neovascular AMD. Inflammation is a stimulus of NV, and thus an anti-inflammatory agent can suppress NV.

Activation of the complement system can lead to inflammation, oxidation, neovascularization and cell lysis. Hence, in some embodiments the therapeutic agent is or includes a complement inhibitor. Examples of complement inhibitors include without limitation those described herein. In some embodiments, the complement inhibitor is or includes a complement factor D inhibitor (e.g., lampalizumab or ACH-4471), a C3 inhibitor (e.g., CB-2782) or a C5 inhibitor (e.g., ARC1905 [ZIMURA®], tesidolumab [LFG316] or RA101495), or any combination or all thereof. In certain embodiments, lampalizumab is used in a subject with a mutation in the gene encoding complement factor I, which may be a biomarker for a more positive response to treatment with lampalizumab. In some embodiments, a TDS comprising a complement inhibitor and a CPP is administered at least in the early stage of AMD (e.g., to prevent or delay the onset of non-central GA). In further embodiments, the TDS is administered at least in the intermediate stage of AMD (e.g., to treat non-central GA, or/and to prevent or delay the onset of central GA or/and neovascular AMD). In still further embodiments, the TDS is administered at least in the advanced stage of atrophic AMD (e.g., to treat central GA, or/and to prevent or delay the onset of neovascular AMD). In additional embodiments, the TDS is administered at least in neovascular AMD to treat neovascular AMD, including types 1, 2 or/and 3 NV.

The death of RPE cells and retinal cells (e.g., photoreceptors) by apoptosis, necrosis, cell lysis or any other mechanism can result in RPE and retinal degeneration and atrophy. Therefore, in some embodiments the therapeutic agent is or includes a neuroprotector. Examples of neuroprotectors include without limitation those described herein. In some embodiments, the neuroprotector is selected from glatiramer acetate, neurotrophic factors, apoptosis inhibitors, necrosis inhibitors, complement inhibitors, antioxidants, and combinations thereof. In certain embodiments, the neuroprotector is or includes glatiramer acetate or/and a neurotrophic factor (e.g., CNTF, BDNF or GDNF). In some embodiments, a TDS comprising a neuroprotector and a CPP is administered at least in the early stage of AMD. In further embodiments, the TDS is administered at least in the intermediate stage of AMD. In still further embodiments, the TDS is administered at least in the advanced stage of atrophic AMD. In additional embodiments, the TDS is administered at least in neovascular AMD.

The growth of new blood vessels and vascular leakage therefrom in type 1, 2 or 3 NV can lead to loss of central vision within 24 months of disease onset if left untreated. Hence, in some embodiments the therapeutic agent is or includes an anti-angiogenic agent. Examples of anti-angiogenic agents include without limitation those described herein. In certain embodiments, the anti-angiogenic agent is or includes an agent that inhibits the action of a vascular endothelial growth factor (e.g., VEGF-A, VEGF-B or placental growth factor) or a receptor therefor (e.g., aflibercept [EYLEA®], brolucizumab, bevacizumab [AVASTIN®] or ranibizumab [LUCENTIS®]), or/and an agent that inhibits the action of a platelet-derived growth factor (e.g., PDGF-A, PDGF-B, PDGF-C, PDGF-D or PDGF-A/B) or a receptor therefor (e.g., E10030 [FOVISTA®] or REGN2176-3). In some embodiments, a TDS comprising an anti-angiogenic agent and a CPP is administered at least in neovascular AMD to treat neovascular AMD, including types 1, 2 or/and 3 NV. In additional embodiments, the TDS is administered prior to signs of active neovascularization (e.g., in the advanced or intermediate stage of dry AMD or earlier) to prevent or delay the onset of neovascular AMD, including types 1, 2 or/and 3 NV. The presence of sub-RPE-BL, subretinal or intraretinal fluid, which can signify active neovascularization and leakage of fluid from new blood vessels, can be detected by techniques such as OCT-fluorescein angiography.

A TDS comprising a particular therapeutic agent of a particular category of therapeutic agents can be used to treat AMD. For instance, an apo mimetic (e.g., an apoA-I mimetic such as L-4F or D-4F or an apoE mimetic such as AEM-28-14) or a statin (e.g., atorvastatin or simvastatin) can be used as an anti-dyslipidemic agent to treat AMD. Furthermore, a single TDS, or two or more TDSs, comprising two or more different therapeutic agents of a particular category of therapeutic agents, such as those having different mechanisms of action or different biological targets, can be used to treat AMD. As an example, an apo mimetic (e.g., an apoA-I mimetic such as L-4F or D-4F or an apoE mimetic such as AEM-28-14) and a statin (e.g., atorvastatin or simvastatin) can be used as anti-dyslipidemic agents to treat AMD. As another example, an anti-VEGF/VEGFR agent (e.g., aflibercept, brolucizumab, bevacizumab or ranibizumab) and an anti-PDGF/PDGFR agent (e.g., E10030 or REGN2176-3) can be used as anti-angiogenic agents to treat neovascular AMD.

In addition, a single TDS, or two or more TDSs, comprising two or more different categories of therapeutic agents, such as those targeting different underlying factors of AMD, can be used to treat AMD. For example, a TDS comprising an anti-dyslipidemic agent (e.g., an apo mimetic such as an apoA-I mimetic [e.g., L-4F or D-4F] or an apoE mimetic [e.g., AEM-28-14], or a statin such as atorvastatin or simvastatin) can be used in conjunction with a TDS comprising an anti-inflammatory agent (e.g., an immunosuppressant such as glatiramer acetate or a glucocorticoid), a TDS comprising a complement inhibitor (e.g., a CFD inhibitor such as lampalizumab or ACH-4471, a C3 inhibitor such as CB-2782, or a C5 inhibitor such as ARC1905, LFG316 or RA101495), a TDS comprising a neuroprotector (e.g., a neurotrophic factor such as CNTF, BDNF or GDNF), or a TDS comprising an anti-angiogenic agent (e.g., an anti-VEGF/VEGFR agent such as aflibercept, brolucizumab, bevacizumab or ranibizumab), or any combination or all thereof, to treat atrophic AMD or/and neovascular AMD. As another example, a TDS comprising an anti-angiogenic agent (e.g., an anti-VEGF/VEGFR agent such as aflibercept, brolucizumab, bevacizumab or ranibizumab) can be used in combination with a TDS comprising an anti-inflammatory agent (e.g., a complement inhibitor such as a C5 inhibitor [e.g., ARC1905 or LFG316]) or a TDS comprising an immunosuppressant (e.g., an IL-2 receptor antagonist such as basiliximab or daclizumab, or a TNF-α inhibitor such as adalimumab or infliximab) to treat neovascular AMD. Inflammation is a stimulus of NV, and thus an anti-inflammatory agent or an immunosuppressant can suppress NV.

Alternatively, one or more CPP-containing TDSs comprising one or more different therapeutic agents, or one or more therapeutic agents with a membrane translocation-conferring modification, can be used in combination with one or more other therapeutic agents without the aid of a CPP or a membrane translocation-conferring modification to prevent or treat AMD. As an example, a statin (e.g., atorvastatin or simvastatin) can be administered orally or by eye drop without a CPP or a membrane translocation-conferring modification for the prevention or treatment of AMD (e.g., atrophic or/and neovascular AMD). As another example, an antioxidant (e.g., melatonin, a vitamin [e.g., vitamin E], a carotenoid [e.g., saffron carotenoids], zinc or OT-551, or any combination thereof) can be administered orally or by eye drop without a CPP or a membrane translocation-conferring modification for the prevention or treatment of AMD (e.g., atrophic AMD). For instance, antioxidants in an AREDS or AREDS2 formulation, an ICAPS® formulation, an Ocuvite® formulation or Saffron 2020™ can be taken orally. As a further example, an NSAID (e.g., bromfenac or a salt [e.g., sodium salt] thereof, or a coxib) can be administered by eye drop or orally without a CPP or a membrane translocation-conferring modification for the prevention or treatment of AMD (e.g., atrophic or/and neovascular AMD). As an additional example, an enhancer of choroidal blood flow (e.g., MC-1101) can be administered by eye drop without a CPP or a membrane translocation-conferring modification, e.g., prior to development of AMD or in early AMD to prevent or treat atrophic AMD. A chemical penetration enhancer (CPE) can optionally be used to enhance delivery of a therapeutic agent into the eye by, e.g., eye drop or contact lens.

A TDS comprising a therapeutic agent and a CPP, or a modified (e.g., stapled, prenylated, lipidated or coupled to a small-molecule α-helix mimic) therapeutic agent, can be administered by any suitable mode. In some embodiments, a TDS or a modified therapeutic agent is administered by eye drop. In further embodiments, 1, 2, 3, 4 or more (e.g., 1 or 2) eye drops of a TDS or a modified therapeutic agent are administered 1, 2, 3, 4 or more times (e.g., twice or thrice) daily for at least about 1 week, 2 weeks, 3 weeks, 1 month, 6 weeks, 2 months, 10 weeks, 3 months, 4 months, 5 months, 6 months, 1 year, 1.5 years, 2 years, 3 years, 4 years, 5 years or longer, or until the disease has been successfully treated according to selected outcome measure(s), or for a period of time that can be determined by the treating physician. The number of topical applications per day can be based on, e.g., the rate of clearance of the therapeutic agent from ocular tissues. Because CPP-conjugated nanoparticles, micelles or liposomes encapsulating a therapeutic agent can release the therapeutic agent in a controlled and sustained manner, such a TDS can be administered by eye drop, e.g., once daily, once every 2 or 3 days, twice a week or potentially once a week. All of the foregoing embodiments also apply to a composition comprising a therapeutic agent and a CPE, with or without a CPP.

In other embodiments, a CPP-containing TDS, a modified therapeutic agent, or a composition comprising a therapeutic agent and a CPE with or without a CPP is administered by means of a contact lens (e.g., a corneal lens or a scleral lens). A contact lens can be designed to deliver the therapeutic agent into the eye over a certain period of time, such as at least about 1 day, 2 days, 3 days, 1 week or longer.

A TDS or a modified therapeutic agent can also be used pro re nata (as needed). For example, a TDS or a modified therapeutic agent can be administered by eye drop or contact lens until achievement of selected outcome measure(s) (e.g., elimination of all or most soft drusen or reduction of soft drusen volume to a certain level), at which time use of the therapeutic agent can optionally be stopped. Drusen volume can be quantified by non-invasive techniques such as SDOCT. If monitoring shows that the disease has returned (e.g., the presence of a few medium-size drusen or the presence of a large druse), application of the TDS or the modified therapeutic agent by eye drop or contact lens can be resumed. The same also applies to the use of a composition comprising a therapeutic agent and a CPE, with or without a CPP.

Administration of one or more therapeutic agents the earlier the stage of AMD is advantageous for preventing or slowing the disease progression to more severe forms of AMD (e.g., non-central GA, central GA or neovascular AMD), and for preventing or minimizing complications thereof, such as vision impairment or loss. Use of a cell-penetrating peptide, a chemical penetration enhancer or a membrane translocation-conferring modification (e.g., stapling, prenylation, lipidation or coupling to a small-molecule α-helix mimic) allows a therapeutic agent to be administered non-invasively by eye drop or contact lens in early AMD or even prior to signs of AMD (e.g., atrophic AMD).

X. TREATMENT OF AMD AND OTHER EYE DISEASES

One or more of the therapeutic agents described herein (e.g., an anti-dyslipidemic agent such as an apoA-I or apoE mimetic or/and a statin, optionally in combination with one or more other therapeutic agents) can be used to treat age-related macular degeneration (AMD) and any symptoms or complications associated with AMD. Examples of such symptoms and complications include without limitation accumulation of lipids (including neutral lipids and modified lipids) on the BrM, thickening of the BrM, accumulation of lipid-rich debris, deposition of lipid-rich debris (including basal linear deposits and drusen) between the RPE-BL and the BrM ICL, formation of a diffusion barrier between the RPE and the choriocapillaris, degeneration of photoreceptors, geographic atrophy (including non-central and central GA), RPE atrophy, neovascularization (including types 1, 2 and 3 NV), leakage, bleeding and scarring in the eye, and vision impairment and loss.

As a non-limiting example, an anti-dyslipidemic agent (e.g., an apoA-I mimetic such as L-4F or D-4F or an apoE mimetic such as AEM-28-14, or/and a statin such as atorvastatin or simvastatin) can be used to prevent, delay the onset of, slow the progression of or reduce the extent of vision impairment or loss associated with AMD, or improve vision (e.g., visual acuity) in a subject with AMD. One or more other therapeutic agents can optionally be used. The vision impairment or loss can be associated with atrophic AMD (including non-central or/and central GA) or neovascular AMD (including types 1, 2 or/and 3 NV), or the vision improvement can occur in a subject with atrophic AMD or neovascular AMD.

One or more of the therapeutic agents described herein can also be used to treat other eye diseases and disorders in addition to AMD. Non-limiting examples of other eye diseases and disorders that can be treated with one or more therapeutic agents described herein include juvenile macular degeneration (e.g., Stargardt disease), macular telangiectasia, maculopathy (e.g., age-related maculopathy [ARM] and diabetic maculopathy [DMP] [including partial ischemic DMP]), macular edema (e.g., diabetic macular edema [DME, including clinically significant DME, focal DME and diffuse DME], Irvine-Gass syndrome [postoperative macular edema], and macular edema following RVO [including central RVO and branch RVO]), retinopathy (e.g., diabetic retinopathy [DR, including in patients with DME], proliferative vitreoretinopathy [PVR], Purtscher's retinopathy and radiation retinopathy), retinal artery occlusion (RAO, e.g., central and branch RAO), retinal vein occlusion (RVO, e.g., central RVO [including central RVO with cystoid macular edema {CME}] and branch RVO [including branch RVO with CME]), glaucoma (including low-tension, normal-tension and high-tension glaucoma), ocular hypertension, retinitis (e.g., Coats' disease [exudative retinitis] and retinitis pigmentosa [RP]), chorioretinitis, choroiditis (e.g., serpiginous choroiditis), uveitis (including anterior uveitis, intermediate uveitis, posterior uveitis with or without CME, pan-uveitis and non-infectious uveitis), retinal detachment (e.g., in von Hippel-Lindau disease), retinal pigment epithelium (RPE) detachment, dystrophies of rods or/and cones, and diseases associated with increased intracellular or extracellular lipid storage or accumulation in addition to AMD.

Table 1 provides non-limiting examples of therapeutic agents that can be used to treat AMD and other eye disorders. In some embodiments, each therapeutic agent listed in Table 1 is used alone to treat AMD or another eye disorder. In other embodiments, each therapeutic agent listed in Table 1 is used in combination with one or more other therapeutic agents described herein, such as one or more other therapeutic agents listed in Table 1, to treat AMD or another eye disorder. In certain embodiments, each therapeutic agent listed in Table 1 is used in combination with an apo mimetic (e.g., an apoA-I mimetic such as L-4F or D-4F, or an apoE mimetic such as AEM-28-14) or/and a statin (e.g., atorvastatin or simvastatin) to treat AMD or another eye disorder. In some embodiments, each therapeutic agent listed in Table 1 is delivered into the eye with the aid of a cell-penetrating peptide (CPP) or/and a chemical penetration enhancer (CPE) by means of, e.g., an eye drop or a contact lens (e.g., a corneal lens or a scleral lens). In further embodiments, an apo mimetic (e.g., an apoA-I mimetic such as L-4F or D-4F, or an apoE mimetic such as AEM-28-14) or/and a statin (e.g., atorvastatin or simvastatin) is delivered into the eye with the aid of a CPP or/and a CPE by means of, e.g., an eye drop or a contact lens (e.g., a corneal lens or a scleral lens).

In some embodiments, a therapeutic agent that is a peptide or protein is administered by way of a CPP-containing TDS. A non-polypeptide (e.g., small-molecule) therapeutic agent can also be delivered into the eye with the aid of a CPP (or/and a CPE). In certain embodiments, a therapeutic agent is mixed with a CPP or/and a CPE in an ophthalmic formulation. In some embodiments, the CPP is a polycationic CPP (e.g., POD), an arginine-rich CPP [e.g., a polyarginine such as $R_6$-$R_{11}$ (SEQ ID NO: 268) (e.g., $R_6$ (SEQ ID NO: 258) or $R_9$ (SEQ ID NO: 261)) or a TAT-related CPP such as TAT(49-57)], or an amphipathic CPP (e.g., Pep-1 or penetratin). In certain embodiments, the CPE is or includes a surfactant, such as a non-ionic surfactant (e.g., a saponin or an alkyl glycoside such as 1-O-tetradecyl-β-D-maltoside). In some embodiments, each therapeutic agent listed in Table 1 is mixed with a polyarginine CPP (e.g., $R_6$ (SEQ ID NO: 258) or $R_9$ (SEQ ID NO: 261)), and optionally a CPE, and is delivered into the eye by means of, e.g., an eye drop or a contact lens (e.g., a corneal lens or a scleral lens).

TABLE 1

Therapeutic agents used alone or in combination with one or more other therapeutic agents (e.g., an apoA-I mimetic such as L-4F or D-4F or an apoE mimetic such as AEM-28-14, or/and a statin such as atorvastatin or simvastatin) to treat AMD or other eye disorders

| Function | Exemplary Active Agent | Exemplary Eye Disorders |
| --- | --- | --- |
| Anti-dyslipidemic | | |
| | Omega-3 fatty acid(s) | Dry and wet AMD, macular edema |
| HMG-CoA reductase inhibitor | Atorvastatin | Dry AMD (including GA) and wet AMD |
| HMG-CoA reductase inhibitor | Simvastatin | Dry AMD (including GA) and wet AMD |
| CETP inhibitor | Anacetrapib | AMD (including dry AMD) |
| ApoA-I mimetic | L-4F or D-4F | Dry AMD (incl. GA) and wet AMD |
| ApoE mimetic | AEM-28-14 | Dry AMD (incl. GA) and wet AMD |
| Reconstituted HDL mimetic | CSL-112 | Dry and wet AMD |
| Antioxidant | | |
| Carotenoid | Crocin or/and crocetin | AMD (including dry AMD and GA) |
| Carotenoid | Lutein or/and zeaxanthin | AMD (including dry AMD and GA) |
| ROS and radical scavenger | Vitamin E (eg., α-tocopherol) or/and vitamin C | AMD (including dry AMD and GA) |
| ROS and radical scavenger | Melatonin | AMD (including dry AMD and GA) |
| Cardiolipin peroxidation inhibitor (CPI) | Elamipretide | AMD (including dry AMD), mitochondrial eye diseases (e.g. Leber's hereditary optic neuropathy) |
| CPI | SkQ1 | AMD (including dry AMD), uveitis, glaucoma, dry eye |
| NADPH oxidase inhibitor | GKT-831 | Dry AMD (including GA), wet AMD, DR, DME, RVO, uveitis, allergic conjunctivitis, dry eye |
| NADH:ubiquinone oxidoreductase inhibitor | Metformin | AMD (including dry AMD and GA) |
| Anti-inflammatory | | |
| COX-2 inhibitor | Bromfenac | Dry AMD (including GA), wet AMD, ME, ocular inflammation (e.g., uveitis) |
| Connexin43 hemichannel blocker | Peptide5 (Peptagon ™) | Wet AMD, DR, ME, DME, |
| Complement inhibitor | | |
| | KSI-401 | AMD (including dry AMD and GA) |
| CFD inhibitor | ACH-4471 | AMD (including dry AMD and GA) |
| CFD inhibitor | Lampalizumab | AMD (including dry AMD and GA) |
| CFP (properdin) inhibitor | CLG561 | AMD (including dry AMD and GA) |
| C3 inhibitor | APL-2 | AMD (including dry AMD and GA) |
| C3 inhibitor | CB-2782 | AMD (including dry AMD and GA) |
| C5 inhibitor | ARC1905 (avacincaptad pegol or Zimura ®) | Dry AMD (including GA), wet AMD, Stargardt disease, non-infectious uveitis, von Hippel-Lindau disease |
| C5 inhibitor | Tesidolumah (LFG316) | Dry AMD (including GA), wet AMD, uveitis |
| C5 inhibitor | RA101495 | Dry AMD (including GA), wet AMD, uveitis |
| Immunosuppressant | | |
| Glucocorticoid | Dexamethasone (e.g., EGP-437, Ozurdex ®, Dextenza ™ or DSP-Visulex) | Dry and wet AMD, ME, DME, RVO, uveitis, endophthalmitis, post-cataract surgery inflammation |
| Glucocorticoid | Fluocinolone acetonide (e.g., Iluvien ®) | Dry and wet AMD, DME, uveitis |

TABLE 1-continued

Therapeutic agents used alone or in combination with one or more other therapeutic agents
(e.g., an apoA-I mimetic such as L-4F or D-4F or an apoE mimetic such as AEM-28-14, or/and a statin
such as atorvastatin or simvastatin) to treat AMD or other eye disorders

| Function | Exemplary Active Agent | Exemplary Eye Disorders |
| --- | --- | --- |
| TNF-α inhibitor | Adalimumab | Dry and wet AMD, uveitis |
| Calcineurin inhibitor | Tacrolimus | Dry and wet AMD, uveitis |
| mTOR inhibitor | Rapamycin (sirolimus) | Dry and wet AMD, uveitis |
| Suppressor of M1-related transcription | TMi-018 | Dry AMD (including GA), DR |
| Anti-inflammatory and neuroprotective | | |
| | Glatiramer acetate | AMD (including dry AMD and GA) |
| | Doxycycline | AMD (including dry AMD and GA) |
| | Minocycline | AMD (including dry AMD and GA) |
| PDE inhibitor | Ibudilast | Dry AMD (including GA), wet AMD, allergic conjunctivitis |
| Neuroprotector | | |
| | Brimonidine | AMD (including dry AMD and GA) |
| | Glucose | Dry AMD (including GA), wet AMD, retinitis pigmentosa (RP) |
| | Ciliary neurotrophic factor (CNTF) | Dry AMD (including GA), wet AMD, RP, DR, macular telangiectasia |
| | NT-501 (CNTF-releasing cells) | Dry AMD (including GA), wet AMD, RP, DR, macular telangiectasia |
| | Brain-derived neurotrophic factor (BDNF) | Dry AMD (including GA), wet AMD, RP, DR, macular telangiectasia |
| | Glial cell-derived neurotrophic factor (GDNF) | Dry AMD (including GA), wet AMD, RP, DR, macular telangiectasia |
| Apoptosis/Fas inhibitor | ONL-1204 | Dry & wet AMD, retinal detachment, RP |
| Visual cycle modulator | | |
| RBP4 inhibitor | LBS-008 | AMD (including dry AMD), Stargardt disease |
| RPE65 inhibitor | Emixustat | AMD (including dry AMD), DR (e.g., proliferative DR), Stargardt disease |
| Anti-angiogenic | | |
| VEGF inhibitor | Abicipar pegol | Wet AMD, DR, DME, post-RVO ME |
| VEGF inhibitor | Aflibercept (e.g., Eylea ® or OTX-IVT) | Wet AMD, DR, DME, post-RVO ME |
| VEGF inhibitor | Conbercept | Wet AMD, DR, DME, post-RVO ME |
| VEGF inhibitor | OPT-302 | Wet AMD, DR, DME, post-RVO ME |
| VEGF inhibitor | Bevacizumab (Avastin ®) | Wet AMD, DR, DME, post-RVO ME |
| VEGF inhibitor | Brolucizumab | Wet AMD, DR, DME, post-RVO ME |
| VEGF inhibitor | Ranibizumab (e.g., Lucentis ® or TransCon ranibizumab) | Wet AMD, DR, DME, post-RVO ME |
| VEGF inhibitor | ENV1305 | Wet AMD, DR, DME, post-RVO ME |
| VEGF inhibitor | KSI-301 | Wet AMD, DR, DME, post-RVO ME |
| VEGF inhibitor | ACU-6151 | Wet AMD, DR, DME, post-RVO ME dry AMD (including GA) |
| VEGF/PDGF inhibitor | Squalamine | Wet AMD, DR, DME, post-RVO ME |
| VEGF/PDGF/FGF inhibitor | Decorin | Wet AMD, DR, DME, post-RVO ME, RP |
| VEGF-signaling inhibitor | OCU200 | Wet AMD, DR, DME, post-RVO ME |
| VEGFR tyrosine kinase (TK) inhibitor | KPI-285 | Wet AMD, DR, DME, post-RVO ME |
| VEGFR/PDGFR TK inhibitor | Sunitinib (e.g., GB-102) | Wet AMD, DR, DME, post-RVO ME |
| VEGFR/PDGFR TK inhibitor | X-82 | Wet AMD, DR, DME, post-RVO ME |
| VEGFR/PDGFR/FGFR TK inhibitor | Pazopanib | Wet AMD, DR, DME, post-RVO ME |
| PDGF inhibitor | E10030 [Fovista ®] | Wet AMD, DR, DME, post-RVO ME |
| VEGF/angiopoietin-2 (ANG-2) inhibitor | ABP-201 | Wet AMD, DR, DME, post-RVO ME |
| VEGF/ANG-2 inhibitor | RG7716 | Wet AMD, DR, DME, post-RVO ME |
| Integrin inhibitor | ALG-1001 (Luminate ®) | Wet AMD, DR, DME, post-RVO ME |
| Integrin inhibitor | SF0166 | Wet AMD, DR, DME, post-RVO ME |
| MMP inhibitor | Minocycline (e.g., NM108) | Wet AMD, DR, DME, post-RVO ME uveitis |

TABLE 1-continued

Therapeutic agents used alone or in combination with one or more other therapeutic agents
(e.g., an apoA-I mimetic such as L-4F or D-4F or an apoE mimetic such as AEM-28-14, or/and a statin
such as atorvastatin or simvastatin) to treat AMD or other eye disorders

| Function | Exemplary Active Agent | Exemplary Eye Disorders |
| --- | --- | --- |
| Tissue factor inhibitor | ICON-1 | Wet AMD, DR, DME, post-RVO ME |
| SRPK1 inhibitor | SPHINX31 | Wet AMD, DR, DME, post-RVO ME |
| Kallikrein inhibitor | KVD001 | Wet AMD, DR, DME, post-RVO ME |
| Antifibrotic/antiscarring | | |
| TGF-β inhibitor | Decorin | PVR |
| TGF-β inhibitor | IL-10 | PVR |
| Antiproliferative | 5-Fluorouracil (5-FU) | PVR |
| VE-PTP inhibitor | AKB-9778 | DR (including non-proliferative DR) |
| Vascular modulator | | |
| Vasodilator | MC-1101 | AMD (including dry AMD) |
| α$_2$-adrenergic receptor agonist | Brimonidine | Glaucoma |
| Unknown | RO7171009 | AMD (including dry AMD and GA) |
| Crystallin stabilizer | VP1-001 | Lens disorders (e.g., cataracts and presbyopia) |
| Cell replacement | | |
| hESC-derived RPE cells | OpRegen ® cells | AMD (including dry AMD and GA) |
| hESC-derived RPE cells | CPCB-RPE1 cells | AMD (including dry AMD and GA) |
| hESC-derived RPE cells | MA09-hRPE cells | AMD (including dry AMD and GA) |
| Human retinal progenitor cells | jCell cells | AMD (including dry AMD and GA), RP |
| Human umbilical tissue-derived cells | Palucorcel (CNTO 2476) | AMD (including dry AMD and GA), RP |

As an illustrative example, glucose can be used to treat an eye disorder characterized by loss of cone photoreceptor function, such as retinitis pigmentosa (RP), dry AMD (incluging GA) or wet AMD. Degeneration or death of rod photoreceptors in RP and AMD prevents glucose release from RPE cells. Cone photoreceptors starved of glucose have impaired function and can no longer synthesize the visual pigment-rich cone outer segment (COS), resulting in COS loss and reduction or loss of central vision, although viable cone nuclei remain. Glucose therapy reactivates degenerative or dormant cones and restores cone function and COS synthesis, thereby improving central vision in RP and AMD. See, e.g., W. Wang et al., *Cell Reports*, 15:372-385 (2016), and H. Kaplan et al., *Trans. Vis. Sci. Tech.*, 6:5 (2017). Glucose can be used alone or in combination with one or more other therapeutic agents described herein (e.g., a neurotrophic factor such as CNTF, BDNF or GDNF, an anti-inflammatory agent such as an NSAID [e.g., bromfenac], or an anti-dyslipidemic agent such as an apoA-I mimetic [e.g., L-4F or D-4F] or an apoE mimetic [e.g., AEM-28-14], or/and a statin [e.g., atorvastatin or simvastatin]) to treat an eye disorder characterized by loss of cone function, such as RP or AMD. In some embodiments, glucose, and optionally an additional therapeutic agent (e.g., a neurotrophic factor, an anti-inflammatory agent or an anti-dyslipidemic agent), is delivered into the eye with the aid of a CPP or/and a CPE by means of, e.g., an eye drop or a contact lens (e.g., a corneal lens or a scleral lens). In certain embodiments, glucose and an additional therapeutic agent (e.g., a neurotrophic factor, an anti-inflammatory agent or an anti-dyslipidemic agent) in the same formulation are delivered into the eye with the aid of a CPP or/and a CPE by means of, e.g., an eye drop or a contact lens (e.g., a corneal lens or a scleral lens).

As another example, one or more therapeutic agents can be used to treat proliferative vitreoretinopathy (PVR). In some embodiments, the one or more therapeutic agents are selected from TGF-β inhibitors (e.g., decorin, tranilast and IL-10), PDGF inhibitors, PDGFR kinase inhibitors (e.g., AG1295), antiproliferative agents (e.g., alkylphosphocholine, daunorubicin, etoposide, 5-fluorouracil, glucosamine, hypericin, retinoic acid, tacrolimus and taxol), cell-migration inhibitors (e.g., rho kinase [ROCK] inhibitors such as fasudil), anti-inflammatory agents (e.g., TNF-α inhibitors, IL-6 inhibitors and glucocorticoids [e.g., triamcinolone acetonide]), and combinations thereof. In certain embodiments, the one or more therapeutic agents are delivered into the eye using a CPP or/and a CPE by means of, e.g., an eye drop or a contact lens (e.g., a corneal lens or a scleral lens).

In some embodiments, an anti-dyslipidemic agent (e.g., an apoA-I mimetic such as L-4F or D-4F or an apoE mimetic such as AEM-28-14, or/and a statin such as atorvastatin or simvastatin), either alone or in combination with one or more other therapeutic agents, is used to treat an eye disorder other than AMD. In certain embodiments, an anti-dyslipidemic agent having anti-inflammatory property (e.g., an apoA-I mimetic such as L-4F or D-4F or an apoE mimetic such as AEM-28-14), either alone or in combination with another therapeutic agent, is used to treat an inflammatory eye disorder, such as uveitis. In such a case, the apo mimetic (e.g., L-4F, D-4F or AEM-28-14) acts as an anti-inflammatory agent and can be utilized in place of, e.g., a steroidal or non-steroidal anti-inflammatory drug. In further embodiments, an anti-dyslipidemic agent (e.g., an apoA-I mimetic such as L-4F or D-4F or an apoE mimetic such as AEM-28-14), in conjunction with an anti-VEGF/VEGFR agent, a neuroprotector, a kinase inhibitor or c-peptide (connecting peptide), or any combination or all thereof, is used to treat diabetic retinopathy.

In additional embodiments, an anti-dyslipidemic agent (e.g., an apoA-I mimetic such as L-4F or D-4F or an apoE mimetic such as AEM-28-14, or/and a statin such as atorvastatin or simvastatin) is used in combination with an anti-angiogenic agent (e.g., an anti-VEGF/VEGFR agent such as aflibercept, brolucizumab, bevacizumab or ranibizumab, or/and an anti-PDGF/PDGFR agent such as E10030 or REGN2176-3) to treat other eye disorders in addition to AMD. Examples of other eye disorders that can be treated with such a combination include without limitation DMP (including partial ischemic DMP), DME (including clinically significant DME, focal DME and diffuse DME), diabetic retinopathy (including in patients with DME), RVO (including central RVO [e.g., central RVO with CME] and branch RVO [e.g., branch RVO with CME]), macular edema following RVO (including central RVO and branch RVO), Irvine-Gass syndrome (postoperative macular edema), and uveitis (including uveitis posterior with CME). Beneficial properties of an anti-dyslipidemic agent (e.g., an apo mimetic or a statin), such as the strong anti-inflammatory property of apoA-I mimetics and apoE mimetics and the antioxidant property of statins, can increase the effectiveness of an anti-angiogenic agent (e.g., an anti-VEGF/VEGFR agent or an anti-PDGF/PDGFR agent) in the treatment of such eye disorders.

In further embodiments, a neuroprotector, optionally in combination with one or more other therapeutic agents, is used to treat a degenerative (e.g., neurodegenerative) eye disorder. Examples of neuroprotectors include without limitation those described herein. In some embodiments, the neuroprotector is or includes a neurotrophic factor. Examples of neurotrophic factors include without limitation those described herein. In certain embodiments, the neurotrophic factor is or includes CNTF, GDNF, BDNF or NGF, or any combination thereof. Examples of degenerative (e.g., neurodegenerative) eye disorders include without limitation those described herein. In certain embodiments, the degenerative (e.g., neurodegenerative) eye disorder is AMD (atrophic or neovascular), diabetic retinopathy, retinitis pigmentosa or a dystrophy of rods or/and cones.

Embodiments relating to the treatment of AMD using one or more therapeutic agents (e.g., an anti-dyslipidemic agent such as an apoA-I or apoE mimetic or/and a statin, optionally in combination with one or more other therapeutic agents) and described elsewhere herein also apply to the treatment of other eye disorders using one or more such therapeutic agents. Such embodiments include without limitation embodiments relating to therapeutic agents mixed with, non-covalently associated with or covalently bonded to a cell-penetrating peptide, therapeutic agents encapsulated in CPP-conjugated nanoparticles, micelles or liposomes, therapeutic agents coupled to a small-molecule α-helix mimic, and modified (e.g., stapled, prenylated or lipidated) therapeutic agents, each of which can be administered by any suitable mode, such as by eye drop or contact lens (e.g., corneal lens or scleral lens).

XI. ADMINISTRATION OF THERAPEUTIC AGENTS

The therapeutic agents described herein can be administered to a subject by any suitable method, including any suitable means for local or systemic administration. In certain embodiments, the therapeutic agents are administered by eye drop, contact lens (e.g., corneal lens or scleral lens), intravitreal injection or implant, subconjunctival injection or implant, subretinal injection or implant, sub-Tenon's injection or implant, peribulbar injection, oral ingestion, intravenous injection or infusion, or subcutaneous injection or infusion.

In some embodiments, one or more, or all, of the therapeutic agent(s) are administered locally. Local administration of a therapeutic agent can deliver the agent to the target site(s) more effectively, avoid first-pass metabolism and require a lower administration dose of the agent, and thereby can reduce any side effect caused by the agent. As the pathological events of AMD or another eye disorder occur in the eye, the therapeutic agent(s) used to treat AMD or another eye disorder can be locally administered to the eye for more effective treatment. For example, the lipid-containing material (e.g., lipids, lipoproteins and apolipoproteins) that accumulates in the Bruch's membrane (BrM), the sub-RPE-BL space and the subretinal space appears to be of intraocular origin (e.g., secreted by retinal pigment epithelium [RPE]cells). Therefore, a more effective reduction in the accumulation of such material can involve local administration of one or more anti-dyslipidemic agents to the target sites in the eye.

Potential routes/modes of local administration include without limitation intraaqueous (the aqueous humor), peribulbar, retrobulbar, suprachoroidal, subconjunctival, intraocular, periocular, subretinal, intrascleral, posterior juxtascleral, trans-scleral, sub-Tenon's, intravitreal and transvitreal. Subretinal administration administers a therapeutic agent below the retina, such as, e.g., the subretinal space, the RPE, the sub-RPE-BL space or the choroid, or any combination or all thereof. Potential sites of local administration include, but are not limited to, the anterior chamber (aqueous humor) and the posterior chamber of the eye, the vitreous humor (vitreous body), the retina (including the macula or/and the photoreceptor layer), the subretinal space, the RPE, the sub-RPE-BL space, the choroid (including the BrM and the choriocapillaris endothelium), the sclera, and the sub-Tenon's capsule/space.

In some embodiments, a therapeutic agent is delivered across the sclera and the choroid to the vitreous humor, from where it can diffuse to the target tissue(s), e.g., the retina (e.g., the photoreceptors), the subretinal space, the RPE, the sub-RPE-BL space or the BrM, or any combination or all thereof. In other embodiments, a therapeutic agent is delivered across the sclera and the choroid to the target tissue(s), e.g., the retina (e.g., the photoreceptors), the subretinal space, the RPE or/and the sub-RPE-BL space, from where it can diffuse to the BrM if the BrM is a target tissue. In further embodiments, a therapeutic agent is administered intraocularly into the anterior or posterior chamber of the eye, the vitreous humor, the retina or the subretinal space, for example.

Potential means of local administration include without limitation injection, implantation, and means for local topical administration to the eye, such as eye drop and contact lens (e.g., corneal lens and scleral lens). In some embodiments, one or more of the therapeutic agent(s) are administered by intravitreal (e.g., micro-intravitreal), subconjunctival, subretinal or sub-Tenon's injection or implantation. As an example, an apolipoprotein mimetic (e.g., an apoA-I mimetic such as L-4F or an apoE mimetic such as AEM-28-14) can be injected into the vitreous humor, underneath the conjunctiva, below the retina or into the sub-Tenon's capsule of the eye once every 1 month, 6 weeks, 2 months, 10 weeks or 3 months for a period of time determined by the treating physician (e.g., at least about 6 months, 12 months, 18 months, 24 months or longer) to treat, e.g., atrophic AMD (including non-central or/and central geographic atrophy) or/and neovascular AMD. As another example, an anti-angiogenic agent (e.g., an anti-VEGF/VEGFR agent such as aflibercept, brolucizumab, bevacizumab or ranibizumab) can be intravitreally injected once every 1 month, 6 weeks, 2 months, 10 weeks or 3 months for a period of time determined by the treating physician (e.g., at least about 6 months, 12 months, 18 months, 24 months or longer) to treat, e.g., neovascular AMD.

A method that can administer a therapeutic agent less frequently than intravitreal injection is a posterior juxtascleral depot. For example, Retaane® is a blunt, tinted, posterior juxtascleral depot cannula that delivers a certain amount (e.g., about 15 mg) of anecortave acetate onto the sclera directly behind the macula while leaving the globe intact. Anecortave acetate can be administered once every 6 months using this delivery method, compared to monthly, bimonthly or trimonthly intravitreal injections of ranibizumab, aflibercept or brolucizumab, respectively. Moreover, the posterior juxtascleral depot method greatly decreases the risk of intraocular infection, endophthalmitis and detachment of the retina that may occur with frequent intravitreal injections.

Although local administration of a therapeutic agent to the eye for the treatment of AMD or another eye disorder may have advantages such as greater efficacy and reduced side effects, systemic administration of a therapeutic agent may be desired in certain circumstances. As an example, oral administration of a therapeutic agent can increase patient compliance due to ease of use and non-invasiveness if, e.g., a topical formulation for local delivery (e.g., eye drop or contact lens) cannot be developed for that therapeutic agent. As another example, a pathological event of AMD may have a non-local component. For instance, the amount of lipid-containing material RPE cells secrete into the BrM, the sub-RPE-BL space and the subretinal space may be affected in part by the uptake of plasma lipids (e.g., cholesterol and fatty acids) and lipoproteins (e.g., LDLs) by RPE cells. In such a case, it may be desirable to administer systemically one or more anti-dyslipidemic agents that decrease the production of such lipids and lipoproteins by the liver.

In some embodiments, one or more of the therapeutic agent(s) are administered systemically. Potential routes of systemic administration include without limitation oral, parenteral (e.g., intradermal, subcutaneous, intramuscular, intravascular, intravenous, intra-arterial, intraperitoneal, intramedullary, intrathecal and topical), intracavitary, and topical (e.g., transdermal, transmucosal, intranasal [e.g., by nasal spray or drop], pulmonary [e.g., by oral or nasal inhalation], buccal, sublingual, rectal [e.g., by suppository] and vaginal [e.g., by suppository]).

In certain embodiments, one or more anti-dyslipidemic agents are administered systemically. For example, in certain embodiments a statin or/and a fibrate are administered orally, or/and a GLP-1 receptor agonist is administered subcutaneously. In further embodiments, one or more antioxidants are administered systemically. As an example, in certain embodiments vitamins (e.g., vitamin C and vitamin E), carotenoids (e.g., β-carotene, saffron carotenoids and xanthophylls) or/and zinc are administered orally. In yet further embodiments, one or more anti-inflammatory agents are administered systemically. For example, in certain embodiments an NSAID (e.g., a coxib) is administered orally, or/and a complement inhibitor (e.g., an anti-C5 antibody such as LFG316) is administered intravenously.

In some embodiments, one or more polypeptide therapeutics (e.g., an endogenous angiogenesis inhibitor such as a soluble VEGFR [e.g., VEGFR1], or angiostatin or/and endostatin) are administered by means of a viral (e.g., adenoviral or lentiviral) vector expressing the polypeptide therapeutic(s). As an example, AVA-101 comprises an adeno-associated virus 2 (AAV2) vector containing a gene that encodes soluble VEGFR1 (FLT-1). Local administration of AVA-101 into the eye (e.g., the RPE or choriocapillary endothelium) results in expression of soluble VEGFR1 by the host retinal cells. The soluble VEGFR1 protein binds to VEGF in the extracellular space, which prevents VEGF from binding to membrane-bound VEGFRs and thereby inhibits angiogenesis. AVA-101 can be administered as, e.g., a single subretinal injection for the treatment of, e.g., neovascular AMD (including types 1, 2 or/and 3 neovascularization), which precludes the need for multiple or frequent injections.

In additional embodiments, one or more polypeptide therapeutics (e.g., a neuroprotector [e.g., ciliary neurotrophic factor] or an anti-angiogenic agent [e.g., an anti-VEGF agent such as a soluble VEGFR]) are administered by means of genetically engineered cells (e.g., NTC-201 cells) producing the polypeptide therapeutic(s) and encapsulated in polymeric particles or a polymeric implant. As an example, an expression vector containing a gene encoding ciliary neurotrophic factor (CNTF) is transfected into RPE cells to produce genetically engineered NTC-201 cells. The NTC-201 cells are encapsulated, e.g., in a semipermeable hollow fiber-membrane capsule that is contained in a scaffold of six strands of polyethylene terephthalate yarn. The capsule and the scaffold maintain the cells (e.g., growth support and delivery of nutrients). After implantation of the encapsulated cell-based drug-delivery system in, e.g., the vitreous cavity (e.g., via access through the sclera), the NTC-201 cells produce and secrete CNTF through the semipermeable capsule. Such an encapsulated cell technology (e.g., NT-501) provides a controlled, continuous and sustained delivery of CNTF, and prolongs the half-life of CNTF from about 1-3 minutes to about 20-50 months. Intraocular delivery of CNTF using such an encapsulated cell technology can, e.g., reduce photoreceptor loss associated with the degeneration of cells of the retina, and hence can be used to prevent, delay the onset of or slow the progression of, e.g., geographic atrophy (including central GA), neovascular AMD or/and vision loss.

One or more polypeptide therapeutics can also be delivered via administration of naturally occurring cells that produce and release such polypeptides. For example, cells derived from umbilical cord tissue can rescue photoreceptors and visual functions, reportedly through the production and release of neuroprotectors such as neurotrophic factors.

The therapeutically effective amount and the frequency of administration of, and the length of treatment with, a particular therapeutic agent for the treatment of AMD or another eye disease may depend on various factors, including the eye disease, the severity of the disease, the potency of the therapeutic agent, the mode of administration, the age, body weight, general health, gender and diet of the subject, and the response of the subject to the treatment, and can be determined by the treating physician. In some embodiments, the dosing regimen of one or more of the therapeutic agent(s) comprises one or more loading doses followed by one or more maintenance doses. The one or more loading doses are designed to establish a therapeutically effective level of the therapeutic agent at the target site(s) more quickly, and the one or more maintenance doses are designed to establish a therapeutically effective level of the therapeutic agent for the period of treatment. The loading dose can be provided, e.g., by administering a dose that is larger than (e.g., 2, 3, 4 or 5 times larger than) the maintenance dose, or by administering a dose substantially similar to the maintenance dose more frequently (e.g., 2, 3, 4 or 5 times more frequently) at the beginning of treatment. As an example, for the treatment of neovascular AMD (including types 1, 2 or/and 3 neovascularization), in certain embodiments three loading doses of the anti-angiogenic agent aflibercept are administered by intravitreal injection (about 2 mg monthly for 3 months) followed by a maintenance dose (about 2 mg) once every 2 months for a period of time as determined by the treating physician.

In the early, intermediate and advanced stages of AMD, and in atrophic AMD and neovascular AMD, the progression and treatment of AMD can be monitored using various methods known in the art (called "diagnostic" methods herein for simplicity). Such methods include without limitation structural SDOCT (which reveals drusen and RPE and can quantify total drusen volume and monitor progression of the disease), hyperspectral autofluorescence (which can detect fluorophores unique to drusen and basal linear deposits), color fundus photography, quantitative fundus autofluorescence (qAF) and OCT-fluorescein angiography (FA), and can examine parameters such as cone-mediated vision (e.g., best-corrected visual acuity [BCVA, which persists until late in the disease], visual acuity with an Early Treatment Diabetic Retinopathy Study (ETDRS) chart or a Snellen chart, contrast sensitivity with a Pelli-Robson chart, low-luminance visual acuity [visual acuity measured with a neutral-density filter to reduce retinal illuminance], and development of metamorphopsia) and rod-mediated vision (e.g., dark adaptation kinetics [which is a sensitive measure of macular function that tracks with progression of the disease]). For example, treatment is expected to keep stable, or to improve, photopic (daylight) vision mediated by cone photoreceptors and scotopic (night) vision mediated by rod photoreceptors. As another example, the health of RPE cells can be assessed with qAF, where stability of or increase in qAF intensity can indicate stable or improved RPE health, as a reduction in qAF intensity can signify degeneration of RPE cells. qAF can be used to quantify the area or size of geographic atrophy, and hence to monitor the progression of non-central GA or central GA, as was done in the MAHALO Phase II study on lampalizumab. The health of RPE cells can also be assessed with SDOCT, where the presence of hyper-reflective foci located vertically above drusen within the retina indicates migratory RPE cells, which signifies that the RPE layer is about to disintegrate just before atrophy of RPE cells and photoreceptors. Poor RPE health can be an indicator of poor visual outcome in atrophic AMD and neovascular AMD. As a further example, OCT-FA can detect the presence of sub-RPE-BL, subretinal or intraretinal fluid, which can signify active neovascularization and leakage of fluid from new blood vessels.

Employment of diagnostic methods allows the course of treatment of early, intermediate or advanced AMD, or atrophic AMD or neovascular AMD, using one or more therapeutic agents (e.g., an anti-dyslipidemic agent such as an apo mimetic or a statin, an anti-angiogenic agent or a complement inhibitor, or any combination or all thereof), to be monitored and adjusted. As an example, an anti-dyslipidemic agent (e.g., an apo mimetic such as an apoA-I mimetic [e.g., L-4F] or an apoE mimetic [e.g., AEM-28-14]) can be administered by injection (e.g., intravitreal, subconjunctival, subretinal or sub-Tenon's injection) for the treatment of early, intermediate or advanced AMD, or atrophic AMD or neovascular AMD. During the initial phase of treatment, the anti-dyslipidemic agent can be administered in a certain frequency of injections and in a certain dose per injection. If one or more diagnostic methods show substantial improvement in the disease, or stability in the disease after a significant length of treatment (e.g., SDOCT shows substantial reduction of soft drusen volume, or stability in soft drusen volume after a significant length of treatment), the anti-dyslipidemic agent can be injected less frequently or/and in a lower dose per injection, or the anti-dyslipidemic agent can be injected less frequently and in a higher dose per injection so that a substantially similar total dose is administered over a certain time period. On the other hand, if one or more diagnostic methods show a worsening of the disease, or no change in the disease (particularly in a more severe form of the disease, such as non-central or central geographic atrophy or neovascular AMD) after the initial phase of treatment (e.g., SDOCT shows an increase in soft drusen volume, or no change in soft drusen volume after the initial phase of treatment), the anti-dyslipidemic agent can be injected more frequently or/and in a higher dose per injection. If one or more diagnostic methods show stark improvement in the disease (e.g., SDOCT shows elimination of all or most soft drusen), treatment with the anti-dyslipidemic agent can be paused or stopped. However, if one or more diagnostic methods show return of the disease after a certain period of time (e.g., SDOCT shows an appreciable or significant amount of soft drusen), treatment with the anti-dyslipidemic agent, such as the treatment regimen that had resulted in the stark improvement, can be resumed. The progression and treatment of AMD can be monitored using diagnostic methods to adjust the treatment accordingly. Such a treatment regimen can be called an "as-needed" or "pro re nata" regimen. An as-needed regimen involves routine clinic visits (e.g., once every 4, 6 or 8 weeks) so that one or more diagnostic methods can be performed to monitor the progression and treatment of AMD, although the therapeutic agent might not be administered during a clinic visit depending on the results of the diagnostic tests.

As another example of treatment of early, intermediate or advanced AMD, or atrophic AMD or neovascular AMD, with an anti-dyslipidemic agent (e.g., an apo mimetic such as an apoA-I mimetic [e.g., L-4F] or an apoE mimetic [e.g., AEM-28-14]) administered by injection (e.g., intravitreal, subconjunctival, subretinal or sub-Tenon's injection), the anti-dyslipidemic agent can be administered in a certain frequency of injections (e.g., once monthly) and in a certain dose per injection during the initial phase of treatment. During the second phase of treatment, the anti-dyslipidemic agent can be injected less frequently (e.g., once every 6 or 8 weeks), and in the same dose per injection as the initial dose per injection or in a higher dose per injection so that a substantially similar total dose is administered over a certain time period. The second phase of treatment can last for a selected period of time. During an optional third phase of treatment, the anti-dyslipidemic agent can be injected even less frequently (e.g., once every 10 or 12 weeks), and in the same dose per injection as the initial dose per injection or in a higher dose per injection so that a substantially similar total dose is administered over a certain time period. The optional third phase of treatment can last for a selected period of time. And so on. Such a treatment regimen can be called a "treat-and-extend" regimen. In the initial/first phase, the second phase, the optional third phase and any additional optional phase of treatment, one or more diagnostic methods can be performed to monitor the progression and treatment of AMD and possibly to adjust the treatment depending on the results of the diagnostic tests. For example, if one or more diagnostic methods show a worsening of the disease (e.g., SDOCT shows an increase in soft drusen volume), the anti-dyslipidemic agent can be injected more frequently or/and in a higher dose per injection. In contrast, if one or more diagnostic methods show stability or an improvement in the disease (e.g., SDOCT shows stability or a reduction of soft drusen volume), the anti-dyslipidemic agent can be injected less frequently or/and in a lower dose per injection, or the anti-dyslipidemic agent can be injected less frequently and in a higher dose per injection so that a substantially similar total dose is administered over a certain time period. Unlike an as-needed regimen, a treat-and-extend regimen does not involve routine diagnostic visits, but the therapeutic agent is administered in routine treatment visits (whose frequency decreases in the second phase and the optional third phase of treatment), even though the therapeutic agent, or the dose administered, might not be medically needed at that time. Frequent clinic visits (whether for monitoring or/and treatment) and frequent (e.g., monthly) injections can have negative consequences, such as decreased patient compliance, adverse medical effects (e.g. tachyphylaxis), and increased healthcare cost. A potential advantage of a treat-and-extend regimen over an as-needed regimen is that it can decrease the total number of clinic visits made for monitoring and treatment.

As an illustrative example of a treat-and-extend regimen, for the treatment of neovascular AMD an anti-angiogenic agent (e.g., an anti-VEGF agent such as bevacizumab, ranibizumab or aflibercept), whether alone or in combination with one or more other therapeutic agents (e.g., an anti-inflammatory agent or/and an anti-dyslipidemic agent) can be injected (e.g., intravitreally) once every 4, 6 or 8 weeks until achievement of a maximal effect, such as substantially complete resolution of subretinal fluid or/and intraretinal fluid without new retinal hemorrhage, or no further reduction of subretinal fluid or/and intraretinal fluid in OCT-FA for at least two consecutive clinic visits in the absence of new retinal hemorrhage. In such a case, the anti-angiogenic agent can be injected less frequently (the interval between injections can be extended by, e.g., about 2 or 4 weeks). If the disease remains stable, the interval between injections can be extended by, e.g., about 2 or 4 weeks at a time, and the total extension period can be up to, e.g., about 3, 4, 5 or 6 months. If the patient shows a relatively mild deterioration in the disease (e.g., reappearance of a relatively small amount of subretinal fluid or/and intraretinal fluid or a relatively small increase in the amount thereof), the interval between injections of the anti-angiogenic agent can be shortened by, e.g., about 1 or 2 weeks. If the disease deterioration is severe, frequent injections (e.g., once every 4, 6 or 8 weeks) of the anti-angiogenic agent can be resumed. Similar principles are also applicable to a treat-and-extend regimen for the treatment of atrophic AMD or neovascular AMD with any other kind of therapeutic agent, including without limitation an anti-dyslipidemic agent (e.g., an apo mimetic such as an apoA-I mimetic [e.g., L-4F] or an apoE mimetic [e.g., AEM-28-14]) and a complement inhibitor (e.g., a complement factor D inhibitor such as lampalizumab, a C3 inhibitor such as CB-2782, or a C5 inhibitor such as ARC1905 or LFG316).

Alternative to an as-needed regimen or a treat-and-extend regimen, for the treatment of early, intermediate or advanced AMD, or atrophic AMD or neovascular AMD, a therapeutic agent (e.g., an anti-dyslipidemic agent, an anti-angiogenic agent or a complement inhibitor) can be administered in substantially the same frequency of administration and in substantially the same dose per administration for substantially the entire length of treatment selected by the treating physician or until one or more diagnostic methods indicate that the disease has been successfully treated according to any selected outcome measure(s). Such a treatment regimen can be called a "fixed-routine" regimen.

XII. PHARMACEUTICAL COMPOSITIONS, DELIVERY SYSTEMS AND KITS

The disclosure provides pharmaceutical compositions comprising one or more therapeutic agents described herein or a pharmaceutically acceptable salt thereof, and one or more pharmaceutically acceptable carriers or excipients. A pharmaceutical composition generally contains a therapeutically effective amount of a therapeutic agent, but can contain an appropriate fraction thereof. If two or more therapeutic agents are used to treat an eye disorder (e.g., AMD), the therapeutic agents can be contained in the same pharmaceutical composition or in different compositions.

A pharmaceutical composition contains a therapeutic agent in substantially pure form. In some embodiments, the purity of a macromolecule (e.g., peptide, protein, polynucleotide or peptide-nucleic acid) therapeutic is at least about 90%, 95%, 96%, 97%, 98% or 99% (e.g., at least about 95% or 98%). In further embodiments, the purity of a small-molecule therapeutic is at least about 95%, 96%, 97%, 98% or 99% (e.g., at least about 98% or 99%).

Pharmaceutical compositions/formulations can be prepared in sterile form. For example, compositions/formulations for parenteral administration by injection or infusion generally are sterile. Compositions/formulations for administration into the eye by eye drop or injection can also be prepared in sterile form. Sterile compositions/formulations are compounded or manufactured according to pharmaceutical-grade sterilization standards known to those of skill in the art, such as those disclosed in or required by the United States Pharmacopeia Chapters 797, 1072 and 1211, and 21 Code of Federal Regulations 211.

Pharmaceutically acceptable carriers and excipients include pharmaceutically acceptable vehicles, substances and materials. Non-limiting examples of types of excipients include liquid and solid fillers, diluents, binders, lubricants, glidants, surfactants, dispersing agents, disintegration agents, emulsifying agents, wetting agents, suspending agents, thickeners, solvents, isotonic/iso-osmotic agents, buffers, pH adjusters, absorption-delaying agents, stabilizers, antioxidants, preservatives, antimicrobial agents, antibacterial agents, antifungal agents, chelating agents, adjuvants, sweetening agents, flavoring agents, coloring agents, encapsulating materials and coating materials. The use of such excipients in pharmaceutical formulations is known in the art. For example, conventional vehicles and carriers include without limitation aqueous solvents {e.g., saline, buffered saline (e.g., phosphate-buffered saline [PBS]) and isotonic solutions (e.g., Ringer's solution)}, organic solvents (e.g., dimethyl sulfoxide [DMSO] and alcohols [e.g., ethanol, glycerol and propylene glycol]), and oils (e.g., vegetable oils such as olive oil and sesame oil). Except insofar as any conventional carrier or excipient is incompatible with a therapeutic agent, the disclosure encompasses the use of conventional carriers and excipients in formulations containing the therapeutic agents described herein. See, e.g., Remington: The Science and Practice of Pharmacy, 21st Ed., Lippincott Williams & Wilkins (Philadelphia, Pa.) (2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla.) (2004).

As an illustrative example, one or more therapeutic agents can be formulated for delivery into the eye (e.g., by eye drop, contact lens or intravitreal, subconjunctival, subretinal or sub-Tenon's injection). Carriers and excipients that can be used to make such formulations include without limitation solvents (e.g., aqueous solvents such as water, saline and PBS), isotonic/iso-osmotic agents (e.g., NaCl and sugars [e.g., sucrose]), pH adjusters (e.g., sodium dihydrogen phosphate and disodium hydrogen phosphate), and emulsifiers (e.g., non-ionic surfactants such as polysorbates [e.g., polysorbate 20]).

To enhance delivery of a therapeutic agent into the eye, in some embodiments a pharmaceutical composition comprises one or more cell-penetrating peptides (CPPs) or/and one or more chemical penetration enhancers (CPEs) mixed with the therapeutic agent. Use of a CPP can also enable delivery of a therapeutic agent into target cells in the eye, such as delivery of a neurotrophic factor-expressing plasmid DNA into RPE cells. In further embodiments, a pharmaceutical composition comprises any CPP-containing transepithelial, transmembrane or transmucosal drug-delivery system (TDS) described herein.

If a therapeutic agent is a peptide or protein, a formulation can contain one or more substances that increase peptide/protein solubility, inhibit peptide/protein aggregation, reduce solution viscosity or increase peptide/protein stability, or any combination or all thereof. Examples of such substances include without limitation hydrophilic or polar amino acids (e.g., arginine and histidine), polyols (e.g., myo-inositol, mannitol and sorbitol), saccharides {e.g., glucose (including D-glucose [dextrose]), lactose, sucrose and trehalose}, osmolytes (e.g., trehalose, taurine, amino acids [e.g., glycine, sarcosine, alanine, proline, serine, β-alanine and γ-aminobutyric acid], and betaines [e.g., trimethylglycine and trimethylamine N-oxide]), and non-ionic surfactants {e.g., alkyl polyglycosides, ProTek® alkylsaccharides (e.g., a monosaccharide [e.g., glucose] or a disaccharide [e.g., maltose or sucrose] coupled to a long-chain fatty acid or a corresponding long-chain alcohol), and polypropylene glycol/polyethylene glycol block co-polymers (e.g., poloxamers [e.g., Pluronic™ F-68], and Genapol® PF-10 and variants thereof)}. Because such substances increase peptide/protein solubility, they can be used to increase peptide/protein concentration and hence decrease the volume needed to administer a given amount of the peptide or protein, which can have beneficial effects such as reduced ocular pressure (e.g., in intravitreal injection). In addition, such substances can be employed to stabilize peptides and proteins during the preparation, storage and reconstitution of lyophilized peptides and proteins.

In some embodiments, a therapeutic agent, whether a small molecule or a macromolecule, is administered by means of an eye drop. In other embodiments, a small molecule or macromolecule therapeutic agent is administered by means of a contact lens (e.g., a corneal lens or a scleral lens). Delivery of the therapeutic agent into the eye can be aided by use of a CPP or/and a CPE as described elsewhere herein.

In further embodiments, a small-molecule drug is delivered passively into the eye by means of a Visulex-P eye applicator system. In other embodiments, a macromolecule drug is delivered actively into the eye by means of a Visulex-I eye applicator system that uses iontophoresis to induce electro-osmosis. Both Visulex systems are non-invasive, trans-scleral, scleral lens-like drug-delivery systems that topically apply the drug onto the scleral surface of the eye, and within about 5-10 minutes, the drug diffuses through the trans-scleral pathway from the front of the eye to the posterior sections of the eye. Upon penetration through, e.g., conjunctival and scleral pores, the drug traverses the highly permeable spherical layer of the suprachoroidal space of the eye.

In some embodiments, one or more of the therapeutic agent(s) independently are delivered from a sustained-release composition. As used herein, the term "sustained-release composition" encompasses sustained-release, prolonged-release, extended-release, slow-release, delayed-release and controlled-release compositions, systems and devices. Use of a sustained-release composition can have benefits, such as an improved profile of the amount of the drug delivered to the target site over a time period, and improved patient compliance and health due to fewer invasive procedures (e.g., injections into the eye) being performed for administration of the drug. In some embodiments, the sustained-release composition is a drug-encapsulation system, such as, e.g., nanoparticles, microparticles, a cylinder or a capsule made of, e.g., a biodegradable polymer or/and a hydrogel. In certain embodiments, the sustained-release composition comprises a hydrogel. Non-limiting examples of polymers of which a hydrogel can be composed include polyvinyl alcohol, acrylate polymers (e.g., sodium polyacrylate), and other homopolymers and copolymers having a relatively large number of hydrophilic groups (e.g., hydroxyl or/and carboxylate groups). In other embodiments, the sustained-release drug-encapsulation system comprises a membrane-enclosed reservoir, wherein the reservoir contains a drug and the membrane is permeable to the drug.

In certain embodiments, the sustained-release composition is composed of a hydrogel formed by combining a cellulosic polymer (e.g., hydroxypropyl methyl cellulose or a derivative thereof) and polystyrene nanoparticles. Such a hydrogel can be locally administered to the eye by, e.g., eye drop, injection or implantation. The polymer chains of the cellulosic polymer and the polystyrene nanoparticles can form relaxed bonds under pressure, which allows the hydrogel to flow readily when pushed through a needle, but can form solidified bonds within seconds of release of the pressure, which allows the hydrogel to transform into a drug-carrying capsule in the eye. In certain embodiments, the hydrogel is loaded with a peptide or protein, such as an apolipoprotein mimetic or an anti-VEGF/VEGFR agent. The peptide or protein can be released from the hydrogel as the edges of the hydrogel are gradually eroded by exposure to water in the eye, which allows the peptide or protein to be released from the hydrogel over the course of months and possibly years.

OTX-TKI is a sustained-release implant composed of a bioresorbable hydrogel and containing particles of a receptor tyrosine kinase inhibitor (e.g., a VEGFR TKI for the treatment of, e.g., wet AMD) in an injectable fiber. OTX-TKI can be implanted by, e.g., intravitreal injection and can deliver the drug to the target tissues over a period of about 6 months. Similarly, OTX-IVT is a sustained-release, intravitreal implant designed to deliver an anti-VEGF agent (e.g., aflibercept) over a period of about 4-6 months. The OTX-TKI or OTX-IVT sustained-release implant can be adapted to deliver other kinds of therapeutic agents alternative to or in addition to a TKI or an anti-VEGF agent, such as an anti-dyslipidemic agent (e.g., an apo mimetic such as an apoA-I mimetic [e.g., L-4F or D-4F] or an apoE mimetic [e.g., AEM-28-14], or a statin [e.g., atorvastatin or simvastatin]).

In some embodiments, the sustained-release composition is a polymeric implant (e.g., a cylinder, a capsule or any other suitable form) or polymeric nanoparticles or microparticles, wherein the polymeric particles can be delivered, e.g., by eye drop or injection or from an implant. In some embodiments, the polymeric implant or polymeric nanoparticles or microparticles are composed of a biodegradable polymer (one or more biodegradable homopolymers, one or more biodegradable copolymers, or a mixture thereof). In certain embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. The biodegradable polymer of the polymeric implant or polymeric nanoparticles or microparticles can be selected so that the polymer substantially completely degrades around the time the period of treatment is expected to end, and so that the byproducts of the polymer's degradation, like the polymer, are biocompatible.

Non-limiting examples of biodegradable polymers include polyesters, poly(ca-hydroxyacids), polylactide, polyglycolide, poly(ε-caprolactone), polydioxanone, poly(hydroxyalkanoates), poly(hydroxypropionates), poly(3-hydroxypropionate), poly(hydroxybutyrates), poly(3-hydroxybutyrate), poly(4-hydroxybutyrate), poly(hydroxypentanoates), poly(3-hydroxypentanoate), poly(hydroxyvalerates), poly(3-hydroxyvalerate), poly(4-hydroxyvalerate), poly(hydroxyoctanoates), poly(2-hydroxyoctanoate), poly(3-hydroxyoctanoate), polysalicylate/polysalicylic acid, polycarbonates, poly(trimethylene carbonate), poly(ethylene carbonate), poly(propylene carbonate), tyrosine-derived polycarbonates, L-tyrosine-derived polycarbonates, polyiminocarbonates, poly(DTH iminocarbonate), poly(bisphenol A iminocarbonate), poly(amino acids), poly(ethyl glutamate), poly(propylene fumarate), polyanhydrides, polyorthoesters, poly(DETOSU-1,6HD), poly(DETOSU-t-CDM), polyurethanes, polyphosphazenes, polyimides, polyamides, nylons, nylon 12, polyoxyethylated castor oil, poly(ethylene glycol), polyvinylpyrrolidone, poly(L-lactide-co-D-lactide), poly(L-lactide-co-D,L-lactide), poly(D-lactide-co-D,L-lactide), poly(lactide-co-glycolide), poly(lactide-co-ε-caprolactone), poly(glycolide-co-ε-caprolactone), poly(lactide-co-dioxanone), poly(glycolide-co-dioxanone), poly(lactide-co-trimethylene carbonate), poly(glycolide-co-trimethylene carbonate), poly(lactide-co-ethylene carbonate), poly(glycolide-co-ethylene carbonate), poly(lactide-co-propylene carbonate), poly(glycolide-co-propylene carbonate), poly(lactide-co-2-methyl-2-carboxyl-propylene carbonate), poly(glycolide-co-2-methyl-2-carboxyl-propylene carbonate), poly(lactide-co-hydroxybutyrate), poly(lactide-co-3-hydroxybutyrate), poly(lactide-co-4-hydroxybutyrate), poly(glycolide-co-hydroxybutyrate), poly(glycolide-co-3-hydroxybutyrate), poly(glycolide-co-4-hydroxybutyrate), poly(lactide-co-hydroxyvalerate), poly(lactide-co-3-hydroxyvalerate), poly(lactide-co-4-hydroxyvalerate), poly(glycolide-co-hydroxyvalerate), poly(glycolide-co-3-hydroxyvalerate), poly(glycolide-co-4-hydroxyvalerate), poly(3-hydroxybutyrate-co-4-hydroxybutyrate), poly(hydroxybutyrate-co-hydroxyvalerate), poly(3-hydroxybutyrate-co-3-hydroxyvalerate), poly(3-hydroxybutyrate-co-4-hydroxyvalerate), poly(4-hydroxybutyrate-co-3-hydroxyvalerate), poly(4-hydroxybutyrate-co-4-hydroxyvalerate), poly(ε-caprolactone-co-fumarate), poly(ε-caprolactone-co-propylene fumarate), poly(ester-co-ether), poly(lactide-co-ethylene glycol), poly(glycolide-co-ethylene glycol), poly(ε-caprolactone-co-ethylene glycol), poly(ester-co-amide), poly(DETOSU-1,6HD-co-DETOSU-t-CDM), poly(lactide-co-cellulose ester), poly(lactide-co-cellulose acetate), poly(lactide-co-cellulose butyrate), poly(lactide-co-cellulose acetate butyrate), poly(lactide-co-cellulose propionate), poly(glycolide-co-cellulose ester), poly(glycolide-co-cellulose acetate), poly(glycolide-co-cellulose butyrate), poly(glycolide-co-cellulose acetate butyrate), poly(glycolide-co-cellulose propionate), poly(lactide-co-glycolide-co-ε-caprolactone), poly(lactide-co-glycolide-co-trimethylene carbonate), poly(lactide-co-ε-caprolactone-co-trimethylene carbonate), poly(glycolide-co-ε-caprolactone-co-trimethylene carbonate), poly(3-hydroxybutyrate-co-3-hydroxyvalerate-co-4-hydroxybutyrate), poly(3-hydroxybutyrate-co-4-hydroxyvalerate-co-4-hydroxybutyrate), collagen, casein, polysaccharides, cellulose, cellulose esters, cellulose acetate, cellulose butyrate, cellulose acetate butyrate, cellulose propionate, chitin, chitosan, dextran, starch, modified starch, and copolymers and blends thereof, wherein lactide includes L-lactide, D-lactide and D,L-lactide.

As an illustrative example, sustained-release compositions comprising one or more peptides or proteins (e.g., an apoliprotein mimetic [e.g., an apoA-I or apoE mimetic] or/and an antibody or a fragment thereof [e.g., an anti-VEGF antibody or a fragment thereof]) for injection (e.g., intravitreal, subconjunctival, subretinal or sub-Tenon's injection) can be composed of one or more biodegradable polymers, such as hexyl-substituted poly(lactic acid) (hexPLA). Hex-PLA is a hydrophobic polyester having a semi-solid aggregate state, which facilitates formulation. The peptide/protein can be micronized and incorporated into a liquid hexPLA polymer matrix by cryo-milling, forming a homogeneous and injectable suspension. The peptide/protein can have good compatibility with the hexPLA polymer, good storage stability (e.g., at about 4° C. for an extended period [e.g., about 3 months or longer]), and better stability inside the polymer when shielded from the surrounding aqueous medium. Formulations of the peptide/protein with hexPLA can have a drug loading of, e.g., about 1-5% or 5-10%, and the hexPLA can have a molecular weight (MW) of, e.g., about 1000-2000 g/mol, 2000-3000 g/mol or 3000-4000 g/mol. The formulations can form spherical depots in an aqueous medium (e.g., a buffer) and release the peptide/protein for an extended period (e.g., about 1, 2, 3, 4, 5 or 6 months). The release rate of the peptide/protein can be influenced by the polymer viscosity based on the polymer MW, and by the drug loading to a lesser extent, which permits fine-tuning of the drug-release profile. The peptide/protein can maintain its structure when incorporated into the polymer matrix, and can maintain its biological activity (e.g., high affinity for its biological target) after being released from the polymer matrix.

Alternative to being released from polymeric nanoparticles or microparticles, a solid therapeutic agent can be administered in the form of nanoparticles or microparticles comprising primarily or consisting essentially of the therapeutic agent. Compared to the therapeutic being substantially completely dissolved in an aqueous medium upon administration, the therapeutic in the form of such nanoparticles or microparticles would substantially completely dissolve over time after administration, and thereby would have a longer duration of action and require fewer administrations (e.g., injections). Furthermore, such nanoparticles or microparticles may form a depot for prolonged delivery of the therapeutic. Such nanoparticles or microparticles can optionally contain a relatively small amount of one or more excipients. Nanoparticles or microparticles comprising primarily or consisting essentially of a therapeutic agent can be administered locally by, e.g., injection (e.g., intravitreal, subconjunctival, subretinal or sub-Tenon's injection), eye drop or implant (e.g., intravitreal, subretinal or sub-Tenon's implant).

In some embodiments, a sustained-release composition releases a low or relatively low, but therapeutically effective, dose of one or more therapeutic agents over a period of about 1 week, 2 weeks, 3 weeks, 1 month, 6 weeks, 2 months, 3 months, 6 months, 1 year, 1.5 years, 2 years, 3 years or longer.

An example of a sustained-release polymeric implant is ILUVIEN®. ILUVIEN® is an intravitreal implant in the form of a tiny tube which is made of a polyimide and sealed with a silicone adhesive on one end and polyvinyl alcohol on the other end, and which releases a very small amount of the corticosteroid fluocinolone acetonide for up to 3 years. Another example of a sustained-release polymeric implant is OZURDEX®. OZURDEX® is a biodegradable, intravitreal implant that delivers an extended release of the corticosteroid dexamethasone using the NOVADUR® solid polymer delivery system. Other therapeutic agents that can be delivered via a sustained-release, biodegradable intravitreal implant include without limitation the neuroprotector brimonidine.

A further example of a sustained-release ocular drug-delivery system is that described in U.S. Pat. No. 6,375,972 by Guo et al. Guo's system comprises an inner drug core containing a drug, and an inner tube impermeable to passage of the drug, wherein the inner tube has first and second ends and covers at least a portion of the inner drug core, and the inner tube is sized and formed of a material so that the inner tube is dimensionally stable to accept the inner drug core without changing shape. An impermeable member is positioned at the inner tube's first end and prevents passage of the drug out of the inner drug core through the inner tube's first end. A permeable member is positioned at the inner tube's second end and allows diffusion of the drug out of the inner drug core through the inner tube's second end. Guo's sustained-release system can be applied by injection or implantation to the vitreous humor, under the retina or onto the sclera, for example.

An additional example of a controlled-release ocular drug-delivery system is that described in U.S. Pat. No. 6,413,540 by Yaacobi. Yaacobi's system comprises a body having a scleral surface for placement proximate to the sclera, and a well having an opening to the scleral surface and an inner core containing a drug. The system delivers the drug at a controlled rate through the sclera to or through the choroid and to the retina.

Another exemplary ocular drug-delivery device is an osmotic pump, such as that described by Ambati et al. Ambati's osmotic pump delivered separately IgG and an anti-ICAM-1 monoclonal antibody across the sclera to the choroid and the retina, with negligible systemic absorption. J. Ambati et al., *Invest. Opthalmol. Vis. Sci.,* 41:1186-1191 (2000).

Another system for controlled delivery of a drug to the posterior segment of the eye is described in M. Bhattacharya et al., *J. Controlled Release,* 251:37-48 (2017). The N-terminus of a peptide-based cleavable linker (PCL) is conjugated to a cell-penetrating peptide (e.g., a charged peptide), and the C-terminus of the PCL is conjugated to a peptide drug. The peptide drug can be, e.g., an apo mimetic such as an apoA-I mimetic (e.g., L-4F or D-4F) or an apoE mimetic (e.g., AEM-28-14). To increase resistance to proteolysis, one or more, or all, of the amino acid residues of the peptide drug can have the D-stereochemistry (e.g., D-4F having all D-amino acids). The PCL is sensitive to an enzyme (e.g., cathepsin D) that is expressed at a relatively high level in the target cells (e.g., RPE cells). The CPP-PCL-peptide drug conjugate can be, e.g., intravitreally injected, and is taken up by target RPE cells via endocytosis. In the lysosome of RPE cells, cathepsin D cleaves the PCL, thereby releasing the peptide drug in the RPE cells. The amino acid sequence of the PCL controls the cleavage/release rate of the peptide drug. The RPE cells act as intracellular drug depots that deliver the peptide drug to the surrounding tissues, including the neural retina and the Bruch's membrane, in a controlled and sustained manner. Alternative to a peptide drug, the PCL can be conjugated to any kind of drug (e.g., a small molecule such as a statin) that can be attached to an amino acid. Furthermore, the CPP or another kind of cell-targeting moiety can be designed to target different types of cells. Alternatively, a CPP or a cell-targeting moiety need not be employed and the PCL can be conjugated to, e.g., a biodegradable polymer, such as a polymeric implant or polymeric nanoparticles or microparticles, where the amino acid sequence of the PCL can be designed to control the enzymatically assisted release of the peptide or non-peptide drug in the target tissue or environment.

Drug-eluting contact lenses (e.g., corneal lenses and scleral lenses) can also be used as sustained-release drug-delivery systems. Such contact lenses can be regarded as implantable devices or as compositions for topical administration. The release duration of drug-eluting contact lenses can be increased by, e.g., molecular imprinting, dispersion of barriers or nanoparticles/microparticles, increasing drug binding to a polymer, or sandwiching a polymer [e.g., poly(lactide-co-glycolide)] layer in a lens, or any combination or all thereof. Contact lenses can provide extended drug release for, e.g., hours to days as desired, and can increase patient compliance due to their ease of use and minimal invasiveness.

In some embodiments, one or more therapeutic agents (whether a macromolecule [e.g., a polypeptide, polynucleotide or peptide-nucleic acid] or a small molecule) independently are contained in liposomes or micelles. In certain embodiments, the liposomes or micelles are composed of one or more phospholipids. Non-limiting examples of phospholipids include phosphatidic acids (e.g., DEPA, DLPA, DMPA, DOPA, DPPA and DSPA), phosphatidylcholines (e.g., DDPC, DEPC, DLPC, DLOPC, DMPC, DOPC, DPPC, DSPC, MPPC, MSPC, PLPC, PMPC, POPC, PSPC, SMPC, SOPC and SPPC), phosphatidylethanolamines (e.g., DEPE, DLPE, DMPE, DOPE, DPPE, DSPE and POPE), phosphatidylglycerols (e.g., DEPG, DLPG, DMPG, DOPG, DPPG, DSPG and POPG), phosphatidylserines (e.g., DLPS, DMPS, DOPS, DPPS and DSPS), and salts (e.g., sodium and ammonium salts) thereof. In certain embodiments, liposomes or micelles are composed of one or more phosphatidylcholines. Liposomes have a hydrophilic core, so liposomes are particularly suited for delivery of hydrophilic therapeutic agents, whereas micelles have a hydrophobic core, so micelles are particularly suited for delivery of hydrophobic therapeutic agents. Liposomes and micelles can permeate across biological membranes. To enhance the permeation of liposomes and micelles across epithelia, membranes and tissue barriers, liposomes and micelles can be conjugated to molecules of a cell-penetrating peptide as described elsewhere herein. Liposomes and micelles composed of a fusogenic lipid (e.g., DPPG) can fuse with the plasma membrane of cells and thereby deliver a therapeutic agent into those cells. Liposomes and micelles can provide sustained release of the therapeutic agent based in part on the rate of degradation of the liposomes and micelles. Liposomes and micelles can be administered locally or systemically (e.g., orally or parenterally). In certain embodiments, liposomes and micelles, whether or not conjugated to a CPP, are administered by eye drop or contact lens (e.g., corneal lens or scleral lens).

In some embodiments, an anti-angiogenic agent (e.g., an anti-VEGF/VEGFR agent) and an anti-inflammatory agent (e.g., an apolipoprotein mimetic [e.g., an apoA-I mimetic], a CRP inhibitor, a complement inhibitor, an inflammasome inhibitor, a corticosteroid or an NSAID, or any combination thereof) are contained in the same or different liposomes or micelles, or nanoparticles or microparticles composed of a biodegradable polymer, and are administered for the treatment of, e.g., neovascular AMD (including types 1, 2 or/and 3 neovascularization). In certain embodiments, the liposomes, micelles, nanoparticles or microparticles are administered locally, e.g., by eye drop or injection (e.g., intravitreal, subconjunctival, subretinal or sub-Tenon's injection).

A pharmaceutical composition comprising one or more therapeutic agents can be presented in unit dosage form as a single dose wherein all active and inactive ingredients are combined in a suitable system, and components do not need to be mixed to form the composition to be administered. A unit dosage form generally contains a therapeutically effective dose of a therapeutic agent, but can contain an appropriate fraction thereof. Examples of a unit dosage form include a tablet, capsule or pill for oral administration, a contact lens (e.g., a corneal lens or a scleral lens), and an eye drop formulation where one, two or more eye drops can be designed to provide a therapeutically effective dose of a therapeutic agent. Another example of a unit dosage form is a single-use pen comprising a pre-filled syringe containing one or more therapeutic agents and excipients dissolved or suspended in a suitable carrier (e.g., buffered saline), a needle and a needle cover for parenteral (e.g., intravenous or subcutaneous) injection or local (e.g., intravitreal) injection into the eye.

Alternatively, a pharmaceutical composition comprising one or more therapeutic agents can be presented as a kit in which the one or more therapeutic agents, excipients and carriers (e.g., solvents) are provided in two or more separate containers (e.g., ampules, vials, tubes, bottles or syringes) and need to be combined to prepare the composition to be administered. In some embodiments, two or more therapeutic agents (e.g., an apoA-I mimetic or an apoE mimetic plus an anti-angiogenic agent, a neuroprotector, an anti-inflammatory agent, a complement inhibitor, an antioxidant or an agent that curtails lipid production) are combined in the same formulation shortly or just before the formulation is administered (e.g., by injection). The one or more therapeutic agents can be provided in any suitable form (e.g., in a stable medium or lyophilized). The kit can contain implements for administering the composition (e.g., a syringe, a filter or filter needle, and an injection needle for injecting a solution or suspension). The kit can also contain instructions for storing the contents of the kit, and for preparing and administering the composition.

A kit can contain all active and inactive ingredients in unit dosage form or the active ingredient(s) and inactive ingredients in two or more separate containers, and can contain instructions for administering or using the pharmaceutical composition to treat AMD or another eye disorder.

In some embodiments, a kit contains a TDS or a pharmaceutical composition comprising one or more therapeutic agents and a CPP, and instructions for administering or using the TDS or the pharmaceutical composition to treat AMD or another eye disorder. In certain embodiments, the TDS or the pharmaceutical composition is administered by eye drop. In other embodiments, the TDS or the pharmaceutical composition is administered by a contact lens (e.g., a corneal lens or a scleral lens).

XIII. SALT FORMS

Compounds/molecules (e.g., apolipoprotein mimetics such as L-4F and AEM-28-14, and statins such as atorvastatin) may exist in a non-salt form (e.g., a free base or a free acid, or having no basic or acidic atom or functional group) or as salts if they can form salts. Compounds that can form salts can be used in the non-salt form or in the form of pharmaceutically acceptable salts. If a compound has, e.g., a basic nitrogen atom, the compound can form an addition salt with an acid (e.g., a mineral acid [such as HCl, HBr, HI, nitric acid, phosphoric acid or sulfuric acid] or an organic acid [such as a carboxylic acid or a sulfonic acid]). Suitable acids for use in the preparation of pharmaceutically acceptable salts include without limitation acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, D-gluconic acid, D-glucuronic acid, L-glutamic acid, alpha-oxo-glutaric acid, glycolic acid, hippuric acid, hydrobromic acid, hydrochloric acid, hydroiodic acid, (±)-DL-lactic acid, (+)-L-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, propionic acid, L-pyroglutamic acid, pyruvic acid, saccharic acid, salicylic acid, 4-amino-salicylic acid, sebacic acid, stearic acid, succinic acid, sulfuric acid, tannic acid, (±)-DL-tartaric acid, (+)-L-tartaric acid, thiocyanic acid, p-toluenesulfonic acid, undecylenic acid, and valeric acid.

If a compound has an acidic group (e.g., a carboxyl group), the compound can form an addition salt with a base. Pharmaceutically acceptable base addition salts can be formed with, e.g., metals (e.g., alkali metals or alkaline earth metals) or amines (e.g., organic amines). Non-limiting examples of metals useful as cations include alkali metals (e.g., lithium, sodium, potassium and cesium), alkaline earth metals (e.g., magnesium and calcium), aluminum and zinc. Metal cations can be provided by way of, e.g., inorganic bases such as hydroxides, carbonates and hydrogen carbonates. Non-limiting examples of organic amines useful for forming base addition salts include chloroprocaine, choline, cyclohexylamine, dibenzylamine, N,N'-dibenzylethylenediamine, dicyclohexylamine, diethanolamine, ethylenediamine, N-ethylpiperidine, histidine, isopropylamine, N-methylglucamine, procaine, pyrazine, triethylamine and trimethylamine. Pharmaceutically acceptable salts are discussed in detail in Handbook of Pharmaceutical Salts, Properties, Selection and Use, P. Stahl and C. Wermuth, Eds., Wiley-VCH (2011).

XIV. REPRESENTATIVE EMBODIMENTS

The following embodiments of the disclosure are provided by way of example only:

1. A transepithelial, transmembrane or transmucosal drug-delivery system (TDS) comprising a therapeutic agent and a cell-penetrating peptide (CPP).
2. The TDS of embodiment 1, wherein the therapeutic agent is or comprises an anti-dyslipidemic agent, an antioxidant, an anti-inflammatory agent, a complement inhibitor, a neuroprotector or an anti-angiogenic agent, or any combination thereof.
3. The TDS of embodiment 2, wherein the therapeutic agent is or comprises an anti-dyslipidemic agent.
4. The TDS of embodiment 3, wherein the anti-dyslipidemic agent is or comprises an apolipoprotein (apo) mimetic.
5. The TDS of embodiment 4, wherein the apo mimetic comprises at least one amphipathic α-helical domain.
6. The TDS of embodiment 4 or 5, wherein the apo mimetic is an apoA-I mimetic.
7. The TDS of embodiment 6, wherein the apoA-I mimetic is 4F or a variant or salt thereof.
8. The TDS of embodiment 7, wherein the apoA-I mimetic is L-4F or D-4F or a salt thereof, each optionally having a protecting group at the N-terminus or/and the C-terminus (e.g., Ac-DWFKAFYDKVAEKFKEAF-NH$_2$ (SEQ ID NO: 1)).
9. The TDS of embodiment 4 or 5, wherein the apo mimetic is an apoE mimetic.
10. The TDS of embodiment 9, wherein the apoE mimetic is AEM-28-14 or a variant or salt thereof.
11. The TDS of any one of embodiments 3 to 10, wherein the anti-dyslipidemic agent is or comprises a statin.
12. The TDS of embodiment 11, wherein the statin is atorvastatin, cerivastatin, fluvastatin, mevastatin, a monacolin (e.g., monacolin K [lovastatin]), pitavastatin, pravastatin, rosuvastatin or simvastatin, or an analog, derivative or salt thereof.
13. The TDS of embodiment 11 or 12, wherein the statin is a substantially hydrophobic/lipophilic statin.
14. The TDS of any one of embodiments 11 to 13, wherein the statin is atorvastatin or simvastatin or a salt thereof.
15. The TDS of any one of the preceding embodiments, wherein the therapeutic agent is a polypeptide (e.g., a peptide or a protein), a small molecule, a polynucleotide (e.g., a plasmid DNA, a microRNA, an anti-sense polynucleotide or an siRNA) or an anti-sense peptide-nucleic acid (PNA).
16. The TDS of any one of the preceding embodiments, wherein the CPP comprises at least 2, 3, 4, 5 or 6 basic natural or/and non-natural amino acid residues.
17. The TDS of embodiment 16, wherein the CPP comprises at least 6 basic natural or/and non-natural amino acid residues.
18. The TDS of embodiment 16 or 17, wherein the CPP comprises at least 2, 3, 4, 5 or 6 consecutive basic natural or/and non-natural amino acid residues.
19. The TDS of any of embodiments 16 to 18, wherein the basic natural and non-natural amino acid residues are selected from the L- and D-isomers of arginine, homoarginine, lysine, ornithine, histidine,

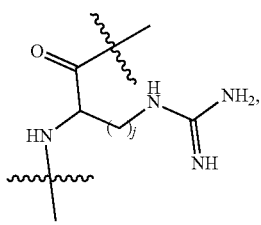

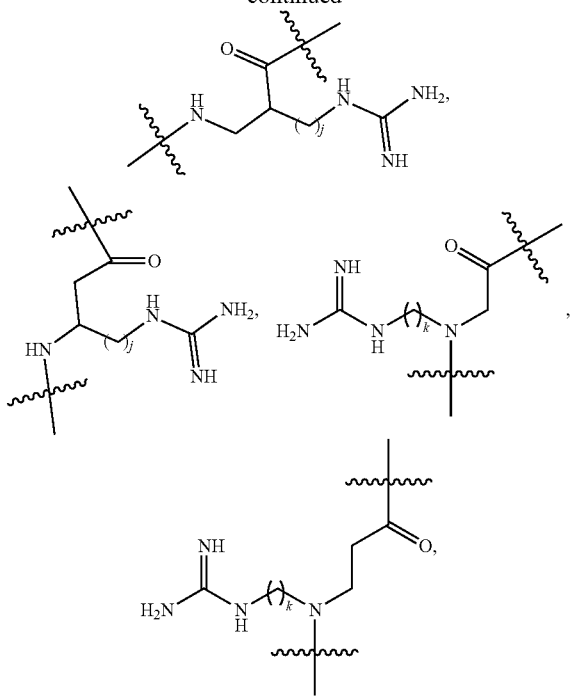

and combinations thereof, wherein:
j is 1, 2, 3, 4, 5 or 6; and
k is 2, 3, 4, 5 or 6.
20. The TDS of embodiment 19, wherein the basic amino acid residues are or comprise arginine or/and lysine.
21. The TDS of any one of embodiments 16 to 20, wherein the CPP is a polycationic CPP having a net positive charge of at least +3, +4, +5 or +6 at a pH of about 7.4.
22. The TDS of embodiment 21, wherein the polycationic CPP is selected from:
1) GGG(ARKKAAKA)$_4$ (peptide for ocular delivery [POD]) (SEQ ID NO: 2), which is capable of nuclear targeting;
2) CGGG(ARKKAAKA)$_4$ (cysteine added to the N-terminus of POD) (SEQ ID NO: 3), which is capable of nuclear targeting;
3) RLRWR (AIP6) (SEQ ID NO: 4);
4) RRLSYSRRRF (SynB3) (SEQ ID NO: 5);
5) KKLFKKILKKL (BP16) (SEQ ID NO: 6);
6) YKQCHKKGGKKGSG (NrTP1 derived from crotamine) (SEQ ID NO: 7), which is capable of nuclear targeting;
7) CRWRWKCCKK [crotamine(30-39)] (SEQ ID NO: 8), which is not capable of nuclear targeting;
8) TKRRITPKDVIDVRSVTTRINT {[E148R]Mce1A (130-151)} (SEQ ID NO: 9);
9) TKRRITPKDVIDVRSVTTKINT {[E148K]Mce1A (130-151)} (SEQ ID NO: 10);
10) TKRRITPKRVIRVRSVTTEINT {[D138R, D141R] Mce1A(130-151)} (SEQ ID NO: 11);
11) TKRRITPKKVIKVRSVTTEINT {[D138K, D141K] Mce1A(130-151)} (SEQ ID NO: 12);
12) TKRRITPKRVIRVRSVTTRINT {[D138R, D141R, E148R]Mce1A(130-151)} (SEQ ID NO: 13);
13) TKRRITPKKVIKVRSVTTKINT {[D138K, D141K, E148K]Mce1A(130-151)} (SEQ ID NO: 14);
14) GGSQPKKKRK (Ostacolo pep-6) (SEQ ID NO: 15);
15) GGKKKRKV (Ostacolo pep-7) (SEQ ID NO: 16);

16) RKKRRRESRKKRRRES (Diatos peptide vector 3 [DPV3]) (SEQ ID NO: 17);
17) GRPRESGKKRKRKRLKP (DPV6) (SEQ ID NO: 18);
18) GKRKKKGKLGKKRDP (DPV7) (SEQ ID NO: 19);
19) GKRKKKGKLGKKRPRSR (DPV7b) (SEQ ID NO: 20);
20) RKKRRRESRRARRSPRHL (DPV3/10) (SEQ ID NO: 21);
21) SRRARRSPRESGKKRKRKR (DPV10/6) (SEQ ID NO: 22);
22) VKRGLKLRHVRPRVTRMDV (DPV1047) (SEQ ID NO: 23), which is capable of nuclear targeting;
23) SRRARRSPRHLGSG (DPV10) (SEQ ID NO: 24), which is capable of nuclear targeting;
24) LRRERQSRLRRERQSR (DPV15) (SEQ ID NO: 25), which is capable of nuclear targeting;
25) GAYDLRRRERQSRLRRRERQSR (DPV15b) (SEQ ID NO: 26), which is capable of nuclear targeting;
the corresponding peptides having all D-amino acid residues; and
the corresponding peptides (L- and D-isomers) having the reverse order of amino acid sequence;
wherein:
  each peptide can optionally have one or more, or all, D-amino acid residues;
  each peptide can optionally have a protecting group at the N-terminus or/and the C-terminus (e.g., acetyl at the N-terminus or/and —NH$_2$ at the C-terminus);
  each peptide can optionally have a cysteamide group at the C-terminus; and
  each peptide can optionally have one, two or more hydrophobic/lipophilic groups (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and polyethylene glycol (PEG) moieties (those comprising, e.g., about 2-20 or 2-10 PEG units) attached to the N-terminus, the C-terminus or/and side chain(s).

23. The TDS of any one of embodiments 16 to 21, wherein the CPP comprises 6, 7, 8, 9, 10, 11, 12, 13, 14, 15 or more consecutive residues of and wherein:
  j is 1, 2, 3, 4, 5 or 6;
  the CPP can optionally have one or more, or all, D-amino acid residues;
  the CPP can optionally have a protecting group at the N-terminus or/and the C-terminus (e.g., acetyl at the N-terminus or/and —NH$_2$ at the C-terminus);
  the CPP can optionally have a cysteamide group at the C-terminus; and
  the CPP can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.

24. The TDS of embodiment 23, wherein j is 3 (arginine), 4 (homoarginine), 5 or 6.

25. The TDS of embodiment 23 or 24, wherein the CPP comprises 6, 7, 8, 9, 10 or 11 consecutive residues of 26. The TDS of any one of embodiments 23 to 25, wherein the CPP has all D-amino acid residues.

27. The TDS of any one of embodiments 23 to 26, wherein the CPP has a hydrophobic group (e.g., stearyl or stearoyl) attached to the N-terminus.

28. The TDS of any one of embodiments 23 to 27, wherein the CPP is a homopolymer.

29. The TDS of any one of embodiments 16 to 21, wherein the CPP comprises 6, 7, 8, 9, 10, 11, 12, 13, 14, 15 or more consecutive residues of and wherein:
  j is 1, 2, 3, 4, 5 or 6;
  the CPP can optionally have one or more, or all, D-amino acid residues;
  the CPP can optionally have a protecting group at the N-terminus or/and the C-terminus (e.g., acetyl at the N-terminus or/and —NH$_2$ at the C-terminus);
  the CPP can optionally have a cysteamide group at the C-terminus; and
  the CPP can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.

30. The TDS of embodiment 29, wherein j is 3, 4, 5 or 6 (e.g., 3).

31. The TDS of embodiment 29 or 30, wherein the CPP comprises 6, 7, 8, 9, 10 or 11 consecutive residues of

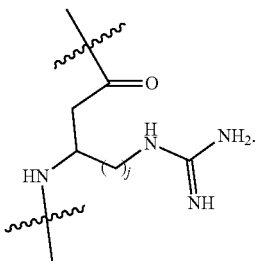

32. The TDS of any one of embodiments 29 to 31, wherein the CPP has a hydrophobic group (e.g., stearyl or stearoyl) attached to the N-terminus.

33. The TDS of any one of embodiments 29 to 32, wherein the CPP is a homopolymer.

34. The TDS of any one of embodiments 16 to 21, wherein the CPP comprises 6, 7, 8, 9, 10, 11, 12, 13, 14, 15 or more consecutive residues of

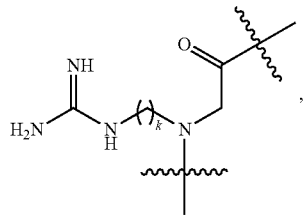

and wherein:
  k is 2, 3, 4, 5 or 6;
  the CPP can optionally have a protecting group at the N-terminus or/and the C-terminus (e.g., acetyl at the N-terminus or/and —NH$_2$ at the C-terminus);
  the CPP can optionally have a cysteamide group at the C-terminus; and
  the CPP can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.

35. The TDS of embodiment 34, wherein k is 3, 4, 5 or 6 (e.g., 6).

36. The TDS of embodiment 34 or 35, wherein the CPP comprises 6, 7, 8, 9, 10 or 11 (e.g., 9) consecutive residues of

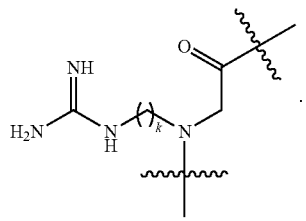

37. The TDS of any-one of embodiments 34 to 36, wherein k is 6 and the CPP comprises 9 consecutive residues of

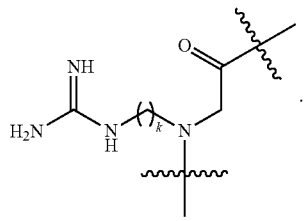

38. The TDS of any one of embodiments 34 to 37, wherein the CPP is a homopolymer.

39. The TDS of any one of embodiments 16 to 21, wherein the CPP is an arginine-rich CPP comprising 5, 6, 7, 8 or more arginine residues.

40. The TDS of embodiment 39, wherein the arginine-rich CPP is a polyarginine comprising 6, 7, 8, 9, 10, 11, 12, 13, 14, 15 or more consecutive arginine residues, and wherein:
  the polyarginine can optionally have one or more, or all, D-arginine residues;
  the polyarginine can optionally have a protecting group at the N-terminus or/and the C-terminus (e.g., acetyl at the N-terminus or/and —NH$_2$ at the C-terminus);
  the polyarginine can optionally have a cysteamide group at the C-terminus; and
  the polyarginine can optionally have a hydrophobic/lipophilic group (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and a PEG moiety (comprising, e.g., about 2-20 or 2-10 PEG units) attached to the N-terminus or/and the C-terminus.

41. The TDS of embodiment 40, wherein the polyarginine is a homopolymer, such as RRRRRR ($R_6$) (SEQ ID NO: 258), $R_7$ (SEQ ID NO: 259), $R_8$ (SEQ ID NO: 260), $R_9$ (SEQ ID NO: 261), $R_{10}$ (SEQ ID NO: 262), $R_{11}$ (SEQ ID NO: 263), $R_{12}$ (SEQ ID NO: 264), $R_{13}$ (SEQ ID NO: 265), $R_{14}$ (SEQ ID NO: 266) or $R_{15}$ (SEQ ID NO: 267).

42. The TDS of embodiment 41, wherein the polyarginine is $R_6$ (SEQ ID NO: 258), $R_7$ (SEQ ID NO: 259), $R_8$ (SEQ ID NO: 260), $R_9$ (SEQ ID NO: 261), $R_{10}$ (SEQ ID NO: 262) or $R_{11}$ (SEQ ID NO: 263) (e.g., $R_6$ (SEQ ID NO: 258) or $R_9$ (SEQ ID NO: 261)).

43. The TDS of any one of embodiments 40 to 42, wherein the polyarginine has all D-arginine residues (e.g., D-$R_6$, D-$R_7$, D-$R_8$, D-$R_9$, D-$R_{10}$ or D-$R_{11}$).

44. The TDS of any one of embodiments 40 to 43, wherein the polyarginine has a hydrophobic group (e.g., stearyl or stearoyl) attached to the N-terminus (e.g., the L- or D-isomer of $R_6$ (SEQ ID NO: 258), $R_7$ (SEQ ID NO: 259), $R_8$ (SEQ ID NO: 260), $R_9$ (SEQ ID NO: 261), $R_{10}$ (SEQ ID NO: 262) or $R_{11}$ (SEQ ID NO: 263) stearylated or stearoylated at the N-terminus).

45. The TDS of any one of embodiments 40, 43 and 44, wherein the polyarginine has one, two or more tryptophan residues at the N-terminus or/and the C-terminus, such as $R_6$W (SEQ ID NO: 269), $R_7$W (SEQ ID NO: 270), $R_8$W (SEQ ID NO: 271), $R_9$W (SEQ ID NO: 272), $R_{10}$W (SEQ ID NO: 273) or $R_{11}$W (SEQ ID NO: 274).

46. The TDS of any one of embodiments 40 and 43 to 45, wherein the polyarginine has a hydrophobic sequence at the N-terminus or/and the C-terminus.

47. The TDS of embodiment 46, wherein the hydrophobic sequence is FFLIPKG (SEQ ID NO: 60) (penetration-accelerating sequence [Pas]), such as in Pas$R_6$ (SEQ ID NO:

276), PasR$_7$ (SEQ ID NO: 277), PasR$_8$ (SEQ ID NO: 278), PasR$_9$ (SEQ ID NO: 279), PasR$_{10}$ (SEQ ID NO: 280) or PasR$_{11}$ (SEQ ID NO: 281).

48. The TDS of embodiment 39, wherein the arginine-rich CPP is selected from:
   1) YGRKKRRQRRR [HIV-1 TAT(47-57)] (SEQ ID NO: 27) and the corresponding isomer having all D-amino acids, both of which are capable of nuclear targeting;
   2) GRKKRRQRRR [TAT(48-57)] (SEQ ID NO: 28) and the corresponding isomer having all D-amino acids, both of which are capable of nuclear targeting;
   3) RKKRRQRRR [TAT(49-57)] (SEQ ID NO: 29) and the corresponding isomer having all D-amino acids, both of which are capable of nuclear targeting;
   4) GRKKRRQRRRPPQ [TAT(48-60)] (SEQ ID NO: 30) and the corresponding isomer having all D-amino acids, both of which are capable of nuclear targeting;
   5) CGGGGYGRKKRRQRRR (SEQ ID NO: 31) [CGGGG (SEQ ID NO: 32) added to the N-terminus of TAT(47-57)], which is capable of nuclear targeting;
   6) GRKKRRQRRRCG [CG added to the C-terminus of TAT(48-57)] (SEQ ID NO: 33), which is capable of nuclear targeting;
   7) RKKRRQRRRC [Cys added to C-terminus of TAT(49-57)] (SEQ ID NO: 34), which is capable of nuclear targeting;
   8) RKKRRARRR {[Q54A]TAT(49-57)} (SEQ ID NO: 35);
   9) YGRRRRRRRRR {[K50R, K51R, Q54R]TAT(47-57)} (SEQ ID NO: 36);
   10) GRKKRRQRRRPWQ {[P59W]TAT(48-60)} (SEQ ID NO: 37);
   11) GRRRRRRRRRPPQ {[K50R, K51R, Q54R]TAT(48-60)} (SEQ ID NO: 38);
   12) RKKRRQRRRRKKRRQRRR [dimer of TAT(49-57)] (SEQ ID NO: 39);
   13) C(YGRKKRRQRRRG)$_{2-4}$(Rosenecker TAT$_{24}$) (SEQ ID NO: 40), wherein the Cys sulfhydryl group is optionally modified by dithiodipyridine reaction, and each oligomer is capable of nuclear targeting;
   14) C(YGRKERRQERRG)$_2$ (Rosenecker TAT$_2$-M1) (SEQ ID NO: 41), wherein the Cys sulfhydryl group is optionally modified by dithiodipyridine reaction, and the dimer is not capable of nuclear targeting;
   15) RRRQRRKKRGY {TAT(47-57) in reverse order [Rev-TAT(47-57)]} (SEQ ID NO: 42) and the corresponding isomer having all D-amino acids;
   16) RRRQRRKKRG {TAT(48-57) in reverse order [Rev-TAT(48-57)]} (SEQ ID NO: 43) and the corresponding isomer having all D-amino acids;
   17) RRRQRRKKR {TAT(49-57) in reverse order [Rev-TAT(49-57)]} (SEQ ID NO: 44) and the corresponding isomer having all D-amino acids;
   18) QPPRRRQRRKKRG {TAT(48-60) in reverse order [Rev-TAT(48-60)]} (SEQ ID NO: 45) and the corresponding isomer having all D-amino acids;
   19) TRQARRNRRRRWRERQR [HIV-1 Rev(34-50)] (SEQ ID NO: 46);
   20) TRRQRTRRARRNR [HTLV-2 Rex(4-16)] (SEQ ID NO: 47);
   21) RRIPNRRPRR (an HRSV-derived peptide) (SEQ ID NO: 48);
   22) KMTRAQRRAAARRNRWTAR [BMV Gag(7-25)] (SEQ ID NO: 49);
   23) KLTRAQRRAAARKNKRNTR [CCMV Gag(7-25)] (SEQ ID NO: 50);
   24) RRRRNRTRRNRRRVR [FHV Coat(35-49)] (SEQ ID NO: 51);
   25) NAKTRRHERRRKLAIER [P22 N(14-30)] (SEQ ID NO: 52);
   26) KRARNTEAARRSRARKLQRMKQ [yeast GCN4 (231-252)] (SEQ ID NO: 53), which is capable of nuclear targeting;
   27) RIKAERKRMRNRIAASKSRKRKLERIAR [human cJun(252-279)] (SEQ ID NO: 54);
   28) KRRIRRERNKMAAAKSRNRRRELTDT [human cFos(139-164)] (SEQ ID NO: 55);
   29) VSRRRRRRGGRRRR (low molecular weight protamine [LMWP]) (SEQ ID NO: 56);
   30) RRWRRWNRFNRRRCR (IMT-P8) (SEQ ID NO: 57);
   31) HWSYILRPRRRRRRK (SEQ ID NO: 58);
   32) RCGRASRCRVRWMRRRRI (BEN_1079) (SEQ ID NO: 59);
   the corresponding peptides having all D-amino acid residues; and
   the corresponding peptides (L- and D-isomers) having the reverse order of amino acid sequence;
   wherein:
      each peptide can optionally have one or more, or all, D-amino acid residues;
      each peptide can optionally have a protecting group at the N-terminus or/and the C-terminus (e.g., acetyl at the N-terminus or/and —NH$_2$ at the C-terminus);
      each peptide can optionally have a cysteamide group at the C-terminus; and
      each peptide can optionally have one, two or more hydrophobic/lipophilic groups (e.g., C$_8$-C$_{20}$ alkyl [e.g., decyl, lauryl, myristyl, palmityl or stearyl], C$_8$-C$_{20}$ acyl [e.g., decanoyl, lauroyl, myristoyl, palmitoyl or stearoyl], or steroidal [e.g., cholesteryl]) or/and PEG moieties (those comprising, e.g., about 2-20 or 2-10 PEG units) attached to the N-terminus, the C-terminus or/and side chain(s).

49. The TDS of any one of embodiments 1 to 21, wherein the CPP is an amphipathic CPP comprising polar or/and charged (e.g., basic or/and acidic) amino acid residues, and non-polar or hydrophobic amino acid residues (e.g., comprising hydrophilic residues alternating or interspersed with hydrophobic residues, or one or more hydrophilic regions and one or more hydrophobic regions).

50. The TDS of embodiment 49, wherein the amphipathic CPP is selected from:
   1) KETWWETWWTEWSQPKKKRKV (Pep-1) (SEQ ID NO: 61), optionally having acetyl at the N-terminus or/and cysteamide at the C-terminus, which is capable of nuclear targeting;
   2) KETWFETWFTEWSQPKKKRKV (Pep-2) (SEQ ID NO: 62), optionally having acetyl at the N-terminus or/and cysteamide at the C-terminus, which is capable of nuclear targeting;
   3) KWFETWFTEWPKKRK (Pep-3) (SEQ ID NO: 63), optionally acetylated or PEGylated at the N-terminus or/and having cysteamide at the C-terminus;
   4) KATWFETWFTEWSQPKKKRKV (Pep-21) (SEQ ID NO: 64), optionally having acetyl at the N-terminus or/and cysteamide at the C-terminus, which is capable of nuclear targeting;
   5) KETWFETWFAEWSQPKKKRKV (Pep-29) (SEQ ID NO: 65), optionally having acetyl at the N-terminus or/and cysteamide at the C-terminus, which is capable of nuclear targeting;

6) KETWFETWFTAWSQPKKKRKV (Pep-30) (SEQ ID NO: 66), optionally having acetyl at the N-terminus or/and cysteamide at the C-terminus, which is capable of nuclear targeting;
7) KETWFETWFTEWAQPKKKRKV (Pep-32) (SEQ ID NO: 67), optionally having acetyl at the N-terminus or/and cysteamide at the C-terminus, which is capable of nuclear targeting;
8) KETWFETWFTEWSAPKKKRKV (Pep-33) (SEQ ID NO: 68), optionally having acetyl at the N-terminus or/and cysteamide at the C-terminus, which is capable of nuclear targeting;
9) KETWFETWFTEWSQPKKKRKA (Pep-40) (SEQ ID NO: 69), optionally having acetyl at the N-terminus or/and cysteamide at the C-terminus;
10) KETWFETWFTEWSQPKKKRKV (Pep-43) (SEQ ID NO: 62), optionally having acetyl at the N-terminus or/and cysteamide at the C-terminus, which is capable of nuclear targeting;
11) GGKETWWETW (Ostacolo pep-2) (SEQ ID NO: 70);
12) GGWWETWWTE (Ostacolo pep-3) (SEQ ID NO: 71);
13) GGTWWTEWSQ (Ostacolo pep-4) (SEQ ID NO: 72);
14) GGTEWSQPKK (Ostacolo pep-5) (SEQ ID NO: 73);
15) GALFLGFLGAAGSTMGAWSQPKKKRKV (aka MPG) (SEQ ID NO: 74), optionally having acetyl at the N-terminus or/and cysteamide at the C-terminus, which is capable of nuclear targeting;
16) GALFLGFLGAAGSTMGAWSQPKSKRKV {aka MPGΔ$^{NLS}$ (MPG having a mutation in the nuclear localization sequence [NLS])} (SEQ ID NO: 75), optionally having acetyl at the N-terminus or/and cysteamide at the C-terminus, which is not capable of nuclear targeting;
17) RRRRRRRRRGALFLAFLAAALSLMG (R9-ΔMPG [R$_9$ (SEQ ID NO: 261) attached to an MPG variant]) (SEQ ID NO: 76);
18) MGLGLHLLVLAAALQGAWSQPKKKRKV (P1) (SEQ ID NO: 77), which is capable of nuclear targeting;
19) GLWRALWRLLRSLWRLLWRA (aka CADY-R) (SEQ ID NO: 78), optionally having acetyl at the N-terminus or/and cysteamide at the C-terminus;
20) GLWRALWRLLRSLWRLLWKA (aka CADY-K) (SEQ ID NO: 79), optionally having acetyl at the N-terminus or/and cysteamide at the C-terminus;
21) GLFKALLKLLKSLWKLLLKA (ppTG1) (SEQ ID NO: 80);
22) GLFRALLRLLRSLWRLLLRA (ppTG20) (SEQ ID NO: 81);
23) GLFEALLELLESLWELLLEA (JTS1) (SEQ ID NO: 82);
24) GLFEALLELLESLWELLEACCYKAKKKKKKKKWKKKKQS (JTS1-K13) (SEQ ID NO: 83);
25) WEAKLAKALAKALAKHLAKALAKALKACEA (aka KALA) (SEQ ID NO: 84);
26) WEAALAEALAEALAEHLAEALAEALEALAA (aka GALA) (SEQ ID NO: 85);
27) GWTLNSAGYLLGKINLKALAALAKKIL (transportan [TP]) (SEQ ID NO: 86);
28) LNSAGYLLGKINLKALAALAKKIL (TP7) (SEQ ID NO: 87);
29) GWTLNSAGYLLGKLKALAALAKKIL (TP9) (SEQ ID NO: 88);
30) AGYLLGKINLKALAALAKKIL (TP10) (SEQ ID NO: 89), optionally having stearyl or stearoyl at the N-terminus;
31) AGYLLGKINLKPLAALAKKIL (TP10-2) (SEQ ID NO: 90);
32) LNSAGYLLGKALAALAKKIL (TP13) (SEQ ID NO: 91);
33) AGYLLGKLLOOLAAAALOOLL (PepFect 14 [PF14]) (SEQ ID NO: 92), optionally having stearyl or stearoyl at the N-terminus, wherein "O" is ornithine;
34) KWKLFKKIGAVLKVLTTG (CM$_{18}$-Tat$_{11}$) (SEQ ID NO: 93);
35) KLALKLALKALKAALKLA (model amphipathic peptide [MAP]) (SEQ ID NO: 94);
36) QLALQLALQALQAALQLA [MAP17 or MAP(Q)] (SEQ ID NO: 95);
37) LKTLTETLKELTKTLTEL (MAP12) (SEQ ID NO: 96);
38) KALAKALAKALA (a MAP analog) (SEQ ID NO: 97);
39) RRWWRRWRR (aka W/R) (SEQ ID NO: 98);
40) WLRRIKAWLRRIKAWLRRIKA (aka WLR or W3) (SEQ ID NO: 99);
41) YARAAARQARA (aka YARA or PTD4) (SEQ ID NO: 100);
42) VRLPPPVRLPPPVRLPPP (sweet arrow peptide [SAP]) (SEQ ID NO: 101);
43) VKLPPPVKLPPPVKLPPP [SAP(K)] (SEQ ID NO: 102);
44) VELPPPVELPPPVELPPP [SAP(E)] (SEQ ID NO: 103);
45) (PPR)$_{3-6}$(SEQ ID NO: 104);
46) (PRR)$_{3-6}$(SEQ ID NO: 105);
47) GPSQPTYPGDDAPVRDLIRFYRDLQRYLNVVTRHRY (aPP4R1) (SEQ ID NO: 106);
48) GPSQPTYPGDDAPVRDLIRFYRDLRRYLNVVTRHRY (aPP5R1) (SEQ ID NO: 107);
49) GPSQPTYPGDDAPVRDLRRFYRDLRRYLNVVTRHRY (aPP6R1) (SEQ ID NO: 108);
50) GSPWGLQHHPPRT (439A) (SEQ ID NO: 109);
51) RLSGMNEVLSFRWL (SG3) (SEQ ID NO: 110);
52) KLWMRWYSPTTRRYG (IVV-14) (SEQ ID NO: 111);
53) PYSRPHVQLWYPNRESCRSLIRSLGP (BEN_0805) (SEQ ID NO: 112);
54) YTAIAWVKAFIRKLRK (YTA2) (SEQ ID NO: 113);
55) IAWVKAFIRKLRKGPLG (YTA4) (SEQ ID NO: 114);
56) FKIYDKKVRTRVVKH (SVM1, a CPP predicted by support vector machine model and shown to be a CPP) (SEQ ID NO: 115);
57) RASKRDGSWVKKLHRILE (SVM2) (SEQ ID NO: 116);
58) KGTYKKKLMRIPLKGT (SVM3) (SEQ ID NO: 117);
59) LYKKGPAKKGRPPLRGWFH (SVM4) (SEQ ID NO: 118);
60) the helical polyarginine mimic (HPRM) designated P11 [H. Tang et al., *Chem. Sci.*, 4:3839-3844 (2013)];
61) the HPRM designated P13 [Tang (supra)];
62) the HPRM designated P14 [Tang (supra)];
63) DAATATRGRSAASRPTERPRAPARSASRPRRPVE [HSV-1 VP22(267-301)] (SEQ ID NO: 119), which is capable of nuclear targeting;

64) PLSSIFSRIGDP [HBV PreS2(41-52)] (SEQ ID NO: 120);
65) DPKGDPKGVTVTVTVTVTGKGDPKPD (VT5) (SEQ ID NO: 121);
66) YLLDGMTNTIENARQGAARVTSWLGRQL-RIAGKRLEGRSK [pestivirus envelope glycoprotein E$^{rns}$(181-220)] (SEQ ID NO: 122), which is capable of nuclear targeting;
67) DGMTNTIENARQGAARVTSWLGRQLRIAGKR-LEGRSKTWF [E$^{rns}$(184-223)] (SEQ ID NO: 123), which is capable of nuclear targeting;
68) ENARQGAARVTSWLGRQLRIAGKRLEGR-SKTWFGAYA [E$^{rns}$(191-227)] (SEQ ID NO: 124), which is capable of nuclear targeting;
69) ENARQGAARVTSWLGRQLRIAGKRLEGR-SKTWF [E$^{rns}$(191-223)] (SEQ ID NO: 125), which is capable of nuclear targeting;
70) ENARQGAARVTSWLGRQLRIAGKRLEGRSK [E$^{rns}$(191-220)] (SEQ ID NO: 126), which is capable of nuclear targeting;
71) RQGAARVTSWLGRQLRIAGKRLEGRSK [E$^{rns}$(194-220)] (SEQ ID NO: 127), which is capable of nuclear targeting;
72) RQGAARVTSWLGRQLRIAGKRLEGR [E$^{rns}$(194-218)] (SEQ ID NO: 128), which is capable of nuclear targeting;
73) GNGKLIKGRTPIKFGKADCDRPPKHSQNGMGK {ribotoxin 2 L3 loop(57-89) [R2L3(57-89)]} (SEQ ID NO: 129), which is capable of nuclear targeting;
74) KLIKGRTPIKFGKADCDRPPKHSQNGMGK [R2L3(60-89)] (SEQ ID NO: 130), which is capable of nuclear targeting;
75) KLIKGRTPIKFGK [R2L3(60-73)] (SEQ ID NO: 131);
76) RGGRLSYSRRRFSTSTGR (SynBI) (SEQ ID NO: 132);
77) ALWKTLLKKVLKAPKKKRKV (S4$_{13}$-PV$_{rev}$) (SEQ ID NO: 133), optionally having acetyl at the N-terminus or/and —NH$_2$ at the C-terminus, which is capable of nuclear targeting;
78) ALWKTLLKKVLKA {[M4K]dermaseptin S4(1-13) without NLS} (SEQ ID NO: 134);
79) GIGKFLHSAKKFGKAFVGEIMNS (magainin 2) (SEQ ID NO: 135);
80) GIGKWLHSAKKFGKAFVGEIMNS ([F5W]magainin 2) (SEQ ID NO: 136);
81) GIGKFLHSAKKWGKAFVGQIMNC ([F12W, E19Q, S23C]magainin 2) (SEQ ID NO: 137);
82) VLTTGLPALISWIRRRHRRHC (p5RHH, a melittin variant) (SEQ ID NO: 138);
83) TRSSRAGLQFPVGRVHRLLRK [buforin 2 (BUF2)] (SEQ ID NO: 139), which is capable of nuclear targeting;
84) RAGLQFPVGRVHRLLRK [BUF2(5-21)] (SEQ ID NO: 140);
85) AGLQFPVGRVHRLLRK [BUF2(6-21)] (SEQ ID NO: 141);
86) GLQFPVGRVHRLLRK [BUF2(7-21)] (SEQ ID NO: 142);
87) LQFPVGRVHRLLRK [BUF2(8-21)] (SEQ ID NO: 143);
88) QFPVGRVHRLLRK [BUF2(9-21)] (SEQ ID NO: 144);
89) FPVGRVHRLLRK [BUF2(10-21)] (SEQ ID NO: 145);
90) PVGRVHRLLRK [BUF2(11-21)] (SEQ ID NO: 146);
91) LLGDFFRKSKEKIGKEFKRIVQRIKD-FLRNLVPRTES (human cathelicidin LL-37) (SEQ ID NO: 147);
92) KCFQWQRNMRKVRGPPVSCIKR {human lactoferrin(38-59) [hLF(38-59)]} (SEQ ID NO: 148), optionally having an intramolecular disulfide bridge between the two terminal cysteine residues, which is capable of nuclear targeting;
93) KCFQWQRNMRKVRGPPVSC [hLF(38-56)] (SEQ ID NO: 149), optionally having an intramolecular disulfide bridge between the two terminal cysteine residues;
94) RRIRPRPPRLPRPRPRPLPFPRPG (bactenecin 7 [Bac7]) (SEQ ID NO: 150);
95) RRIRPRP [Bac7(1-7)] (SEQ ID NO: 151);
96) PRPLPFPRP [Bac7(15-24)] (SEQ ID NO: 152);
97) VDKGSYLPRPTPPRPIYNRN (pyrrhocoricin) (SEQ ID NO: 153);
98) LGTYTQDFNKFHTFPQTAIGVGAP {human calcitonin(9-32) [hCT(9-32)]} (SEQ ID NO: 154);
99) LGTYTQDFNKFHTFAQTAIGVGAP {[P23A]hCT(9-32)} (SEQ ID NO: 155);
100) LGTYTQDFNKFHTFPQTAIGVWAP {[G30W]hCT(9-32)} (SEQ ID NO: 156);
101) KFHTFPQTAIGVGAP [hCT(18-32)] (SEQ ID NO: 157);
102) MVRRFLVTLRIRRACGPPRVRV [p14ARF(1-22)] (SEQ ID NO: 158);
103) MVTVLFRRLRIRRACGPPRVRV [M918 inverting positions 3-8 of p14ARF(1-22)] (SEQ ID NO: 159);
104) RLVSYNGIIFFLK (CD44 binding peptide [CD44BP]) (SEQ ID NO: 160);
105) FNLPLPSRPLLR (a peptide binding to CD44 found by phage display) (SEQ ID NO: 161);
106) MASIWVGHRG (AA3H [the N-terminus of an annexin A isoform]) (SEQ ID NO: 162);
107) LLIILRRRIRKQAHAHSK (murine peptide vascular endothelial cadherin [pVEC]) (SEQ ID NO: 163), which is capable of nuclear targeting;
108) LSTAADMQGVVTDGMASG [azurin(50-67)], aka p18] (SEQ ID NO: 164);
109) RQIKIWFQNRRMKWKK [penetratin or Antennapedia homeodomain-/AntpHD-(43-58)](SEQ ID NO: 165) and the corresponding isomer having all D-amino acids, both of which are capable of nuclear targeting;
110) RQIKIWFPNRRMKWKK {[Q50P]AntpHD(43-58)} (SEQ ID NO: 166);
111) RQPKIWFPNRRKPWKK {[I45P, Q50P, M54K, K55P]AntpHD(43-58)} (SEQ ID NO: 167);
112) RQIRIWFQNRRMRWRR (penetratin-Arg in which all Lys residues are replaced with Arg) (SEQ ID NO: 168);
113) RQIKIWFQKNRRMKWKK (Lys inserted at position 9 of penetratin) (SEQ ID NO: 169);
114) LIRLWSHLIHIWFQNRRLKWKKK (EB1, a penetratin variant) (SEQ ID NO: 170);
115) RHIKIWFQNRRMKWKK (PDX-1, which is [Q2H] penetratin) (SEQ ID NO: 171), which is capable of nuclear targeting;
116) RVIRVWFQNKRCKDKK (Islet-1 homeodomain third helix) (SEQ ID NO: 172), which is capable of nuclear targeting;
117) SQIKIWFQNKRAKIKK (Engrailed-2 homeodomain third helix) (SEQ ID NO: 173), which is capable of nuclear targeting;

118) RQVTIWFQNRRVKEKK (HoxA-13 homeodomain third helix) (SEQ ID NO: 174), which is capable of nuclear targeting;
119) KQINNWFINQRKRHWK (Knotted-1 homeodomain third helix) (SEQ ID NO: 175), which is capable of nuclear targeting;
120) AAVALLPAVLLALLAPVQRKRQKLMP (MTS signal peptide plus NLS of NF-icB p50) (SEQ ID NO: 176), which is capable of nuclear targeting;
121) AAVALLPAVLLALLAKNNLKDCGLF (SEQ ID NO: 177);
122) AAVALLPAVLLALLAKNNLKECGLY (SEQ ID NO: 178);
123) MGLGLHLLVLAAALQGAKKKRKV [Ig(v)] (SEQ ID NO: 179), which is capable of nuclear targeting;
124) MVKSKIGSWILVLFVAMWSDVGLCKKRPKP {bovine prion protein(1-30) [bPrPp(1-30)]} (SEQ ID NO: 180), which is capable of nuclear targeting;
125) MANLGYWLLALFVTMWTDVGLCKKRPKP [murine prion protein(1-28) [mPrPp(1-28)] } (SEQ ID NO: 181), which is capable of nuclear targeting;
the corresponding peptides having all D-amino acid residues; and
the corresponding peptides (L- and D-isomers) having the reverse order of amino acid sequence;
wherein:
each peptide can optionally have one or more, or all, D-amino acid residues;
each peptide can optionally have a protecting group at the N-terminus or/and the C-terminus (e.g., acetyl at the N-terminus or/and —NH$_2$ at the C-terminus);
each peptide can optionally have a cysteamide group at the C-terminus; and
each peptide can optionally have one, two or more hydrophobic/lipophilic groups (e.g., $C_8$-$C_{20}$ alkyl [e.g., decyl, lauryl, myristyl, palmityl or stearyl], $C_8$-$C_{20}$ acyl [e.g., decanoyl, lauroyl, myristoyl, palmitoyl or stearoyl], or steroidal [e.g., cholesteryl]) or/and PEG moieties (those comprising, e.g., about 2-20 or 2-10 PEG units) attached to the N-terminus, the C-terminus or/and side chain(s).

51. The TDS of any one of embodiments 1 to 15, wherein the CPP is a hydrophobic CPP rich in non-polar or hydrophobic amino acid residues, and wherein the hydrophobic CPP can optionally have a low net charge (e.g., a net charge of +/−1 or +/−2 at a pH of about 7.4).

52. The TDS of embodiment 51, wherein the hydrophobic CPP is selected from:
1) GALFLGFLGAAGSTMGA (MPG without the NLS and linker) (SEQ ID NO: 182);
2) AAVALLPAVLLALLAP (membrane-translocating sequence peptide [MTS] derived from the hydrophobic H-region of the signal peptide of Kaposi fibroblast growth factor [K-FGF]) (SEQ ID NO: 183);
3) AAVALLPAVLLKLLAP ([A12K]MTS) (SEQ ID NO: 184);
4) AAVLLPVLLAAP (an MTS variant) (SEQ ID NO: 185);
5) PIEVCMYREP (FGF12) (SEQ ID NO: 186);
6) VTVLALGALAGVGVG (integrin (33 signal peptide) (SEQ ID NO: 187);
7) CSIPPEVKFNKPFVYLI (C105Y) (SEQ ID NO: 188);
8) PFVYLI (the mimimal cell-penetrating sequence of C105Y) (SEQ ID NO: 189);
9) SDLWEMMMVSLACQY (Janda pep7) (SEQ ID NO: 190);
10) GPFHFYQFLFPPV (435B) (SEQ ID NO: 191);
11) PLILLRLLR (SEQ ID NO: 192), optionally having GQF added to the C-terminus;
12) PLIYLRLLR (SEQ ID NO: 193), optionally having GQF added to the C-terminus;
13) PLILLFKLL (SEQ ID NO: 194), optionally having GQF added to the C-terminus;
14) PLGYLFLLR (SEQ ID NO: 195), optionally having GQF added to the C-terminus;
15) PLIYPFLRL (SEQ ID NO: 196), optionally having GQF added to the C-terminus;
16) VPTLK (a Bax-inhibiting peptide [BIP]) (SEQ ID NO: 197);
17) VPTLE (a BIP) (SEQ ID NO: 198);
18) VPTLQ (a BIP) (SEQ ID NO: 199);
19) VPALK (a BIP) (SEQ ID NO: 200);
20) VPALR (a BIP) (SEQ ID NO: 201);
21) VPMIK (a BIP) (SEQ ID NO: 202);
22) VPMLK (a BIP) (SEQ ID NO: 203);
23) VSALK (a BIP) (SEQ ID NO: 204);
24) IPALK (a BIP) (SEQ ID NO: 205);
25) IPMLK (a BIP) (SEQ ID NO: 206);
26) PMLKE (a BIP) (SEQ ID NO: 207);
27) KLPVT (a BIP) (SEQ ID NO: 208);
28) KLGVM (a BIP) (SEQ ID NO: 209);
29) ELPVM (a BIP) (SEQ ID NO: 210);
30) QLPVM (a BIP) (SEQ ID NO: 211);
the corresponding peptides having all D-amino acid residues; and
the corresponding peptides (L- and D-isomers) having the reverse order of amino acid sequence;
wherein:
each peptide can optionally have one or more, or all, D-amino acid residues;
each peptide can optionally have a protecting group at the N-terminus or/and the C-terminus (e.g., acetyl at the N-terminus or/and —NH$_2$ at the C-terminus);
each peptide can optionally have a cysteamide group at the C-terminus; and each peptide can optionally have one, two or more PEG moieties (those comprising, e.g., about 2-20 or 2-10 PEG units) attached to the N-terminus, the C-terminus or/and side chain(s).

53. The TDS of any one of embodiments 1 to 15, wherein the CPP is selected from:
1) TKRRITPKDVIDVRSVTTEINT [Mce1A(130-151), aka Inv3] (SEQ ID NO: 212);
2) RLIYLRLLR (SEQ ID NO: 213), optionally having GQF added to the C-terminus;
3) PLRLLRLLR (SEQ ID NO: 214), optionally having GQF added to the C-terminus;
4) RKILLRLLR (SEQ ID NO: 215), optionally having GQF added to the C-terminus;
5) PLRLRFLLR (SEQ ID NO: 216), optionally having GQF added to the C-terminus;
6) RLIRLFLLR (SEQ ID NO: 217), optionally having GQF added to the C-terminus;
7) RLILLFRRL (SEQ ID NO: 218), optionally having GQF added to the C-terminus;
8) RRILLQLLR (SEQ ID NO: 219), optionally having GQF added to the C-terminus;
9) PLGRPQLRR (SEQ ID NO: 220), optionally having GQF added to the C-terminus;
10) DDILLQLLD (SEQ ID NO: 221), optionally having GQF added to the C-terminus;
11) VSLKK (a BIP) (SEQ ID NO: 222);
12) VSGKK (a BIP) (SEQ ID NO: 223);

13) 50% M$^{Gal}_{10}$ [J. Kramer et al., *ACS Cent. Sci.*, 1:83-88 (2015)];
14) 50% M$^{Glc}_{10}$ [Kramer (supra)];
15) CC12 [C. Chen et al., *Biomaterials*, 112:218-233 (2017)];
the corresponding peptides having all D-amino acid residues; and
the corresponding peptides (L- and D-isomers) having the reverse order of amino acid sequence;
wherein:
  each peptide can optionally have one or more, or all, D-amino acid residues;
  each peptide can optionally have a protecting group at the N-terminus or/and the C-terminus (e.g., acetyl at the N-terminus or/and —NH$_2$ at the C-terminus);
  each peptide can optionally have a cysteamide group at the C-terminus; and
  each peptide can optionally have one, two or more hydrophobic/lipophilic groups (e.g., C$_8$-C$_{20}$ alkyl [e.g., decyl, lauryl, myristyl, palmityl or stearyl], C$_8$-C$_{20}$ acyl [e.g., decanoyl, lauroyl, myristoyl, palmitoyl or stearoyl], or steroidal [e.g., cholesteryl]) or/and PEG moieties (those comprising, e.g., about 2-20 or 2-10 PEG units) attached to the N-terminus, the C-terminus or/and side chain(s).

54. The TDS of any one of the preceding embodiments, wherein the therapeutic agent is mixed with the CPP.

55. The TDS of any one of the preceding embodiments, wherein the therapeutic agent is non-covalently bound to or associated with the CPP.

56. The TDS of embodiment 55, which is a complex (e.g., a stable complex) between the therapeutic agent and the CPP.

57. The TDS of embodiment 55 or 56, wherein the therapeutic agent and the CPP form a charged complex having a net charge, or the therapeutic and the CPP form a complex, or are non-covalently associated with one another, via charge-based or electrostatic interaction or/and hydrogen bonding between the therapeutic agent and the CPP.

58. The TDS of embodiment 57, wherein the CPP is a polycationic CPP, an arginine-rich CPP [e.g., a polyarginine such as R$_6$-R$_{11}$ (SEQ ID NO: 268) (e.g., R$_6$ (SEQ ID NO: 258) or R$_9$ (SEQ ID NO: 261)) or a TAT-related CPP such as TAT(49-57)], or an amphipathic CPP (e.g., Pep-1 or penetratin).

59. The TDS of embodiment 55 or 56, wherein the therapeutic agent and the CPP form a complex, or are non-covalently associated with one another, via hydrophobic interaction or/and hydrogen bonding between the therapeutic agent and the CPP.

60. The TDS of embodiment 59, wherein the CPP is an amphipathic CPP (e.g., Pep-1 or penetratin) or a hydrophobic CPP.

61. The TDS of any one of embodiments 55 to 60, wherein the therapeutic agent and the CPP form a complex, or are non-covalently associated with one another, via both electrostatic interaction and hydrophobic interaction, and optionally hydrogen bonding, between the therapeutic agent and the CPP.

62. The TDS of embodiment 61, wherein the CPP is an amphipathic CPP (e.g., Pep-1 or penetratin).

63. The TDS of any one of embodiments 56 to 62, wherein the complex is formed in a molar ratio of the CPP to the therapeutic agent from about 1:1 to about 20:1 (e.g., from about 1:1 to about 5:1, such as about 1:1, 2:1 or 3:1).

64. The TDS of any one of embodiments 54 to 63, which is in the form of a nanoparticle (e.g., a stable nanoparticle) comprising molecules of the CPP around one or more molecules of the therapeutic agent.

65. The TDS of embodiment 64, wherein the CPP forming the nanoparticle containing the therapeutic agent is an amphipathic CPP (e.g., Pep-1), a polycationic CPP (e.g., POD) or an arginine-rich CPP (e.g., a polyarginine such as R$_6$-R$_{11}$ (SEQ ID NO: 268) [e.g., R$_6$ (SEQ ID NO: 258) or R$_9$ (SEQ ID NO: 261)]).

66. The TDS of embodiment 64 or 65, wherein the nanoparticle is formed in a molar ratio of the CPP to the therapeutic agent from about 10:1 to about 20:1 (e.g., from about 10:1 to about 15:1, or from about 15:1 to about 20:1).

67. The TDS of any one of embodiments 1 to 53, wherein the therapeutic agent is covalently bonded to the CPP, and wherein:
  the therapeutic agent can be bonded to the CPP at the N-terminus, the C-terminus or a side chain of the therapeutic agent if the therapeutic agent is a polypeptide; and
  the CPP can be bonded to the therapeutic agent at the N-terminus, the C-terminus or a side chain of the CPP.

68. The TDS of embodiment 67, wherein the bond between the therapeutic agent and the CPP, whether a direct bond or an indirect bond (e.g., via a linker), is cleavable (e.g., chemically or enzymatically cleavable).

69. The TDS of embodiment 67 or 68, wherein the therapeutic agent is directly or indirectly bonded to the CPP via a disulfide bond, an amide bond, an ester bond, a hydrazone bond an oxime bond a thiazolidine bond a thioether bond, or a succinimide-thioether bond 70. The TDS of any one of embodiments 67 to 69, wherein the therapeutic agent is directly bonded to the CPP.

71. The TDS of any one of embodiments 67 to 69, wherein the therapeutic agent is indirectly bonded to the CPP via a cleavable or non-cleavable linker.

72. The TDS of embodiment 71, wherein the linker is selected from

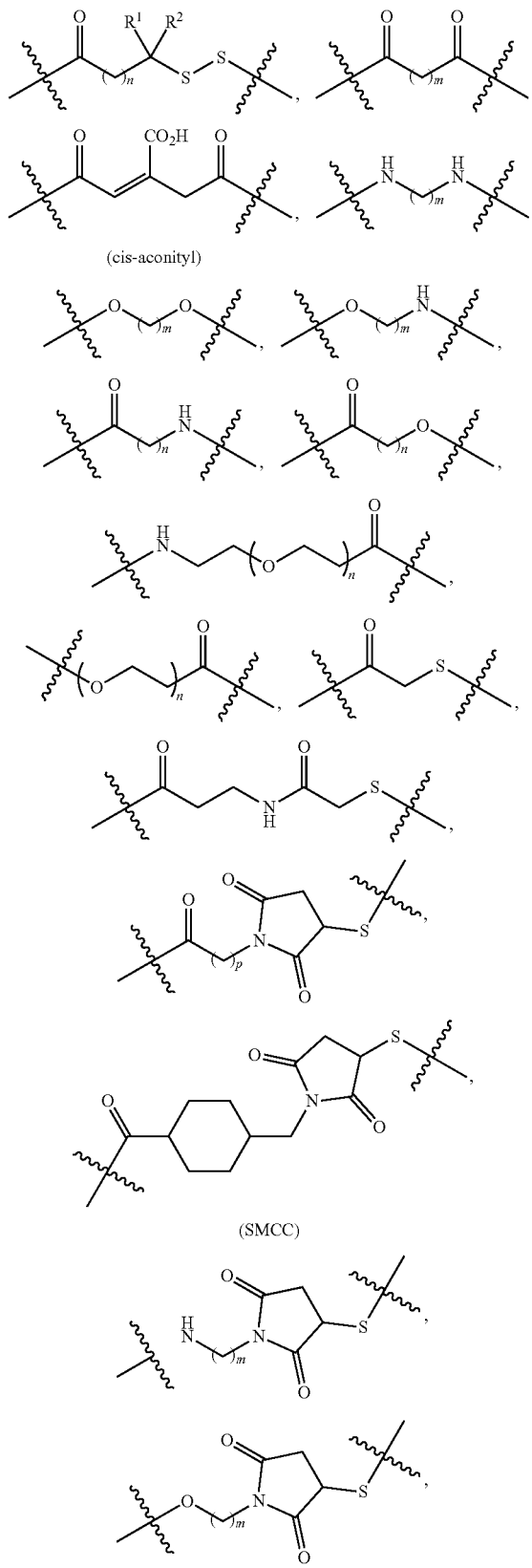

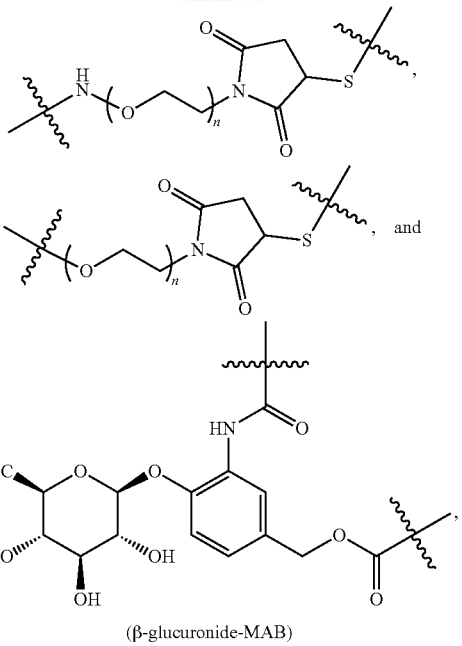

(β-glucuronide-MAB)

and wherein:
m is 2, 3, 4, 5 or 6 (e.g., 2);
n is 1, 2, 3, 4, 5 or 6 (e.g., 1 or 2);
p is 2, 3, 4, 5 or 6 (e.g., 3 or 5);
S next to a squiggly line can be the sulfur atom of, e.g., a cysteine, —SCH$_2$CH$_2$NHC(=O)-(cysteamide) or —SCH$_2$CH$_2$C(=O)— group; and
R$^1$ and R$^2$ independently are hydrogen or —CH$_3$ (i.e., R$^1$=R$^2$=H, or R$^1$=H and R$^2$=—CH$_3$, or R$^1$=R$^2$=—CH$_3$).

73. The TDS of embodiment 71, wherein the linker is a peptide linker comprising at least 2, 3, 4, 5 or 6 natural or/and non-natural amino acid residues, and optionally one or more non-peptidic moieties.

74. The TDS of embodiment 73, wherein the peptide linker is an enzymatically cleavable peptide linker.

75. The TDS of embodiment 74, wherein the enzymatically cleavable peptide linker is selected from:
1) Val-Cit, wherein Cit is citrulline;

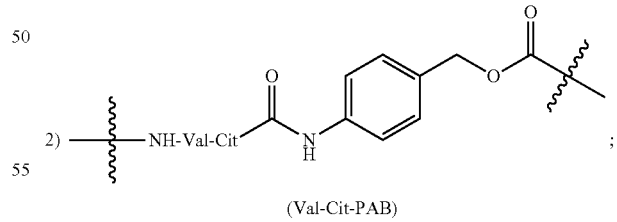

(Val-Cit-PAB)

3) Gly-Gly-Gly-Val-Cit-PAB (SEQ ID NO: 224);
4) Phe-Lys;
5) Phe-Lys-PAB;
6) Ala-Ala-Asn-PAB;
7) GFLG (SEQ ID NO: 225);
8) ALAL (SEQ ID NO: 226);
9) GKPILFFRLKr, optionally having Lys added to the N-terminus or/and Glu added to the C-terminus, wherein the lower case "r" denotes D-Arg;

10) GKPILFFRLK-Cit (SEQ ID NO: 227), optionally having Lys added to the N-terminus or/and Glu added to the C-terminus, wherein Cit is is citrulline;

11) GSKPILFFRLKr, optionally having Lys added to the N-terminus or/and Glu added to the C-terminus, wherein the lower case "r" denotes D-Arg;

12) PILFFRLGK (SEQ ID NO: 228), optionally having Lys added to the N-terminus or/and Glu added to the C-terminus; and 13) GSPILFFRLGK (SEQ ID NO: 229), optionally having Lys added to the N-terminus or/and Glu added to the C-terminus.

76. The TDS of any one of embodiments 67 to 75, wherein the therapeutic agent is a polypeptide (e.g., an apoA-I mimetic such as L-4F or D-4F or an apoE mimetic such as AEM-28-14) and the CPP is a polyarginine (e.g., $R_6$ (SEQ ID NO: 258), $R_7$ (SEQ ID NO: 259), $R_8$ (SEQ ID NO: 260) or $R_9$ (SEQ ID NO: 261)), and the CPP is directly or indirectly (e.g., via a linker) bonded to the N-terminus, the C-terminus or a side chain of the therapeutic agent.

77. The TDS of embodiment 76, wherein the CPP is directly bonded to the N-terminus of the therapeutic agent.

78. The TDS of any one of embodiments 1 to 53, which is a nanoparticle, micelle or liposome encapsulating a plurality of molecules of the therapeutic agent, wherein a plurality of molecules of the CPP are directly or indirectly (e.g., via a linker) attached to the surface of the nanoparticle, micelle or liposome.

79. The TDS of embodiment 78, wherein a plurality of poly(ethylene glycol) moieties are directly or indirectly (e.g., via a linker) attached to the surface of the nanoparticle, micelle or liposome.

80. The TDS of embodiment 78 or 79, wherein the nanoparticle, micelle or liposome is composed of one or more biodegradable polymers, one or more polysaccharides (e.g., chitosan), or one or more lipids (e.g., a solid lipid such as glycerol behenate, glycerol palmitostearate or wax cetyl palmitate, and optionally a liquid lipid such as a medium-chain triglyceride [e.g., Miglyol® 812]), and optionally a surfactant (e.g., for stabilization of a lipid nanoparticle).

81. The TDS of any one of embodiments 78 to 80, which is a nanoparticle or micelle composed of a biodegradable polymer (e.g., a natural homopolymer, a synthetic homopolymer, a natural copolymer or a synthetic copolymer, or any combination or blend thereof).

82. The TDS of embodiment 81, wherein the nanoparticle is composed of poly(lactic acid) (PLA), poly(glycolic acid) (PGA) or poly(ε-caprolactone) (PCL), or a copolymer thereof [e.g., poly(lactic-co-glycolic acid) (PLGA)], or a copolymer thereof with poly(ethylene glycol) (e.g., PLGA-PEG), wherein lactic acid is L-lactic acid, D-lactic acid or D,L-lactic acid.

83. The TDS of embodiment 81, wherein the micelle is composed of an amphiphilic block copolymer, such as a lactosome composed of, e.g., three poly(sarcosine) blocks and a poly(lactic acid) block, wherein lactic acid is L-lactic acid, D-lactic acid or D,L-lactic acid.

84. The TDS of any one of embodiments 78 to 80, which is a micelle composed of one or more surfactants or phospholipids.

85. The TDS of any one of embodiments 78 to 80, which is a liposome composed of one or more phospholipids (e.g., one or more phosphatidylcholines).

86. The TDS of any one of embodiments 78 to 85, wherein the CPP is or comprises a polycationic CPP (e.g., POD), an arginine-rich CPP [e.g., a polyarginine such as $R_6$-$R_{11}$ (SEQ ID NO: 268) (e.g., $R_6$ (SEQ ID NO: 258), $R_9$ (SEQ ID NO: 261) or $R_{11}$ (SEQ ID NO: 263)), or a TAT-related CPP such as TAT(49-57) or TAT(47-57)], or an amphipathic CPP (e.g., Pep-1, penetratin or EB1), or any combination thereof.

87. The TDS of any one of the preceding embodiments, which is capable of delivering the therapeutic agent into the eye.

88. The TDS of embodiment 87, which is capable of delivering the therapeutic agent into the posterior segment (e.g., the vitreous or/and the retina) of the eye.

89. The TDS of embodiment 87 or 88, which is capable of delivering the therapeutic agent into the eye when administered by an eye drop or a contact lens (e.g., a corneal lens or a scleral lens).

90. A pharmaceutical composition comprising a therapeutic agent and a cell-penetrating peptide (CPP), and one or more pharmaceutically acceptable carriers or excipients.

91. The composition of embodiment 90, wherein the therapeutic agent is or comprises an anti-dyslipidemic agent, an antioxidant, an anti-inflammatory agent, a complement inhibitor, a neuroprotector or an anti-angiogenic agent, or any combination thereof.

92. The composition of embodiment 91, wherein the therapeutic agent is or comprises an anti-dyslipidemic agent.

93. The composition of embodiment 92, wherein the anti-dyslipidemic agent is or comprises an apolipoprotein (apo) mimetic (e.g., an apoA-I mimetic such as L-4F or D-4F or a salt thereof, or an apoE mimetic such as AEM-28-14 or a salt thereof).

94. The composition of embodiment 92 or 93, wherein the anti-dyslipidemic agent is or comprises a statin (e.g., atorvastatin or simvastatin or a salt thereof).

95. The composition of any one of embodiments 90 to 94, wherein the molar ratio of the CPP to the therapeutic agent is from about 1:1 to about 20:1.

96. The composition of embodiment 95, wherein the molar ratio of the CPP to the therapeutic agent is from about 1:1 to about 5:1 or from about 1:1 to about 3:1, or is about 1:1, 2:1 or 3:1 (e.g., about 1:1).

97. The composition of embodiment 95, wherein the molar ratio of the CPP to the therapeutic agent is from about 10:1 to about 20:1 (e.g., from about 10:1 to about 15:1, or from about 15:1 to about 20:1).

98. The composition of any one of embodiments 90 to 97, which comprises the transepithelial, transmembrane or transmucosal drug-delivery system (TDS) of any one of embodiments 1 to 89.

99. The composition of any one of embodiments 90 to 98, which is formulated as an eye drop.

100. The composition of any one of embodiments 90 to 98, which is formulated for administration by a contact lens (e.g., a corneal lens or a scleral lens).

101. A method of treating an eye disorder, comprising administering to a subject in need of treatment a therapeutically effective amount of the transepithelial, transmembrane or transmucosal drug-delivery system (TDS) of any one of embodiments 1 to 89 or the pharmaceutical composition of any one of embodiments 90 to 100.

102. The method of embodiment 101, wherein the eye disorder is age-related macular degeneration (AMD).

103. The method of embodiment 102, wherein the TDS or the composition is administered prior to development of AMD to prevent or delay the onset of AMD.

104. The method of embodiment 102 or 103, wherein the TDS or the composition is administered at least in the early stage of AMD (e.g., to prevent or delay the onset of non-central geographic atrophy [GA]).

105. The method of any one of embodiments 102 to 104, wherein the TDS or the composition is administered at least in the intermediate stage of AMD (e.g., to treat non-central GA, or/and to prevent or delay the onset of central GA or/and neovascular AMD).

106. The method of any one of embodiments 102 to 105, wherein the TDS or the composition is administered at least in the advanced stage of atrophic AMD (e.g., to treat central GA, or/and to prevent or delay the onset of neovascular AMD).

107. The method of any one of embodiments 102 to 106, wherein the TDS or the composition is administered at least in neovascular AMD to treat neovascular AMD.

108. The method of any one of embodiments 101 to 107, wherein the TDS or the composition is administered as or by means of an eye drop.

109. The method of any one of embodiments 101 to 107, wherein the TDS or the composition is administered by means of a contact lens (e.g., a corneal lens or a scleral lens).

110. The method of any one of embodiments 101 to 109, further comprising administering one or more additional therapeutic agents.

111. The method of embodiment 110, wherein the one or more additional therapeutic agents are selected from anti-dyslipidemic agents; PPAR-α agonists, PPAR-δ agonists and PPAR-γ agonists; anti-amyloid agents and inhibitors of other toxic substances (e.g., aldehydes); inhibitors of lipofuscin or components thereof; antioxidants; neuroprotectors (neuroprotectants); apoptosis inhibitors and necrosis inhibitors; C-reactive protein inhibitors; inhibitors of the complement system or components (e.g., proteins) thereof; inhibitors of inflammasomes; anti-inflammatory agents; immunosuppressants; modulators (inhibitors and activators) of matrix metalloproteinases and other inhibitors of cell migration; anti-angiogenic agents; low-level light therapies, laser therapies, photodynamic therapies and radiation therapies; agents that preserve or improve the health of the endothelium or/and the blood flow of the vascular system of the eye; cell (e.g., RPE cell) replacement therapies; and combinations thereof.

112. The method of embodiment 111, wherein the one or more additional therapeutic agents comprise an anti-dyslipidemic agent, an antioxidant, an anti-inflammatory agent, a complement inhibitor, a neuroprotector or an anti-angiogenic agent, or any combination or all thereof.

113. The method of any one of embodiments 110 to 112, wherein the one or more additional therapeutic agents are administered locally to, into, in or around the eye by eye drop, contact lens (e.g., corneal lens or scleral lens), injection (e.g., intravitreal, subconjunctival, subretinal or sub-Tenon's injection), or implant (e.g., intravitreal, intraaqueous, subretinal or sub-Tenon's implant).

114. The method of embodiment 113, wherein the one or more additional therapeutic agents are mixed with, non-covalently associated with or covalently bonded to a cell-penetrating peptide (CPP), or are encapsulated in a CPP-modified nanoparticle, micelle or liposome, and are administered by eye drop or contact lens.

115. The method of embodiment 114, wherein the one or more additional therapeutic agents are or comprise an anti-angiogenic agent (e.g., aflibercept [EYLEA®], bevacizumab [AVASTIN®], ranibizumab [LUCENTIS®] or brolucizumab), and wherein the anti-angiogenic agent is mixed with or non-covalently associated with a CPP {e.g., a polycationic CPP, an arginine-rich CPP (e.g., a polyarginine such as $R_6$-$R_{11}$ (SEQ ID NO: 268) [e.g., $R_6$ (SEQ ID NO: 258) or $R_9$ (SEQ ID NO: 261)]), or an amphipathic CPP (e.g., Pep-1)} and is administered by eye drop.

116. A transepithelial, transmembrane or transmucosal drug-delivery system (TDS) of any one of embodiments 1 to 89 or a pharmaceutical composition of any one of embodiments 90 to 100 for use in the treatment of an eye disorder, optionally in combination with an additional therapeutic agent.

117. Use of a transepithelial, transmembrane or transmucosal drug-delivery system (TDS) of any one of embodiments 1 to 89, or use of a therapeutic agent and a cell-penetrating peptide (CPP), in the preparation of a medicament for the treatment of an eye disorder, optionally in combination with an additional therapeutic agent.

118. The TDS or the pharmaceutical composition for use according to embodiment 116, or the use of embodiment 117, wherein the eye disorder is atrophic or neovascular AMD.

119. A method of treating an eye disorder, comprising administering to a subject in need of treatment a therapeutically effective amount of a therapeutic agent listed in Table 1.

120. The method of embodiment 119, further comprising administering an additional therapeutic agent.

121. The method of embodiment 120, wherein the additional therapeutic agent is or comprises an apolipoprotein mimetic peptide (e.g., an apoA-I mimetic such as L-4F or D-4F, or an apoE mimetic such as AEM-28-14) or/and a statin (e.g., atorvastatin or simvastatin).

122. The method of any one of embodiments 119 to 121, wherein the therapeutic agent listed in Table 1 is delivered into the eye with the aid of a cell-penetrating peptide (CPP) or/and a chemical penetration enhancer (CPE) by means of, e.g., an eye drop or a contact lens (e.g., a corneal lens or a scleral lens).

123. The method of any one of embodiments 120 to 122, wherein the additional therapeutic agent is delivered into the eye with the aid of a CPP or/and a CPE by means of, e.g., an eye drop or a contact lens (e.g., a corneal lens or a scleral lens).

124. The method of embodiment 122 or 123, wherein the therapeutic agent listed in Table 1 or the additional therapeutic agent is a polypeptide (e.g., a peptide or a protein), and the polypeptide is administered by way of a CPP-containing transepithelial, transmembrane or transmucosal drug-delivery system (TDS).

125. The method of any one of embodiments 122 to 124, wherein the therapeutic agent listed in Table 1 or the additional therapeutic agent is mixed with the CPP or/and the CPE in an ophthalmic formulation.

126. The method of any one of embodiments 122 to 125, wherein the CPP is a polycationic CPP (e.g., POD), an arginine-rich CPP [e.g., a polyarginine such as $R_6$-$R_{11}$ (SEQ ID NO: 268) (e.g., $R_6$ (SEQ ID NO: 258) or $R_9$ (SEQ ID NO: 261)) or a TAT-related CPP such as TAT(49-57)], or an amphipathic CPP (e.g., Pep-1 or penetratin).

127. The method of any one of embodiments 122 to 126, wherein the CPE is or comprises a surfactant, such as a non-ionic surfactant (e.g., a saponin or an alkyl glycoside such as 1-O-tetradecyl-β-D-maltoside).

128. The method of any one of embodiments 119 to 127, wherein the eye disorder is atrophic or neovascular AMD.

129. A kit comprising:
a transepithelial, transmembrane or transmucosal drug-delivery system (TDS) of any one of embodiments 1 to 89 or a pharmaceutical composition of any one of embodiments 90 to 100; and instructions for using or administering the TDS or the composition to treat an eye disorder.
130. The kit of embodiment 129, wherein the TDS or the composition is administered as or by means of an eye drop.
131. The kit of embodiment 129, wherein the TDS or the composition is administered by means of a contact lens (e.g., a corneal lens or a scleral lens).
132. The kit of any one of embodiments 129 to 131, wherein the eye disorder is atrophic or neovascular AMD.

XV. EXAMPLES

The following examples are intended only to illustrate the disclosure. Other assays, studies, procedures, methodologies, materials, reagents and conditions may alternatively be used or conducted as appropriate.

Example 1. Reduction of Lipid Deposits from Bruch's Membrane in Geriatric Monkeys by L-4F The macaque study was conducted according to accepted guidelines. Nine female geriatric macaques (*Macaca fascicularis*, all more than 20 years of age) with naturally occurring age-related maculopathy (exhibiting age-related drusenoid macular changes/maculopathy resembling early AMD in humans) were intravitreally injected with a sterile balanced salt solution (BSS) of the apoA-I mimetic L-4F, Ac-DWFKAFYDKVAEKFKEAF-$NH_2$ (SEQ ID NO: 1) acetate salt (n=7), or a placebo (a sterile BSS of scrambled L-4F [sL-4F] having the same amino acids but in a non-functional order) (n=2). One eye per animal received 6 monthly injections of the same escalating dosages of L-4F or scrambled L-4F (total of 625 μg) in a 50 μL volume. The second eye per animal was not injected and was just observed. The injected eye exhibited worse drusenoid changes than the uninjected eye per animal at baseline. Table 2 shows the dosing regimen used in the macaque study.

TABLE 2

|  | Day | Amount Injected (μg) | Concentration (mg/mL) | Volume Injected |
| --- | --- | --- | --- | --- |
| Placebo | 1 | 25 | 0.5 | 50 μL |
| (scrambled L-4F) | 29 | 50 | 1.0 | one eye only |
| (n = 2) | 57 | 100 | 2.0 |  |
|  | 85 | 125 | 2.5 |  |
|  | 113 | 150 | 3.0 |  |
|  | 141 | 175 | 3.5 |  |
| L-4F | 1 | 25 | 0.5 | 50 μL |
| (n = 7) | 29 | 50 | 1.0 | one eye only |
|  | 57 | 100 | 2.0 |  |
|  | 85 | 125 | 2.5 |  |
|  | 113 | 150 | 3.0 |  |
|  | 141 | 175 | 3.5 |  |

Clinical laboratory tests including serology, hemograms and liver enzymes were conducted, and ophthalmic examinations were also performed, including fundus photographs, optical coherence tomography (OCT), intraocular pressure testing and blood sampling. After 7 months, all animals were sacrificed and eyes were immediately prepared for histology. Histochemistry was performed with oil red O for neutral lipids and filipin for esterified cholesterol. Immunohistochemistry was performed against complement factor D (CFD) and the membrane attack complex (MAC, C5b-9), both being markers of activation of the alternative complement pathway.

For staining with oil red O (ORO), specimens were treated with a 0.3% oil red O (Sigma-Aldrich Biochemie GmbH, Hamburg, Germany) solution (in 99% isopropanol) for 30 min at room temperature (RT), followed by immersion in a 60% isopropanol solution for 12 min. After the specimens were washed with deionized water for 3 min, counter-staining was conducted with hematoxylin (Carl Roth GmbH, Karlsruhe, Germany). The specimens were then mounted with mounting solution (Aquatex from Merck Millipore, Darmstadt, Germany), covered with a glass cover slip (Menzel-Graeser GmbH), and examined using a fully automated inverted light microscope for life science (DMI 6000 from Leica Microsystems Wetzlar, Germany). Image analysis was performed by grading the intensity of ORO staining (red color) of the Bruch's membrane (BrM) with scores ranging from 0 to 4, according to a qualitative evaluation assessed in four different regions in two separate slices from each eye (a total of 8 different regions from each eye). Qualitative ORO staining scores at the BrM and the choroid: 0=no staining; 1=+; 2=++; 3=+++; 4=++++.

For staining with filipin, specimens were washed once with deionized water for 5 min and then treated with 70% ethanol for 45 min. After being washed with deionized water for 5 min, the specimens were treated with cholesterol esterase (8.12 units/mL) diluted in 0.1 M potassium phosphate buffer (PPB, pH 7.4) for 3.5 hr at 37° C. The specimens were then washed sequentially with PPB and with phosphate buffered saline (PBS) twice for 3 min, followed by a wash with cold (4° C.) PBS overnight. Filipin staining was then performed with 250 μg/mL filipin (Sigma-Aldrich Biochemie GmbH, Hamburg, Germany), diluted in N,N-dimethylformamide (Merck Millipore, Darmstadt, Germany), for 60 min at RT with light shielding. The specimens were then washed sequentially with PBS and deionized water, mounted with a mounting solution (Mowiol®, Carl Roth GmbH, Karlsruhe, Germany), covered with a glass cover slip, and examined using an inverted fluorescence microscope (DMI 6000 from Leica Microsystems, Wetzlar, Germany). Filipin fluorescence was observed using a UV filter set (λex/λem=350 nm/455 nm). As a negative control, cholesterol esterase was replaced by PBS, which prevented the release of cholesterol from cholesteryl ester and subsequent binding by filipin. Semiquantitative analysis of fluorescence intensity of filipin at three separate regions of the BrM was done on three different slides from the same eye (a total of 9 different regions from each eye).

Assays for immunohistochemistry of the membrane attack complex (MAC, C5b-9) and complement factor D (CFD) were performed identically except for employment of monoclonal antibodies specific for each complement component. Specimens were treated with 10 μg/mL protease K (Sigma-Aldrich Biochemie GmbH, Hamburg, Germany) in PBS for antigen retrieval for 30 min at RT. Subsequently the sections were blocked with a solution of goat serum (5% goat serum, 0.3% Triton X-100 in PBS) for 60 min at RT. The specimens were then reacted with a first antibody against either C5b-9 (diluted 1:30 in PBS, mouse monoclonal antibody, Dako Deutschland GmbH, Hamburg, Germany) or complement factor D (diluted 1:200 in PBS, mouse monoclonal antibody, Santa Cruz Biotechnology, Dallas, Tex., USA) overnight at 4° C. After being washed with PBS, the specimens were reacted with a second antibody (diluted 1:200 in PBS, Alexa Fluor 488 anti-mouse, Life Technologies Deutschland GmbH, Darmstadt, Germany) for 1 hr at 37° C. After the specimens were washed with PBS three times, nucleus staining was conducted with DAPI (1 μg/mL, Life Technologies GmbH, Darmstadt, Germany) for 10 min. The specimens then were washed with PBS three times, mounted with anti-fade solution (Mowiol®, Carl Roth GmbH, Karlsruhe, Germany), and covered with a glass cover slip for microscopic examination. Fluorescence microscopy was conducted using an inverted fluorescence microscope (DMI 6000 from Leica Microsystems, Wetzlar, Germany) and a filter set for $\lambda ex/\lambda em=470$ nm/525 nm. For the semiquantitative analysis of fluorescence intensity of C5b-9, 3-5 different regions in one slide were analyzed for 3 different slides from each eye (a total of 9-15 different regions from each eye). For the semiquantitative analysis of fluorescence intensity of complement factor D, 3 distinct regions for each eye were evaluated.

Figure 2:
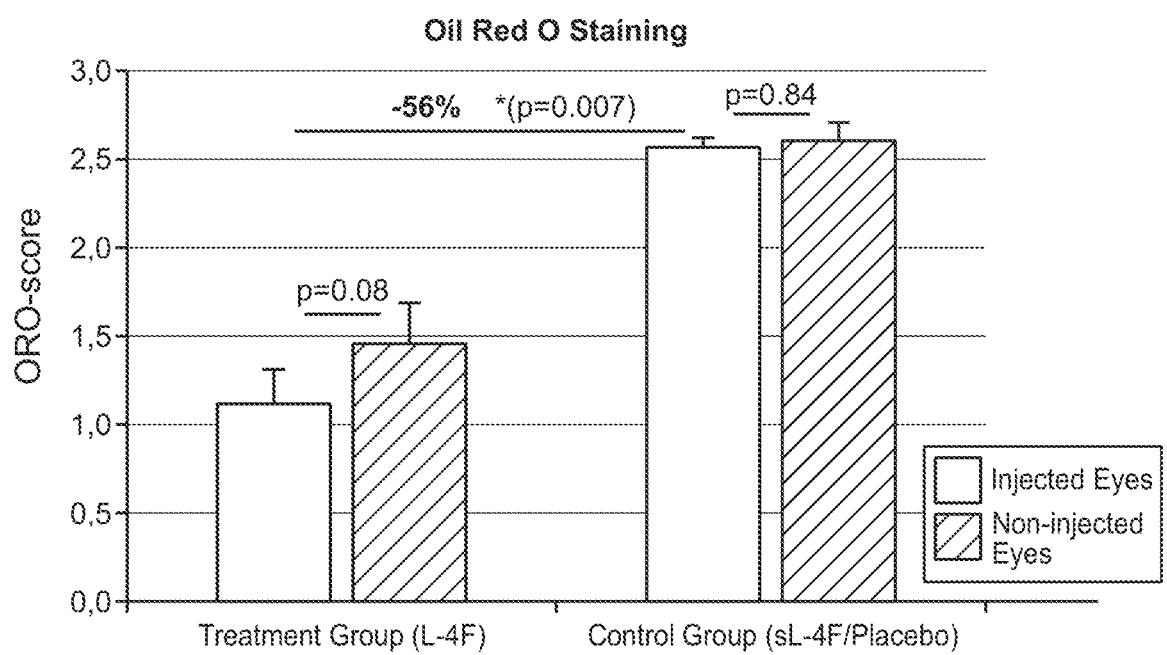
FIG. 2 shows the scoring of staining of neutral lipids in and on the Bruch's membrane with oil red O (ORO) in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.
Figure 3:
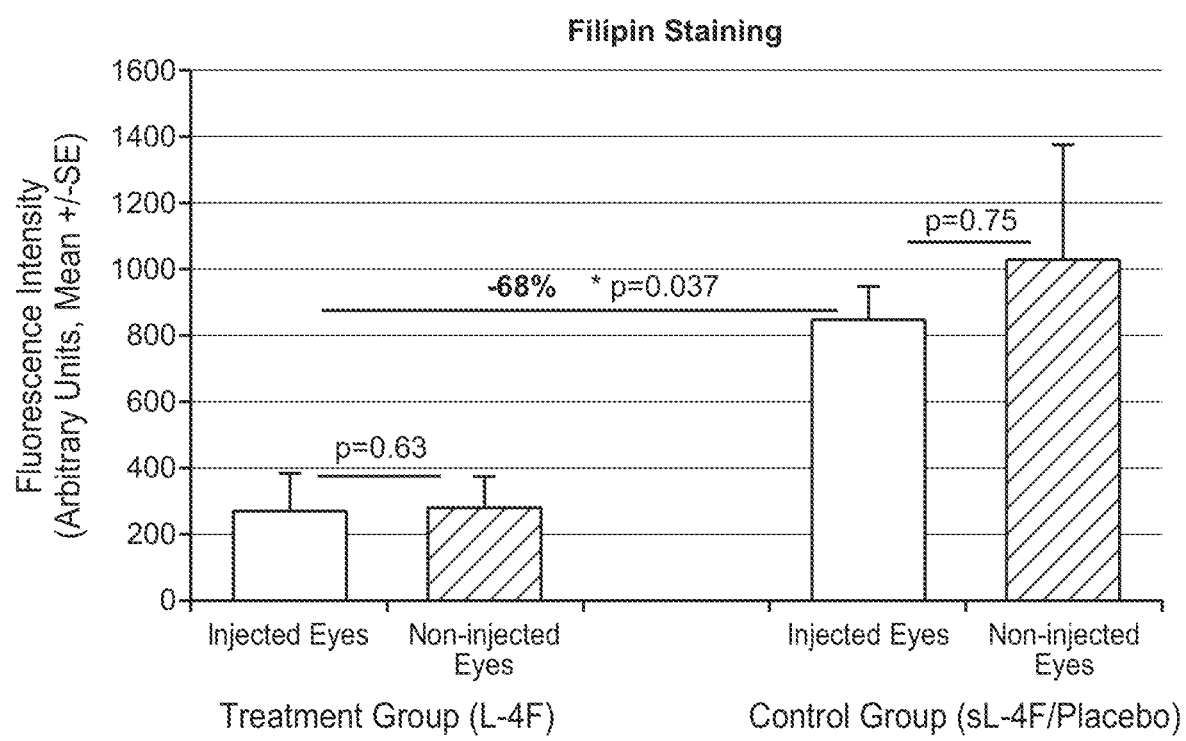
FIG. 3 shows the intensity of staining of esterified cholesterol in the Bruch's membrane with filipin in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.

Both control animals injected with the placebo (scrambled L-4F) exhibited in both eyes an intense and specific staining of the Bruch's membrane (BrM) and choriocapillaris with oil red O for neutral lipids and filipin for esterified cholesterol. For example, staining with oil red O showed that in both control animals, a large amount of lipids was present in and on the BrM. By contrast, in staining with oil red O eyes injected with L-4F exhibited a reduction of lipid deposits from the BrM by about 56% after 6 months compared to eyes injected with placebo. FIG. 2 shows the scoring of staining of neutral lipids in and on the Bruch's membrane with oil red O (ORO) in the injected eye and the fellow non-injected eye of macaques receiving 6 monthly intravitreal injections of L-4F or placebo (scrambled L-4F). Semiquantitative evaluation of filipin fluorescence revealed a reduction of esterified cholesterol in the BrM by about 68% in eyes injected with L-4F compared to placebo-injected eyes. FIG. 3 shows the intensity of staining of esterified cholesterol in the Bruch's membrane with filipin in the injected eye and the fellow non-injected eye of macaques receiving 6 monthly intravitreal injections of L-4F or placebo (scrambled L-4F).

Figure 4:
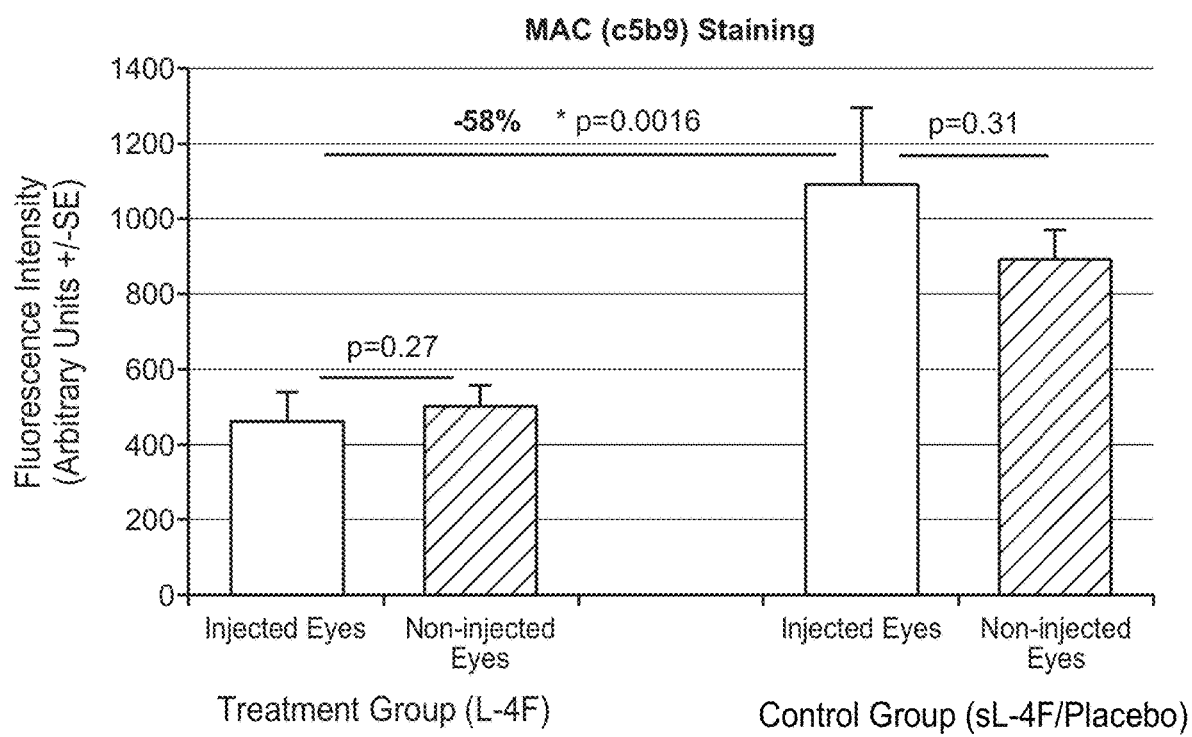
FIG. 4 shows the intensity of staining of the membrane attack complex (MAC, C5b-9) in the Bruch's membrane and the choriocapillaris in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.
Figure 5:
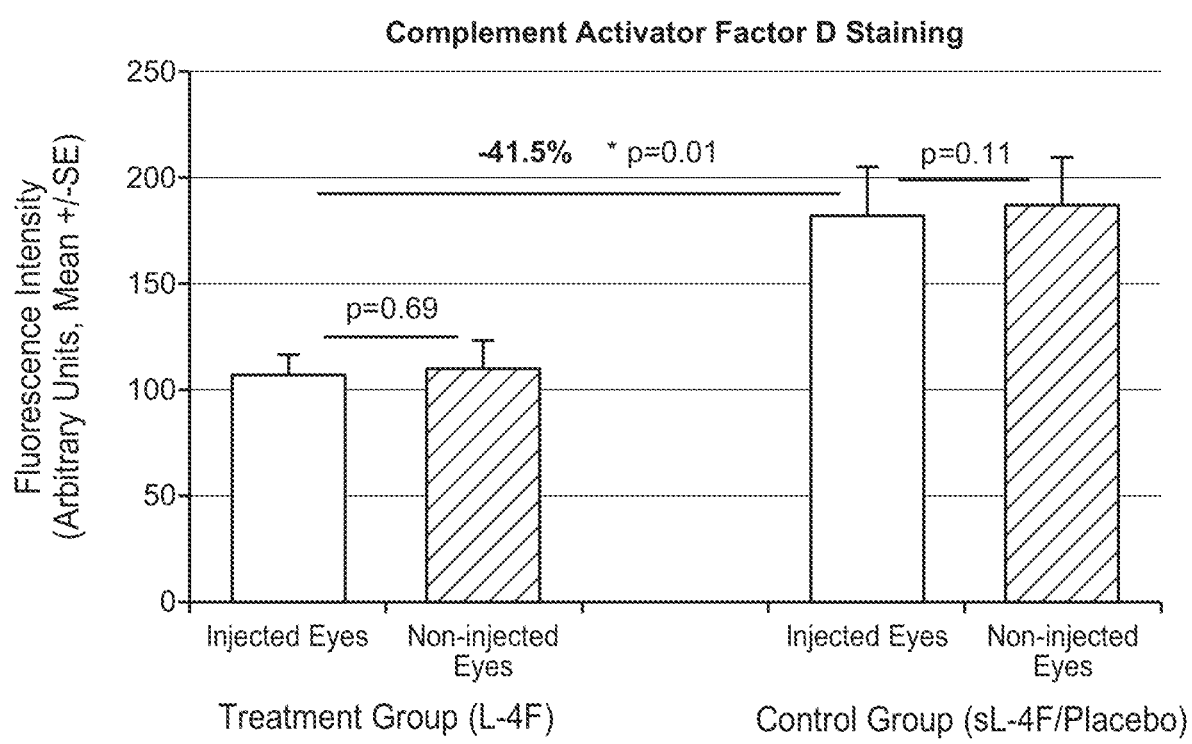
FIG. 5 shows the intensity of staining of complement factor D in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.

Through semiquantitative analysis of fluorescence intensity of the respective specific antibodies, eyes injected with L-4F exhibited a decreased level of MAC (C5b-9) in the BrM and the choriocapillaris by about 58% and a decreased level of complement factor D by about 41% compared to eyes injected with the scrambled peptide. FIG. 4 shows the intensity of staining of the membrane attack complex (MAC, C5b-9) in the Bruch's membrane and the choriocapillaris in the injected eye and the fellow non-injected eye of macaques receiving 6 monthly intravitreal injections of L-4F or placebo (scrambled L-4F). FIG. 5 shows the intensity of staining of complement factor D in the injected eye and the fellow non-injected eye of macaques receiving 6 monthly intravitreal injections of L-4F or placebo (scrambled L-4F).

Figure 6:
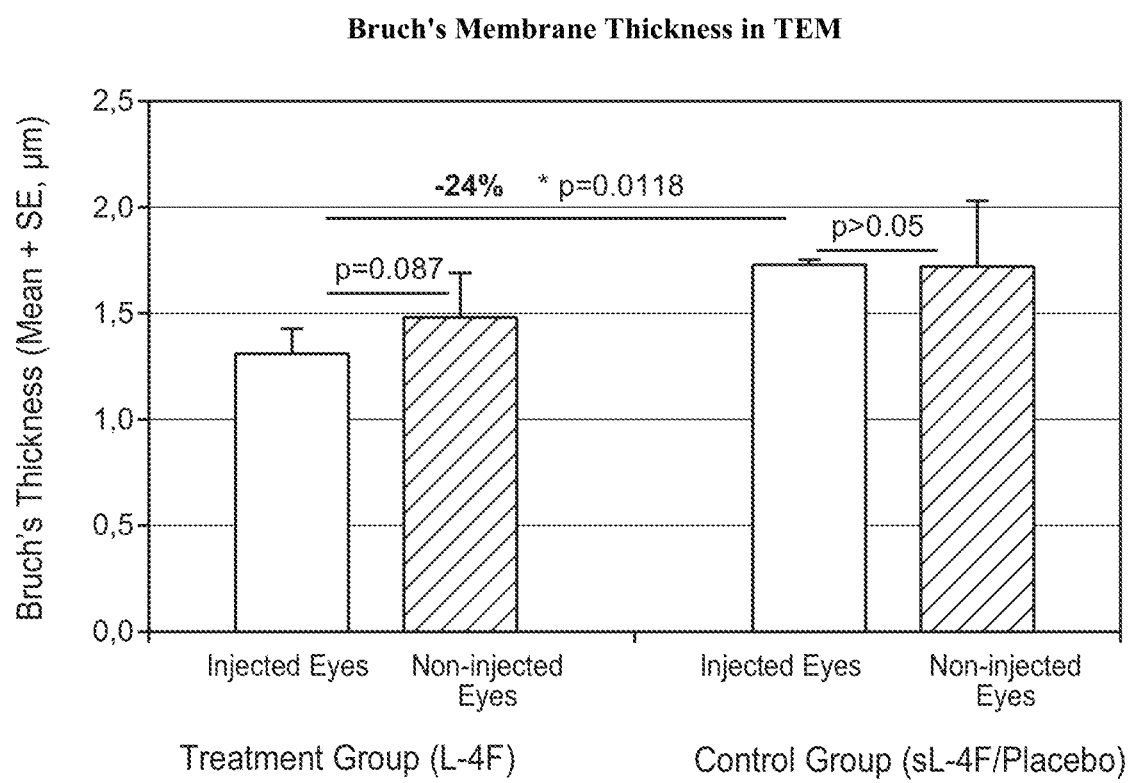
FIG. 6 shows the thickness of the Bruch's membrane measured at the temporal outer macula in the injected eye and the fellow non-injected eye of macaques receiving 6 monthly intravitreal injections of L-4F or placebo (scrambled L-4F). Statistical analysis: 1) paired t-test between injected eyes and non-injected eyes in the same group; 2) unpaired t-test between injected eyes in the treatment (L-4F) group and the control (placebo) group.

Lipid deposition in the Bruch's membrane contributes to thickening of the BrM. Bruch's membrane thickness was measured at the temporal outer macula of enucleated eyes examined by electron microscopy post-mortem. Eyes injected with L-4F exhibited reduction of BrM thickness (1.31 µm±SE 0.11) by about 24% compared to eyes injected with placebo (1.73 µm±SE 0.02). FIG. 6 shows the thickness of the Bruch's membrane measured at the temporal outer macula in the injected eye and the fellow non-injected eye of macaques receiving 6 monthly intravitreal injections of L-4F or placebo (scrambled L-4F).

L-4F had similar effects on the fellow non-injected eye as on the injected eye after 6 monthly intravitreal injections (see FIGS. 2-6). Without intending to be bound by theory, L-4F intravitreally injected into one eye reached the BrM and from there could have entered the choriocapillaris and hence systemic circulation and ultimately the fellow non-injected eye. Also without intending to be bound by theory, the magnitude of L-4F's therapeutic effects in the fellow non-injected eye could have been due in part to the relatively small body weight of the macaques relative to eye size and the primarily vegetarian diet of the macaques, which exhibited no atherosclerosis, a potential target for L-4F in systemic circulation.

L-4F was well tolerated in all of the macaques, as none of the macaques intravitreally injected with L-4F experienced any significant adverse event or side effect. For example, 6 monthly intravitreal injections of L-4F did not increase the blood level of high-sensitivity C-reactive protein (hsCRP) compared to the blood level of hsCRP on the day prior to the first injection of L-4F. Circulating hsCRP, which is mainly produced in the liver, is a non-specific marker for systemic inflammation.

In summary, the apoA-I mimetic L-4F functioned as an effective lipid scavenger and removed lipid deposits from the BrM in a monkey model of age-related maculopathy. Removal of lipid deposits from the BrM restored BrM integrity as examined by electron microscopy. In addition, downstream effects of lipid deposition such as local inflammation were reduced, as demonstrated by the marked reduction of complement activation in eyes injected with L-4F.

Example 2. Ex Vivo Delivery of Anti-Dyslipidemic Agents into Porcine Eyes without or with a Cell-Penetrating Peptide Adult porcine eyes are obtained from a local slaughterhouse, stored on ice, and used within 3 hours of animal death. The eyes are irrigated with PBS and then have an approximately 50 µL eye drop applied to the cornea. The eye drop contains an anti-dyslipidemic agent (e.g., an apoA-I mimetic such as L-4F or D-4F, an apoE mimetic such as AEM-28-14, or a statin such as atorvastatin or simvastatin) alone in PBS or mixed with, non-covalently associated with or covalently bonded to a cell-penetrating peptide (e.g., an arginine-rich CPP such as a polyarginine [e.g., $R_6$ (SEQ ID NO: 258) or $R_9$ (SEQ ID NO: 261)], or an amphipathic CPP [e.g., Pep-1 or penetratin]). The anti-dyslipidemic agent is attached to a fluorescent tag (e.g., fluorescein) if there is no commercially available antibody for performing ELISA on the anti-dyslipidemic agent. After about 45 minutes of incubation at room temperature, the eyes are washed three times with PBS, and then the vitreous and the retina are removed. The vitreous is freeze-thawed and homogenized, and the retinal tissues are freeze-thawed and homogenized in about 100 µL sterile PBS. The level of the anti-dyslipidemic agent in each of the vitreal and retinal homogenates is measured by fluorescense or ELISA.

Similar ex vivo assays can be conducted to evaluate different anti-dyslipidemic agents, different CPPs, other kinds of therapeutic agents (e.g., antioxidants, anti-inflammatory agents, complement inhibitors, neuroprotectors and anti-angiogenic agents), therapeutic agents encapsulated in CPP-conjugated nanoparticles, micelles or liposomes, therapeutic agents coupled to a small-molecule α-helix mimic (e.g., 2G-SMoC or 4G-SMoC), and modified (e.g., stapled, prenylated or lipidated) therapeutic agents.

Example 3. Evaluation of Anti-Dyslipidemic Agents in a Mouse Model of Early AMD without or with a Cell-Penetrating Peptide The apoE$^{null}$ mouse accumulates esterified cholesterol (EC) in the Bruch's membrane (BrM). In mice and humans, EC localizes only to the BrM. Because EC in the BrM is an important precursor of AMD lesions, the apoE$^{null}$ mouse is a useful model for AMD-relevant lipid accumulation. Female apoE$^{null}$ mice develop more lipid deposits than male mice.

Female apoE$^{null}$ mice on a C57BL/6J background and about 10-11 months of age (Jackson Laboratory, Bar Harbor, Me.) are randomly assigned to receive eye drops of: 1) only sterile PBS; 2) an anti-dyslipidemic agent (e.g., an apoA-I mimetic such as L-4F or D-4F, an apoE mimetic such as AEM-28-14, or a statin such as atorvastatin or simvastatin) mixed with, non-covalently associated with or covalently bonded to a cell-penetrating peptide (e.g., an arginine-rich CPP such as a polyarginine [e.g., $R_6$ (SEQ ID NO: 258) or $R_9$ (SEQ ID NO: 261)], or an amphipathic CPP [e.g., Pep-1 or penetratin]); 3) only the anti-dyslipidemic agent in sterile PBS; or 4) only the CPP in sterile PBS. Each group has at least six mice (n≥6). One eye of each mouse receives one eye drop of about 5 μL twice daily (applied topically about 12 hours apart and at the same times each day) for 30 days. The anti-dyslipidemic agent is attached to a fluorescent tag (e.g., fluorescein). The other eye of each mouse serves as a control. After 30 days the mice are euthanized, and both eyes of each mouse are immediately enucleated and prepared for histology. The levels of EC in whole mounts of the BrM are measured by fluorescence, and the BrM ultrastructure is evaluated by transmission electron microscopy.

Similar studies can be conducted to evaluate different doses of the anti-dyslipidemic agent mixed with, non-covalently associated with or covalently bonded to the CPP (taking into account, e.g., the concentrations of the anti-dyslipidemic agent and the CPP in the eye drop, the volume of an eye drop and the number of eye drops applied daily), different lengths of treatment (e.g., 2 months, 3 months or 6 months), different anti-dyslipidemic agents, different CPPs, anti-dyslipidemic agents encapsulated in CPP-conjugated nanoparticles, micelles or liposomes, anti-dyslipidemic agents coupled to a small-molecule α-helix mimic (e.g., 2G-SMoC or 4G-SMoC), and modified (e.g., stapled, prenylated or lipidated) anti-dyslipidemic agents.

Example 4. Phase I/II Safety/Efficacy Studies of Anti-Dyslipidemic Agents with Cell-Penetrating Peptides Randomized, open-label, dose-escalation Phase I/II studies are conducted to evaluate the safety, tolerability, pharmacokinetics and effective dose of an anti-dyslipidemic agent mixed with, non-covalently associated with or covalently bonded to a cell-penetrating peptide and administered by eye drop to subjects with AMD (e.g., intermediate-stage AMD). Soft drusen are a high-risk factor for progression of AMD and are clinically well-recognized lipid-rich sub-RPE-BL deposits that are hallmarks for AMD. The cumulative dose of the anti-dyslipidemic agent until drusen reduction to a certain level as well the maximum tolerated dose provide important information about the optimum dose(s) of the anti-dyslipidemic agent in other studies, including those where the anti-dyslipidemic agent is administered in combination with one or more other therapeutic agents (e.g., an anti-inflammatory agent, a neuroprotector or an anti-angiogenic agent) for the treatment of atrophic AMD or neovascular AMD.

In Phase I/II studies, one, two or more 50 μL eye drops (e.g., a single eye drop) of an anti-dyslipidemic agent (e.g., an apoA-I mimetic such as L-4F or D-4F, an apoE mimetic such as AEM-28-14, or a statin such as atorvastatin or simvastatin) mixed with, non-covalently associated with or covalently bonded to a cell-penetrating peptide (e.g., an arginine-rich CPP such as a polyarginine [e.g., $R_6$ (SEQ ID NO: 258) or $R_9$ (SEQ ID NO: 261)], or an amphipathic CPP [e.g., Pep-1 or penetratin]) are administered to the surface of one eye one, two or more times (e.g., twice) daily for, e.g., about 6 or 12 months. The other eye does not receive any eye drop and serves as intra-individual control eye. Primary outcome measures include, e.g., reduction of soft drusen (e.g., reduction of total drusen volume by about 30%) as quantified by spectral domain optical coherence tomography (SDOCT) and stability of or increase in quantitative fundus autofluorescence (qAF) intensity. Secondary outcome measures include, e.g., stability or improvement of vision, such as metamorphopsia, dark adaptometry and best-corrected visual acuity (BCVA) from baseline. Measurements/monitoring are taken/done at the end of the treatment period and up to, e.g., about 3 or 6 months after the end of the treatment period, and can also be taken/done during the treatment period, such as every 1 month, 2 months or 3 months during the treatment period.

Similar studies can be conducted to evaluate different doses of the anti-dyslipidemic agent mixed with, non-covalently associated with or covalently bonded to the CPP (taking into account, e.g., the concentrations of the anti-dyslipidemic agent and the CPP in the eye drop, the volume of an eye drop and the number of eye drops applied daily), different lengths of treatment (e.g., 18 months or 24 months), different anti-dyslipidemic agents, different CPPs, anti-dyslipidemic agents encapsulated in CPP-conjugated nanoparticles, micelles or liposomes, anti-dyslipidemic agents coupled to a small-molecule α-helix mimic (e.g., 2G-SMoC or 4G-SMoC), and modified (e.g., stapled, prenylated or lipidated) anti-dyslipidemic agents.

Example 5. CPP-Assisted Delivery of Atorvastatin Across an Egg Shell Membrane

Atorvastatin was dissolved in DMSO and titrated into water. The CPP hexa-arginine (SEQ ID NO: 258) (5 mg/mL) and atorvastatin were mixed in water by vortex for 30 seconds, while atorvastatin alone was mixed in water by vortex for 30 seconds as a control. As a proxy for topical delivery into the eye by eye drop, 50 μL of atorvastatin plus hexa-arginine (SEQ ID NO: 258) or atorvastatin alone was applied to one side of the outer shell membrane of a chicken egg, and the material that crossed the membrane in water was collected after 2 minutes. The presence of atorvastatin was detected by electrospray mass spectroscopy. The peak at 559 m/z (M$^+$) in FIG. 7A demonstrates that atorvastatin crossed the egg shell membrane with the aid of hexa-arginine (SEQ ID NO: 258), whereas the absence of a peak at 559 m/z in FIG. 7B demonstrates that atorvastatin did not cross the membrane in the absence of hexa-arginine (SEQ ID NO: 258).

Example 6. CPP-Assisted Delivery of Lutein Across an Egg Shell Membrane

Lutein was dissolved in DMSO (10 mg/mL) and titrated into water. The CPP hexa-arginine (SEQ ID NO: 258) (5 mg/mL) and lutein were mixed in water by vortex for 30 seconds, while lutein alone was mixed in water by vortex for 30 seconds as a control. As a proxy for topical delivery into the eye by eye drop, 50 μL of lutein plus hexa-arginine (SEQ ID NO: 258) or lutein alone was applied to one side of the outer shell membrane of a chicken egg, and the material that crossed the membrane in water was collected after 2 minutes. The level of lutein was measured by absorbance. The experiment was conducted three times (n=3). 26±8% of the applied amount of lutein crossed the egg shell membrane with the aid of hexa-arginine (SEQ ID NO: 258), whereas lutein did not cross the membrane in the absence of hexa-arginine (SEQ ID NO: 258) (FIG. 8).

Example 7. CPP-Assisted Delivery of Zeaxanthin Across an Egg Shell Membrane

Zeaxanthin was dissolved in DMF (10 mg/mL) and titrated into water. The CPP hexa-arginine (SEQ ID NO: 258) (5 mg/mL) and zeaxanthin were mixed in water by vortex for 30 seconds, while zeaxanthin alone was mixed in water by vortex for 30 seconds as a control. As a proxy for topical delivery into the eye by eye drop, 50 µL of zeaxanthin plus hexa-arginine (SEQ ID NO: 258) or zeaxanthin alone was applied to one side of the outer shell membrane of a chicken egg, and the material that crossed the membrane in water was collected after 2 minutes. The level of zeaxanthin was measured by absorbance. The experiment was conducted three times (n=3). 15±5% of the applied amount of zeaxanthin crossed the egg shell membrane with the aid of hexa-arginine (SEQ ID NO: 258), whereas a very small amount of zeaxanthin crossed the membrane in the absence of hexa-arginine (SEQ ID NO: 258) (FIG. 9).

Example 8. CPP-Assisted Delivery of Lutein and Zeaxanthin Across an Egg Shell Membrane Lutein was dissolved in DMSO (10 mg/mL) and titrated into water, zeaxanthin was dissolved in DMF (10 mg/mL) and titrated into water, and then lutein and zeaxanthin were mixed in a 1:1 ratio. The CPP hexa-arginine (SEQ ID NO: 258) (5 mg/mL), lutein and zeaxanthin were mixed in water by vortex for 30 seconds, while lutein and zeaxanthin without CPP were mixed in water by vortex for 30 seconds as a control. As a proxy for topical delivery into the eye by eye drop, 50 µL of lutein and zeaxanthin plus hexa-arginine (SEQ ID NO: 258), or lutein and zeaxanthin without CPP, was applied to one side of the outer shell membrane of a chicken egg, and the material that crossed the membrane in water was collected after 2 minutes. The level of lutein and zeaxanthin was measured by absorbance. The experiment was conducted three times (n=3). 21±6% of the applied amount of lutein and zeaxanthin crossed the egg shell membrane with the aid of hexa-arginine (SEQ ID NO: 258), whereas a very small amount of lutein and zeaxanthin crossed the membrane in the absence of hexa-arginine (SEQ ID NO: 258) (FIG. 10).

Example 9. CPP-Assisted Delivery of Dexamethasone Across an Egg Shell Membrane

Dexamethasone was dissolved in DMSO and titrated into water. The CPP hexa-arginine (SEQ ID NO: 258) (5 mg/mL) and dexamethasone were mixed in water by vortex for 30 seconds, while dexamethasone alone was mixed in water by vortex for 30 seconds as a control. As a proxy for topical delivery into the eye by eye drop, 50 µL of dexamethasone plus hexa-arginine (SEQ ID NO: 258) or dexamethasone alone was applied to one side of the outer shell membrane of a chicken egg, and the material that crossed the membrane in water was collected after 2 minutes. The presence of dexamethasone was detected by electrospray mass spectroscopy. The peaks at 415 m/z (M+Na), 807 m/z (2M+Na) and 1199 m/z (3M+Na) in FIG. 11A demonstrate that dexamethasone crossed the egg shell membrane with the aid of hexa-arginine (SEQ ID NO: 258), whereas the absence of a peak at 415 m/z, 807 m/z or 1199 m/z in FIG. 11B demonstrates that dexamethasone did not cross the membrane in the absence of hexa-arginine (SEQ ID NO: 258).

Example 10. CPP-Assisted Delivery of Tacrolimus Across an Egg Shell Membrane

Tacrolimus was dissolved in DMSO and titrated into water. The CPP hexa-arginine (SEQ ID NO: 258) (5 mg/mL) and tacrolimus were mixed in water by vortex for 30 seconds, while tacrolimus alone was mixed in water by vortex for 30 seconds as a control. As a proxy for topical delivery into the eye by eye drop, 50 µL of tacrolimus plus hexa-arginine (SEQ ID NO: 258) or tacrolimus alone was applied to one side of the outer shell membrane of a chicken egg, and the material that crossed the membrane in water was collected after 2 minutes. The presence of tacrolimus was detected by electrospray mass spectroscopy. The peaks at 826 m/z (M+Na) and 842 m/z (M+K) in FIG. 12A demonstrate that tacrolimus crossed the egg shell membrane with the aid of hexa-arginine (SEQ ID NO: 258), whereas the absence of a peak at 826 m/z or 842 m/z in FIG. 12B demonstrates that tacrolimus did not cross the membrane in the absence of hexa-arginine (SEQ ID NO: 258).

Example 11. CPP-Assisted Delivery of Adalimumab Across an Egg Shell Membrane

Adalimumab was fluorescently tagged and purified. The CPP hexa-arginine (SEQ ID NO: 258) (5 mg/mL) and adalimumab (333 µg/mL) were mixed in PBS by vortex for 30 seconds, while adalimumab alone was mixed in PBS by vortex for 30 seconds as a control. As a proxy for topical delivery into the eye by eye drop, 50 µL of adalimumab plus hexa-arginine (SEQ ID NO: 258) or adalimumab alone was applied to one side of the outer shell membrane of a chicken egg, and the material that crossed the membrane in PBS was collected after 2 minutes. The level of adalimumab was measured by fluorescence. The experiment was conducted three times (n=3). FIG. 13 shows that the amount of adalimumab which crossed the egg shell membrane with the aid of hexa-arginine (SEQ ID NO: 258) (fluorescence of 6071±1241) was markedly greater than the amount of adalimumab which crossed the membrane in the absence of hexa-arginine (SEQ ID NO: 258) (fluorescence of 1359±3).

Example 12. CPP-Assisted Delivery of Glucose Across an Egg Shell Membrane

The CPP hexa-arginine (SEQ ID NO: 258) (5 mg/mL) and glucose were mixed in water by vortex for 30 seconds, while glucose alone was mixed in water by vortex for 30 seconds as a control. As a proxy for topical delivery into the eye by eye drop, 50 µL of glucose plus hexa-arginine (SEQ ID NO: 258) or glucose alone was applied to one side of the outer shell membrane of a chicken egg, and the material that crossed the membrane in water was collected after 2 minutes. The presence of glucose was detected by electrospray mass spectroscopy. The peak at 203 m/z (M+Na) in FIG. 14 demonstrates that glucose crossed the egg shell membrane in the presence of hexa-arginine (SEQ ID NO: 258). A peak at 203 m/z was also present in the mass spectrum (not shown) when glucose was applied to the membrane without hexa-arginine (SEQ ID NO: 258). However, the area of the 203 m/z peak for glucose plus hexa-arginine (SEQ ID NO: 258) was substantially greater than the area of the 203 m/z peak for glucose without hexa-arginine (SEQ ID NO: 258) (523,483 vs 57,172), indicating that a substantially greater amount of glucose crossed the membrane in the presence of hexa-arginine (SEQ ID NO: 258).

Example 13. CPP-Assisted Delivery of BDNF Across an Egg Shell Membrane

The CPP hexa-arginine (SEQ ID NO: 258) (5 mg/mL) and brain-derived neurotrophic factor (BDNF, 20 µg/mL) were mixed in PBS by vortex for 30 seconds, while BDNF alone was mixed in PBS by vortex for 30 seconds as a control. As a proxy for topical delivery into the eye by eye drop, 50 µL of BDNF plus hexa-arginine (SEQ ID NO: 258) or BDNF alone was applied to one side of the outer shell membrane of a chicken egg, and the material that crossed the membrane in PBS was collected after 2 minutes. The level of BDNF was measured by ELISA. The experiment was conducted three times (n=3). 23±1% of the applied amount of BDNF crossed the egg shell membrane with the aid of hexa-arginine (SEQ ID NO: 258), whereas BDNF did not cross the membrane in the absence of hexa-arginine (SEQ ID NO: 258) (FIG. 15).

Example 14. CPP-Assisted Delivery of GDNF Across an Egg Shell Membrane

The CPP hexa-arginine (SEQ ID NO: 258) (5 mg/mL) and glial cell-derived neurotrophic factor (GDNF, 33 µg/mL) were mixed in PBS by vortex for 30 seconds, while GDNF alone was mixed in PBS by vortex for 30 seconds as a control. As a proxy for topical delivery into the eye by eye drop, 50 µL of GDNF plus hexa-arginine (SEQ ID NO: 258) or GDNF alone was applied to one side of the outer shell membrane of a chicken egg, and the material that crossed the membrane in PBS was collected after 2 minutes. The level of GDNF was measured by ELISA. The experiment was conducted three times (n=3). 76±40% of the applied amount of GDNF crossed the egg shell membrane with the aid of hexa-arginine (SEQ ID NO: 258), whereas GDNF did not cross the membrane in the absence of hexa-arginine (SEQ ID NO: 258) (FIG. 16).

Example 15. CPP-Assisted Delivery of FGF Across an Egg Shell Membrane

The CPP hexa-arginine (SEQ ID NO: 258) (5 mg/mL) and fibroblast growth factor (FGF, 20 µg/mL) were mixed in PBS by vortex for 30 seconds, while FGF alone was mixed in PBS by vortex for 30 seconds as a control. As a proxy for topical delivery into the eye by eye drop, 50 µL of FGF plus hexa-arginine (SEQ ID NO: 258) or FGF alone was applied to one side of the outer shell membrane of a chicken egg, and the material that crossed the membrane in PBS was collected after 2 minutes. The level of FGF was measured by ELISA. The experiment was conducted three times (n=3). 74±32% of the applied amount of FGF crossed the egg shell membrane with the aid of hexa-arginine (SEQ ID NO: 258), whereas FGF did not cross the membrane in the absence of hexa-arginine (SEQ ID NO: 258) (FIG. 17).

Example 16. CPP-Assisted Delivery of L-4F into Porcine Eye Ex Vivo

The apoA-I mimetic L-4F was fluorescently tagged and purified. The CPP hexa-arginine (SEQ ID NO: 258) (5 mg/mL) and L-4F (1.25 mg/mL) were mixed in PBS by vortex for 30 seconds, while L-4F (1.25 mg/mL) alone and hexa-arginine (SEQ ID NO: 258) (5 mg/mL) alone were separately mixed in PBS by vortex for 30 seconds as controls. An eye drop of 50 µL of L-4F plus hexa-arginine (SEQ ID NO: 258), or L-4F alone, or hexa-arginine (SEQ ID NO: 258) alone or PBS alone was applied topically to the front of a porcine eye ex vivo, and then the eye was dissected 10 minutes after topical application. The level of L-4F in the posterior segment (the vitreous and the retina) of the eye was measured by fluorescence. FIG. 18 shows that a significantly greater amount of L-4F was delivered into the posterior segment of the porcine eye ex vivo with the aid of hexa-arginine (SEQ ID NO: 258) than without the CPP.

Example 17. CPP-Assisted Delivery of Bevacizumab into Rat Eye In Vivo

The CPP hexa-arginine (SEQ ID NO: 258) (5 mg/mL) and bevacizumab (25 mg/mL) were mixed in PBS by vortex for 30 seconds. An eye drop of 50 µL of bevacizumab plus hexa-arginine (SEQ ID NO: 258) was applied topically to the front of one of the eyes of a live rat, and then the rat was sacrificed 60 minutes after topical application. The level of bevacizumab in the posterior segment (the vitreous and the retina) of the treated eye and that in the fellow untreated eye were measured by human IgG ELISA. FIG. 19 shows that bevacizumab was delivered into the posterior segment of the treated rat eye in vivo with the aid of hexa-arginine (SEQ ID NO: 258). Bevacizumab was not detected in the untreated eye or in the bloodstream, which demonstrates that bevacizumab entered into the posterior segment of the treated eye directly via the topical application rather than indirectly via the systemic circulation.

It is understood that, while particular embodiments have been illustrated and described, various modifications may be made thereto and are contemplated herein. It is also understood that the disclosure is not limited by the specific examples provided herein. The description and illustration of embodiments and examples of the disclosure herein are not intended to be construed in a limiting sense. It is further understood that aspects of the disclosure are not limited to the specific depictions, configurations or relative proportions set forth herein, which may depend on a variety of conditions and variables. Various modifications and variations in form and detail of the embodiments and examples of the disclosure will be apparent to a person skilled in the art. It is therefore contemplated that the disclosure also covers any and all such modifications, variations and equivalents.

What is claimed is:

1. A transepithelial, transmembrane or transmucosal drug-delivery system (TDS) comprising a therapeutic agent and a cell-penetrating peptide (CPP), wherein:
   the therapeutic agent is a small molecule;
   the CPP is a polycationic CPP, an arginine-rich CPP or an amphipathic CPP;
   the therapeutic agent is not covalently bound to the CPP; and
   the TDS is capable of delivering the therapeutic agent into the eye;
with the proviso that
   the TDS is not a therapeutic agent-containing CPP-conjugated nanoparticle, micelle or liposome.

2. The TDS of claim 1, which is capable of delivering the therapeutic agent into the posterior segment of the eye.

3. The TDS of claim 1, which is capable of delivering the therapeutic agent into the eye when administered by an eye drop or a contact lens.

4. The TDS of claim 1, wherein the therapeutic agent is a statin.

5. The TDS of claim 1, wherein the polycationic CPP is the peptide for ocular delivery (POD).

6. The TDS of claim 1, wherein the arginine-rich CPP is a polyarginine or a TAT-related CPP.

7. The TDS of claim 1, wherein the amphipathic CPP is Pep-1 or penetratin.

8. The TDS of claim 1, wherein the therapeutic agent is an agent that preserves or improves the health of the endothelium or/and the blood flow of the vascular system of the eye, an anti-dyslipidemic agent, an antioxidant, an anti-inflammatory agent, a complement inhibitor, a neuroprotector or an anti-angiogenic agent, or any combination thereof.

9. A pharmaceutical composition comprising a therapeutic agent, a cell-penetrating peptide (CPP) and one or more pharmaceutically acceptable carriers or excipients, wherein:
   the therapeutic agent is a small molecule;
   the CPP is a polycationic CPP, an arginine-rich CPP or an amphipathic CPP;
   the therapeutic agent is not covalently bound to the CPP; and
   the pharmaceutical composition is formulated for administration to the eye;
with the proviso that
   the pharmaceutical composition does not comprise a therapeutic agent-containing CPP-conjugated nanoparticle, micelle or liposome.

10. The pharmaceutical composition of claim 9, wherein the therapeutic agent is a statin.

11. The pharmaceutical composition of claim 9, wherein the polycationic CPP is the peptide for ocular delivery (POD), the arginine-rich CPP is a polyarginine or a TAT-related CPP, and the amphipathic CPP is Pep-1 or penetratin.

12. The pharmaceutical composition of claim 9, which is formulated for administration by an eye drop or a contact lens.

13. The pharmaceutical composition of claim 9, wherein the therapeutic agent is an agent that preserves or improves the health of the endothelium or/and the blood flow of the vascular system of the eye, an anti-dyslipidemic agent, an antioxidant, an anti-inflammatory agent, a complement inhibitor, a neuroprotector or an anti-angiogenic agent, or any combination thereof.

14. A method of treating an eye disorder, comprising administering to a subject in need of treatment a therapeutically effective amount of the transepithelial, transmembrane or transmucosal drug-delivery system (TDS) of claim 1.

15. The method of claim 14, wherein the eye disorder is atrophic or neovascular age-related macular degeneration.

16. The method of claim 14, further comprising administering one or more additional therapeutic agents.

17. The method of claim 14, wherein the TDS comprises a therapeutic agent which is an agent that preserves or improves the health of the endothelium or/and the blood flow of the vascular system of the eye, an anti-dyslipidemic agent, an antioxidant, an anti-inflammatory agent, a complement inhibitor, a neuroprotector or an anti-angiogenic agent, or any combination thereof.

18. The method of claim 14, wherein the TDS comprises a cell-penetrating peptide (CPP) which is a polycationic CPP selected from the peptide for ocular delivery (POD), an arginine-rich CPP selected from polyarginines and TAT-related CPPs, or an amphipathic CPP selected from Pep-1 and penetratin.

19. The method of claim 14, wherein the TDS is administered to an eye of the subject by means of an eye drop or a contact lens.

* * * * *